US012421288B2

(12) United States Patent
Engelhart et al.

(10) Patent No.: US 12,421,288 B2
(45) Date of Patent: Sep. 23, 2025

(54) INTERFERON ALPHA-2 VARIANTS

(71) Applicant: A-Alpha Bio, Seattle, WA (US)

(72) Inventors: Emily Engelhart, Seattle, WA (US); Davis Goodnight, Seattle, WA (US); Kyle Minch, Seattle, WA (US); Ryan Swanson, Seattle, WA (US)

(73) Assignee: A-Alpha Bio, Seattle, WA (US)

( * ) Notice: Subject to any disclaimer, the term of this patent is extended or adjusted under 35 U.S.C. 154(b) by 0 days.

(21) Appl. No.: 18/607,194

(22) Filed: Mar. 15, 2024

(65) Prior Publication Data

US 2024/0309062 A1 Sep. 19, 2024

Related U.S. Application Data

(60) Provisional application No. 63/497,089, filed on Apr. 19, 2023, provisional application No. 63/452,654, filed on Mar. 16, 2023.

(51) Int. Cl.
*C07K 14/56* (2006.01)
*C07K 16/28* (2006.01)

(52) U.S. Cl.
CPC .......... *C07K 14/56* (2013.01); *C07K 16/2815* (2013.01); *C07K 2319/30* (2013.01)

(58) Field of Classification Search
None
See application file for complete search history.

(56) References Cited

U.S. PATENT DOCUMENTS

| | | | |
|---|---|---|---|
| 5,866,692 | A | 2/1999 | Shitara et al. |
| 5,997,867 | A | 12/1999 | Waldmann et al. |
| 10,988,759 | B2 | 4/2021 | Baker et al. |
| 11,136,573 | B2 | 10/2021 | Baker et al. |
| 11,474,111 | B2 | 10/2022 | Younger et al. |
| 11,726,097 | B2 | 8/2023 | Younger et al. |
| 11,820,970 | B2 | 11/2023 | Baker et al. |
| 2002/0025304 | A1 | 2/2002 | Croze et al. |
| 2002/0137677 | A1 | 9/2002 | Sprecher et al. |
| 2005/0124044 | A1 | 6/2005 | Cunningham et al. |
| 2008/0166319 | A1 | 7/2008 | Schreiber et al. |
| 2010/0196309 | A1 | 8/2010 | Bondensgaard et al. |
| 2020/0071375 | A1 | 3/2020 | Kotenko et al. |
| 2021/0324028 | A1 | 10/2021 | Yeung et al. |
| 2022/0251543 | A1 | 8/2022 | Younger et al. |
| 2025/0059247 | A1 | 2/2025 | Goodnight et al. |

FOREIGN PATENT DOCUMENTS

| | | | |
|---|---|---|---|
| WO | WO 1999/58572 | 11/1999 | |
| WO | WO-2007000769 A2 * | 1/2007 | .............. A61P 37/02 |
| WO | WO-2013059885 A2 * | 5/2013 | ........... A61K 47/642 |

OTHER PUBLICATIONS

Malhotra A., Methods Enzymol. 2009;463:239-58. doi: 10.1016/S0076-6879(09)63016-0. PMID: 19892176.*
Shen et al., "Engineered IL-21 cytokine muteins fused to anti-PD-1 antibodies can improve CD8+ T cell function and anti-tumor immunity," Frontiers in Immunology, May 8, 2020, 11:832, 14 pages.
Wilkinson et al., "Systematic analysis of the varied designs of 819 therapeutic antibodies and Fc fusion proteins assigned international nonproprietary names," Mabs, Dec. 2022, 4(1):2123299, 15 pages.
PCT International Search Report and Written Opinion in International Appln. No. PCT/US2024/020211, mailed on Aug. 13, 2024, 13 pages.
Younger et al., "High-throughput characterization of protein-protein interactions by reprogramming yeast mating," Proceedings of the National Academy of Sciences, Nov. 2017, 114(46):12166-71.
PCT International Search Report and Written Opinion in International Appln. No. PCT/US2024/042270, mailed on Feb. 14, 2025, 14 pages.

* cited by examiner

*Primary Examiner* — Michael Szperka
(74) *Attorney, Agent, or Firm* — Fish & Richardson P.C.

(57) ABSTRACT

Provided herein are human interferon alpha-2 (IFNA2) variants that have decreased or no detectable binding to the human interferon-alpha/beta receptor beta 2 (IFNAR2) as compared to the wild-type human IFNA2 polypeptide. Also provided herein are fusion proteins comprising an antibody or fragment thereof, and a human IFNA2 variant, wherein the IFNA2 variant is covalently linked to the antibody, and wherein the IFNA2 variant has decreased or no detectable binding to the human interferon-alpha/beta receptor beta (IFNAR2) as compared to the wild-type human IFNA2 polypeptide.

16 Claims, 27 Drawing Sheets

Specification includes a Sequence Listing.

IFNAR2

| IFNA2 | Human | Cyno | Mouse | Rat |
|---|---|---|---|---|
| Human | 2.2 | 2.5 | 3.5 | 2.9 |
| Cyno | 1.8 | 2.3 | 4.2 | 3.2 |
| Mouse | 3.8 | 4.3 | 4.7 | 3.7 |
| Rat | 4.5 | 4.7 | 1.7 | 1.6 |

FIG. 1

INTERFERON ALPHA-2 VARIANTS

CROSS-REFERENCE TO RELATED APPLICATIONS

This application claims the benefit of U.S. Provisional Patent Application No. 63/452,654, filed on Mar. 16, 2023, and U.S. Provisional Patent Application No. 63/497,089, filed on Apr. 19, 2023, the contents of which are incorporated herein by reference in their entirety.

SEQUENCE LISTING

This application contains a Sequence Listing that has been submitted electronically as an XML file named "52911-0009001_SL.xml." The XML file, created on Apr. 26, 2024, is 603,963 bytes in size. The material in the XML file is hereby incorporated by reference in its entirety.

TECHNICAL FIELD

The present disclosure provides human interferon alpha-2 (IFNA2) variants, methods for making thereof, and methods for measuring binding affinities between IFNA2 variants and human interferon alpha/beta receptor 2 (IFNAR2). The provided IFNA2 variants and fusion proteins comprising IFNA2 variants can have therapeutic use. Also provided are methods of stimulating an immune response or suppressing cellular/tumor proliferation in a mammal, and methods of treating a disorder (e.g., cancer) using the IFNA2 variants or the fusion proteins of such IFNA2 variants.

BACKGROUND

Cytokines, including IFNA2, are potent immune modulators with potential therapeutic value in immuno-oncology and infectious disease. However, in human subjects their potency can present challenges, including only modest efficacies accompanied by significant toxicities and adverse side effects due to immune activation in healthy tissues. Therefore, there exists a need for therapeutic agents based on a targeted cytokine, which would be of great clinical value in treatments of various diseases including cancer.

SUMMARY

The present disclosure provides human interferon alpha-2 (IFNA2) variants and fusion proteins including those variants. In a therapeutic context, these cytokine variants can be targeted to a particular immune cell type of interest by linking the cytokine to an antibody or portion thereof against a specific cell surface marker. To ensure immune activation occurs only at the cell type of interest, the disclosure provides "detuned" cytokine variants, e.g., IFNA2 variants, with weakened affinity for their receptors (in this case, IFNA2 variants with weakened affinity for interferon alpha/beta receptor 2 IFNAR2). Detuning the cytokine can decrease or eliminate toxicities and adverse side effects by localizing the cytokine activity to a specific cellular or tumor context. By reducing affinity for the receptor, the activity of the detuned cytokines is decreased for most cell types, e.g., in healthy tissues, which, in turn, decreases potential toxicity of the molecule when administered as a therapy. However, at the surface of the cell type targeted by the antibody, the residual activity of the cytokine is sufficient to bind its receptor and activate pro-inflammatory pathways leading to immune activation.

The compositions and methods provided herein are based, at least in part, on the identification of IFNA2 variants with decreased affinity for the IFNAR2 receptor by high-throughput screening using a protein-protein interaction (PPI) assay based on a yeast sexual agglutination method, termed AlphaSeq™ (see, e.g., U.S. Pat. Nos. 10,988,759 and 11,136,573).

Cytokine signaling can trigger multifaceted and even opposing activities in different cell types, often leading to toxicity or poor response rates in the therapeutic setting. Targeting specific cellular signaling, such as defined immune subsets or antigen experienced cells at the tumor, has the potential to widen a cytokine therapeutic index and improve patient outcomes.

In a first aspect, the disclosure provides isolated human interferon alpha-2 (IFNA2) variants, wherein the IFNA2 variants have decreased or no detectable binding to the human interferon-alpha/beta receptor beta 2 (IFNAR2) as compared to the wild-type human IFNA2 polypeptide. In some embodiments, the isolated IFNA2 variant has a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2.

In some embodiments, the isolated IFNA2 variants include one or more amino acid substitutions at one or more positions of the wild-type human IFNA2 polypeptide (SEQ ID NO: 1) selected from the group consisting of: H30, S31, L32, S34, R35, R36, L38, L40, L41, A42, Q43, M44, R45, R46, I47, S48, L49, F50, S51, L53, K54, D55, R56, H57, D58, F59, F61, P62, Q63, Q69, K72, V78, M82, Q84, I86, K93, A98, L103, K106, Y108, T109, E110, Q113, N116, N116, E119, A120, G125, V126, T129, P132, M134, 1139, A141, R143, Y145, Q147, R148, E155, K156, K157, P160, V165, R167, A168, E169, I170, M171, R172, S173, S175, L176, S177, N179, S183, R185, S186, K187, and E188.

In some embodiments, the IFNA2 variants include an H30X amino acid substitution in SEQ ID NO: 1, where X represents any amino acid. In some embodiments, the isolated IFNA2 variant includes an H30A or H30D amino acid substitution in SEQ ID NO: 1.

In some embodiments, the IFNA2 variants include an S31X amino acid substitution in SEQ ID NO: 1, where X represents any amino acid. In some embodiments, the IFNA2 variant includes an S31D amino acid substitution in SEQ ID NO: 1.

In some embodiments, the IFNA2 variants include an L32X amino acid substitution in SEQ ID NO: 1, where X represents any amino acid. In some embodiments, the IFNA2 variant includes an L32D or L32E amino acid substitution in SEQ ID NO: 1.

In some embodiments, the IFNA2 variants include an S34X amino acid substitution in SEQ ID NO: 1, where X represents any amino acid. In some embodiments, the IFNA2 variant includes an S34A amino acid substitution in SEQ ID NO: 1.

In some embodiments, the IFNA2 variants include an R35X amino acid substitution in SEQ ID NO: 1, where X represents any amino acid. In some embodiments, the IFNA2 variant includes an R35N amino acid substitution in SEQ ID NO: 1.

In some embodiments, the IFNA2 variants include an R36X amino acid substitution in SEQ ID NO: 1, where X represents any amino acid. In some embodiments, the IFNA2 variant includes an R36G amino acid substitution in SEQ ID NO: 1.

In some embodiments, the IFNA2 variants include an L38X amino acid substitution in SEQ ID NO: 1, where X represents any amino acid. In some embodiments, the IFNA2 variant includes an L38H, L38Y, L38G, L38P, L38S, L38T, L38Q, or L38N amino acid substitution in SEQ ID NO: 1.

In some embodiments, the IFNA2 variants include an L40X amino acid substitution in SEQ ID NO: 1, where X represents any amino acid. In some embodiments, the IFNA2 variant includes an L40R, L40G, L40Q, or L40D amino acid substitution in SEQ ID NO: 1.

In some embodiments, the IFNA2 variants include an L41X amino acid substitution in SEQ ID NO: 1, where X represents any amino acid. In some embodiments, the IFNA2 variant includes an L41H, L41D, L41K, L41G, or L41A amino acid substitution in SEQ ID NO: 1.

In some embodiments, the IFNA2 variants include an A42X amino acid substitution in SEQ ID NO: 1, where X represents any amino acid. In some embodiments, the IFNA2 variant includes an A42G or A42M amino acid substitution in SEQ ID NO: 1.

In some embodiments, the IFNA2 variants include an Q43X amino acid substitution in SEQ ID NO: 1, where X represents any amino acid. In some embodiments, the IFNA2 variant includes an Q43P amino acid substitution in SEQ ID NO: 1.

In some embodiments, the IFNA2 variants include an M44X amino acid substitution in SEQ ID NO: 1, where X represents any amino acid. In some embodiments, the IFNA2 variant includes an M44Q amino acid substitution in SEQ ID NO: 1.

In some embodiments, the IFNA2 variants include an R45X amino acid substitution in SEQ ID NO: 1, where X represents any amino acid. In some embodiments, the IFNA2 variant includes an R45P amino acid substitution in SEQ ID NO: 1.

In some embodiments, the IFNA2 variants include an R46X amino acid substitution in SEQ ID NO: 1, where X represents any amino acid. In some embodiments, the IFNA2 variant includes an R46P, R46D, R46F, R46Y, R46N, R46S, R46I, R46G, R46A, R46H, or R46T amino acid substitution in SEQ ID NO: 1.

In some embodiments, the IFNA2 variants include an 147X amino acid substitution in SEQ ID NO: 1, where X represents any amino acid. In some embodiments, the IFNA2 variant includes an I47P, 147D, 147S, or I47E amino acid substitution in SEQ ID NO: 1.

In some embodiments, the IFNA2 variants include an S48X amino acid substitution in SEQ ID NO: 1, where X represents any amino acid. In some embodiments, the IFNA2 variant includes an S48Y or S48H amino acid substitution in SEQ ID NO: 1.

In some embodiments, the IFNA2 variants include an L49X amino acid substitution in SEQ ID NO: 1, where X represents any amino acid. In some embodiments, the IFNA2 variant includes an L49H, L49I, L49K, L49V, L49Y, L49F, L49G, L49E, or L49P amino acid substitution in SEQ ID NO: 1.

In some embodiments, the IFNA2 variants include an F50X amino acid substitution in SEQ ID NO: 1, where X represents any amino acid. In some embodiments, the IFNA2 variant includes an F50D, F50N, F50G, F50Q, F50S, F50M, F50H, or F50A amino acid substitution in SEQ ID NO: 1.

In some embodiments, the IFNA2 variants include an S51X amino acid substitution in SEQ ID NO: 1, where X represents any amino acid. In some embodiments, the IFNA2 variant includes an S51D or S51E amino acid substitution in SEQ ID NO: 1.

In some embodiments, the IFNA2 variants include an L53X amino acid substitution in SEQ ID NO: 1, where X represents any amino acid. In some embodiments, the IFNA2 variant includes an L53D, L53E, L53G, L53A, L53N, L53V, or L53S amino acid substitution in SEQ ID NO: 1.

In some embodiments, the IFNA2 variants include an K54X amino acid substitution in SEQ ID NO: 1, where X represents any amino acid. In some embodiments, the IFNA2 variant includes an K54L, K54I, or K54M amino acid substitution in SEQ ID NO: 1.

In some embodiments, the IFNA2 variants include an D55X amino acid substitution in SEQ ID NO: 1, where X represents any amino acid. In some embodiments, the IFNA2 variant includes an D55T, D55N, or D55Q amino acid substitution in SEQ ID NO: 1.

In some embodiments, the IFNA2 variants include an R56X amino acid substitution in SEQ ID NO: 1, where X represents any amino acid. In some embodiments, the IFNA2 variant includes an R56D, R56G, R56K, R56N, R56V, R56T, R56A, R56L, R56H amino acid substitution in SEQ ID NO: 1.

In some embodiments, the IFNA2 variants include an H57X amino acid substitution in SEQ ID NO: 1, where X represents any amino acid. In some embodiments, the IFNA2 variant includes an H57P amino acid substitution in SEQ ID NO: 1.

In some embodiments, the IFNA2 variants include an D58X amino acid substitution in SEQ ID NO: 1, where X represents any amino acid. In some embodiments, the IFNA2 variant includes an D58Q amino acid substitution in SEQ ID NO: 1.

In some embodiments, the IFNA2 variants include an F59X amino acid substitution in SEQ ID NO: 1, where X represents any amino acid. In some embodiments, the IFNA2 variant includes an F59Q, F59E, F59I, F59N, F59A, F59G, F59T, or F59Y amino acid substitution in SEQ ID NO: 1.

In some embodiments, the IFNA2 variants include an F61X amino acid substitution in SEQ ID NO: 1, where X represents any amino acid. In some embodiments, the IFNA2 variant includes an F61G, F61I, F61V, F61P, F61Q, F61A, or F61S amino acid substitution in SEQ ID NO: 1.

In some embodiments, the IFNA2 variants include an P62X amino acid substitution in SEQ ID NO: 1, where X represents any amino acid. In some embodiments, the IFNA2 variant includes an P62I amino acid substitution in SEQ ID NO: 1.

In some embodiments, the IFNA2 variants include an Q63X amino acid substitution in SEQ ID NO: 1, where X represents any amino acid. In some embodiments, the IFNA2 variant includes an Q63E amino acid substitution in SEQ ID NO: 1.

In some embodiments, the IFNA2 variants include an Q69X amino acid substitution in SEQ ID NO: 1, where X represents any amino acid. In some embodiments, the IFNA2 variant includes an Q69S amino acid substitution in SEQ ID NO: 1.

In some embodiments, the IFNA2 variants include an K72X amino acid substitution in SEQ ID NO: 1, where X represents any amino acid. In some embodiments, the IFNA2 variant includes an K72D amino acid substitution in SEQ ID NO: 1.

In some embodiments, the IFNA2 variants include an V78X amino acid substitution in SEQ ID NO: 1, where X represents any amino acid. In some embodiments, the IFNA2 variant includes an V78E or V78G amino acid substitution in SEQ ID NO: 1.

In some embodiments, the IFNA2 variants include an M82X amino acid substitution in SEQ ID NO: 1, where X represents any amino acid. In some embodiments, the IFNA2 variant includes an M82W, M82K, M82R, M82G, or M82S amino acid substitution in SEQ ID NO: 1.

In some embodiments, the IFNA2 variants include an 186X amino acid substitution in SEQ ID NO: 1, where X represents any amino acid. In some embodiments, the IFNA2 variant includes an I86L amino acid substitution in SEQ ID NO: 1.

In some embodiments, the IFNA2 variants include an K93X amino acid substitution in SEQ ID NO: 1, where X represents any amino acid. In some embodiments, the IFNA2 variant includes an K93E or K93V amino acid substitution in SEQ ID NO: 1.

In some embodiments, the IFNA2 variants include an A98X amino acid substitution in SEQ ID NO: 1, where X represents any amino acid. In some embodiments, the IFNA2 variant includes an A98E amino acid substitution in SEQ ID NO: 1.

In some embodiments, the IFNA2 variants include an L103X amino acid substitution in SEQ ID NO: 1, where X represents any amino acid. In some embodiments, the IFNA2 variant includes an L103E or L103D amino acid substitution in SEQ ID NO: 1.

In some embodiments, the IFNA2 variants include an K106X amino acid substitution in SEQ ID NO: 1, where X represents any amino acid. In some embodiments, the IFNA2 variant includes an K106L or K106D amino acid substitution in SEQ ID NO: 1.

In some embodiments, the IFNA2 variants include an Y108X amino acid substitution in SEQ ID NO: 1, where X represents any amino acid. In some embodiments, the IFNA2 variant includes an Y108K amino acid substitution in SEQ ID NO: 1.

In some embodiments, the IFNA2 variants include an T109X amino acid substitution in SEQ ID NO: 1, where X represents any amino acid. In some embodiments, the IFNA2 variant includes an T109W amino acid substitution in SEQ ID NO: 1.

In some embodiments, the IFNA2 variants include an E110X amino acid substitution in SEQ ID NO: 1, where X represents any amino acid. In some embodiments, the IFNA2 variant includes an E110P or E110S amino acid substitution in SEQ ID NO: 1.

In some embodiments, the IFNA2 variants include an Q113X amino acid substitution in SEQ ID NO: 1, where X represents any amino acid. In some embodiments, the IFNA2 variant includes an Q113W amino acid substitution in SEQ ID NO: 1.

In some embodiments, the IFNA2 variants include an N116X amino acid substitution in SEQ ID NO: 1, where X represents any amino acid. In some embodiments, the IFNA2 variant includes an N116W, N116M, N116F, or N116Q amino acid substitution in SEQ ID NO: 1.

In some embodiments, the IFNA2 variants include an E119X amino acid substitution in SEQ ID NO: 1, where X represents any amino acid. In some embodiments, the IFNA2 variant includes an E119Y or E119F amino acid substitution in SEQ ID NO: 1.

In some embodiments, the IFNA2 variants include an A120X amino acid substitution in SEQ ID NO: 1, where X represents any amino acid. In some embodiments, the IFNA2 variant includes an A120M amino acid substitution in SEQ ID NO: 1.

In some embodiments, the IFNA2 variants include an G125X amino acid substitution in SEQ ID NO: 1, where X represents any amino acid. In some embodiments, the IFNA2 variant includes an G125V amino acid substitution in SEQ ID NO: 1.

In some embodiments, the IFNA2 variants include an V126X amino acid substitution in SEQ ID NO: 1, where X represents any amino acid. In some embodiments, the IFNA2 variant includes an V126W or V126Y amino acid substitution in SEQ ID NO: 1.

In some embodiments, the IFNA2 variants include an T129X amino acid substitution in SEQ ID NO: 1, where X represents any amino acid. In some embodiments, the IFNA2 variant includes an T129G amino acid substitution in SEQ ID NO: 1.

In some embodiments, the IFNA2 variants include an P132X amino acid substitution in SEQ ID NO: 1, where X represents any amino acid. In some embodiments, the IFNA2 variant includes an P132W amino acid substitution in SEQ ID NO: 1.

In some embodiments, the IFNA2 variants include an M134X amino acid substitution in SEQ ID NO: 1, where X represents any amino acid. In some embodiments, the IFNA2 variant includes an M134Y amino acid substitution in SEQ ID NO: 1.

In some embodiments, the IFNA2 variants include an M139X amino acid substitution in SEQ ID NO: 1, where X represents any amino acid. In some embodiments, the IFNA2 variant includes an I139Y or I1139F amino acid substitution in SEQ ID NO: 1.

In some embodiments, the IFNA2 variants include an A141X amino acid substitution in SEQ ID NO: 1, where X represents any amino acid. In some embodiments, the IFNA2 variant includes an A141E or A141I amino acid substitution in SEQ ID NO: 1.

In some embodiments, the IFNA2 variants include an R143X amino acid substitution in SEQ ID NO: 1, where X represents any amino acid. In some embodiments, the IFNA2 variant includes an R143F amino acid substitution in SEQ ID NO: 1.

In some embodiments, the IFNA2 variants include an Q147X amino acid substitution in SEQ ID NO: 1, where X represents any amino acid. In some embodiments, the IFNA2 variant includes an Q147S amino acid substitution in SEQ ID NO: 1.

In some embodiments, the IFNA2 variants include an R148X amino acid substitution in SEQ ID NO: 1, where X represents any amino acid. In some embodiments, the IFNA2 variant includes an R148Y amino acid substitution in SEQ ID NO: 1.

In some embodiments, the IFNA2 variants include an E155X amino acid substitution in SEQ ID NO: 1, where X represents any amino acid. In some embodiments, the IFNA2 variant includes an E155H amino acid substitution in SEQ ID NO: 1.

In some embodiments, the IFNA2 variants include an K156X amino acid substitution in SEQ ID NO: 1, where X represents any amino acid. In some embodiments, the IFNA2 variant includes an K156D, K156L, or K156W amino acid substitution in SEQ ID NO: 1.

In some embodiments, the IFNA2 variants include an K157X amino acid substitution in SEQ ID NO: 1, where X represents any amino acid. In some embodiments, the IFNA2 variant includes an K157Y amino acid substitution in SEQ ID NO: 1.

In some embodiments, the IFNA2 variants include an P160X amino acid substitution in SEQ ID NO: 1, where X represents any amino acid. In some embodiments, the IFNA2 variant includes an P160E, P160F, P160W, P160Y, or P160T amino acid substitution in SEQ ID NO: 1.

In some embodiments, the IFNA2 variants include an V165X amino acid substitution in SEQ ID NO: 1, where X represents any amino acid. In some embodiments, the IFNA2 variant includes an V165Y, V165E, V165H, V165K, V165W, V165F, V165Q, V165L, V165M, V165S, V165R, V165N, V165D, or V165I amino acid substitution in SEQ ID NO: 1.

In some embodiments, the IFNA2 variants include an R167X amino acid substitution in SEQ ID NO: 1, where X represents any amino acid. In some embodiments, the IFNA2 variant includes an R167W, R167I, R167M, R167S, R167E, R167L, R167V, R167A, R167G, or R167H amino acid substitution in SEQ ID NO: 1.

In some embodiments, the IFNA2 variants include an A168X amino acid substitution in SEQ ID NO: 1, where X represents any amino acid. In some embodiments, the IFNA2 variant includes an A168R, A168H, A168K, A168Y, A168G, A168F, A168D, A168M, or A168Q amino acid substitution in SEQ ID NO: 1.

In some embodiments, the IFNA2 variants include an E169X amino acid substitution in SEQ ID NO: 1, where X represents any amino acid. In some embodiments, the IFNA2 variant includes an E169T, E169S, or E169G amino acid substitution in SEQ ID NO: 1.

In some embodiments, the IFNA2 variants include an 1170X amino acid substitution in SEQ ID NO: 1, where X represents any amino acid. In some embodiments, the IFNA2 variant includes an I170L amino acid substitution in SEQ ID NO: 1.

In some embodiments, the IFNA2 variants include an M171X amino acid substitution in SEQ ID NO: 1, where X represents any amino acid. In some embodiments, the IFNA2 variant includes an M171R, M171S, M171T, M171N, M171A, M171Y, M171W, M171F, M171K, M171E, M171G, M171L, M171I, or M171V amino acid substitution in SEQ ID NO: 1.

In some embodiments, the IFNA2 variants include an R172X amino acid substitution in SEQ ID NO: 1, where X represents any amino acid. In some embodiments, the IFNA2 variant includes an R172D, R172W, R172N, R172A, R172V, R172G, R172T, R172S, R172Y, R172L, R172M, or R172K amino acid substitution in SEQ ID NO: 1.

In some embodiments, the IFNA2 variants include an S173X amino acid substitution in SEQ ID NO: 1, where X represents any amino acid. In some embodiments, the IFNA2 variant includes an S173K, S173R, S173H, S173E, S173N, S173W, or S173Y amino acid substitution in SEQ ID NO: 1.

In some embodiments, the IFNA2 variants includes an S175X amino acid substitution in SEQ ID NO: 1, where X represents any amino acid. In some embodiments, the IFNA2 variant includes an S175R, S175K, S175M, S175L, S175P, S175I, S175V, S175W, S175Y, S175G, S175E, S175Q, or S175T amino acid substitution in SEQ ID NO: 1.

In some embodiments, the IFNA2 variants include an L176X amino acid substitution in SEQ ID NO: 1, where X represents any amino acid. In some embodiments, the IFNA2 variant includes an L176N, L176G, L176H, L176A, L176P, L176D, L176R, L176Q, L176E, or L176V amino acid substitution in SEQ ID NO: 1.

In some embodiments, the IFNA2 variants include an S177X amino acid substitution in SEQ ID NO: 1, where X represents any amino acid. In some embodiments, the IFNA2 variant includes an S177D or S177R amino acid substitution in SEQ ID NO: 1.

In some embodiments, the IFNA2 variants include an N179X amino acid substitution in SEQ ID NO: 1, where X represents any amino acid. In some embodiments, the IFNA2 variant includes an N179G amino acid substitution in SEQ ID NO: 1.

In some embodiments, the IFNA2 variants include an S183X amino acid substitution in SEQ ID NO: 1, where X represents any amino acid. In some embodiments, the IFNA2 variant includes an S183W, S183F, S183M, S183E, S183Y, S183K, or S183L amino acid substitution in SEQ ID NO: 1.

In some embodiments, the IFNA2 variants include an R185X amino acid substitution in SEQ ID NO: 1, where X represents any amino acid. In some embodiments, the IFNA2 variant includes an R185D, R185E, or R185Q amino acid substitution in SEQ ID NO: 1.

In some embodiments, the IFNA2 variants include an S186X amino acid substitution in SEQ ID NO: 1, where X represents any amino acid. In some embodiments, the IFNA2 variant includes an S186L, S186I, or S186D amino acid substitution in SEQ ID NO: 1.

In some embodiments, the IFNA2 variants include an K187X amino acid substitution in SEQ ID NO: 1, where X represents any amino acid. In some embodiments, the IFNA2 variant includes an K187R, K187L, K187E, K187Y, K187V, K187M, K187F, K187I, K187W, or K187G amino acid substitution in SEQ ID NO: 1.

In some embodiments, the IFNA2 variants include an E188X amino acid substitution in SEQ ID NO: 1, where X represents any amino acid. In some embodiments, the IFNA2 variant includes an E188I amino acid substitution in SEQ ID NO: 1.

In another aspect, the disclosure provides isolated IFNA2 variants, wherein the IFNA2 variants include two or more amino acid substitutions, wherein the two or more amino acid substitutions include a combination of substitutions selected from the group consisting of: M44N+A168R, L49P+S175P, L49P+S173H, L49P+M171W, L49P+M171G, L49P+S173R, M44N+S175P, L49P+M171V, L49P+M171K, L49P+M171S, L49P+S175R, L49P+M171R, L49P+L176G, L49P+M171Y, L49P+L176N, L49P+S173Q, L49P+L176H, L49P+L176R, L49P+M171A, L49P+M171T, L49P+L176A, L49P+M171F, M44N+S175K, L49P+S175K, L49P+L176E, L49P+E169T, L49P+M171L, L49P+L176Q, L49P+K187E, L49P+S173N, M44N+L176H, M44N+S175R, L49P+S177N, L49P+S173W, L49P+S177D, L49P+R185D, L49P+E169S, L49P+S175G, L49P+S177L, L49P+R172K, L49P+R185E, L49P+K187M, L49P+K187W, L49P+S159Q, M44N+L176Q, M44N+R185E, L49P+S175Q, L49P+S175M, L49P+E155V, L49P+K187D, L49P+S175W, L49P+L176V, L49P+S173L, M44N+S175G, L49P+R185G, L49P+R143W, L49P+1149T, L49P+R185L, L49P+R185S, L49P+S177H, L49P+K106D, M44N+R185N, L49P+K187V, L49P+K106W, L49P+K135T, M44N+V128I, M44N+R185D, L49P+K106P, L49P+S183M, L49P+S183D, L49P+K156A, L49P+S183L, M44N+K187D, L49P+R185M, L49P+R185N, M44N+A168L, L49P+S175L, L49P+R185Q, L49P+K187G, M44N+S177E, L49P+W163L, L49P+

R185W, L49P+K187T, L49P+T109W, M44N+P160E, M44N+K106T, L49P+R185T, L49P+S175I, L49P+S173F, M44N+R185L, L49P+S183E, L49P+K187N, M44N+K187F, L49P+S159D, M44N+K106I, L49P+S175Y, L49P+L184N, L49P+I170L, L49P+V166S, L49P+K187A, L49P+S186D, L49P+L111F, L49P+K154Q, L49P+K106T, L49P+E136D, L49P+K106M, L49P+F107W, M44N+R185Y, M44N+V165I, M44N+K187W, L49P+R185I, M44N+R185T, M44N+R185V, M44N+Q113A, M44N+T178K, L49P+K156V, L49P+K187S, M44N+Q114I, L49P+T131E, M44N+S183E, L49P+Y152W, L49P+V128E, L49P+E155K, L49P+S175T, L49P+E155R, L49P+V166T, and L49P+T178F in the wild-type IFNA2 amino acid sequence (SEQ ID NO: 1).

In another aspect, the disclosure provides isolated fusion proteins including an antibody or a binding fragment thereof including an Fc domain; and a human IFNA2 variant, wherein the IFNA2 variant is covalently linked to the antibody or binding fragment thereof, and wherein the IFNA2 variant has decreased or no detectable binding to the human interferon-alpha/beta receptor beta (IFNAR2) as compared to the wild-type human IFNA2 polypeptide. In some embodiments, the IFNA2 variant has a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2.

In another aspect, the disclosure provides isolated fusion proteins including an antibody or a binding fragment thereof including an Fc domain; and a human IFNA2 variant, wherein the IFNA2 variant is covalently linked to the Fc domain of the antibody or binding fragment thereof, and wherein the Fc domain has decreased or no detectable antibody dependent cellular cytotoxicity (ADCC) activity compared to the wild-type Fc. In some embodiments, the antibody or binding fragment thereof includes an amino acid sequence of SEQ ID NO: 4, 5, 6, 7, 8, or 9. In some embodiments, the antibody or binding fragment thereof has an isotype that is selected from the group consisting of NG, DANG, LALA, and LALA-PG. In some embodiments, the antibody or binding fragment thereof binds to an antigen selected from the group consisting of CD8, TIGIT, CLEC9A, LILRB4, LILRB2, PD-1, CD160, BTLA, and TNFRSF9.

In some embodiments, the antibody is selected from the group consisting of an anti-CTLA-4 antibody, an anti-CD3 antibody, an anti-CD4 antibody, an anti-CD8 antibody, an anti-4-1 BB antibody, an anti-PD-I antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-HVEM antibody, an anti-BTLA antibody, an anti-CD40 antibody, an anti-CD40L antibody, anti-CD47 antibody, an anti-CSFIR antibody, an anti-MARCO antibody, an anti-CXCR4 antibodies, an anti-VEGFR1 antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD52 antibody, an anti-CCR4 antibody, an anti-CCR5 antibody, an anti-CD200R antibody, an anti-VlSG4 antibody, an anti-CCR2 antibody, an anti-LILRB2 antibody, an anti-CXCR4 antibody, an anti-CD206 antibody, an anti-CD163 antibody, an anti-KLRGl antibody, an anti-FLT3 antibody, an anti-B7-H4 antibody, an anti-B7-H3 antibody, an KLRGl antibody, and an anti-GITR antibody, anti-CD160 antibody, anti-KLRD1 antibody, anti-KLRC1 antibody, anti-BTLA antibody, and anti-LILRB4 antibody.

In some embodiments, the IFNA2 variants are covalently linked to the antibody or binding fragment thereof by a polypeptide linker. In some embodiments, the polypeptide linker is selected from the group consisting of (G4S) 2 and (G4S) 3. In some embodiments, the polypeptide linker is a polypeptide tag selected from the group consisting of FLAG, MYC, HA, and 6Xhis.

In another aspect, the disclosure provides isolated cell lines that produce any one of the IFNA2 variants or any one of the fusion proteins disclosed herein. In some embodiments, the isolated cell lines are a CHO cell line or an HEK293 cell line.

In another aspect, the disclosure provides isolated nucleic acids encoding any one of the IFNA2 variants or any one of the fusion proteins disclosed herein.

In another aspect, the disclosure provides recombinant expression vectors including the nucleic acids encoding any one of the IFNA2 variants or any one of the fusion proteins disclosed herein.

In another aspect, the disclosure provides host cells including the isolated nucleic acids encoding any one of the IFNA2 variants or any one of the fusion proteins disclosed herein or the recombinant expression vector including the nucleic acid encoding any one of the IFNA2 variants or any one of the fusion proteins disclosed herein.

In another aspect, the disclosure provides pharmaceutical compositions including any one of the IFNA2 variants or any one of the fusion proteins disclosed herein, and a pharmaceutically acceptable carrier.

In another aspect, the disclosure provides methods of treating a disease in a subject in need thereof, the methods including administering to the subject an effective amount, e.g., a therapeutically effective amount, of a pharmaceutical composition as described herein including any one of the IFNA2 variants or any one of the fusion proteins disclosed herein, and a pharmaceutically acceptable carrier, such that one or more symptoms associated with the disease is ameliorated in the subject.

In some embodiments, the disease is cancer. In some embodiments, the cancer is a solid cancer or a liquid, e.g., blood-borne, cancer. In some embodiments, the solid cancer is selected from the group consisting of gastric cancer, small intestine cancer, sarcoma, head and neck cancer, thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer, bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma.

In some embodiments, the liquid cancer is selected from the group consisting of multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell/histiocyte-rich large B-cell lymphoma, primary central nervous system lymphoma, primary cutaneous diffuse large B-cell lymphoma (leg type), EBY positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHVS-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cells related cancer. In some embodiments, the cancer is relapsed, refractory, or metastatic.

In some embodiments, the methods further include administering an effective amount of a second therapeutic agent, optionally wherein the administration is separate, sequential, or simultaneous. In some embodiments, the second therapeutic agent is an antibody selected from the group consisting of an anti-CTLA-4 antibody, an anti-CD3 antibody, an anti-CD4 antibody, an anti-CD8 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-IL-8 antibody, an anti-IL-15 antibody, an anti-HVEM antibody, an anti-BTLA antibody, an anti-CD40 antibody, an anti-CD40L antibody, anti-CD47 antibody, an anti-CSFIR antibody, an anti-CSFl antibody, an anti-IL-7R antibody, an anti-MARCO antibody, an antiCXCR4 antibodies, an anti-VEGF antibody, an anti-VEGFRl antibody, an anti-VEGFR2 antibody, an anti-TNFR1 antibody, an anti-TNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD 52 antibody, an anti-CCR4 antibody, an anti-CCRS antibody, an antiCD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRGl antibody, an anti-FLT3 antibody, an anti-B7-H4 antibody, an anti-B7-H3 antibody, an KLRGl antibody, a BTNlAl antibody, and an anti-GITR antibody.

In some embodiments, the second therapeutic agent is a cytokine, an immunocytokine, TNFa, a PAP inhibitor, an oncolytic virus, a kinase inhibitor, an ALK inhibitor, a MEK inhibitor, an IDO inhibitor, a GLSl inhibitor, a tyrosine kinase inhibitor, a CART cell or T cell therapy, a TLR agonist, or a tumor vaccine.

In another aspect, the disclosure provides pharmaceutical compositions including any one of the IFNA2 variants or any one of the fusion proteins disclosed herein, for use in the treatment of cancer, optionally wherein the cancer is a solid cancer or a liquid cancer and/or the cancer is relapsed, refractory, or metastatic. In some embodiments, the use is in combination with a second therapeutic agent, optionally wherein the combination is for administration simultaneously, concurrently, or simultaneously.

In another aspect, the disclosure provides isolated human interferon alpha-2 (IFNA2) variants, wherein the IFNA2 variants have decreased or no detectable binding to the human interferon-alpha/beta receptor beta 2 (IFNAR2) as compared to the wild-type human IFNA2 polypeptide, and wherein the IFNA2 variants comprise a polypeptide sequence of any one of SEQ ID NOs 10-416 and 439-538.

In some embodiments, the IFNA2 variants have a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2. In some embodiments, the isolated IFNA2 variants comprise a polypeptide sequence of any one of SEQ ID NOs 67, 79, 85, 99-101, 117, 118, 121, 159, 161, and 165.

In another aspect, the disclosure provides isolated nucleic acids encoding the IFNA2 variants.

In another aspect, the disclosure provides recombinant expression vectors comprising the isolated nucleic acids.

In another aspect, the disclosure provides host cells comprising the recombinant expression vectors.

In another aspect, the disclosure provides isolated fusion proteins including an antibody or binding fragment thereof, and an isolated human IFNA2 variant, wherein the IFNA2 variant is covalently linked to the antibody or binding fragment thereof, and wherein the IFNA2 variant has decreased or no detectable binding to the human interferon-alpha/beta receptor beta (IFNAR2) as compared to the wild-type human IFNA2 polypeptide, and wherein the IFNA2 variant comprises a polypeptide sequence of any one of SEQ ID NOs 10-416 and 439-538. In some embodiments, the antibody or binding fragment thereof comprises an Fc domain. In some embodiments, the isolated fusion proteins comprise a polypeptide sequence of any one of SEQ ID NOs 539-550 and 560-574. In some embodiments, the antibody is an anti-CD8 antibody. In some embodiments, the isolated fusion protein comprises a polypeptide sequence of any one of SEQ ID NOs 552-559.

In some embodiments, the isolated fusion proteins include an IFNA2 variant that has a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2. In some embodiments, the IFNA2 variant is covalently linked to the antibody by a polypeptide linker. In some embodiments, the polypeptide linker is selected from the group consisting of (G4S) 2 and (G4S) 3. In some embodiments, the polypeptide linker is a polypeptide tag selected from the group consisting of FLAG, MYC, HA, and 6Xhis.

In another aspect, the disclosure provides isolated cell lines that produce the fusion proteins described herein.

In additional aspects, the disclosure provides isolated nucleic acid encoding the fusion proteins described herein.

In another aspect, the disclosure provides recombinant expression vectors comprising the nucleic acids described herein.

In other aspects, the disclosure provides host cells comprising the recombinant expression vectors described herein.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned.

Optimal alignment of sequences for comparison may be conducted using the MegAlign® program in the Lasergene® suite of bioinformatics software (DNASTAR®, Inc., Madison, Wis.), using default parameters. This program embodies several alignment schemes described in the following references: Dayhoff, M. 0., 1978, A model of evolutionary change in proteins-Matrices for detecting distant relationships. In Dayhoff, M. 0. (ed.) Atlas of Protein Sequence and Structure, National Biomedical Research Foundation, Washington D.C. Vol. 5, Suppl. 3, pp. 345-358; Hein J., 1990, Unified Approach to Alignment and Phylogenes pp. 626-645 Methods in Enzymology vol. 183, Academic Press, Inc., San Diego, Calif.; Higgins, D. G. and Sharp, P. M., 1989, CABIOS 5:151-153; Myers, E. W. and Muller W., 1988, CABIOS 4:11-17; Robinson, E. D., 1971, Comb. Theor. 11:105; Santou, N., Nes, M., 1987, Mo!. Biol. Evol. 4:406-425; Sneath, P. H. A. and Sokal, R. R., 1973, Numerical Taxonomy the Principles and Practice of Numerical Taxonomy, Freeman Press, San Francisco, Calif.; Wilbur, W. J. and Lipman, D. J., 1983, Proc. Natl. Acad. Sci. USA 80:726-730.

As defined herein, a "percentage of sequence identity" is determined by comparing two optimally aligned sequences over a window of comparison of at least 20 positions, wherein the portion of the polynucleotide or polypeptide sequence in the comparison window may comprise additions or deletions (i.e., gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

As used herein, "protein-protein interaction" or "PPI" refers to physical contacts of high specificity established between two or more proteins (or polypeptides) as a result of biochemical events driven by electrostatic forces including the hydrophobic effect. Many are physical contacts with molecular associations between chains that occur in a cell or in a living organism in a specific biomolecular context. In some embodiments, the protein-protein interactions are strong enough to replace the function of the native sexual agglutination proteins. For example, it can be possible to couple mating efficiency to the interaction strength of a particular protein-protein interaction. In certain embodiments, the assay can characterize or determine protein-protein interactions between synthetic adhesion proteins (SAPs).

As used herein, a "synthetic adhesion protein" refers to any protein or polypeptide to be assayed for binding to or interacting with any other any protein or polypeptide. The proteins can be heterologous or exogenously expressed. Synthetic adhesion proteins are referred to as such because they are not typically associated with the adhesion required for agglutination as natively performed by the sexual agglutination proteins. In certain embodiments, the synthetic adhesion proteins have sufficiently strong interactions to allow agglutination in yeast where the native sexual agglutination proteins are not natively expressed. In some embodiments, the SAPs of the first and second expression cassettes of the first and second nucleic acid constructs, respectively, bind to a cell wall GPI anchored protein. In some embodiments, the SAPs can be fused to a cell wall GPI anchored protein or fused to a protein that forms a disulfide bond with a cell wall GPI anchored protein. In some embodiments, the SAP of the first expression cassette of the first nucleic acid construct is fused to the sexual agglutination protein Aga2, and the SAP of the first expression cassette of the second nucleic acid construct is fused to the sexual agglutination protein Aga2.

As used herein, "affinity" is a measure of the strength of the binding interaction between a single biomolecule to its ligand or binding partner. Affinity is usually measured and described using the equilibrium dissociation constant, Kn. The lower the Kn value, the greater the affinity between the protein and its binding partner. Affinity may be affected by hydrogen bonding, electrostatic interactions, hydrophobic and Van der Waals forces between the binding partners, or by the presence of other molecules, e.g., binding agonists or antagonists.

In some implementations, affinity may be described using arbitrary units, wherein a certain binding affinity within an assay, for example the binding affinity between two wildtype protein binding partners or the wild-type species of a first protein binding partner and the wild-type species of a second protein binding partner, is set to an arbitrary unit of 1.0 and binding affinities for other pairs of protein binding partners, for example the mutant species of a first protein binding partner and the mutant species of a second protein binding partner, are measured relative proportionally to that certain binding affinity.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 1 is a heatmap of AlphaSeq™ predicted affinities ($\log_{10}$ Kd nM) for the IFNA2/IFNAR2 validation network. Strong binding is considered below 3, weak binding is considered between 3 and 4, no detectable binding is considered above 4.

DETAILED DESCRIPTION

Figure 2A:
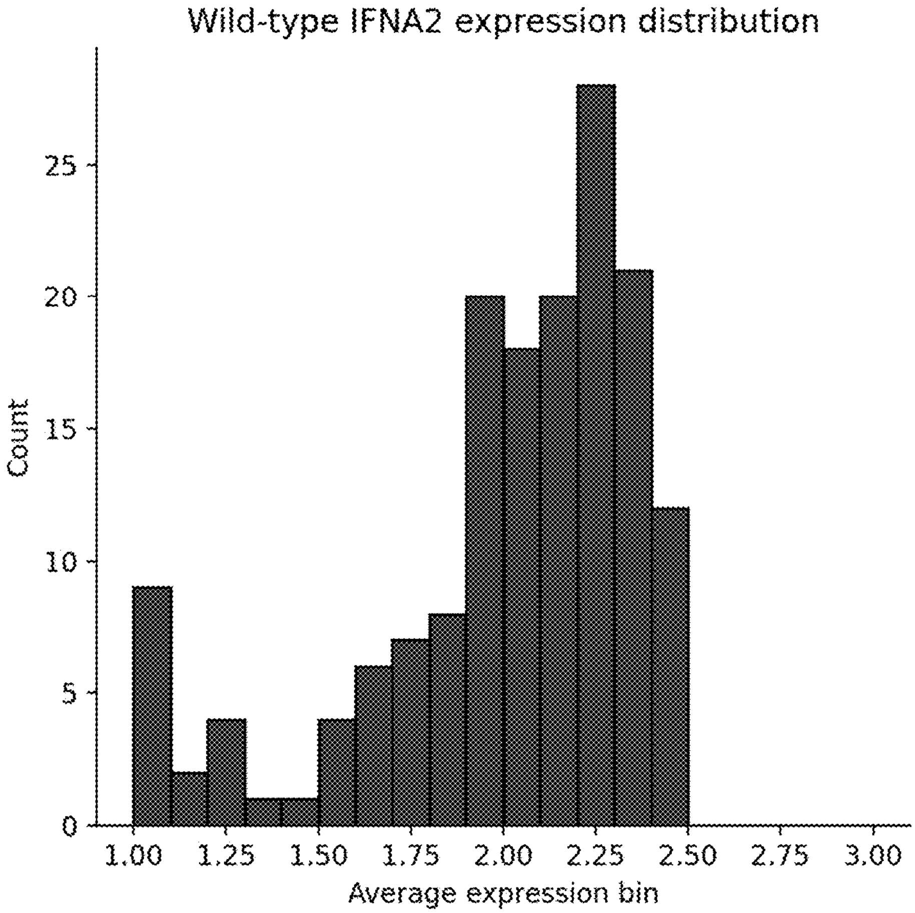
FIG. 2A is a histogram of expression values for wild-type replicates of IFNA2. A value of 3 is the maximum possible expression in this assay and a value of 1 is the minimum possible expression.

The present disclosure provides detuned human interferon alpha-2 (IFNA2) variants and fusion proteins including those variants. By "detuned" is meant that the wildtype IFNA2 is engineered to have a reduced or weakened affinity for the interferon alpha/beta receptor 2 IFNAR2). Different modifications of the wildtype IFNA2 results in a large number of detuned IFNA2 variants.

In a therapeutic context, these detuned variants can be targeted to a particular immune cell type of interest by linking the detuned variants to an antibody or portion thereof against a specific cell surface marker. By reducing affinity for the receptor, the activity of the detuned cytokines is decreased for most cell types, e.g., in healthy tissues, which, in turn, decreases potential toxicity of the molecule when administered as a therapy. However, at the surface of the cell type targeted by the antibody, the residual activity of the cytokine is sufficient to bind its receptor and activate pro-inflammatory pathways leading to immune activation.

Cytokine signaling can trigger multifaceted and even opposing activities in different cell types, meaning that even if cytokine activity is limited specifically to the cells expressing the antibody targeted antigen activation of other cell types may be detrimental to the therapeutic efficacy of the cytokine. Targeting cytokine-dependent activation to only a subset of the immune cells present in a tumor, for example, activated T cells as opposed to all cells with a cytokine receptor, can allow improved targeting of the therapeutic effects of the molecule.

The compositions disclosed herein are human IFNA2 variants and fusion proteins made from these variants. As measured by, e.g., AlphaSeq™, and demonstrated in further detail in the Examples, the IFNA2 variants of the compositions and methods disclosed herein have decreased or no detectable binding to the IFNAR2 receptor, as compared to the wild-type human IFNA2 polypeptide or a wild-type IFNA2 fusion polypeptide. In some embodiments, these reduced affinity IFNA2 variants, when presented as an antibody fusion chimeric protein, are targeted selectively to desired cell types (those cells expressing the antibody target). Cell types that express the IFNAR2 receptor complex, but not the antibody target, are activated less, or not activated at all, compared to those cells which express both components. Accordingly, the IFNA2 variants and the IFNA2 fusion proteins of the compositions and methods disclosed herein selectively modulate the activation of cell subsets to promote biological activity, such as an anti-tumor activity, efficaciously and safely.

Methods of Determining IFNA2 Variants

In some embodiments, measuring the affinity of the cytokine IFNA2 to its receptor interferon alpha/beta receptor 2 (IFNAR2) is performed using a high-throughput synthetic yeast agglutination protein-protein interaction (PPI) screening platform termed AlphaSeq™. Synthetic yeast agglutination relies on reprogramming yeast sexual agglutination—a naturally-occurring protein-protein interaction—to link protein-protein interaction strength with mating efficiency between a-type recombinant haploid yeast cells and α-type recombinant haploid yeast cells in liquid culture. For a screen of IFNA2 variants for binding affinity to IFNAR2 based on synthetic yeast agglutination, mating efficiency, represented by the number of diploid yeast cells formed in a turbulent liquid culture, is a proxy for affinity between IFNA2 and IFNAR2.

The AlphaSeq™ method is disclosed in, e.g., U.S. Pat. Nos. 10,988,759 and 11,136,573, which are incorporated herein by reference in their entireties. AlphaSeq™ can be used to perform library-by-library screens of a library of variants of one protein binding partner, e.g., IFNA2, against a library of variants of another protein binding partner, e.g., IFNAR2. AlphaSeq™ can be also used to perform a library-based screen of a library of variants of one protein binding partner, e.g., IFNA2, against a single species of another protein binding partner, e.g., wild-type human IFNAR2 or wild-type mouse IFNAR2. Each variant, i.e., protein of interest (POI) is assigned a unique oligonucleotide molecular barcode, and after diploid formation events, these protein-specific barcodes can be recombined and sequenced to identify the individual synthetic adhesion proteins (SAPs) that mediated the corresponding diploid formation event. Quantifying sequencing reads of unique barcode-barcode combinations acts as a proxy measure of the number of diploid formation events, and thus, PPI affinity.

In some embodiments, affinity between a library of IFNA2 variants and IFNAR2 is measured by the AlphaSeq™ method which is based on yeast sexual agglutination. In native yeast sexual agglutination, in a turbulent liquid culture, MATa and MATa haploid cells stick to one another due to the binding of sexual agglutinin proteins, which allows them to mate. The native sexual agglutinin proteins consist of Agal and Aga2, expressed by MATa cells, and Sagl, expressed by MATa cells. Agal and Sagl form GPI anchors with the cell wall and extend outside of the cell wall with glycosylated stalks. Aga2 is secreted by MATa cells and forms a disulfide bond with Agal. The interaction between Aga2 and Sag1 is essential for wild-type sexual agglutination.

The native sexual agglutinin interaction can be replaced with an engineered one by expressing Agal in both mating types and fusing complementary binders to Aga2. In this case, a synthetic adhesion protein (SAP) comprises the fusion of Aga2 and the binder of interest, e.g., the library of IFNA2 variants expressed by cells of one mating type and IFNAR2 expressed by cells of the other mating type. Interaction of the SAPs therefore mediates adhesion, and subsequently the agglutination process. In some embodiments, instead of direct agglutination, it may be possible to express SAPs for a multivalent target, such that agglutination and mating only occurs in the presence of the target.

In some embodiments, each MATa and MATa haploid cell contains a SAP fused to Aga2 integrated into a target chromosome (for example, chromosome III). Upon mating, both copies of the target chromosome are present in the same diploid cell. In addition to the SAP/Aga2 cassette, each copy of the target chromosome has a unique primer binding site, one of a plurality of unique oligonucleotide barcodes operably linked to the particular SAP, and a lox recombination site.

The plurality of oligonucleotide barcodes can be synthesized and assembled with the library of SAP expression cassettes such that a single SAP species is operably linked to a plurality of unique oligonucleotide barcodes. Upon expression of Cre recombinase, a chromosomal translocation occurs at the lox sites, resulting in a juxtaposition of the primer binding sites and barcodes onto the same copy of the target chromosome. A PCR is then performed to amplify a region of the chromosome containing the barcodes from both SAPs, such that sequences comprising unique barcode-barcode pairs, each representing a diploid formation event, are amplified. In a batched mating, the result is a pool of fragments, each containing the unique barcode-barcode pair associated with two SAPs that were responsible for the single diploid formation event. Paired-end next generation sequencing is then used to match the barcodes and determine the number of diploid formation events mediated by that SAP pair.

In some embodiments, the a-agglutinin, Sag 1, is knocked out in MATa cells to eliminate native agglutination. MATa and MATa cells are able to synthesize lysine or leucine, respectively. Diploids can then be selected for in media lacking both amino acids. MATa cells express ZEV4, a BE inducible transcription factor that activates Cre recombinase expression in diploid cells. MATa and MATa cells express mCherry and mTurquoise, respectively, for identification of strain types with flow cytometry. MATa and MATα cells constitutively express Agal along with a uniquely barcoded SAP fused to Aga2. When Cre recombinase expression is induced in diploids with βE, a chromosomal translocation at lox sites consolidates both SAP-Aga2 fusion expression cassettes onto the same chromosome. A single fragment containing the unique barcode-barcode sequence associated with that diploid formation event is then amplified by PCR with primers annealing to Pf and Pr (primers specific to the primers from the first and second nucleic acid constructs integrated at the genomic target site) and sequenced to quantify the number of diploid formation events and identify the interacting SAP pair.

In some embodiments, a CRE recombinase translocation scheme is utilized for high throughput analysis for interactions between synthetic adhesion proteins from a library to library screen, or, e.g., the library of IFNA2 variants expressed by cells of one mating type and IFNAR2 expressed by cells of the other mating type. When CRE recombinase expression is induced in diploids with BE, a chromosomal translocation at lox sites consolidates both SAP-Aga2 expression cassettes onto the same chromosome. A single fragment containing the unique barcode-barcode sequence associated with that diploid formation event is then amplified by PCR with primers annealing to primer binding sites from each of the first and second nucleic acid constructs and sequenced (for example, using a paired end analysis of next generation sequencing) to quantify the number of diploid formation events and identify the interacting SAP pair, e.g., a unique variant of IFNA2 and IFNAR2, thereby yielding an estimation of the affinity between the variant of IFNA2 and IFNAR2.

In some embodiments, the methods for measuring the affinity of a cytokine and its receptor include a library of cytokine variants, e.g., variants of IFNA2, comprising a plurality of cytokine variants and a receptor or library of receptor variants, e.g., IFNAR2 or variants of IFNAR2. The cytokine variants and the receptor or library of receptor variants can be user-designated or randomly added mutants of a protein and the wild-type protein. In some embodiments, the amino acid substitutions may be generated by site saturation mutagenesis (SSM) to produce an SSM library of the cytokine and the receptor. In some embodiments, the variants and the receptor variants can be generated by alanine scanning. In some embodiments, the cytokine variants and the receptor variants can be generated by random mutagenesis, such as with error prone PCR, or another method to introduce variation into the amino acid sequence of the expressed protein. The cytokine variant library comprising a plurality of cytokine variants and the receptor variant library comprising a plurality of receptor variants are assayed for binding affinity, such that affinity is measured for interaction between each of the plurality of variants and the wild-type receptor or each of the plurality of receptor variants individually, in a parallelized high-throughput manner.

In some embodiments, the cytokine variants and the receptor or receptor variants are full-length proteins. In some embodiments, the cytokine variants and the receptor or receptor variants are truncated proteins. In some embodiments, the cytokine variants and the receptor or receptor variants are fusion proteins. In some embodiments, the cytokine variants and the receptor or receptor variants are tagged proteins. Tagged proteins include proteins that are epitope tagged, e.g., FLAG-tagged, HA-tagged, His-tagged, Myc-tagged, among others known in the art. The cytokine variants and the receptor or receptor variants can each be any of the following: a full-length protein, truncated protein, fusion protein, tagged protein, or combinations thereof.

In some embodiments, the methods for measuring the affinity of a cytokine and its receptor include bio-layer interferometry (BLI). BLI measures kinetics and biomolecular interactions on a basis of wave interference. To prepare for BLI analysis between two unique biomolecules, the ligand is first immobilized onto a bio compatible biosensor while the analyte is in solution. After this, the biosensor tip is dipped into the solution and the target molecule will begin to associate with the analyte, producing a layer on top of the biosensor tip. This creates two separate surfaces: the substrate itself, and the substrate interacting with the molecule immobilized on the biosensor tip. This can create a thin-film interference, in which the created layer acts as a thin film bound by these two surfaces. White light from a tungsten lamp is shone onto the biosensor tip and reflected off both surfaces, creating two unique reflection patterns with different intensities.

In some cases, it is possible that cytokine variants, e.g., IFNA2 variants, can be measured by various affinity determination methods, e.g., AlphaSeq™ and/or BLI to have no detectable binding to the cytokine's receptor, e.g., IFNAR2, while still inducing signaling in cells in vitro or in vivo. In such cases, a cytokine variant exhibiting no detectable binding to its receptor as measured by AlphaSeq™ or BLI, or a fusion protein comprising the cytokine variant, can potentially have therapeutic efficacy.

IFNA2 Variants

IFNA2 variants (e.g., human IFNA2 variants) as described herein have decreased or no detectable binding to the IFNAR2 receptor and/or reduced interaction between IFNA2 and the IFNAR2 receptor, as compared to the wild-type human IFNA2 polypeptide, as described in further detail in the Examples section. The IFNA2 variants provided herein are recited in Tables 1-5 as comprising amino acid substitutions numbered according to the wild-type sequence of IFNA2:

(SEQ ID NO: 1)

```
MALTFALLVALLVLSCKSSCSVGCDLPQTHSLGSRRTLMLLAQMR

RISLFSCLKDRHDFGFPQEEFGNQFQKAETIPVLHEMIQQIFNLF

STKDSSAAWDETLLDKFYTELYQQLNDLEACVIQGVGVTETPLMK

EDSILAVRKYFQRITLYLKEKKYSPCAWEVVRAEIMRSFSLSTNL

QESLRSKE
```

For example, a variant with the name "IFNA2b_V165Y" has an amino acid substitution in SEQ ID NO: 1 at location 165, where the existing valine is replaced with tyrosine.

Tables 1-3 also recite affinities between IFNA2 and the human interferon alpha/beta receptor 2 (IFNAR2) as measured by AlphaSeq™ (in nM). A value of 3 is the maximum possible expression in this assay and a value of 1 is the minimum possible expression. The amino acid sequence of human interferon alpha/beta receptor 2 (IFNAR2) is provided below:

(SEQ ID NO: 2)

```
MLLSQNAFIFRSLNLVLMVYISLVFGISYDSPDYTDESCTFKISL

RNFRSILSWELKNHSIVPTHYTLLYTIMSKPEDLKVVKNCANTTR

SFCDLTDEWRSTHEAYVTVLEGFSGNTTLFSCSHNFWLAIDMSFE

PPEFEIVGFTNHINVMVKFPSIVEEELQFDLSLVIEEQSEGIVKK

HKPEIKGNMSGNFTYIIDKLIPNTNYCVSVYLEHSDEQAVIKSPL

KCTLLPPGQESESAESAKIGGIITVFLIALVLTSTIVTLKWIGYI

CLRNSLPKVLNFHNFLAWPFPNLPPLEAMDMVEVIYINRKKKVWD

YNYDDESDSDTEAAPRTSGGGYTMHGLTVRPLGQASATSTESQLI

DPESEEEPDLPEVDVELPTMPKDSPQQLELLSGPCERRKSPLQDP

FPEEDYSSTEGSGGRITFNVDLNSVFLRVLDDEDSDDLEAPLMLS

SHLEEMVDPEDPDNVQSNHLLASGEGTQPTFPSPSSEGLWSEDAP

SDQSDTSESDVDLGDGYIMR
```

As shown in Table 1 below, disclosed herein are 280 IFNA2 variants comprising single amino acid substitutions, with amino acid substitutions throughout the length of the wild-type IFNA2 polypeptide (SEQ ID NO: 1) with reduced affinity for human IFNAR2. Any variant found to bind human IFNAR2 with an affinity weaker than 100 nM ($\log_{10}$ nM=2) as measured by AlphaSeq™ and found to have an average expression bin >2.0 is included in Table 1. Table 1 is sorted in order of descending Kd, with the highest values representing the lowest affinity of IFNA2 for human IFNAR2. Table 1 also provides the polypeptide sequences of the 280 IFNA2 variants comprising single amino acid substitutions as SEQ ID NOs 10-289. The polypeptide sequences describe the mature IFNA2b protein, which does not include a 23-amino acid signal peptide that is cleaved from the N-terminus to produce the mature protein.

TABLE 1

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ V165Y | 175684 | 2.08 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEYVRAEIMRSFS<br>LSTNLQESLRSKE | 10 |
| IFNA2b_ R56D | 166760 | 2.62 | CDLPQTHSLGSRRTLMLLAQMRRISLFSCLKDDHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 11 |
| IFNA2b_ F59Q | 165921 | 2.04 | CDLPQTHSLGSRRTLMLLAQMRRISLFSCLKDRHDQGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 12 |
| IFNA2b_ F50D | 134718 | 2.29 | CDLPQTHSLGSRRTLMLLAQMRRISLDSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 13 |
| IFNA2b_ L41H | 129330 | 2.10 | CDLPQTHSLGSRRTLMLHAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 14 |
| IFNA2b_ A168R | 126400 | 2.28 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRREIMRSFS<br>LSTNLQESLRSKE | 15 |
| IFNA2b_ F59E | 125833 | 2.35 | CDLPQTHSLGSRRTLMLLAQMRRISLFSCLKDRHDEGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 16 |
| IFNA2b_ V165E | 98339 | 2.37 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEEVRAEIMRSFS<br>LSTNLQESLRSKE | 17 |
| IFNA2b_ R56G | 96394 | 2.48 | CDLPQTHSLGSRRTLMLLAQMRRISLFSCLKDGHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 18 |
| IFNA2b_ L53D | 94074 | 2.32 | CDLPQTHSLGSRRTLMLLAQMRRISLFSCDKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 19 |
| IFNA2b_ L53E | 92621 | 2.21 | CDLPQTHSLGSRRTLMLLAQMRRISLFSCEKDRHDFGF<br>PQEEFGNQFQKAETIPVLHEMIQQIFNLESTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 20 |
| IFNA2b_ L53G | 91022 | 2.16 | CDLPQTHSLGSRRTLMLLAQMRRISLFSCGKDRHDFGF<br>PQEEFGNQFQKAETIPVLHEMIQQIFNLESTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 21 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ L53A | 88720 | 2.29 | CDLPQTHSLGSRRTLMLLAQMRRISLFSCAKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 22 |
| IFNA2b_ M171R | 87906 | 2.38 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIRRSFS<br>LSTNLQESLRSKE | 23 |
| IFNA2b_ R56K | 86786 | 2.37 | CDLPQTHSLGSRRTLMLLAQMRRISLFSCLKDKHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 24 |
| IFNA2b_ V165H | 82118 | 2.15 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEHVRAEIMRSFS<br>LSTNLQESLRSKE | 25 |
| IFNA2b_ V165K | 80784 | 2.27 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEKVRAEIMRSFS<br>LSTNLQESLRSKE | 26 |
| IFNA2b_ M171S | 79034 | 2.16 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEISRSFS<br>LSTNLQESLRSKE | 27 |
| IFNA2b_ L41D | 76944 | 2.25 | CDLPQTHSLGSRRTLMLDAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 28 |
| IFNA2b_ F59I | 73763 | 2.19 | CDLPQTHSLGSRRTLMLLAQMRRISLFSCLKDRHDIGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 29 |
| IFNA2b_ R56N | 69054 | 2.38 | CDLPQTHSLGSRRTLMLLAQMRRISLFSCLKDNHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 30 |
| IFNA2b_ H57P | 65172 | 2.27 | CDLPQTHSLGSRRTLMLLAQMRRISLFSCLKDRPDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRAEIMRSFS<br>LSTNLQESLRSKE | 31 |
| IFNA2b_ R167W | 64832 | 2.12 | CDLPQTHSLGSRRTLMLLAQMRRISLFSCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVWAEIMRSFS<br>LSTNLQESLRSKE | 32 |
| IFNA2b_ A168H | 63555 | 2.32 | CDLPQTHSLGSRRTLMLLAQMRRISLESCLKDRHDFGF<br>PQEEFGNQFQKAETIPVLHEMIQQIFNLFSTKDSSAAW<br>DETLLDKFYTELYQQLNDLEACVIQGVGVTETPLMKED<br>SILAVRKYFQRITLYLKEKKYSPCAWEVVRHEIMRSFS<br>LSTNLQESLRSKE | 33 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ F59N | 61610 | 2.04 | CDLPQTHSLGSRRTLMLLAQMRRISLFSCLKDRHDNGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 34 |
| IFNA2b_ M171T | 61176 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEITRSFS LSTNLQESLRSKE | 35 |
| IFNA2b_ V165W | 55443 | 2.22 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEWVRAEIMRSFS LSTNLQESLRSKE | 36 |
| IFNA2b_ L49H | 52734 | 2.21 | CDLPQTHSLGSRRTLMLLAQMRRISHFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 37 |
| IFNA2b_ V165F | 52584 | 2.35 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEFVRAEIMRSFS LSTNLQESLRSKE | 38 |
| IFNA2b_ L53N | 51981 | 2.37 | CDLPQTHSLGSRRTLMLLAQMRRISLFSCNKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 39 |
| IFNA2b_ F59A | 51955 | 2.19 | CDLPQTHSLGSRRTLMLLAQMRRISLFSCLKDRHDAGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 40 |
| IFNA2b_ A168K | 50815 | 2.43 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRKEIMRSFS LSTNLQESLRSKE | 41 |
| IFNA2b_ R172D | 50691 | 2.50 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMDSFS LSTNLQESLRSKE | 42 |
| IFNA2b_ R167I | 49479 | 2.00 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVIAEIMRSFS LSTNLQESLRSKE | 43 |
| IFNA2b_ L41K | 48574 | 2.06 | CDLPQTHSLGSRRTLMLKAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 44 |
| IFNA2b_ F59G | 46593 | 2.18 | CDLPQTHSLGSRRTLMLLAQMRRISLFSCLKDRHDGGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 45 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ R56V | 44697 | 2.18 | CDLPQTHSLGSRRTLMLLAQMRRISLFSCLKDVHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 46 |
| IFNA2b_ R172W | 44067 | 2.02 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMWSFS LSTNLQESLRSKE | 47 |
| IFNA2b_ R56T | 43611 | 2.38 | CDLPQTHSLGSRRTLMLLAQMRRISLFSCLKDTHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 48 |
| IFNA2b_ L49I | 43249 | 2.07 | CDLPQTHSLGSRRTLMLLAQMRRISIFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 49 |
| IFNA2b_ R172N | 41999 | 2.23 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMNSFS LSTNLQESLRSKE | 50 |
| IFNA2b_ M171N | 40624 | 2.39 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEINRSFS LSTNLQESLRSKE | 51 |
| IFNA2b_ L49K | 38419 | 2.46 | CDLPQTHSLGSRRTLMLLAQMRRISKFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 52 |
| IFNA2b_ V165Q | 38210 | 2.36 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEQVRAEIMRSFS LSTNLQESLRSKE | 53 |
| IFNA2b_ L53V | 36997 | 2.30 | CDLPQTHSLGSRRTLMLLAQMRRISLFSCVKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 54 |
| IFNA2b_ L53S | 34978 | 2.13 | CDLPQTHSLGSRRTLMLLAQMRRISLFSCSKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 55 |
| IFNA2b_ L41G | 34802 | 2.27 | CDLPQTHSLGSRRTLMLGAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 56 |
| IFNA2b_ R56A | 34146 | 2.41 | CDLPQTHSLGSRRTLMLLAQMRRISLFSCLKDAHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 57 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ F59T | 33225 | 2.05 | CDLPQTHSLGSRRTLMLLAQMRRISLFSCLKDRHDTGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 58 |
| IFNA2b_ R56L | 29487 | 2.09 | CDLPQTHSLGSRRTLMLLAQMRRISLFSCLKDLHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 59 |
| IFNA2b_ S173K | 28783 | 2.12 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRKFS LSTNLQESLRSKE | 60 |
| IFNA2b_ R56H | 28741 | 2.06 | CDLPQTHSLGSRRTLMLLAQMRRISLFSCLKDHHDFGF PQEEFGNQFQKAETIPVLHEMIQQIENLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 61 |
| IFNA2b_ R167M | 28607 | 2.41 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVMAEIMRSFS LSTNLQESLRSKE | 62 |
| IFNA2b_ R172A | 27318 | 2.16 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMASFS LSTNLQESLRSKE | 63 |
| IFNA2b_ R167S | 27280 | 2.27 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVSAEIMRSFS LSTNLQESLRSKE | 64 |
| IFNA2b_ R172V | 26443 | 2.21 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMVSFS LSTNLQESLRSKE | 65 |
| IFNA2b_ V165L | 26316 | 2.11 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWELVRAEIMRSFS LSTNLQESLRSKE | 66 |
| IFNA2b_ I47P | 24600 | 2.62 | CDLPQTHSLGSRRTLMLLAQMRRPSLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 67 |
| IFNA2b_ S173R | 23892 | 2.30 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRRFS LSTNLQESLRSKE | 68 |
| IFNA2b_ R167E | 22135 | 2.04 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVEAEIMRSFS LSTNLQESLRSKE | 69 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ M171A | 21491 | 2.46 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIARSFS LSTNLQESLRSKE | 70 |
| IFNA2b_ M171Y | 21334 | 2.40 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIYRSFS LSTNLQESLRSKE | 71 |
| IFNA2b_ M171W | 20819 | 2.17 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIWRSFS LSTNLQESLRSKE | 72 |
| IFNA2b_ V165M | 20710 | 2.29 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEMVRAEIMRSFS LSTNLQESLRSKE | 73 |
| IFNA2b_ M171F | 19164 | 2.37 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIFRSFS LSTNLQESLRSKE | 74 |
| IFNA2b_ A168Y | 19085 | 2.00 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRYEIMRSFS LSTNLQESLRSKE | 75 |
| IFNA2b_ V165S | 15489 | 2.16 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWESVRAEIMRSFS LSTNLQESLRSKE | 76 |
| IFNA2b_ V165R | 14751 | 2.24 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWERVRAEIMRSFS LSTNLQESLRSKE | 77 |
| IFNA2b_ S175R | 10833 | 2.41 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFR LSTNLQESLRSKE | 78 |
| IFNA2b_ A168G | 10757 | 2.43 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRGEIMRSFS LSTNLQESLRSKE | 79 |
| IFNA2b_ R172G | 10734 | 2.40 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMGSFS LSTNLQESLRSKE | 80 |
| IFNA2b_ M171K | 10717 | 2.46 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIKRSFS LSTNLQESLRSKE | 81 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_M171E | 9929 | 2.44 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIERSFS LSTNLQESLRSKE | 82 |
| IFNA2b_R46P | 9510 | 2.33 | CDLPQTHSLGSRRTLMLLAQMRPISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 83 |
| IFNA2b_R46D | 9254 | 2.47 | CDLPQTHSLGSRRTLMLLAQMRDISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 84 |
| IFNA2b_R172T | 8755 | 2.12 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMTSFS LSTNLQESLRSKE | 85 |
| IFNA2b_R167L | 8584 | 2.49 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVLAEIMRSFS LSTNLQESLRSKE | 86 |
| IFNA2b_F59Y | 6708 | 2.06 | CDLPQTHSLGSRRTLMLLAQMRRISLESCLKDRHDYGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 87 |
| IFNA2b_L176N | 6510 | 2.05 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS NSTNLQESLRSKE | 88 |
| IFNA2b_E169T | 5745 | 2.20 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRATIMRSFS LSTNLQESLRSKE | 89 |
| IFNA2b_L176G | 5479 | 2.22 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS GSTNLQESLRSKE | 90 |
| IFNA2b_R167V | 5478 | 2.61 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVVAEIMRSFS LSTNLQESLRSKE | 91 |
| IFNA2b_R172S | 5071 | 2.19 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMSSFS LSTNLQESLRSKE | 92 |
| IFNA2b_S173H | 4507 | 2.31 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRHFS LSTNLQESLRSKE | 93 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ M171G | 4143 | 2.14 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIGRSFS LSTNLQESLRSKE | 94 |
| IFNA2b_ L49V | 3993 | 2.17 | CDLPQTHSLGSRRTLMLLAQMRRISVFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 95 |
| IFNA2b_ F50N | 3391 | 2.25 | CDLPQTHSLGSRRTLMLLAQMRRISLNSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 96 |
| IFNA2b_ R167A | 3372 | 2.51 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVAAEIMRSFS LSTNLQESLRSKE | 97 |
| IFNA2b_ I47D | 3254 | 2.31 | CDLPQTHSLGSRRTLMLLAQMRRDSLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 98 |
| IFNA2b_ R46F | 3193 | 2.09 | CDLPQTHSLGSRRTLMLLAQMRFISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 99 |
| IFNA2b_ S175K | 3055 | 2.34 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFK LSTNLQESLRSKE | 100 |
| IFNA2b_ M171L | 3029 | 2.01 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEILRSFS LSTNLQESLRSKE | 101 |
| IFNA2b_ V126W | 2783 | 2.11 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGWGVTETPLMKED SILAVRKYFQRITLYLKEKKYSPCAWEVVRAEIMRSFS LSTNLQESLRSKE | 102 |
| IFNA2b_ S175M | 2457 | 2.04 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFM LSTNLQESLRSKE | 103 |
| IFNA2b_ L176H | 2358 | 2.35 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS HSTNLQESLRSKE | 104 |
| IFNA2b_ A168F | 2284 | 2.35 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRFEIMRSFS LSTNLQESLRSKE | 105 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ M171I | 2133 | 2.14 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIIRSFS LSTNLQESLRSKE | 106 |
| IFNA2b_ R167G | 2115 | 2.09 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVGAEIMRSFS LSTNLQESLRSKE | 107 |
| IFNA2b_ V165N | 2052 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWENVRAEIMRSFS LSTNLQESLRSKE | 108 |
| IFNA2b_ R46Y | 2015 | 2.00 | CDLPQTHSLGSRRTLMLLAQMRYISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 109 |
| IFNA2b_ M171V | 1871 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIVRSFS LSTNLQESLRSKE | 110 |
| IFNA2b_ L38H | 1824 | 2.01 | CDLPQTHSLGSRRTHMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 111 |
| IFNA2b_ L176A | 1591 | 2.07 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS ASTNLQESLRSKE | 112 |
| IFNA2b_ L41A | 1455 | 2.03 | CDLPQTHSLGSRRTLMLAAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 113 |
| IFNA2b_ L176P | 1398 | 2.13 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS PSTNLQESLRSKE | 114 |
| IFNA2b_ L176D | 1305 | 2.42 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS DSTNLQESLRSKE | 115 |
| IFNA2b_ S34A | 1225 | 2.17 | CDLPQTHSLGARRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 116 |
| IFNA2b_ S183W | 1206 | 2.33 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQEWLRSKE | 117 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ N116W | 1182 | 2.05 | CDLPQTHSLGSRRTLMLLAQMRRISLFSCLKDRHDFGF PQEEFGNQFQKAETIPVLHEMIQQIENLESTKDSSAAW DETLLDKFYTELYQQLWDLEACVIQGVGVTETPLMKED SILAVRKYFQRITLYLKEKKYSPCAWEVVRAEIMRSFS LSTNLQESLRSKE | 118 |
| IFNA2b_ S173E | 1003 | 2.24 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMREFS LSTNLQESLRSKE | 119 |
| IFNA2b_ S175L | 991 | 2.15 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFL LSTNLQESLRSKE | 120 |
| IFNA2b_ F50G | 863 | 2.15 | CDLPQTHSLGSRRTLMLLAQMRRISLGSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 121 |
| IFNA2b_ M82W | 861 | 2.11 | CDLPQTHSLGSRRTLMLLAQMRRISLFSCLKDRHDFGF PQEEFGNQFQKAETIPVLHEWIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 122 |
| IFNA2b_ L176R | 854 | 2.30 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS RSTNLQESLRSKE | 123 |
| IFNA2b_ S175P | 831 | 2.22 | CDLPQTHSLGSRRTLMLLAQMRRISLESCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFP LSTNLQESLRSKE | 124 |
| IFNA2b_ E188I | 781 | 2.13 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKI | 125 |
| IFNA2b_ S175I | 777 | 2.08 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFI LSTNLQESLRSKE | 126 |
| IFNA2b_ D55T | 774 | 2.12 | CDLPQTHSLGSRRTLMLLAQMRRISLFSCLKTRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 127 |
| IFNA2b_ L49Y | 689 | 2.26 | CDLPQTHSLGSRRTLMLLAQMRRISYFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 128 |
| IFNA2b_ R172Y | 688 | 2.28 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMYSFS LSTNLQESLRSKE | 129 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ I139Y | 683 | 2.02 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SYLAVRKYFQRITLYLKEKKYSPCAWEVVRAEIMRSFS LSTNLQESLRSKE | 130 |
| IFNA2b_ K187R | 678 | 2.64 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSRE | 131 |
| IFNA2b_ M82K | 661 | 2.03 | CDLPQTHSLGSRRTLMLLAQMRRISLFSCLKDRHDFGF PQEEFGNQFQKAETIPVLHEKIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 132 |
| IFNA2b_ S177D | 654 | 2.18 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LDTNLQESLRSKE | 133 |
| IFNA2b_ M82R | 653 | 2.13 | CDLPQTHSLGSRRTLMLLAQMRRISLFSCLKDRHDFGF PQEEFGNQFQKAETIPVLHERIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 134 |
| IFNA2b_ Q43P | 641 | 2.02 | CDLPQTHSLGSRRTLMLLAPMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 135 |
| IFNA2b_ F50Q | 631 | 2.31 | CDLPQTHSLGSRRTLMLLAQMRRISLQSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 136 |
| IFNA2b_ R46N | 572 | 2.62 | CDLPQTHSLGSRRTLMLLAQMRNISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 137 |
| IFNA2b_ L38Y | 556 | 2.21 | CDLPQTHSLGSRRTYMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 138 |
| IFNA2b_ F50S | 549 | 2.35 | CDLPQTHSLGSRRTLMLLAQMRRISLSSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 139 |
| IFNA2b_ L38G | 548 | 2.26 | CDLPQTHSLGSRRTGMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 140 |
| IFNA2b_ R172L | 518 | 2.08 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMLSFS LSTNLQESLRSKE | 141 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ Q63E | 497 | 2.24 | CDLPQTHSLGSRRTLMLLAQMRRISLFSCLKDRHDFGF PEEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 142 |
| IFNA2b_ L49F | 495 | 2.29 | CDLPQTHSLGSRRTLMLLAQMRRISFFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 143 |
| IFNA2b_ G125V | 483 | 2.15 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQVVGVTETPLMKED SILAVRKYFQRITLYLKEKKYSPCAWEVVRAEIMRSFS LSTNLQESLRSKE | 144 |
| IFNA2b_ R172M | 447 | 2.15 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMMSFS LSTNLQESLRSKE | 145 |
| IFNA2b_ L176Q | 446 | 2.26 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS QSTNLQESLRSKE | 146 |
| IFNA2b_ S175V | 442 | 2.04 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFV LSTNLQESLRSKE | 147 |
| IFNA2b_ L38P | 425 | 2.28 | CDLPQTHSLGSRRTPMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 148 |
| IFNA2b_ P160E | 414 | 2.43 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSECAWEVVRAEIMRSFS LSTNLQESLRSKE | 149 |
| IFNA2b_ R46S | 371 | 2.17 | CDLPQTHSLGSRRTLMLLAQMRSISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 150 |
| IFNA2b_ S173N | 368 | 2.15 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRNFS LSTNLQESLRSKE | 151 |
| IFNA2b_ L40R | 359 | 2.01 | CDLPQTHSLGSRRTLMRLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 152 |
| IFNA2b_ R148Y | 343 | 2.24 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQYITLYLKEKKYSPCAWEVVRAEIMRSFS LSTNLQESLRSKE | 153 |

TABLE 1-continued

IFNA2 Variants Comprising Single Amino Acid
Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_S48Y | 328 | 2.13 | CDLPQTHSLGSRRTLMLLAQMRRIYLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 154 |
| IFNA2b_F50M | 318 | 2.09 | CDLPQTHSLGSRRTLMLLAQMRRISLMSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 155 |
| IFNA2b_R46I | 302 | 2.08 | CDLPQTHSLGSRRTLMLLAQMRIISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 156 |
| IFNA2b_K106L | 302 | 2.25 | CDLPQTHSLGSRRTLMLLAQMRRISLFSCLKDRHDFGF PQEEFGNQFQKAETIPVLHEMIQQIFNLFSTKDSSAAW DETLLDLFYTELYQQLNDLEACVIQGVGVTETPLMKED SILAVRKYFQRITLYLKEKKYSPCAWEVVRAEIMRSFS LSTNLQESLRSKE | 157 |
| IFNA2b_S31D | 301 | 2.13 | CDLPQTHDLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 158 |
| IFNA2b_F61G | 299 | 2.11 | CDLPQTHSLGSRRTLMLLAQMRRISLFSCLKDRHDFGG PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 159 |
| IFNA2b_I139F | 293 | 2.31 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SFLAVRKYFQRITLYLKEKKYSPCAWEVVRAEIMRSFS LSTNLQESLRSKE | 160 |
| IFNA2b_R185D | 292 | 2.23 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLDSKE | 161 |
| IFNA2b_R46G | 292 | 2.19 | CDLPQTHSLGSRRTLMLLAQMRGISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 162 |
| IFNA2b_Q147S | 286 | 2.52 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFSRITLYLKEKKYSPCAWEVVRAEIMRSFS LSTNLQESLRSKE | 163 |
| IFNA2b_R45P | 284 | 2.15 | CDLPQTHSLGSRRTLMLLAQMPRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 164 |
| IFNA2b_M82G | 284 | 2.13 | CDLPQTHSLGSRRTLMLLAQMRRISLFSCLKDRHDFGF PQEEFGNQFQKAETIPVLHEGIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 165 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ L49G | 265 | 2.34 | CDLPQTHSLGSRRTLMLLAQMRRISGFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 166 |
| IFNA2b_ L176E | 256 | 2.45 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS ESTNLQESLRSKE | 167 |
| IFNA2b_ K187L | 251 | 2.44 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSLE | 168 |
| IFNA2b_ L40G | 250 | 2.29 | CDLPQTHSLGSRRTLMGLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 169 |
| IFNA2b_ R172K | 247 | 2.50 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMKSFS LSTNLQESLRSKE | 170 |
| IFNA2b_ V78E | 240 | 2.04 | CDLPQTHSLGSRRTLMLLAQMRRISLFSCLKDRHDFGF PQEEFGNQFQKAETIPELHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 171 |
| IFNA2b_ F61I | 239 | 2.11 | CDLPQTHSLGSRRTLMLLAQMRRISLFSCLKDRHDFGI PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 172 |
| IFNA2b_ L176V | 239 | 2.09 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS VSTNLQESLRSKE | 173 |
| IFNA2b_ E169S | 239 | 2.17 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRASIMRSFS LSTNLQESLRSKE | 174 |
| IFNA2b_ K54L | 237 | 2.27 | CDLPQTHSLGSRRTLMLLAQMRRISLFSCLLDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 175 |
| IFNA2b_ E169G | 236 | 2.07 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAGIMRSFS LSTNLQESLRSKE | 176 |
| IFNA2b_ F61V | 236 | 2.10 | CDLPQTHSLGSRRTLMLLAQMRRISLFSCLKDRHDFGV PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 177 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ S173W | 231 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRWFS LSTNLQESLRSKE | 178 |
| IFNA2b_ F61P | 228 | 2.23 | CDLPQTHSLGSRRTLMLLAQMRRISLFSCLKDRHDFGP PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 179 |
| IFNA2b_ S186L | 218 | 2.23 | CDLPQTHSLGSRRTLMLLAQMRRISLFSCLKDRHDFGF PQEEFGNQFQKAETIPVLHEMIQQIENLESTKDSSAAW DETLLDKFYTELYQQLNDLEACVIQGVGVTETPLMKED SILAVRKYFQRITLYLKEKKYSPCAWEVVRAEIMRSFS LSTNLQESLRLKE | 180 |
| IFNA2b_ K187E | 216 | 2.46 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSEE | 181 |
| IFNA2b_ K187Y | 214 | 2.38 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSYE | 182 |
| IFNA2b_ S175W | 211 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFW LSTNLQESLRSKE | 183 |
| IFNA2b_ L38S | 209 | 2.39 | CDLPQTHSLGSRRTSMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 184 |
| IFNA2b_ L49E | 209 | 2.33 | CDLPQTHSLGSRRTLMLLAQMRRISEFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 185 |
| IFNA2b_ F61Q | 208 | 2.29 | CDLPQTHSLGSRRTLMLLAQMRRISLFSCLKDRHDFGQ PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 186 |
| IFNA2b_ Q113W | 207 | 2.35 | CDLPQTHSLGSRRTLMLLAQMRRISLFSCLKDRHDFGF PQEEFGNQFQKAETIPVLHEMIQQIFNLFSTKDSSAAW DETLLDKFYTELYWQLNDLEACVIQGVGVTETPLMKED SILAVRKYFQRITLYLKEKKYSPCAWEVVRAEIMRSFS LSTNLQESLRSKE | 187 |
| IFNA2b_ K54I | 206 | 2.15 | CDLPQTHSLGSRRTLMLLAQMRRISLFSCLIDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 188 |
| IFNA2b_ K156D | 204 | 2.24 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEDKYSPCAWEVVRAEIMRSFS LSTNLQESLRSKE | 189 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ P132W | 203 | 2.03 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETWLMKED SILAVRKYFQRITLYLKEKKYSPCAWEVVRAEIMRSFS LSTNLQESLRSKE | 190 |
| IFNA2b_ S51D | 202 | 2.07 | CDLPQTHSLGSRRTLMLLAQMRRISLFDCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 191 |
| IFNA2b_ M44Q | 202 | 2.11 | CDLPQTHSLGSRRTLMLLAQQRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 192 |
| IFNA2b_ E119Y | 200 | 2.03 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLYACVIQGVGVTETPLMKED SILAVRKYFQRITLYLKEKKYSPCAWEVVRAEIMRSFS LSTNLQESLRSKE | 193 |
| IFNA2b_ A168D | 200 | 2.50 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRDEIMRSFS LSTNLQESLRSKE | 194 |
| IFNA2b_ F50H | 199 | 2.26 | CDLPQTHSLGSRRTLMLLAQMRRISLHSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 195 |
| IFNA2b_ S51E | 198 | 2.03 | CDLPQTHSLGSRRTLMLLAQMRRISLFECLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 196 |
| IFNA2b_ S183F | 197 | 2.51 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQEFLRSKE | 197 |
| IFNA2b_ P160F | 194 | 2.05 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSFCAWEVVRAEIMRSFS LSTNLQESLRSKE | 198 |
| IFNA2b_ 1 E110P | 192 | 2.27 | CDLPQTHSLGSRRTLMLLAQMRRISLFSCLKDRHDFGF PQEEFGNQFQKAETIPVLHEMIQQIFNLFSTKDSSAAW DETLLDKFYTPLYQQLNDLEACVIQGVGVTETPLMKED SILAVRKYFQRITLYLKEKKYSPCAWEVVRAEIMRSFS LSTNLQESLRSKE | 199 |
| IFNA2b_ I170L | 190 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAELMRSFS LSTNLQESLRSKE | 200 |
| IFNA2b_ S175Y | 189 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFY LSTNLQESLRSKE | 201 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ S175G | 189 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFG LSTNLQESLRSKE | 202 |
| IFNA2b_ L40Q | 185 | 2.00 | CDLPQTHSLGSRRTLMQLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 203 |
| IFNA2b_ K187V | 183 | 2.31 | CDLPQTHSLGSRRTLMLLAQMRRISLFSCLKDRHDFGF PQEEFGNQFQKAETIPVLHEMIQQIENLESTKDSSAAW DETLLDKFYTELYQQLNDLEACVIQGVGVTETPLMKED SILAVRKYFQRITLYLKEKKYSPCAWEVVRAEIMRSFS LSTNLQESLRSVE | 204 |
| IFNA2b_ K157Y | 180 | 2.16 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKYYSPCAWEVVRAEIMRSFS LSTNLQESLRSKE | 205 |
| IFNA2b_ N116M | 180 | 2.02 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLMDLEACVIQGVGVTETPLMKED SILAVRKYFQRITLYLKEKKYSPCAWEVVRAEIMRSFS LSTNLQESLRSKE | 206 |
| IFNA2b_ I86L | 180 | 2.11 | CDLPQTHSLGSRRTLMLLAQMRRISLFSCLKDRHDFGF PQEEFGNQFQKAETIPVLHEMIQQLFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 207 |
| IFNA2b_ P62I | 177 | 2.20 | CDLPQTHSLGSRRTLMLLAQMRRISLFSCLKDRHDFGF IQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 208 |
| IFNA2b_ Y145H | 175 | 2.00 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKHFQRITLYLKEKKYSPCAWEVVRAEIMRSFS LSTNLQESLRSKE | 209 |
| IFNA2b_ V126Y | 167 | 2.09 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGYGVTETPLMKED SILAVRKYFQRITLYLKEKKYSPCAWEVVRAEIMRSFS LSTNLQESLRSKE | 210 |
| IFNA2b_ Q69S | 166 | 2.17 | CDLPQTHSLGSRRTLMLLAQMRRISLFSCLKDRHDFGF PQEEFGNSFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 211 |
| IFNA2b_ K187M | 162 | 2.52 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSME | 212 |
| IFNA2b_ N116F | 160 | 2.11 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLFDLEACVIQGVGVTETPLMKED SILAVRKYFQRITLYLKEKKYSPCAWEVVRAEIMRSFS LSTNLQESLRSKE | 213 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ P160W | 159 | 2.24 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSWCAWEVVRAEIMRSFS LSTNLQESLRSKE | 214 |
| IFNA2b_ K187F | 158 | 2.51 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSFE | 215 |
| IFNA2b_ K187I | 158 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSIE | 216 |
| IFNA2b_ L38T | 158 | 2.10 | CDLPQTHSLGSRRTTMLLAQMRRISLESCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 217 |
| IFNA2b_ S183M | 157 | 2.06 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQEMLRSKE | 218 |
| IFNA2b_ V165D | 153 | 2.09 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEDVRAEIMRSFS LSTNLQESLRSKE | 219 |
| IFNA2b_ A42G | 153 | 2.19 | CDLPQTHSLGSRRTLMLLGQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 220 |
| IFNA2b_ K156L | 152 | 2.00 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKELKYSPCAWEVVRAEIMRSFS LSTNLQESLRSKE | 221 |
| IFNA2b_ S183E | 149 | 2.37 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LSTNLQEELRSKE | 222 |
| IFNA2b_ 1 Y108K | 149 | 2.19 | CDLPQTHSLGSRRTLMLLAQMRRISLFSCLKDRHDFGF PQEEFGNQFQKAETIPVLHEMIQQIFNLFSTKDSSAAW DETLLDKFKTELYQQLNDLEACVIQGVGVTETPLMKED SILAVRKYFQRITLYLKEKKYSPCAWEVVRAEIMRSFS LSTNLQESLRSKE | 223 |
| IFNA2b_ D55N | 149 | 2.20 | CDLPQTHSLGSRRTLMLLAQMRRISLFSCLKNRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 224 |
| IFNA2b_ L38Q | 149 | 2.25 | CDLPQTHSLGSRRTQMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 225 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ R185E | 147 | 2.32 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLESKE | 226 |
| IFNA2b_ S186I | 146 | 2.08 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRIKE | 227 |
| IFNA2b_ S175E | 146 | 2.05 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFE LSTNLQESLRSKE | 228 |
| IFNA2b_ L49P | 146 | 2.38 | CDLPQTHSLGSRRTLMLLAQMRRISPFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 229 |
| IFNA2b_ S183Y | 146 | 2.37 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQEYLRSKE | 230 |
| IFNA2b_ R46A | 144 | 2.27 | CDLPQTHSLGSRRTLMLLAQMRAISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 231 |
| IFNA2b_ H30A | 144 | 2.04 | CDLPQTASLGSRRTLMLLAQMRRISLESCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 232 |
| IFNA2b_ R46H | 143 | 2.38 | CDLPQTHSLGSRRTLMLLAQMRHISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 233 |
| IFNA2b_ E110S | 142 | 2.34 | CDLPQTHSLGSRRTLMLLAQMRRISLFSCLKDRHDFGF PQEEFGNQFQKAETIPVLHEMIQQIFNLFSTKDSSAAW DETLLDKFYTSLYQQLNDLEACVIQGVGVTETPLMKED SILAVRKYFQRITLYLKEKKYSPCAWEVVRAEIMRSFS LSTNLQESLRSKE | 234 |
| IFNA2b_ K156W | 141 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEWKYSPCAWEVVRAEIMRSFS LSTNLQESLRSKE | 235 |
| IFNA2b_ R46T | 140 | 2.53 | CDLPQTHSLGSRRTLMLLAQMRTISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 236 |
| IFNA2b_ S175Q | 139 | 2.36 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFQ LSTNLQESLRSKE | 237 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ D58Q | 138 | 2.15 | CDLPQTHSLGSRRTLMLLAQMRRISLFSCLKDRHQFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 238 |
| IFNA2b_ E155H | 137 | 2.21 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKHKKYSPCAWEVVRAEIMRSFS LSTNLQESLRSKE | 239 |
| IFNA2b_ L40D | 136 | 2.12 | CDLPQTHSLGSRRTLMDLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 240 |
| IFNA2b_ A120M | 136 | 2.02 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEMCVIQGVGVTETPLMKED SILAVRKYFQRITLYLKEKKYSPCAWEVVRAEIMRSFS LSTNLQESLRSKE | 241 |
| IFNA2b_ R167H | 135 | 2.02 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVHAEIMRSFS LSTNLQESLRSKE | 242 |
| IFNA2b_ M82S | 134 | 2.11 | CDLPQTHSLGSRRTLMLLAQMRRISLFSCLKDRHDFGF PQEEFGNQFQKAETIPVLHESIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 243 |
| IFNA2b_ A42M | 132 | 2.27 | CDLPQTHSLGSRRTLMLLMQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 244 |
| IFNA2b_ S48H | 131 | 2.10 | CDLPQTHSLGSRRTLMLLAQMRRIHLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 245 |
| IFNA2b_ R143F | 129 | 2.02 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVFKYFQRITLYLKEKKYSPCAWEVVRAEIMRSFS LSTNLQESLRSKE | 246 |
| IFNA2b_ K187W | 129 | 2.49 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSWE | 247 |
| IFNA2b_ I47S | 128 | 2.01 | CDLPQTHSLGSRRTLMLLAQMRRSSLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 248 |
| IFNA2b_ R35N | 128 | 2.43 | CDLPQTHSLGSNRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 249 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ S175T | 128 | 2.13 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFT LSTNLQESLRSKE | 250 |
| IFNA2b_ S173Y | 127 | 2.10 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRYFS LSTNLQESLRSKE | 251 |
| IFNA2b_ A168M | 125 | 2.37 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRMEIMRSFS LSTNLQESLRSKE | 252 |
| IFNA2b_ A98E | 125 | 2.05 | CDLPQTHSLGSRRTLMLLAQMRRISLFSCLKDRHDFGF PQEEFGNQFQKAETIPVLHEMIQQIFNLFSTKDSSAEW DETLLDKFYTELYQQLNDLEACVIQGVGVTETPLMKED SILAVRKYFQRITLYLKEKKYSPCAWEVVRAEIMRSFS LSTNLQESLRSKE | 253 |
| IFNA2b_ S186D | 125 | 2.07 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRDKE | 254 |
| IFNA2b_ M134Y | 124 | 2.31 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLYKED SILAVRKYFQRITLYLKEKKYSPCAWEVVRAEIMRSFS LSTNLQESLRSKE | 255 |
| IFNA2b_ H30D | 124 | 2.12 | CDLPQTDSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 256 |
| IFNA2b_ E119F | 122 | 2.08 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLFACVIQGVGVTETPLMKED SILAVRKYFQRITLYLKEKKYSPCAWEVVRAEIMRSFS LSTNLQESLRSKE | 257 |
| IFNA2b_ V78G | 121 | 2.09 | CDLPQTHSLGSRRTLMLLAQMRRISLESCLKDRHDFGF PQEEFGNQFQKAETIPGLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 258 |
| IFNA2b_ R185Q | 120 | 2.22 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLQSKE | 259 |
| IFNA2b_ K54M | 119 | 2.09 | CDLPQTHSLGSRRTLMLLAQMRRISLFSCLMDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 260 |
| IFNA2b_ L32D | 119 | 2.17 | CDLPQTHSDGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 261 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ L103E | 117 | 2.02 | CDLPQTHSLGSRRTLMLLAQMRRISLFSCLKDRHDFGF PQEEFGNQFQKAETIPVLHEMIQQIFNLFSTKDSSAAW DETELDKFYTELYQQLNDLEACVIQGVGVTETPLMKED SILAVRKYFQRITLYLKEKKYSPCAWEVVRAEIMRSFS LSTNLQESLRSKE | 262 |
| IFNA2b_ K106D | 116 | 2.11 | CDLPQTHSLGSRRTLMLLAQMRRISLFSCLKDRHDFGF PQEEFGNQFQKAETIPVLHEMIQQIFNLFSTKDSSAAW DETLLDDFYTELYQQLNDLEACVIQGVGVTETPLMKED SILAVRKYFQRITLYLKEKKYSPCAWEVVRAEIMRSFS LSTNLQESLRSKE | 263 |
| IFNA2b_ L38N | 114 | 2.13 | CDLPQTHSLGSRRTNMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 264 |
| IFNA2b_ N179G | 114 | 2.31 | CDLPQTHSLGSRRTLMLLAQMRRISLFSCLKDRHDFGF PQEEFGNQFQKAETIPVLHEMIQQIENLESTKDSSAAW DETLLDKFYTELYQQLNDLEACVIQGVGVTETPLMKED SILAVRKYFQRITLYLKEKKYSPCAWEVVRAEIMRSFS LSTGLQESLRSKE | 265 |
| IFNA2b_ V165I | 111 | 2.21 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEIVRAEIMRSFS LSTNLQESLRSKE | 266 |
| IFNA2b_ L103D | 111 | 2.25 | CDLPQTHSLGSRRTLMLLAQMRRISLFSCLKDRHDFGF PQEEFGNQFQKAETIPVLHEMIQQIFNLESTKDSSAAW DETDLDKFYTELYQQLNDLEACVIQGVGVTETPLMKED SILAVRKYFQRITLYLKEKKYSPCAWEVVRAEIMRSFS LSTNLQESLRSKE | 267 |
| IFNA2b_ K187G | 110 | 2.14 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSGE | 268 |
| IFNA2b_ R36G | 110 | 2.01 | CDLPQTHSLGSRGTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 269 |
| IFNA2b_ A141E | 110 | 2.22 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILEVRKYFQRITLYLKEKKYSPCAWEVVRAEIMRSFS LSTNLQESLRSKE | 270 |
| IFNA2b_ T129G | 110 | 2.28 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVGETPLMKED SILAVRKYFQRITLYLKEKKYSPCAWEVVRAEIMRSFS LSTNLQESLRSKE | 271 |
| IFNA2b_ A168Q | 109 | 2.27 | CDLPQTHSLGSRRTLMLLAQMRRISLFSCLKDRHDFGF PQEEFGNQFQKAETIPVLHEMIQQIFNLESTKDSSAAW DETLLDKFYTELYQQLNDLEACVIQGVGVTETPLMKED SILAVRKYFQRITLYLKEKKYSPCAWEVVRQEIMRSFS LSTNLQESLRSKE | 272 |
| IFNA2b_ D55Q | 109 | 2.09 | CDLPQTHSLGSRRTLMLLAQMRRISLFSCLKQRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 273 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ S183K | 109 | 2.02 | CDLPQTHSLGSRRTLMLLAQMRRISLESCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQEKLRSKE | 274 |
| IFNA2b_ S183L | 109 | 2.51 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQELLRSKE | 275 |
| IFNA2b_ N116Q | 108 | 2.08 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLQDLEACVIQGVGVTETPLMKED SILAVRKYFQRITLYLKEKKYSPCAWEVVRAEIMRSFS LSTNLQESLRSKE | 276 |
| IFNA2b_ S177R | 108 | 2.14 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LRTNLQESLRSKE | 277 |
| IFNA2b_ K93E | 108 | 2.13 | CDLPQTHSLGSRRTLMLLAQMRRISLFSCLKDRHDFGF PQEEFGNQFQKAETIPVLHEMIQQIFNLFSTEDSSAAW DETLLDKFYTELYQQLNDLEACVIQGVGVTETPLMKED SILAVRKYFQRITLYLKEKKYSPCAWEVVRAEIMRSFS LSTNLQESLRSKE | 278 |
| IFNA2b_ A141I | 107 | 2.27 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILIVRKYFQRITLYLKEKKYSPCAWEVVRAEIMRSFS LSTNLQESLRSKE | 279 |
| IFNA2b_ T109W | 107 | 2.29 | CDLPQTHSLGSRRTLMLLAQMRRISLFSCLKDRHDFGF PQEEFGNQFQKAETIPVLHEMIQQIFNLFSTKDSSAAW DETLLDKFYWELYQQLNDLEACVIQGVGVTETPLMKED SILAVRKYFQRITLYLKEKKYSPCAWEVVRAEIMRSFS LSTNLQESLRSKE | 280 |
| IFNA2b_ K72D | 106 | 2.20 | CDLPQTHSLGSRRTLMLLAQMRRISLFSCLKDRHDFGF PQEEFGNQFQDAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 281 |
| IFNA2b_ F50A | 105 | 2.33 | CDLPQTHSLGSRRTLMLLAQMRRISLASCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 282 |
| IFNA2b_ F61A | 105 | 2.20 | CDLPQTHSLGSRRTLMLLAQMRRISLFSCLKDRHDFGA PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 283 |

TABLE 1-continued

IFNA2 Variants Comprising Single Amino Acid Substitutions with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_ F61S | 104 | 2.27 | CDLPQTHSLGSRRTLMLLAQMRRISLFSCLKDRHDFGS PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 284 |
| IFNA2b_ P160Y | 103 | 2.27 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSYCAWEVVRAEIMRSFS LSTNLQESLRSKE | 285 |
| IFNA2b_ L32E | 103 | 2.04 | CDLPQTHSEGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 286 |
| IFNA2b_ K93V | 103 | 2.18 | CDLPQTHSLGSRRTLMLLAQMRRISLFSCLKDRHDFGF PQEEFGNQFQKAETIPVLHEMIQQIFNLESTVDSSAAW DETLLDKFYTELYQQLNDLEACVIQGVGVTETPLMKED SILAVRKYFQRITLYLKEKKYSPCAWEVVRAEIMRSFS LSTNLQESLRSKE | 287 |
| IFNA2b_ P160T | 102 | 2.29 | CDLPQTHSLGSRRTLMLLAQMRRISLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSTCAWEVVRAEIMRSFS LSTNLQESLRSKE | 288 |
| IFNA2b_ I47E | 102 | 2.05 | CDLPQTHSLGSRRTLMLLAQMRRESLFSCLKDRHDFGF PQEEFGNQFQKAETIPVLHEMIQQIFNLFSTKDSSAAW DETLLDKFYTELYQQLNDLEACVIQGVGVTETPLMKED SILAVRKYFQRITLYLKEKKYSPCAWEVVRAEIMRSFS LSTNLQESLRSKE | 289 |

Table 2 below shows the results for 12 variants that were selected for further analysis. To qualify for prioritization and further characterization first, >50 diploids must have formed between the IFNA2 variant and human IFNAR2 during the AlphaSeq™ assay. In addition, >2 different substitutions at the specific position in IFNA2 must have given rise to detuning. For a given amino acid residue position, the number of substitutions that led to detuning was termed the "multiplicity" for that position. Preference was also given to variants at positions conserved in cynomolgus monkey, mouse, and rat. Using these criteria, 12 initial variants were identified that spanned 4 affinity bins ranging from ~300 nM (~10-fold weaker than wild-type) to ~10 µM (~300-fold weaker than wild-type).

TABLE 2

Detuned IFNA2 Variants Selected for Further Analysis

| Affinity bin ($log_{10}$nM) | Variant | IFNAR2 affinity ($log_{10}$nM) | Position conserved in mouse/cyno/rat? | Multiplicity |
|---|---|---|---|---|
| ~4 | I47P | 4.39 | cyno only | 4 |
| | A168G | 4.03 | Yes | 9 |
| | R172T | 3.94 | Yes | 12 |
| ~3.5 | R46F | 3.50 | Yes | 11 |
| | S175K | 3.49 | Yes | 13 |
| | M171L | 3.48 | cyno only | 14 |

TABLE 2-continued

Detuned IFNA2 Variants Selected for Further Analysis

| Affinity bin ($log_{10}$nM) | Variant | IFNAR2 affinity ($log_{10}$nM) | Position conserved in mouse/cyno/rat? | Multiplicity |
|---|---|---|---|---|
| ~3 | S183W | 3.08 | cyno only | 7 |
| | N116W | 3.07 | cyno/mouse | 4 |
| | F50G | 2.94 | cyno only | 8 |
| ~2.5 | M82G | 2.45 | cyno only | 5 |
| | F61G | 2.48 | Yes | 7 |
| | R185D | 2.47 | cyno/rat | 3 |

Table 3 provides affinities between human IFNA2 detuned variants comprising two amino acid substitutions, i.e., double mutants, and human IFNAR2. Any double mutant variant found to bind human IFNAR2 with an affinity weaker than 316 nM ($log_{10}$ nM=2.5) and found to have an average expression bin >2.0, but that did not show decreased affinity to mouse IFNAR2 was included in Table 3. Table 3 is sorted in order of descending Kd, with the highest values representing the lowest affinity of IFNA2 for human IFNAR2. For example, a variant with the name "IFNA2b M44N_A168R" has an amino acid substitution in SEQ ID NO: 1 at location 44, where the existing methionine is replaced with asparagine AND a substitution at location 168, where the existing alanine is replaced with arginine. Table 3 also provides the polypeptide sequences of the 127 IFNA2 variants comprising two amino acid substitutions as SEQ ID NOs 290-416. The polypeptide sequences describe the mature IFNA2b protein, which does not include a 23-amino acid signal peptide that is cleaved from the N-terminus to produce the mature protein.

TABLE 3

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_M44N_A168R | 124223 | 2.21 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRREIMRSFSLSTNLQESLRSKE | 290 |
| IFNA2b_L49P_S175P | 37506 | 2.20 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFPLSTNLQESLRSKE | 291 |
| IFNA2b_L49P_S173H | 36825 | 2.07 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRHFSLSTNLQESLRSKE | 292 |
| IFNA2b_L49P_M171W | 28512 | 2.26 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIWRSFSLSTNLQESLRSKE | 293 |
| IFNA2b_L49P_M171G | 24545 | 2.26 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIGRSFSLSTNLQESLRSKE | 294 |
| IFNA2b_L49P_S173R | 23380 | 2.24 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRRFSLSTNLQESLRSKE | 295 |
| IFNA2b_M44N_S175P | 21816 | 2.03 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFPLSTNLQESLRSKE | 296 |
| IFNA2b_L49P_M171V | 21682 | 2.33 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIVRSFSLSTNLQESLRSKE | 297 |
| IFNA2b_L49P_M171K | 17082 | 2.47 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIKRSFSLSTNLQESLRSKE | 298 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_ M171S | 16469 | 2.22 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEISRSFSLSTNLQESLRSKE | 299 |
| IFNA2b_L49P_ S175R | 16007 | 2.16 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFRLSTNLQESLRSKE | 300 |
| IFNA2b_L49P_ M171R | 14780 | 2.28 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIRRSFSLSTNLQESLRSKE | 301 |
| IFNA2b_L49P_ L176G | 13375 | 2.18 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSGSTNLQESLRSKE | 302 |
| IFNA2b_L49P_ M171Y | 12703 | 2.32 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIYRSFSLSTNLQESLRSKE | 303 |
| IFNA2b_L49P_ L176N | 11472 | 2.14 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSNSTNLQESLRSKE | 304 |
| IFNA2b_L49P_ S173Q | 11317 | 2.16 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRQFSLSTNLQESLRSKE | 305 |
| IFNA2b_L49P_ L176H | 10571 | 2.01 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSHSTNLQESLRSKE | 306 |
| IFNA2b_L49P_ L176R | 8793 | 2.07 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSRSTNLQESLRSKE | 307 |
| IFNA2b_L49P_ M171A | 8575 | 2.22 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIARSFSLSTNLQESLRSKE | 308 |
| IFNA2b_L49P_ M171T | 7719 | 2.35 | CDLPQTHSLGSRRTLMLLAQMRRISPFS CLKDRHDFGFPQEEFGNQFQKAETIPVL | 309 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | HEMIQQIFNLFSTKDSSAAWDETLLDKF YTELYQQLNDLEACVIQGVGVTETPLMK EDSILAVRKYFQRITLYLKEKKYSPCAW EVVRAEITRSFSLSTNLQESLRSKE | |
| IFNA2b_L49P_ L176A | 7334 | 2.21 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSASTNLQESLRSKE | 310 |
| IFNA2b_L49P_ M171F | 6922 | 2.18 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIFRSFSLSTNLQESLRSKE | 311 |
| IFNA2b_M44N_ S175K | 4872 | 2.04 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFKLSTNLQESLRSKE | 312 |
| IFNA2b_L49P_ S175K | 4674 | 2.39 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFKLSTNLQESLRSKE | 313 |
| IFNA2b_L49P_ L176E | 4409 | 2.34 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSESTNLQESLRSKE | 314 |
| IFNA2b_L49P_ E169T | 3823 | 2.06 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRATIMRSFSLSTNLQESLRSKE | 315 |
| IFNA2b_L49P_ M171L | 2447 | 2.06 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEILRSFSLSTNLQESLRSKE | 316 |
| IFNA2b_L49P_ L176Q | 2222 | 2.20 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSQSTNLQESLRSKE | 317 |
| IFNA2b_L49P_ K187E | 2093 | 2.16 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSEE | 318 |
| IFNA2b_L49P_ S173N | 1993 | 2.28 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK | 319 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | EDSILAVRKYFQRITLYLKEKKYSPCAW EVVRAEIMRNFSLSTNLQESLRSKE | |
| IFNA2b_M44N_ L176H | 1933 | 2.00 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSHSTNLQESLRSKE | 320 |
| IFNA2b_M44N_ S175R | 1912 | 2.01 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFRLSTNLQESLRSKE | 321 |
| IFNA2b_L49P_ S177N | 1871 | 2.10 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLNTNLQESLRSKE | 322 |
| IFNA2b_L49P_ S173W | 1702 | 2.23 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRWFSLSTNLQESLRSKE | 323 |
| IFNA2b_L49P_ S177D | 1664 | 2.32 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLDTNLQESLRSKE | 324 |
| IFNA2b_L49P_ R185D | 1628 | 2.27 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLDSKE | 325 |
| IFNA2b_L49P_ E169S | 1590 | 2.06 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRASIMRSFSLSTNLQESLRSKE | 326 |
| IFNA2b_L49P_ S175G | 1420 | 2.20 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFGLSTNLQESLRSKE | 327 |
| IFNA2b_L49P_ S177L | 1411 | 2.23 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLLTNLQESLRSKE | 328 |
| IFNA2b_L49P_ R172K | 1359 | 2.40 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMKSFSLSTNLQESLRSKE | 329 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_R185E | 1325 | 2.44 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLESKE | 330 |
| IFNA2b_L49P_K187M | 1178 | 2.50 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSME | 331 |
| IFNA2b_L49P_K187W | 1177 | 2.35 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSWE | 332 |
| IFNA2b_L49P_S159Q | 1156 | 2.18 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYQPCAW EVVRAEIMRSFSLSTNLQESLRSKE | 333 |
| IFNA2b_M44N_L176Q | 1046 | 2.11 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSQSTNLQESLRSKE | 334 |
| IFNA2b_M44N_R185E | 978 | 2.38 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLESKE | 335 |
| IFNA2b_L49P_S175Q | 900 | 2.28 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFQLSTNLQESLRSKE | 336 |
| IFNA2b_L49P_S175M | 821 | 2.23 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFMLSTNLQESLRSKE | 337 |
| IFNA2b_L49P_E155V | 821 | 2.07 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKVKKYSPCAW EVVRAEIMRSFSLSTNLQESLRSKE | 338 |
| IFNA2b_L49P_K187D | 795 | 2.41 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSDE | 339 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_ S175W | 789 | 2.08 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFWLSTNLQESLRSKE | 340 |
| IFNA2b_L49P_ L176V | 788 | 2.34 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSVSTNLQESLRSKE | 341 |
| IFNA2b_L49P_ S173L | 784 | 2.15 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRLESLSTNLQESLRSKE | 342 |
| IFNA2b_M44N_ S175G | 784 | 2.01 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFGLSTNLQESLRSKE | 343 |
| IFNA2b_L49P_ R185G | 735 | 2.29 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLGSKE | 344 |
| IFNA2b_L49P_ R143W | 714 | 2.12 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVWKYFQRITLYLKEKKYSPCAW EVVRAEIMRSFSLSTNLQESLRSKE | 345 |
| IFNA2b_L49P_ I149T | 702 | 2.05 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRTTLYLKEKKYSPCAW EVVRAEIMRSFSLSTNLQESLRSKE | 346 |
| IFNA2b_L49P_ R185L | 661 | 2.49 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLLSKE | 347 |
| IFNA2b_L49P_ R185S | 637 | 2.28 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLSSKE | 348 |
| IFNA2b_L49P_ S177H | 632 | 2.11 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLHTNLQESLRSKE | 349 |
| IFNA2b_L49P_ K106D | 625 | 2.00 | CDLPQTHSLGSRRTLMLLAQMRRISPFS CLKDRHDFGFPQEEFGNQFQKAETIPVL | 350 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | HEMIQQIFNLFSTKDSSAAWDETLLDDF YTELYQQLNDLEACVIQGVGVTETPLMK EDSILAVRKYFQRITLYLKEKKYSPCAW EVVRAEIMRSFSLSTNLQESLRSKE | |
| IFNA2b_M44N_ R185N | 621 | 2.19 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLNSKE | 351 |
| IFNA2b_L49P_ K187V | 569 | 2.44 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSVE | 352 |
| IFNA2b_L49P_ K106W | 563 | 2.34 | CDLPQTHSLGSRRTLMLLAQMRRISPFS CLKDRHDFGFPQEEFGNQFQKAETIPVL HEMIQQIFNLFSTKDSSAAWDETLLDWF YTELYQQLNDLEACVIQGVGVTETPLMK EDSILAVRKYFQRITLYLKEKKYSPCAW EVVRAEIMRSFSLSTNLQESLRSKE | 353 |
| IFNA2b_L49P_ K135T | 562 | 2.31 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMT EDSILAVRKYFQRITLYLKEKKYSPCAW EVVRAEIMRSFSLSTNLQESLRSKE | 354 |
| IFNA2b_M44N_ V128I | 561 | 2.06 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGITETPLMK EDSILAVRKYFQRITLYLKEKKYSPCAW EVVRAEIMRSFSLSTNLQESLRSKE | 355 |
| IFNA2b_M44N_ R185D | 559 | 2.05 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLDSKE | 356 |
| IFNA2b_L49P_ K106P | 543 | 2.15 | CDLPQTHSLGSRRTLMLLAQMRRISPFS CLKDRHDFGFPQEEFGNQFQKAETIPVL HEMIQQIFNLFSTKDSSAAWDETLLDPF YTELYQQLNDLEACVIQGVGVTETPLMK EDSILAVRKYFQRITLYLKEKKYSPCAW EVVRAEIMRSFSLSTNLQESLRSKE | 357 |
| IFNA2b_L49P_ S183M | 542 | 2.34 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQEMLRSKE | 358 |
| IFNA2b_L49P_ S183D | 540 | 2.29 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQEDLRSKE | 359 |
| IFNA2b_L49P_ K156A | 522 | 2.22 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK | 360 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | EDSILAVRKYFQRITLYLKEAKYSPCAW EVVRAEIMRSFSLSTNLQESLRSKE | |
| IFNA2b_L49P_S183L | 512 | 2.46 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQELLRSKE | 361 |
| IFNA2b_M44N_K187D | 511 | 2.42 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSDE | 362 |
| IFNA2b_L49P_R185M | 509 | 2.36 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLMSKE | 363 |
| IFNA2b_L49P_R185N | 505 | 2.42 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLNSKE | 364 |
| IFNA2b_M44N_A168L | 494 | 2.02 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRLEIMRSFSLSTNLQESLRSKE | 365 |
| IFNA2b_L49P_S175L | 492 | 2.23 | CDLPQTHSLGSRRTLMLLAQMRRISPFS CLKDRHDFGFPQEEFGNQFQKAETIPVL HEMIQQIFNLESTKDSSAAWDETLLDKF YTELYQQLNDLEACVIQGVGVTETPLMK EDSILAVRKYFQRITLYLKEKKYSPCAW EVVRAEIMRSFLLSTNLQESLRSKE | 366 |
| IFNA2b_L49P_R185Q | 479 | 2.60 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLQSKE | 367 |
| IFNA2b_L49P_K187G | 475 | 2.27 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSGE | 368 |
| IFNA2b_M44N_S177E | 475 | 2.00 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLETNLQESLRSKE | 369 |
| IFNA2b_L49P_W163L | 467 | 2.07 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAL EVVRAEIMRSFSLSTNLQESLRSKE | 370 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_R185W | 455 | 2.06 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLWSKE | 371 |
| IFNA2b_L49P_K187T | 451 | 2.26 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSTE | 372 |
| IFNA2b_L49P_T109W | 448 | 2.39 | CDLPQTHSLGSRRTLMLLAQMRRISPFS CLKDRHDFGFPQEEFGNQFQKAETIPVL HEMIQQIFNLFSTKDSSAAWDETLLDKF YWELYQQLNDLEACVIQGVGVTETPLMK EDSILAVRKYFQRITLYLKEKKYSPCAW EVVRAEIMRSFSLSTNLQESLRSKE | 373 |
| IFNA2b_M44N_P160E | 444 | 2.06 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSECAW EVVRAEIMRSFSLSTNLQESLRSKE | 374 |
| IFNA2b_M44N_K106T | 438 | 2.03 | CDLPQTHSLGSRRTLMLLAQNRRISLFS CLKDRHDFGFPQEEFGNQFQKAETIPVL HEMIQQIFNLFSTKDSSAAWDETLLDTF YTELYQQLNDLEACVIQGVGVTETPLMK EDSILAVRKYFQRITLYLKEKKYSPCAW EVVRAEIMRSFSLSTNLQESLRSKE | 375 |
| IFNA2b_L49P_R185T | 431 | 2.33 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLTSKE | 376 |
| IFNA2b_L49P_S175I | 429 | 2.14 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFILSTNLQESLRSKE | 377 |
| IFNA2b_L49P_S173F | 423 | 2.22 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRFFSLSTNLQESLRSKE | 378 |
| IFNA2b_M44N_R185L | 418 | 2.36 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLLSKE | 379 |
| IFNA2b_L49P_S183E | 411 | 2.51 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQEELRSKE | 380 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_ K187N | 403 | 2.25 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSNE | 381 |
| IFNA2b_M44N_ K187F | 403 | 2.10 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSFE | 382 |
| IFNA2b_L49P_ S159D | 400 | 2.24 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYDPCAW EVVRAEIMRSFSLSTNLQESLRSKE | 383 |
| IFNA2b_M44N_ K106I | 392 | 2.05 | CDLPQTHSLGSRRTLMLLAQNRRISLFS CLKDRHDFGFPQEEFGNQFQKAETIPVL HEMIQQIFNLFSTKDSSAAWDETLLDIF YTELYQQLNDLEACVIQGVGVTETPLMK EDSILAVRKYFQRITLYLKEKKYSPCAW EVVRAEIMRSFSLSTNLQESLRSKE | 384 |
| IFNA2b_L49P_ S175Y | 391 | 2.01 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFYLSTNLQESLRSKE | 385 |
| IFNA2b_L49P_ L184N | 383 | 2.22 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESNRSKE | 386 |
| IFNA2b_L49P_ I170L | 381 | 2.32 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAELMRSFSLSTNLQESLRSKE | 387 |
| IFNA2b_L49P_ V166S | 381 | 2.10 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVSRAEIMRSFSLSTNLQESLRSKE | 388 |
| IFNA2b_L49P_ K187A | 381 | 2.30 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSAE | 389 |
| IFNA2b_L49P_ S186D | 373 | 2.10 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRDKE | 390 |
| IFNA2b_L49P_ L111F | 373 | 2.13 | CDLPQTHSLGSRRTLMLLAQMRRISPFS CLKDRHDFGFPQEEFGNQFQKAETIPVL | 391 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | HEMIQQIFNLFSTKDSSAAWDETLLDKF YTEFYQQLNDLEACVIQGVGVTETPLMK EDSILAVRKYFQRITLYLKEKKYSPCAW EVVRAEIMRSFSLSTNLQESLRSKE | |
| IFNA2b_L49P_ K154Q | 366 | 2.16 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLQEKKYSPCAW EVVRAEIMRSFSLSTNLQESLRSKE | 392 |
| IFNA2b_L49P_ K106T | 363 | 2.06 | CDLPQTHSLGSRRTLMLLAQMRRISPFS CLKDRHDFGFPQEEFGNQFQKAETIPVL HEMIQQIFNLFSTKDSSAAWDETLLDTF YTELYQQLNDLEACVIQGVGVTETPLMK EDSILAVRKYFQRITLYLKEKKYSPCAW EVVRAEIMRSFSLSTNLQESLRSKE | 393 |
| IFNA2b_L49P_ E136D | 363 | 2.02 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK DDSILAVRKYFQRITLYLKEKKYSPCAW EVVRAEIMRSFSLSTNLQESLRSKE | 394 |
| IFNA2b_L49P_ K106M | 359 | 2.10 | CDLPQTHSLGSRRTLMLLAQMRRISPFS CLKDRHDFGFPQEEFGNQFQKAETIPVL HEMIQQIFNLFSTKDSSAAWDETLLDMF YTELYQQLNDLEACVIQGVGVTETPLMK EDSILAVRKYFQRITLYLKEKKYSPCAW EVVRAEIMRSFSLSTNLQESLRSKE | 395 |
| IFNA2b_L49P_ F107W | 356 | 2.05 | CDLPQTHSLGSRRTLMLLAQMRRISPFS CLKDRHDFGFPQEEFGNQFQKAETIPVL HEMIQQIFNLFSTKDSSAAWDETLLDKW YTELYQQLNDLEACVIQGVGVTETPLMK EDSILAVRKYFQRITLYLKEKKYSPCAW EVVRAEIMRSFSLSTNLQESLRSKE | 396 |
| IFNA2b_M44N_ R185Y | 356 | 2.30 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLYSKE | 397 |
| IFNA2b_M44N_ V165I | 354 | 2.17 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EIVRAEIMRSFSLSTNLQESLRSKE | 398 |
| IFNA2b_M44N_ K187W | 354 | 2.13 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSWE | 399 |
| IFNA2b_L49P_ R185I | 350 | 2.38 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLISKE | 400 |
| IFNA2b_M44N_ R185T | 350 | 2.44 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK | 401 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| | | | EDSILAVRKYFQRITLYLKEKKYSPCAW EVVRAEIMRSFSLSTNLQESLTSKE | |
| IFNA2b_M44N_ R185V | 347 | 2.32 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLVSKE | 402 |
| IFNA2b_M44N_ Q113A | 341 | 2.20 | CDLPQTHSLGSRRTLMLLAQNRRISLFS CLKDRHDFGFPQEEFGNQFQKAETIPVL HEMIQQIFNLFSTKDSSAAWDETLLDKF YTELYAQLNDLEACVIQGVGVTETPLMK EDSILAVRKYFQRITLYLKEKKYSPCAW EVVRAEIMRSFSLSTNLQESLRSKE | 403 |
| IFNA2b_M44N_ T178K | 340 | 2.06 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSKNLQESLRSKE | 404 |
| IFNA2b_L49P_ K156V | 340 | 2.04 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEVKYSPCAW EVVRAEIMRSFSLSTNLQESLRSKE | 405 |
| IFNA2b_L49P_ K187S | 335 | 2.16 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQESLRSSE | 406 |
| IFNA2b_M44N_ Q114I | 334 | 2.06 | CDLPQTHSLGSRRTLMLLAQNRRISLFS CLKDRHDFGFPQEEFGNQFQKAETIPVL HEMIQQIFNLFSTKDSSAAWDETLLDKF YTELYQILNDLEACVIQGVGVTETPLMK EDSILAVRKYFQRITLYLKEKKYSPCAW EVVRAEIMRSFSLSTNLQESLRSKE | 407 |
| IFNA2b_L49P_ T131E | 331 | 2.09 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTEEPLMK EDSILAVRKYFQRITLYLKEKKYSPCAW EVVRAEIMRSFSLSTNLQESLRSKE | 408 |
| IFNA2b_M44N_ S183E | 329 | 2.14 | CDLPQTHSLGSRRTLMLLAQNRRISLFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSTNLQEELRSKE | 409 |
| IFNA2b_L49P_ Y152W | 328 | 2.26 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLWLKEKKYSPCAW EVVRAEIMRSFSLSTNLQESLRSKE | 410 |
| IFNA2b_L49P_ V128E | 326 | 2.38 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGETETPLMK EDSILAVRKYFQRITLYLKEKKYSPCAW EVVRAEIMRSFSLSTNLQESLRSKE | 411 |

TABLE 3-continued

IFNA2 Double Mutants with Detuned Affinity to Human IFNAR2

| Variant | Affinity to human IFNAR2 (nM) | Average expression bin | Polypeptide Sequence | SEQ ID NO |
|---|---|---|---|---|
| IFNA2b_L49P_ E155K | 325 | 2.14 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKKKKYSPCAW EVVRAEIMRSFSLSTNLQESLRSKE | 412 |
| IFNA2b_L49P_ S175T | 325 | 2.07 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFTLSTNLQESLRSKE | 413 |
| IFNA2b_L49P_ E155R | 323 | 2.21 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKRKKYSPCAW EVVRAEIMRSFSLSTNLQESLRSKE | 414 |
| IFNA2b_L49P_ V166T | 323 | 2.08 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVTRAEIMRSFSLSTNLQESLRSKE | 415 |
| IFNA2b_L49P_ T178F | 319 | 2.12 | CDLPQTHSLGSRRTLMLLAQMRRISPFS CLKDRHDFGFPQEEFGNQFQKAETIPVL HEMIQQIFNLFSTKDSSAAWDETLLDKF YTELYQQLNDLEACVIQGVGVTETPLMK EDSILAVRKYFQRITLYLKEKKYSPCAW EVVRAEIMRSFSLSFNLQESLRSKE | 416 |

Table 4 below provides affinities between human IFNA2 detuned variants and mouse IFNAR2 as measured by AlphaSeq™. Any double mutant variant found to bind mouse IFNAR2 with half-log weaker affinity than the wild-type human IFNA2 polypeptide (407 nM for M44N double mutants and 63 nM for L49P double mutants) and found to have an average expression bin >2.0, but that did not show decreased affinity to human IFNAR2 was included in Table 4. Table 4 is sorted in order of descending Kd, with the highest values being the weakest binders. Table 4 also provides the polypeptide sequences of the 22 IFNA2 variants comprising two amino acid substitutions as SEQ ID NOs 417-438. The polypeptide sequences describe the mature IFNA2b protein, which does not include a 23-amino acid signal peptide that is cleaved from the N-terminus to produce the mature protein. The amino acid sequence of mouse IFNAR2 is provided below:

(SEQ ID NO: 3)

MRSRCTVSAVGLLSLCLVVSASLETITPSAFDGYPDEPCTINITIR

NSRLILSWELENKSGPPANYTLWYTVMSKDENLTKVKNCSDTTKSS

-continued

CDVTDKWLEGMESYVVAIVIVHRGDLTVCRCSDYIVPANAPLEPPE

FEIVGFTDHINVTMEFPPVTSKIIQEKMKTTPFVIKEQIGDSVRKK

HEPKVNNVTGNFTFVLRDLLPKTNYCVSLYFDDDPAIKSPLKCIVL

QPGQESGLSESAIVGITTSCLVVMVFVSTIVMLKRIGYICLKDNLP

NVLNFRHFLTWIIPERSPSEAIDRLEIIPTNKKKRLWNYDYEDGSD

SDEEVPTASVTGYTMHGLTGKPLQQTSDTSASPEDPLHEEDSGAEE

SDEAGAGAGAEPELPTEAGAGPSEDPTGPYERRKSVLEDSFPREDN

SSMDEPGDNIIFNVNLNSVFLRVLHDEDASETLSLEEDTILLDEGP

QRTESDLRIAGGDRTQPPLPSLPSQDLWTEDGSSEKSDTSDSDADV

GDGYIMR

TABLE 4

IFNA2 Double Mutants with Detuned Affinity to Mouse IFNAR2

| Variant | Affinity to mouse IFNAR2 (nM) | Average expression bin | Polypeptide Sequence | SEQ ID NO |
|---|---|---|---|---|
| IFNA2b_M44N_A168W | 10825 | 2.21 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRWEIMRSFSLSTNLQESLRSKE | 417 |
| IFNA2b_L49P_R167T | 3004 | 2.31 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVTAEIMRSFSLSTNLQESLRSKE | 418 |
| IFNA2b_L49P_R167L | 1946 | 2.35 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVLAEIMRSFSLSTNLQESLRSKE | 419 |
| IFNA2b_L49P_R167V | 1735 | 2.27 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVVAEIMRSFSLSTNLQESLRSKE | 420 |
| IFNA2b_L49P_A168Y | 1465 | 2.04 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRYEIMRSFSLSTNLQESLRSKE | 421 |
| IFNA2b_M44N_K135I | 1129 | 2.39 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMIEDSILAVRKYFQRITLYLKEKKYSPCAWEVVRAEIMRSFSLSTNLQESLRSKE | 422 |
| IFNA2b_M44N_E130M | 825 | 2.03 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTMTPLMKEDSILAVRKYFQRITLYLKEKKYSPCAWEVVRAEIMRSFSLSTNLQESLRSKE | 423 |
| IFNA2b_L49P_G127D | 769 | 2.17 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVDVTETPLMKEDSILAVRKYFQRITLYLKEKKYSPCAWEVVRAEIMRSFSLSTNLQESLRSKE | 424 |
| IFNA2b_L49P_R167I | 708 | 2.30 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVIAEIMRSFSLSTNLQESLRSKE | 425 |
| IFNA2b_M44N_A120T | 591 | 2.06 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLETCVIQGVGVTETPLMKEDSILAVRKYFQRITLYLKEKKYSPCAWEVVRAEIMRSFSLSTNLQESLRSKE | 426 |
| IFNA2b_L49P_A168D | 586 | 2.32 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRDEIMRSFSLSTNLQESLRSKE | 427 |
| IFNA2b_M44N_E188R | 520 | 2.43 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSKR | 428 |

TABLE 4-continued

IFNA2 Double Mutants with Detuned Affinity to Mouse IFNAR2

| Variant | Affinity to mouse IFNAR2 (nM) | Average expression bin | Polypeptide Sequence | SEQ ID NO |
|---|---|---|---|---|
| IFNA2b_M44N_ V126E | 512 | 2.19 | CDLPQTHSLGSRRTLMLLAQNRRISLFSCLKDRHD FGFPQEEFGNQFQKAETIPVLHEMIQQIFNLFSTK DSSAAWDETLLDKFYTELYQQLNDLEACVIQGEGV TETPLMKEDSILAVRKYFQRITLYLKEKKYSPCAW EVVRAEIMRSFSLSTNLQESLRSKE | 429 |
| IFNA2b_M44N_ K106L | 486 | 2.02 | CDLPQTHSLGSRRTLMLLAQNRRISLFSCLKDRHD FGFPQEEFGNQFQKAETIPVLHEMIQQIFNLFSTK DSSAAWDETLLDLFYTELYQQLNDLEACVIQGVGV TETPLMKEDSILAVRKYFQRITLYLKEKKYSPCAW EVVRAEIMRSFSLSTNLQESLRSKE | 430 |
| IFNA2b_L49P_ L140N | 480 | 2.16 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSINAVRKYFQRITLYLKEKKYSPCAW EVVRAEIMRSFSLSTNLQESLRSKE | 431 |
| IFNA2b_M44N_ V128G | 472 | 2.21 | CDLPQTHSLGSRRTLMLLAQNRRISLFSCLKDRHD FGFPQEEFGNQFQKAETIPVLHEMIQQIFNLESTK DSSAAWDETLLDKFYTELYQQLNDLEACVIQGVGG TETPLMKEDSILAVRKYFQRITLYLKEKKYSPCAW EVVRAEIMRSFSLSTNLQESLRSKE | 432 |
| IFNA2b_M44N_ L180E | 413 | 2.03 | CDLPQTHSLGSRRTLMLLAQNRRISLFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRAEIMRSFSLSTNEQESLRSKE | 433 |
| IFNA2b_L49P_ A168F | 267 | 2.32 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRFEIMRSFSLSTNLQESLRSKE | 434 |
| IFNA2b_L49P_ A168W | 237 | 2.15 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRWEIMRSFSLSTNLQESLRSKE | 435 |
| IFNA2b_L49P_ S175D | 79 | 2.24 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRAEIMRSFDLSTNLQESLRSKE | 436 |
| IFNA2b_L49P_ K156Q | 73 | 2.33 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEQKYSPCAW EVVRAEIMRSFSLSTNLQESLRSKE | 437 |
| IFNA2b_L49P_ A168H | 67 | 2.39 | CDLPQTHSLGSRRTLMLLAQMRRISPFSCLKDRHD FGFPQEEFGNQFQKAETIPVLHEMIQQIFNLFSTK DSSAAWDETLLDKFYTELYQQLNDLEACVIQGVGV TETPLMKEDSILAVRKYFQRITLYLKEKKYSPCAW EVVRHEIMRSFSLSTNLQESLRSKE | 438 |

Table 5 below provides affinities between human IFNA2 detuned variants and both mouse IFNAR2 and human IFNAR2 as measured by AlphaSeq™. For inclusion in Table 5, a double mutant variant must have bound human IFNAR2 with an affinity weaker than 100 nM and mouse IFNAR2 with an affinity weaker than 407 nM (for M44N double mutants) or weaker than 63 nM (for L49P double mutants), and found to have an average expression bin >2.0. Table 5 is sorted in order of descending Kd for mouse IFNAR2, with the highest values representing the lowest affinity of IFNA2 for mouse IFNAR2. Table 5 also provides the polypeptide sequences of the 100 IFNA2 variants comprising two amino acid substitutions as SEQ ID NOs 439-538. The polypeptide sequences describe the mature IFNA2b protein, which does not include a 23-amino acid signal peptide that is cleaved from the N-terminus to produce the mature protein.

TABLE 5

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_M44N_R172N | 3128 | 107006 | 2.15 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMNSFSLSTNLQESLRSKE | 439 |
| IFNA2b_L49P_R167S | 50882 | 65847 | 2.14 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVSAEIMRSFSLSTNLQESLRSKE | 440 |
| IFNA2b_L49P_R167G | 124080 | 52552 | 2.27 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVGAEIMRSFSLSTNLQESLRSKE | 441 |
| IFNA2b_L49P_R172E | 134097 | 47292 | 2.18 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMESFSLSTNLQESLRSKE | 442 |
| IFNA2b_M44N_R172G | 20953 | 37090 | 2.09 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMGSFSLSTNLQESLRSKE | 443 |
| IFNA2b_M44N_S159D | 101711 | 34462 | 2.13 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYDPCAWEVVRAEIMRSFSLSTNLQESLRSKE | 444 |
| IFNA2b_L49P_V165G | 41312 | 34403 | 2.25 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEGVRAEIMRSFSLSTNLQESLRSKE | 445 |
| IFNA2b_L49P_A168E | 22212 | 30329 | 2.26 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVREEIMRSFSLSTNLQESLRSKE | 446 |
| IFNA2b_L49P_V165K | 42706 | 30122 | 2.16 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEKVRAEIMRSFSLSTNLQESLRSKE | 447 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_M44N_K187R | 67968 | 26832 | 2.69 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSRE | 448 |
| IFNA2b_M44N_R143I | 93380 | 26262 | 2.12 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVIKYFQRITLYLKEKKYSPCAWEVVRAEIMRSFSLSTNLQESLRSKE | 449 |
| IFNA2b_L49P_V165D | 52289 | 26107 | 2.26 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEDVRAEIMRSFSLSTNLQESLRSKE | 450 |
| IFNA2b_M44N_K156E | 42746 | 24351 | 2.07 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEEKYSPCAWEVVRAEIMRSFSLSTNLQESLRSKE | 451 |
| IFNA2b_M44N_A168K | 27624 | 23252 | 2.09 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRKEIMRSFSLSTNLQESLRSKE | 452 |
| IFNA2b_L49P_V165F | 38495 | 22900 | 2.19 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEFVRAEIMRSFSLSTNLQESLRSKE | 453 |
| IFNA2b_L49P_R172D | 35042 | 21137 | 2.13 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMDSFSLSTNLQESLRSKE | 454 |
| IFNA2b_M44N_A168Q | 9219 | 19977 | 2.11 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRQEIMRSFSLSTNLQESLRSKE | 455 |
| IFNA2b_L49P_V165Q | 34139 | 18640 | 2.40 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTET | 456 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | PLMKEDSILAVRKYFQRITLYLKEKKY SPCAWEQVRAEIMRSFSLSTNLQESLR SKE | |
| IFNA2b_L49P_ R172N | 123608 | 18095 | 2.28 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMNSFSLSTNLQESLR SKE | 457 |
| IFNA2b_M44N_ A168D | 21921 | 17998 | 2.07 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRDEIMRSFSLSTNLQESLR SKE | 458 |
| IFNA2b_M44N_ K156Q | 11250 | 17982 | 2.16 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEQKY SPCAWEVVRAEIMRSFSLSTNLQESLR SKE | 459 |
| IFNA2b_L49P_ V165S | 27477 | 16839 | 2.29 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWESVRAEIMRSFSLSTNLQESLR SKE | 460 |
| IFNA2b_M44N_ S186K | 505 | 16815 | 2.48 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQESLR KKE | 461 |
| IFNA2b_L49P_ V165Y | 25777 | 16712 | 2.37 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEYVRAEIMRSFSLSTNLQESLR SKE | 462 |
| IFNA2b_L49P_ V165E | 33124 | 16435 | 2.31 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEEVRAEIMRSFSLSTNLQESLR SKE | 463 |
| IFNA2b_M44N_ E155K | 2347 | 15815 | 2.26 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKKKKY SPCAWEVVRAEIMRSFSLSTNLQESLR SKE | 464 |
| IFNA2b_M44N_ S177D | 32781 | 12301 | 2.01 | CDLPQTHSLGSRRTLMLLAQNRRISLF SCLKDRHDFGFPQEEFGNQFQKAETIP VLHEMIQQIFNLFSTKDSSAAWDETLL | 465 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | DKFYTELYQQLNDLEACVIQGVGVTET PLMKEDSILAVRKYFQRITLYLKEKKY SPCAWEVVRAEIMRSFSLDTNLQESLR SKE | |
| IFNA2b_M44N_ M171E | 37739 | 11682 | 2.16 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIERSFSLSTNLQESLR SKE | 466 |
| IFNA2b_M44N_ R172D | 4421 | 10938 | 2.05 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMDSFSLSTNLQESLR SKE | 467 |
| IFNA2b_L49P_ V165M | 26763 | 10461 | 2.20 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEMVRAEIMRSFSLSTNLQESLR SKE | 468 |
| IFNA2b_L49P_ R172W | 31708 | 9946 | 2.22 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMWSFSLSTNLQESLR SKE | 469 |
| IFNA2b_L49P_ V165R | 29326 | 8964 | 2.21 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWERVRAEIMRSFSLSTNLQESLR SKE | 470 |
| IFNA2b_M44N_ R172W | 1846 | 8771 | 2.02 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMWSFSLSTNLQESLR SKE | 471 |
| IFNA2b_L49P_ R172Q | 35529 | 8552 | 2.04 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMQSFSLSTNLQESLR SKE | 472 |
| IFNA2b_M44N_ E155R | 3370 | 7665 | 2.12 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKRKKY SPCAWEVVRAEIMRSFSLSTNLQESLR SKE | 473 |
| IFNA2b_M44N_ R167T | 1656 | 7013 | 2.02 | CDLPQTHSLGSRRTLMLLAQNRRISLF SCLKDRHDFGFPQEEFGNQFQKAETIP | 474 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVTAEIMRSFSLSTNLQESLR<br>SKE | |
| IFNA2b_L49P_R172A | 32411 | 6867 | 2.17 | CDLPQTHSLGSRRTLMLLAQMRRISPF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVRAEIMASFSLSTNLQESLR<br>SKE | 475 |
| IFNA2b_L49P_R167W | 27441 | 6436 | 2.17 | CDLPQTHSLGSRRTLMLLAQMRRISPF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVWAEIMRSFSLSTNLQESLR<br>SKE | 476 |
| IFNA2b_L49P_R172T | 47048 | 6206 | 2.07 | CDLPQTHSLGSRRTLMLLAQMRRISPF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVRAEIMTSFSLSTNLQESLR<br>SKE | 477 |
| IFNA2b_L49P_R172S | 35911 | 6189 | 2.31 | CDLPQTHSLGSRRTLMLLAQMRRISPF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVRAEIMSSFSLSTNLQESLR<br>SKE | 478 |
| IFNA2b_L49P_V165T | 17034 | 5952 | 2.23 | CDLPQTHSLGSRRTLMLLAQMRRISPF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWETVRAEIMRSFSLSTNLQESLR<br>SKE | 479 |
| IFNA2b_M44N_G125Y | 604 | 5816 | 2.17 | CDLPQTHSLGSRRTLMLLAQNRRISLF<br>SCLKDRHDFGFPQEEFGNQFQKAETIP<br>VLHEMIQQIFNLFSTKDSSAAWDETLL<br>DKFYTELYQQLNDLEACVIQYVGVTET<br>PLMKEDSILAVRKYFQRITLYLKEKKY<br>SPCAWEVVRAEIMRSFSLSTNLQESLR<br>SKE | 480 |
| IFNA2b_M44N_R167A | 563 | 5776 | 2.03 | CDLPQTHSLGSRRTLMLLAQNRRISLF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVAAEIMRSFSLSTNLQESLR<br>SKE | 481 |
| IFNA2b_M44N_R167I | 648 | 4896 | 2.08 | CDLPQTHSLGSRRTLMLLAQNRRISLF<br>SCLKDRHDFGFPQEEFGNQFQKAETIP<br>VLHEMIQQIFNLFSTKDSSAAWDETLL<br>DKFYTELYQQLNDLEACVIQGVGVTET<br>PLMKEDSILAVRKYFQRITLYLKEKKY<br>SPCAWEVVIAEIMRSFSLSTNLQESLR<br>SKE | 482 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_L49P_ R167F | 4124 | 4462 | 2.14 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVFAEIMRSFSLSTNLQESLR SKE | 483 |
| IFNA2b_M44N_ L180G | 8262 | 4412 | 2.55 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNGQESLR SKE | 484 |
| IFNA2b_L49P_ V165N | 42637 | 2765 | 2.05 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWENVRAEIMRSFSLSTNLQESLR SKE | 485 |
| IFNA2b_L49P_ R167M | 1892 | 2382 | 2.36 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVMAEIMRSFSLSTNLQESLR SKE | 486 |
| IFNA2b_M44N_ R167L | 670 | 2265 | 2.02 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVLAEIMRSFSLSTNLQESLR SKE | 487 |
| IFNA2b_L49P_ R172G | 76389 | 2257 | 2.48 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMGSFSLSTNLQESLR SKE | 488 |
| IFNA2b_L49P_ R167A | 1945 | 2196 | 2.16 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVAAEIMRSFSLSTNLQESLR SKE | 489 |
| IFNA2b_M44N_ S173R | 145711 | 2030 | 2.16 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRRFSLSTNLQESLR SKE | 490 |
| IFNA2b_M44N_ Q114K | 5759 | 1633 | 2.12 | CDLPQTHSLGSRRTLMLLAQNRRISLF SCLKDRHDFGFPQEEFGNQFQKAETIP VLHEMIQQIFNLFSTKDSSAAWDETLL DKFYTELYQKLNDLEACVIQGVGVTET PLMKEDSILAVRKYFQRITLYLKEKKY SPCAWEVVRAEIMRSFSLSTNLQESLR SKE | 491 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_M44N_A168N | 5644 | 1496 | 2.07 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRNEIMRSFSLSTNLQESLRSKE | 492 |
| IFNA2b_L49P_V165H | 6476 | 1179 | 2.30 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEHVRAEIMRSFSLSTNLQESLRSKE | 493 |
| IFNA2b_M44N_S138W | 2635 | 942 | 2.06 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDWILAVRKYFQRITLYLKEKKYSPCAWEVVRAEIMRSFSLSTNLQESLRSKE | 494 |
| IFNA2b_M44N_L184E | 596 | 811 | 2.07 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESERSKE | 495 |
| IFNA2b_M44N_A168H | 997 | 802 | 2.35 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRHEIMRSFSLSTNLQESLRSKE | 496 |
| IFNA2b_L49P_K135I | 6216 | 697 | 2.26 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMIEDSILAVRKYFQRITLYLKEKKYSPCAWEVVRAEIMRSFSLSTNLQESLRSKE | 497 |
| IFNA2b_M44N_T150L | 584 | 584 | 2.09 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRILLYLKEKKYSPCAWEVVRAEIMRSFSLSTNLQESLRSKE | 498 |
| IFNA2b_L49P_R172V | 12189 | 566 | 2.17 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMVSFSLSTNLQESLRSKE | 499 |
| IFNA2b_M44N_T178F | 346 | 554 | 2.22 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTET | 500 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | PLMKEDSILAVRKYFQRITLYLKEKKY SPCAWEVVRAEIMRSFSLSENLQESLR SKE | |
| IFNA2b_M44N_ A168S | 357 | 545 | 2.11 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRSEIMRSFSLSTNLQESLR SKE | 501 |
| IFNA2b_M44N_ L176R | 52438 | 541 | 2.08 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSRSTNLQESLR SKE | 502 |
| IFNA2b_M44N_ T150G | 559 | 528 | 2.05 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRIGLYLKEKKY SPCAWEVVRAEIMRSFSLSTNLQESLR SKE | 503 |
| IFNA2b_L49P_ S183W | 17279 | 518 | 2.37 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQEWLR SKE | 504 |
| IFNA2b_M44N_ L176E | 686 | 487 | 2.05 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSESTNLQESLR SKE | 505 |
| IFNA2b_M44N_ S175E | 366 | 484 | 2.09 | CDLPQTHSLGSRRTLMLLAQNRRISLF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFELSTNLQESLR SKE | 506 |
| IFNA2b_L49P_ R167H | 2356 | 480 | 2.39 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVHAEIMRSFSLSTNLQESLR SKE | 507 |
| IFNA2b_L49P_ A168K | 38040 | 461 | 2.14 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRKEIMRSFSLSTNLQESLR SKE | 508 |
| IFNA2b_M44N_ S175D | 602 | 420 | 2.43 | CDLPQTHSLGSRRTLMLLAQNRRISLF SCLKDRHDFGFPQEEFGNQFQKAETIP VLHEMIQQIFNLFSTKDSSAAWDETLL | 509 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | DKFYTELYQQLNDLEACVIQGVGVTETPLMKEDSILAVRKYFQRITLYLKEKKYSPCAWEVVRAEIMRSFDLSTNLQESLRSKE | |
| IFNA2b_M44N_K135G | 330 | 416 | 2.18 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMGEDSILAVRKYFQRITLYLKEKKYSPCAWEVVRAEIMRSFSLSTNLQESLRSKE | 510 |
| IFNA2b_L49P_K187R | 8292 | 415 | 2.80 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSRE | 511 |
| IFNA2b_M44N_K187E | 1129 | 415 | 2.14 | CDLPQTHSLGSRRTLMLLAQNRRISLFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSEE | 512 |
| IFNA2b_L49P_A168Q | 361 | 321 | 2.31 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRQEIMRSFSLSTNLQESLRSKE | 513 |
| IFNA2b_L49P_R172I | 30426 | 310 | 2.40 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMISFSLSTNLQESLRSKE | 514 |
| IFNA2b_L49P_A168M | 325 | 293 | 2.36 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRMEIMRSFSLSTNLQESLRSKE | 515 |
| IFNA2b_L49P_R172F | 24117 | 273 | 2.14 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMFSFSLSTNLQESLRSKE | 516 |
| IFNA2b_L49P_R172M | 42476 | 227 | 2.05 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMMSFSLSTNLQESLRSKE | 517 |
| IFNA2b_L49P_L176D | 16777 | 206 | 2.28 | CDLPQTHSLGSRRTLMLLAQMRRISPFSCLKDRHDFGFPQEEFGNQFQKAETIP | 518 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| | | | | VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSDSTNLQESLR SKE | |
| IFNA2b_L49P_ R172Y | 37221 | 203 | 2.16 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMYSFSLSTNLQESLR SKE | 519 |
| IFNA2b_L49P_ M171E | 32692 | 173 | 2.49 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIERSFSLSTNLQESLR SKE | 520 |
| IFNA2b_L49P_ K156D | 1134 | 167 | 2.04 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEDKY SPCAWEVVRAEIMRSFSLSTNLQESLR SKE | 521 |
| IFNA2b_L49P_ A168G | 3491 | 163 | 2.27 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRGEIMRSFSLSTNLQESLR SKE | 522 |
| IFNA2b_L49P_ A168R | 41957 | 146 | 2.07 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRREIMRSFSLSTNLQESLR SKE | 523 |
| IFNA2b_L49P_ R172L | 39292 | 142 | 2.19 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMLSFSLSTNLQESLR SKE | 524 |
| IFNA2b_L49P_ S183F | 6913 | 114 | 2.56 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQEFLR SKE | 525 |
| IFNA2b_L49P_ K187I | 5317 | 106 | 2.46 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQESLR SIE | 526 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_L49P_ M171D | 17237 | 106 | 2.01 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIDRSFSLSTNLQESLR SKE | 527 |
| IFNA2b_L49P_ K187Y | 2369 | 90 | 2.08 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQESLR SYE | 528 |
| IFNA2b_L49P_ K187L | 2780 | 85 | 2.47 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQESLR SLE | 529 |
| IFNA2b_L49P_ N179G | 12068 | 84 | 2.25 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTGLQESLR SKE | 530 |
| IFNA2b_L49P_ K156E | 532 | 83 | 2.44 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEEKY SPCAWEVVRAEIMRSFSLSTNLQESLR SKE | 531 |
| IFNA2b_L49P_ R167K | 553 | 77 | 2.11 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVKAEIMRSFSLSTNLQESLR SKE | 532 |
| IFNA2b_L49P_ S183Y | 2673 | 75 | 2.19 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSLSTNLQEYLR SKE | 533 |
| IFNA2b_L49P_ E164D | 14447 | 75 | 2.31 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWDVVRAEIMRSFSLSTNLQESLR SKE | 534 |
| IFNA2b_L49P_ L176P | 14207 | 69 | 2.05 | CDLPQTHSLGSRRTLMLLAQMRRISPF SCLKDRHDFGFPQEEFGNQFQKAETIP VLHEMIQQIFNLFSTKDSSAAWDETLL DKFYTELYQQLNDLEACVIQGVGVTET PLMKEDSILAVRKYFQRITLYLKEKKY SPCAWEVVRAEIMRSFSPSTNLQESLR SKE | 535 |

TABLE 5-continued

IFNA2 Double Mutants with Detuned Affinity to Mouse IFNAR2 and Human IFNAR2

| Variant | Affinity to human IFNAR2 (nM) | Affinity to mouse IFNAR2 (nM) | Average expression bin | Polypeptide Sequence | SEQ ID NO |
|---|---|---|---|---|---|
| IFNA2b_L49P_K187F | 1115 | 67 | 2.27 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYSPCAWEVVRAEIMRSFSLSTNLQESLRSFE | 536 |
| IFNA2b_L49P_K156T | 437 | 65 | 2.35 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKETKYSPCAWEVVRAEIMRSFSLSTNLQESLRSKE | 537 |
| IFNA2b_L49P_S159H | 445 | 65 | 2.28 | CDLPQTHSLGSRRTLMLLAQMRRISPFSCLKDRHDFGFPQEEFGNQFQKAETIPVLHEMIQQIFNLFSTKDSSAAWDETLLDKFYTELYQQLNDLEACVIQGVGVTETPLMKEDSILAVRKYFQRITLYLKEKKYHPCAWEVVRAEIMRSFSLSTNLQESLRSKE | 538 |

In some embodiments, the IFNA2 variant includes amino acid substitutions having one or more specific substitutions at one or more of positions H30, S31, L32, S34, R35, R36, L38, L40, L41, A42, Q43, M44, R45, R46, I47, S48, L49, F50, S51, L53, K54, D55, R56, H57, D58, F59, F61, P62, Q63, Q69, K72, V78, M82, Q84, 186, K93, A98, L103, K106, Y108, T109, E110, Q113, N116, N116, E119, A120, G125, V126, T129, P132, M134, I139, A141, R143, Y145, Q147, R148, E155, K156, K157, P160, V165, R167, A168, E169, I170, M171, R172, S173, S175, L176, S177, N179, S183, R185, S186, K187, and E188 in the wild-type IFNA2 amino acid sequence (SEQ ID NO: 1).

In some embodiments, the IFNA2 variant includes amino acid substitutions having one or more specific substitutions selected from the group consisting of: H30A, H30D, S31D, L32D, L32E, S34A, R35N, R36G, L38H, L38Y, L38G, L38P, L38S, L38T, L38Q, L38N, L40R, L40G, L40Q, L40D, L41H, L41D, L41K, L41G, L41A, A42G, A42M, Q43P, M44Q, R45P, R46P, R46D, R46F, R46Y, R46N, R46S, R46I, R46G, R46A, R46H, R46T, I47P, I47D, I47S, I47E, S48Y, S48H, L49H, L49I, L49K, L49V, L49Y, L49F, L49G, L49E, L49P, F50D, F50N, F50G, F50Q, F50S, F50M, F50H, F50A, S51D, S51E, L53D, L53E, L53G, L53A, L53N, L53V, L53S, K54L, K54I, K54M, D55T, D55N, D55Q, R56D, R56G, R56K, R56N, R56V, R56T, R56A, R56L, R56H, H57P, D58Q, F59Q, F59E, F59I, F59N, F59A, F59G, F59T, F59Y, F61G, F61I, F61V, F61P, F61Q, F61A, F61S, P62I, Q63E, Q69S, K72D, V78E, V78G, M82W, M82K, M82R, M82G, M82S, I86L, K93E, K93V, A98E, L103E, L103D, K106L, K106D, Y108K, T109W, E110P, E110S, Q113W, N116W, N116M, N116F, N116Q, E119Y, E119F, A120M, G125V, V126W, V126Y, T129G, P132W, M134Y, I139Y, I139F, A141E, A141I, R143F, Q147S, R148Y, E155H, K156D, K156L, K156W, K157Y, P160E, P160F, P160W, P160Y, P160T, V165Y, V165E, V165H, V165K, V165W, V165F, V165Q, V165L, V165M, V165S, V165R, V165N, V165D, V165I, R167W, R167I, R167M, R167S, R167E, R167L, R167V, R167A, R167G, R167H, A168R, A168H, A168K, A168Y, A168G, A168F, A168D, A168M, A168Q, E169T, E169S, E169G, I170L, M171R, M171S, M171T, M171N, M171A, M171Y, M171W, M171F, M171K, M171E, M171G, M171L, M171I, M171V, R172D, R172W, R172N, R172A, R172V, R172G, R172T, R172S, R172Y, R172L, R172M, R172K, S173K, S173R, S173H, S173E, S173N, S173W, S173Y, S175R, S175K, S175M, S175L, S175P, S175I, S175V, S175W, S175Y, S175G, S175E, S175Q, S175T, L176N, L176G, L176H, L176A, L176P, L176D, L176R, L176Q, L176E, L176V, S177D, S177R, N179G, S183W, S183F, S183M, S183E, S183Y, S183K, S183L, R185D, R185E, R185Q, S186L, S186I, S186D, K187R, K187L, K187E, K187Y, K187V, K187M, K187F, K187I, K187W, K187G, and E188I in the wild-type IFNA2 amino acid sequence (SEQ ID NO: 1).

In some embodiments, the IFNA2 variant includes a combination of two specific amino acid substitutions, i.e., a double amino acid substitution, selected from the group consisting of: M44N+A168R, L49P+S175P, L49P+S173H, L49P+M171W, L49P+M171G, L49P+S173R, M44N+S175P, L49P+M171V, L49P+M171K, L49P+M171S, L49P+S175R, L49P+M171R, L49P+L176G, L49P+M171Y, L49P+L176N, L49P+S173Q, L49P+L176H, L49P+L176R, L49P+M171A, L49P+M171T, L49P+L176A, L49P+M171F, M44N+S175K, L49P+S175K, L49P+L176E, L49P+E169T, L49P+M171L, L49P+L176Q, L49P+K187E, L49P+S173N, M44N+L176H, M44N+S175R, L49P+S177N, L49P+S173W, L49P+S177D, L49P+R185D, L49P+E169S, L49P+S175G, L49P+S177L, L49P+R172K, L49P+R185E, L49P+K187M, L49P+K187W, L49P+S159Q, M44N+L176Q, M44N+R185E, L49P+S175Q, L49P+S175M, L49P+E155V, L49P+K187D, L49P+S175W, L49P+L176V, L49P+S173L, M44N+S175G, L49P+R185G, L49P+R143W, L49P+I149T, L49P+R185L, L49P+R185S, L49P+S177H, L49P+K106D, M44N+R185N, L49P+K187V, L49P+K106W, L49P+K135T, M44N+V128I, M44N+R185D, L49P+K106P, L49P+S183M, L49P+S183D, L49P+K156A, L49P+S183L, M44N+K187D, L49P+R185M, L49P+R185N, M44N+A168L, L49P+S175L, L49P+R185Q, L49P+K187G, M44N+S177E, L49P+W163L, L49P+R185W, L49P+K187T, L49P+T109W, M44N+P160E, M44N+K106T, L49P+R185T, L49P+S175I, L49P+S173F, M44N+R185L, L49P+S183E, L49P+K187N, M44N+K187F, L49P+S159D, M44N+K106I, L49P+S175Y, L49P+L184N, L49P+I170L, L49P+V166S, L49P+K187A, L49P+S186D, L49P+L111F, L49P+K154Q, L49P+K106T, L49P+E136D, L49P+K106M, L49P+F107W, M44N+R185Y, M44N+V165I, M44N+K187W, L49P+R185I, M44N+R185T, M44N+R185V, M44N+Q113A, M44N+T178K, L49P+K156V, L49P+K187S, M44N+Q114I, L49P+T131E, M44N+S183E, L49P+Y152W, L49P+V128E, L49P+E155K, L49P+S175T, L49P+E155R, L49P+V166T, and L49P+T178F in the wild-type IFNA2 amino acid sequence (SEQ ID NO: 1).

In some embodiments, the IFNA2 variant has a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2.

IFNA2 Fusion Proteins and Methods of Making

This disclosure provides isolated IFNA2 fusion proteins (e.g., antibody-IFNA2 fusion proteins) that have decreased or no detectable binding to the interferon alpha/beta receptor 2 (IFNAR2). Such IFNA2 fusion proteins can deliver cytokines to a desired cell type while minimizing peripheral exposure and thus reducing overall potential adverse effects.

The isolated fusion proteins include: 1) an antibody comprising an Fc domain; and b) a human IFNA2 protein variant, wherein the IFNA2 is covalently linked to the Fc domain of the antibody.

In some embodiments, one or more polypeptides (e.g., heterologous or homologous sequence) can be inserted between the antibody and the IFNA2 variant of the IFNA2 fusion proteins as described herein. In some embodiments, the polypeptide can be inserted or conjugated at the amino terminus, at the carboxyl terminus, or both the amino and carboxyl termini of the antibody or domain thereof. In some embodiments, the polypeptide includes a polypeptide linker conjugating the antibody and the IFNA2 variant. In some embodiments, the polypeptide comprises one or more linker (s) and tag(s). Examples of a polypeptide tag include, but not are not limited to, a FLAG tag, a 6His tag, an 8His tag, or an AVI tag.

The antibodies useful in the IFNA2 fusion proteins of the present invention can encompass monoclonal antibodies, polyclonal antibodies, antibody fragments (e.g., Fab, Fab', F(ab')2, Fv, Fe, etc.), chimeric antibodies, bispecific antibodies, heteroconjugate antibodies, single chain (ScFv), mutants thereof, fusion proteins comprising an antibody portion (e.g., a domain antibody), humanized antibodies, and any other modified configuration of the immunoglobulin molecule that comprises an antigen recognition site of the required specificity, including glycosylation variants of antibodies, amino acid sequence variants of antibodies, and covalently modified antibodies. The antibodies may be murine, rat, human, or any other origin (including chimeric or humanized antibodies.

In some embodiments, an antibody constant region can be modified to avoid interaction with Fc gamma receptors and/or the complement system. The techniques for preparation of such antibodies are described in WO 99/58572. For example, the constant region may be engineered to more resemble human constant regions to avoid immune response if the antibody is used in clinical trials and treatments in humans. See, e.g., U.S. Pat. Nos. 5,997,867 and 5,866,692.

In still other embodiments, the constant region is a glycosylated for N-linked glycosylation, e.g., the antibodies are engineered to bypass glycosylation. In some embodiments, the constant region is a glycosylated for N-linked glycosylation by mutating the oligosaccharide attachment residue and/or flanking residues that are part of the N-glycosylation recognition sequence in the constant region. For example, N-glycosylation site N297 may be mutated to, e.g., A, Q, K, or H. See, Tao et al., J. Immunology 143:2595-2601, 1989; and Jefferis et al., Immunological Reviews 163:59-76, 1998. In some embodiments, the constant region is enzymatically aglycosylated for N-linked glycosylation (such as removing carbohydrate by the enzyme PNGase), or by expression in a glycosylation deficient host cell.

Other antibody modifications include antibodies that have been modified as described in PCT Publication No. WO 99/58572. These antibodies comprise, in addition to a binding domain directed at the target molecule, an effector domain having an amino acid sequence substantially homologous to all or part of a constant region of a human immunoglobulin heavy chain. These antibodies are capable of binding to the target molecule without triggering significant complement dependent lysis, or cell-mediated destruction of the target. In some embodiments, the effector domain is capable of specifically binding to FcRn and/or FcyRIIb. These are typically based on chimeric domains derived from two or more human immunoglobulin heavy chain CH2 domains. Antibodies modified in this manner are particularly suitable for use in chronic antibody therapy, to avoid inflammatory and other adverse reactions to conventional antibody therapy.

The antibodies used in the IFNA2 fusion proteins of the compositions and methods disclosed herein, listed by International Nonproprietary Name, can include but are not limited to abagovomab, abatacept, abciximababelacimab, abituzumab, abrezekimab, abrilumab, acapatamab, acasunlimab, acazicolcept, acrixolimab, actoxumab, adalimumab, adebrelimab, adecatumumab, adintrevimab, aducanumab, afasevikumab, afelimomab, aflibercept, alacizumab, alefacept, alemtuzumab, alirocumab, alnuctamab, alomfilimab, alsevalimab, altumomab, amatuximab, amivantamab, amlitelimab, amubarvimab, anatumomab, anbenitamab, andecaliximab, anetumab, anifrolumab, anivovetmab, anrukinzumab, anselamimab, ansuvimab, anumigilimab, apamistamab, apitegromab, apolizumab, aprutumab, arcitumomab, ascrinvacumab, aselizumab, asfotase, astegolimab, asunercept, atacicept, atezolizumab, atibuclimab, atidortoxumab, atinumab, atoltivimab, atorolimumab, avdoralimab, avelumab, avizakimab, axatilimab, azintuxizumab, bafisontamab, balstilimab, baminercept, bamlanivimab, bapineuzumab, bapotulimab, barecetamab, barzolvolimab, basiliximab, batiraxcept, batoclimab, bavituximab, bavunalimab, bebtelovimab, bectumomab, bedinvetmab, befovacimab, begelomab, belantamab, belatacept, belimumab, beludavimab, bemarituzumab, benralizumab, bentracimab, benufutamab, bepranemab, berlimatoxumab, bermekimab, bersanlimab, bertilimumab, besilesomab, betifisolimab, bevacizumab, bexmarilimab, bezlotoxumab, biciromab, bifikafusp, bimagrumab, bimekizumab, bintrafusp, birtamimab, bivatuzumab, bleselumab, blinatumomab, blisibimod, blontuvetmab, blosozumab, bococizumab, botensilimab, brazikumab, brentuximab, briakinumab, briobacept, briquilimab, brodalumab, brolucizumab, brontictuzumab, budigalimab, burfiralimab, burosumab, cabiralizumab, cadonilimab, camidanlumab, camoteskimab, camrelizumab, canakinumab, cantuzumab, caplacizumab, capromab, carlumab, carotuximab, casirivimab, catumaxomab, cedelizumab, cemiplimab, cendakimab, cergutuzumab, certolizumab, cetrelimab, cetuximab, cevostamab, cibisatamab, cifurtilimab, cilgavimab, cinpanemab, cinrebafusp, cirevetmab, citatuzumab, cixutumumab, clazakizumab, clenoliximab, clervonafusp, clesrovimab, clivatuzumab, cobolimab, codrituzumab, cofetuzumab, coltuximab, conatumumab, conbercept, concizumab, coprelotamab, cosfroviximab, cosibelimab, crefmirlimab, crenezumab, crexavibart, crizanlizumab, crotedumab, crovalimab, cudarolimab, cusatuzumab, dacetuzumab, daclizumab, dafsolimab, dalantercept, dalotuzumab, dalutrafusp, dapirolizumab, daratumumab, datopotamab, davoceticept, daxdilimab, dectrekumab, demcizumab, demupitamab, denintuzumab, denosumab, depatuxizumab, depemokimab, derlotuximab, detumomab, dezamizumab, dilpacimab, dinutuximab, diridavumab, disitamab, divozilimab, docaravimab, domagrozumab, domvanalimab, donanemab, dorlimomab, dostarlimab, dovanvetmab, dresbuxelimab, drozitumab, dulaglutide, duligotuzumab, dupilumab, durvalumab, dusigitumab, duvortuxizumab, ebdarokimab, eblasakimab, ebronucimab, ecleralimab, ecromeximab, eculizumab, edobacomab, edrecolomab, efalizumab, efanesoctocog, efaprinermin, efavaleukin, efbemalenograstim, efdamrofusp, efepoetin, efgartigimod, efgivanermin, efineptakin, efinopegdutide, efizonerimod, eflapegrastim, eflenograstim, eflepedocokin, eflimrufusp, efmarodocokin, efmitermant, efmoroctocog, efocipegtrutide, efpeglenatid, efpegsomatropin, efprezimod, efrilacedase, efruxifermin, eftansomatropin, eftilagimod, eftozanermin, eftrenonacog, efungumab, efzofitimod, eldelumab, elezanumab, elgemtumab, elipovimab, elotuzumab, elranatamab, elsilimomab, eluvixtamab, emactuzumab, emapalumab, emerfetamab, emfizatamab, emibetuzumab, emicizumab, emirodatamab, enapotamab, enavatuzumab, encelimab, enfortumab, enibarcimab, enlimomab, enoblituzumab, enokizumab, enoticumab, ensituximab, ensomafusp, enuzovimab, envafolimab, epcoritamab, epitumomab, epratuzumab, eptinezumab, eramkafusp, erenumab, erfonrilimab, erlizumab, ertumaxomab, etanercept, etaracizumab, etesevimab, etevritamab, etigilimab, etokimab, etrolizumab, evinacumab, evolocumab, evorpacept, exbivirumab, exidavnemab, ezabenlimab, fanolesomab, faralimomab, faricimab, farletuzumab, fasinumab, favezelimab, fazpilodemab, feladilimab, felvizumab, felzartamab, fezakinumab, fianlimab, ficlatuzumab, fidasimtamab, figitumumab, finotonlimab, firivumab, fiztasovimab, flanvotumab, fletikumab, flotetuzumab, fontolizumab, foralumab, foravirumab, fremanezumab, fresolimumab, frexalimab, frovocimab, frunevetmab, fulranumab, futuximab, galcanezumab, galegenimab, galiximab, gancotamab, ganitumab, gantenerumab, garadacimab, garetosmab, garivulimab, gatipotuzumab, gatralimab, gavilimomab, gedivumab, gefurulimab, gemtuzumab, geptanolimab, gevokizumab, giloralimab, gilvetmab, gimsilumab, ginisortamab, girentuximab, glembatumumab, glenzocimab, glofitamab, goflikicept, golimumab, golocdacimab, gontivimab, gosuranemab, gremubamab, gresonitamab, grisnilimab, gumokimab, guselkumab, ianalumab, ibalizumab, ibritumomab, icrucumab, idactamab, idarucizumab, ieramilimab, ifabotuzumab, ifinatamab, igovomab, iladatuzumab, imalumab, imaprelimab, imciromab, imdevimab, imgatuzumab, imsidolimab, imvotamab, inbakicept, inclacumab, indatuximab, indusatumab, inebilizumab, inezetamab, infliximab, inolimomab, inotuzumab, intetumumab, ipafricept, iparomlimab, ipilimumab, iratumumab, isatuximab, iscalimab, isecarosmab, ispectamab, istiratumab, itepekimab, itolizumab, ivicentamab, ivonescimab, ivuxolimab, ixekizumab, izalontamab, izenivetmab, izuralimab, keliximab, labetuzumab, lacnotuzumab, lacutamab, ladiratuzumab, lampalizumab, lanadelumab, landogrozumab, laprituximab, larcaviximab, latikafusp, latozinemab, lebrikizumab, lecanemab, lemalesomab, lemzoparlimab, lenercept, lenvervimab, lenzilumab, lepunafusp, lerdelimumab, leronlimab, lesabelimab, lesofavumab, letaplimab, letolizumab, levilimab, lexatumumab, libivirumab, licaminlimab, lifastuzumab, ligelizumab, ligufalimab, lilotomab, lintuzumab, linvoseltamab, lirentelimab, lirilumab, litifilimab, livmoniplimab, lodapolimab, lodelcizumab, lokivetmab, lomtegovimab, loncastuximab, lonigutamab, lorigerlimab, lorukafusp, lorvotuzumab, losatuxizumab, lucatumumab, lulizumab, lumiliximab, lumretuzumab, lupartumab, luspatercept, lusvertikimab, lutikizumab, luveltamab, maftivimab, magrolimab, manelimab, manfidokimab, mapatumumab, margetuximab, marstacimab, masavibart, maslimomab, matuzumab, mavrilimumab, mazorelvimab, mecbotamab, melredableukin, melrilimab, mepolizumab, metelimumab, mezagitamab, mibavademab, milatuzumab, minretumomab, mipasetamab, miptenalimab, mirikizumab, miromavimab, mirvetuximab, mirzotamab, mitazalimab, mitumomab, modakafusp, modotuximab, mogamulizumab, monalizumab, morolimumab, mosunetuzumab, motavizumab, moxetumomab, mupadolimab, murlentamab, muromonab, nacolomab, nadecnemab, nadunolimab, namilumab, naptumomab, naratuximab, narnatumab, narsoplimab, natalizumab, navicixizumab, navivumab, naxitamab, nebacumab, necitumumab, nemolizumab, nepuvibart, nerelimomab, nesvacumab, netakimab, nimacimab, nimotuzumab, nipocalimab, nirsevimab, nivatrotamab, nivolumab, nofazinlimab, nofetumomab, nurulimab, obexelimab, obiltoxaximab, obinutuzumab, obrindatamab, ocaratuzumab, ociperlimab, ocrelizumab, odesivimab, odronextamab, odulimomab, ofatumumab, ogalvibart, olamkicept, olaratumab, oleclumab, olendalizumab, olinvacimab, olokizumab, omalizumab, omburtamab, omodenbamab, onartuzumab, onfekafusp, ongericimab, ontamalimab, ontorpacept, ontuxizumab, onvatilimab, opicinumab, opinercept, oportuzumab, opucolimab, ordesekimab, oregovomab, orilanolimab, ormutivimab, orticumab, osemitamab, osocimab, otelixizumab, otilimab, otlertuzumab, oxelumab, ozanezumab, ozoralizumab, ozuriftamab, pabinafusp, pacanalotamab, pacmilimab, pagibaximab, palivizumab, pamrevlumab, panitumumab, panobacumab, paridiprubart, parsatuzumab, pascolizumab, pasotuxizumab, pateclizumab, patritumab, pavurutamab, pelgifatamab, pembrolizumab, penpulimab, pepinemab, perakizumab, peresolimab, pertuzumab, petosemtamab, pexelizumab, pidilizumab, pimivalimab, pimurutamab, pinatuzumab, pintumomab, pivekimab, placulumab, plamotamab, plonmarlimab, plozalizumab, plutavimab, polatuzumab, ponezumab, ponsegromab, porgaviximab, posdinemab, pozelimab, praluzatamab, prasinezumab, prezalumab, priliximab, pritoxaximab, pritumumab, prolgolimab, pucotenlimab, pulocimab, quavonlimab, quetmolimab, quilizumab, quisovalimab, racotumomab, radretumab, rafivirumab, ragifilimab, ralpancizumab, ramatercept, ramucirumab, ranevetmab, ranibizumab, ravagalimab, ravulizumab, raxibacumab, recaticimab, refanezumab, regavirumab, regdanvimab, relatlimab, relfovetmab, remtolumab, reozalimab, reslizumab, retifanlimab, retlirafusp, revdofilimab, rilonacept, rilotumumab, rimteravimab, rinucumab, ripertamab, risankizumab, rituximab, rivabazumab, robatumumab, rocatinlimab, roledumab, rolinsatamab, romilkimab, romlusevimab, romosozumab, rontalizumab, rosmantuzumab, rosnilimab, rosopatamab, rovalpituzumab, rovelizumab, rozanolixizumab, rozibafusp, rulonilimab, runimotamab, ruplizumab, sabatolimab, sacituzumab, samalizumab, samrotamab, sarilumab, sasanlimab, satralizumab, satumomab, secukinumab, selicrelumab, semorinemab, semzuvolimab, serclutamab, seribantumab, serplulimab, setoxaximab, setrusumab, sevirumab, sibeprenlimab, sibrotuzumab, sifalimumab, siltuximab, simlukafusp, simridarlimab, simtuzumab, sintilimab, siplizumab, sirexatamab, sirtratumab, sirukumab, socazolimab, sofituzumab, solanezumab, solitomab, sonelokimab, sontuzumab, sotatercept, sotevtamab, sotigalimab, sotrovimab, sozinibercept, spartalizumab, spesolimab, stamulumab, suciraslimab, sudubrilimab, sugemalimab, sulesomab, suptavumab, surzebiclimab, sutimlimab, suvizumab, suvratoxumab, tabalumab, tabituximab, tacatuzumab, tadocizumab, tafasitamab, tafolecimab, tagitanlimab, talacotuzumab, talizumab, talquetamab, tamgiblimab, tamrintamab, tamtuvetmab, tanezumab, taplitumomab, tarcocimab, tarextumab, tarlatamab, tavolimab, tebentafusp, tebotelimab, tecaginlimab, teclistamab, tefibazumab, telazorlimab, telimomab, telisotuzumab, telitacicept, temelimab, tenatumomab, teneliximab, teplizumab, tepoditamab, teprotumumab, teropavimab, tesidolumab, tesnatilimab, tezepelumab, tibulizumab, tidutamab, tifcemalimab, tigatuzumab, tilavonemab, tildrakizumab, tilogotamab, tilvestamab, timigutuzumab, timolumab, tinurilimab, tiragolumab, tirnovetmab, tislelizumab, tisotumab, tixagevimab, tocilizumab, tomaralimab, tomuzotuximab, toralizumab, toripalimab, torudokimab, tosatoxumab, tositumomab, tovetumab, tozorakimab, tralokinumab, trastuzumab, trebananib, tregalizumab, tremelimumab, trinbelimab, trontinemab, tucotuzumab, tulinercept, tusamitamab, tuvirumab, tuvonralimab, ubamatamab, ublituximab, ulenistamab, ulildlimab, ulocuplumab, unasnemab, upanovimab, upifitamab, urabrelimab, urelumab, urtoxazumab, ustekinumab, utomilumab, vadastuximab, valanafusp, vandortuzumab, vantictumab, vanucizumab, vapaliximab, varisacumab, varlilumab, vatelizumab, vedolizumab, veltuzumab, vepalimomab, vepsitamab, vesencumab, vibecotamab, vibostolimab, vilobelimab, visilizumab, visugromab, vixarelimab, vixtimotamab, vobarilizumab, vobramitamab, vofatamab, volagidemab, volociximab, vonlerolizumab, vopratelimab, vorsetuzumab, votumumab, voxalatamab, vudalimab, vulinacimab, vunakizumab, xeligekimab, xentuzumab, zagotenemab, zalifrelimab, zalutumumab, zamerovimab, zampilimab, zanidatamab, zanolimumab, zansecimab, zelminemab, zeluvalimab, zenocutuzumab, zilovertamab, ziltivekimab, zimberelimab, zinlirvimab, ziralimumab, zolbetuximab, zolimomab, and zuberitamab.

In some embodiments, the antibody or binding fragment thereof used in the IFNA2 fusion protein of the compositions and methods disclosed herein is an effectorless antibody or binding fragment thereof that has an isotype selected from the group consisting of NG, DANG, LALA, and LALA-PG.

In some embodiments, the antibody or binding fragment thereof used in the IFNA2 fusion protein of the compositions and methods disclosed herein, listed by International Nonproprietary Name, is an antibody selected from the group consisting of crefmirlimab, vibostolimab, and tifcemalumab, or a binding fragment thereof.

In some embodiments, the antibody or binding fragment thereof used in the IFNA2 fusion protein of the compositions and methods disclosed herein, is an antibody or binding fragment thereof that binds an antigen selected from the group consisting of human CD8A, human TIGIT, and human BTLA.

The antibody or binding fragment thereof used in the IFNA2 fusion protein of the compositions and methods disclosed herein can comprise an amino acid sequence 80%, 90%, 95%, 96%, 97%, 98%, 99%, or 100% identical to amino acid sequences selected from the group consisting of SEQ ID NO: 4, 5, 6, 7, 8, or 9:

```
                                                 (SEQ ID NO: 4)
EVQLVESGGGLVQPGGSLRLSCAASGFNIKDTYIHFVRQAPGKGLEWIGR

IDPANDNTLYASKFQGKATISADTSKNTAYLQMNSLRAEDTAVYYCGRGY

GYYVFDHWGQGTLVTVSS

                                                 (SEQ ID NO: 5)
DVQITQSPSSLSASVGDRVTITCRTSRSISQYLAWYQQKPGKVPKLLIYS

GSTLQSGVPSRFSGSGSGTDFTLTISSLQPEDVATYYCQQHNENPLTFGG

GTKVEIK

                                                 (SEQ ID NO: 6)
EVQLVQSGAEVKKPGSSVKVSCKASGYTFSSYVMHWVRQAPGQGLEWIGY

IDPYNDGAKYAQKFQGRVTLTSDKSTSTAYMELSSLRSEDTAVYYCARGG

PYGWYFDVWGQGTTVTVSS

                                                 (SEQ ID NO: 7)
DIQMTQSPSSLSASVGDRVTITCRASEHIYSYLSWYQQKPGKVPKLLIYN

AKTLAEGVPSRFSGSGSGTDFTLTISSLQPEDVATYYCQHHFGSPLTFGQ

GTRLEIK

                                                 (SEQ ID NO: 8)
QVQLVQSGAEVKKPGASVKLSCKASGYNFKHTYAHWVRQAPGQGLEWIGR

IDPANGNTKYDPKFQGRATMTADTASNTAYLELSSLRSEDTAVYYCVADH

YGSSLLDYWGQGTLVTVSS

                                                 (SEQ ID NO: 9)
DVVMTQTPLSLSVTPGQPASISCKSSQSLLDSDGKTYLNWFQQRPGQSPR

RLIYLVSKLDSGVPDRFSGSGSGTDFTLKISRVEAEDVGVYYCWQGTYFP

YTFGQGTKLEIK
```

The IFNA2 fusion proteins as described herein can be created by methods known in the art, for example, synthetically or recombinantly. Typically, the fusion proteins are made by preparing and expressing a polynucleotide encoding them using recombinant methods described herein, although they may also be prepared by other means known in the art, including, for example, chemical synthesis.

The antibodies as described herein can be made by any method known in the art. For the production of hybridoma cell lines, the route and schedule of immunization of the host animal are generally in keeping with established and conventional techniques for antibody stimulation and production, as further described herein. General techniques for production of human and mouse antibodies are known in the art and/or are described herein.

It is contemplated that any mammalian subject including humans or antibody producing cells therefrom can be manipulated to serve as the basis for production of mammalian, including human and hybridoma cell lines. Typically, the host animal is inoculated intraperitoneally, intramuscularly, orally, subcutaneously, intraplantar, and/or intradermally with an amount of immunogen, including as described herein.

Hybridomas can be prepared from the lymphocytes and immortalized myeloma cells using the general somatic cell hybridization technique of Kohler, B. and Milstein, C., Nature 256:495-497, 1975 or as modified by Buck, D. W., et al., In Vitro, 18:377-381, 1982. Available myeloma lines, including, but not limited to, X63-Ag8.653 and those from the Salk Institute, Cell Distribution Center, San Diego, Calif., USA, can be used in the hybridization. Generally, the technique involves fusing myeloma cells and lymphoid cells using a fusogen such as polyethylene glycol, or by electrical means well known to those skilled in the art. After the fusion, the cells are separated from the fusion medium and grown in a selective growth medium, such as hypoxanthine-aminopterin-thymidine (HAT) medium, to eliminate unhybridized parent cells. Any of the media described herein, supplemented with or without serum, can be used for culturing hybridomas that secrete monoclonal antibodies. As another alternative to the cell fusion technique, EBY immortalized B cells may be used to produce the monoclonal antibodies of the subject invention. The hybridomas are expanded and subcloned, if desired, and supernatants are assayed for anti-immunogen activity by conventional immunoassay procedures (e.g., radioimmunoassay, enzyme immunoassay, or fluorescence immunoassay).

Hybridomas that can be used as a source of antibodies include all derivatives, and progeny cells, of the parent hybridomas that produce monoclonal antibodies.

Hybridomas that produce antibodies used for the present invention may be grown in vitro or in vivo using known procedures. The monoclonal antibodies may be isolated from the culture media or body fluids by conventional immunoglobulin purification procedures such as ammonium sulfate precipitation, gel electrophoresis, dialysis, chromatography, and ultrafiltration, if desired. Undesired activity, if present, can be removed, for example, by running the preparation over adsorbents made of the immunogen attached to a solid phase and eluting or releasing the desired antibodies off the immunogen. Immunization of a host animal with cells expressing the antibody target, a human target protein, or a fragment containing the target amino acid sequence conjugated to a protein that is immunogenic in the species to be immunized, e.g., keyhole limpet hemocyanin, serum albumin, bovine thyroglobulin, or soybean trypsin inhibitor using a bifunctional or derivatizing agent, for example, maleimidobenzoyl sulfosuccinimide ester (conjugation through cysteine residues), N-hydroxysuccinimide (through lysine residues), glutaraldehyde, succinic anhydride, SOC12, or R1N=C=NR, where R and R1 are different alkyl groups, can yield a population of antibodies (e.g., monoclonal antibodies).

If desired, the antibody (monoclonal or polyclonal) of interest can be sequenced and the polynucleotide sequence may then be cloned into a vector for expression or propagation. The sequence encoding the antibody of interest can be maintained in a vector in a host cell and the host cell can then be expanded and frozen for future use. Production of recombinant monoclonal antibodies in cell culture can be carried out through cloning of antibody genes from B cells by means known in the art. See, e.g. Tiller et al., J. Immunol. Methods 329, 112, 2008; U.S. Pat. No. 7,314,622.

In some embodiments, antibodies as described herein are glycosylated at conserved positions in their constant regions (Jefferis and Lund, 1997, Chem. Immunol. 65:111-128; Wright and Morrison, 1997, TibTECH 15:26-32). The oligosaccharide side chains of the immunoglobulins affect the protein's function (Boyd et al., 1996, Mol. Immunol. 32:1311-1318; Wittwe and Howard, 1990, Biochem. 29:4175-4180) and the intramolecular interaction between portions of the glycoprotein, which can affect the conformation and presented three-dimensional surface of the glycoprotein (Jefferis and Lund, supra; Wyss and Wagner, 1996, Current Opin. Biotech. 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, antibodies produced by CHO cells with tetracyclineregulated expression of ~(1,4)-N-acetylglucosaminyltransferase III (GnTIII), a glycosyltransferase catalyzing formation of bisecting GicNAc, was reported to have improved ADCC activity (Umana et al., 1999, Nature Biotech. 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except praline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the tripeptide sequences (for N-linked glycosylation sites) described above. The alteration may also be made by the addition of, or substitution by, one or more serine or threonine residues to the sequence of the original antibody (for O-linked glycosylation sites).

The glycosylation pattern of antibodies can also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, J. Biol. Chem. 272:9062-9070).

In addition to the choice of host cells, factors that affect glycosylation during recombinant production of antibodies include growth mode, media formulation, culture density, oxygenation, pH, purification schemes and the like.

Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example, using endoglycosidase H (Endo H), N-glycosidase F, endoglycosidase F 1, endoglycosidase F2, endoglycosidase F3. In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation.

Modifications can be used, for example, for attachment of labels for immunoassay. Modified polypeptides are made using established procedures in the art and can be screened using standard assays known in the art, some of which are described below and in the Examples.

The IFNA2 fusion proteins and/or the IFNA2 variants of this invention may be linked to a labeling agent such as a fluorescent molecule, a radioactive molecule, or any other labels known in the art. Labels are known in the art which generally provide (either directly or indirectly) a signal.

In some embodiments, the IFNA2 fusion protein includes an antibody including or consisting of an Fc domain and an IFNA2 variant having one or more specific substitutions at one or more of positions H30, S31, L32, S34, R35, R36, L38, L40, L41, A42, Q43, M44, R45, R46, 147, S48, L49, F50, S51, L53, K54, D55, R56, H57, D58, F59, F61, P62, Q63, Q69, K72, V78, M82, Q84, 186, K93, A98, L103, K106, Y108, T109, E110, Q113, N116, N116, E119, A120, G125, V126, T129, P132, M134, I139, A141, R143, Y145, Q147, R148, E155, K156, K157, P160, V165, R167, A168, E169, I170, M171, R172, S173, S175, L176, S177, N179, S183, R185, S186, K187, and E188 in the wild-type IFNA2 amino acid sequence (SEQ ID NO: 1).

In some embodiments, the IFNA2 fusion protein includes an antibody comprising a Fc domain and an IFNA2 variant comprising one or more specific substitutions selected from the group consisting of: H30A, H30D, S31D, L32D, L32E, S34A, R35N, R36G, L38H, L38Y, L38G, L38P, L38S, L38T, L38Q, L38N, L40R, L40G, L40Q, L40D, L41H, L41D, L41K, L41G, L41A, A42G, A42M, Q43P, M44Q, R45P, R46P, R46D, R46F, R46Y, R46N, R46S, R46I, R46G, R46A, R46H, R46T, 147P, 147D, I47S, I47E, S48Y, S48H, L49H, L49I, L49K, L49V, L49Y, L49F, L49G, L49E, L49P, F50D, F50N, F50G, F50Q, F50S, F50M, F50H, F50A, S51D, S51E, L53D, L53E, L53G, L53A, L53N, L53V, L53S, K54L, K54I, K54M, D55T, D55N, D55Q, R56D, R56G, R56K, R56N, R56V, R56T, R56A, R56L, R56H, H57P, D58Q, F59Q, F59E, F59I, F59N, F59A, F59G, F59T, F59Y, F61G, F61I, F61V, F61P, F61Q, F61A, F61S, P62I, Q63E, Q69S, K72D, V78E, V78G, M82W, M82K, M82R, M82G, M82S, I86L, K93E, K93V, A98E, L103E, L103D, K106L, K106D, Y108K, T109W, E110P, E110S, Q113W, N116W, N116M, N116F, N116Q, E119Y, E119F, A120M, G125V, V126W, V126Y, T129G, P132W, M134Y, I139Y, I139F, A141E, A141I, R143F, Q147S, R148Y, E155H, K156D, K156L, K156W, K157Y, P160E, P160F, P160W, P160Y, P160T, V165Y, V165E, V165H, V165K, V165W, V165F, V165Q, V165L, V165M, V165S, V165R, V165N, V165D, V165I, R167W, R167I, R167M, R167S, R167E, R167L, R167V, R167A, R167G, R167H, A168R, A168H, A168K, A168Y, A168G, A168F, A168D, A168M, A168Q, E169T, E169S, E169G, I170L, M171R, M171S, M171T, M171N, M171A, M171Y, M171W, M171F, M171K, M171E, M171G, M171L, M171I, M171V, R172D, R172W, R172N, R172A, R172V, R172G, R172T, R172S, R172Y, R172L, R172M, R172K, S173K, S173R, S173H, S173E, S173N, S173W, S173Y, S175R, S175K, S175M, S175L, S175P, S175I, S175V, S175W, S175Y, S175G, S175E, S175Q, S175T, L176N, L176G, L176H, L176A, L176P, L176D, L176R, L176Q, L176E, L176V, S177D, S177R, N179G, S183W, S183F, S183M, S183E, S183Y, S183K, S183L, R185D, R185E, R185Q, S186L, S186I, S186D, K187R, K187L, K187E, K187Y, K187V, K187M, K187F, K187I, K187W, K187G, and E188I in the wild-type IFNA2 amino acid sequence (SEQ ID NO: 1).

In some embodiments, the IFNA2 fusion protein includes an antibody comprising an Fc domain and an IFNA2 variant including a combination of two specific amino acid substitutions, i.e., a double amino acid substitution, selected from the group consisting of: M44N+A168R, L49P+S175P, L49P+S173H, L49P+M171W, L49P+M171G, L49P+S173R, M44N+S175P, L49P+M171V, L49P+M171K, L49P+M171S, L49P+S175R, L49P+M171R, L49P+L176G, L49P+M171Y, L49P+L176N, L49P+S173Q, L49P+L176H, L49P+L176R, L49P+M171A, L49P+M171T, L49P+L176A, L49P+M171F, M44N+S175K, L49P+S175K, L49P+L176E, L49P+E169T, L49P+M171L, L49P+L176Q, L49P+K187E, L49P+S173N, M44N+L176H, M44N+S175R, L49P+S177N, L49P+S173W, L49P+S177D, L49P+R185D, L49P+E169S, L49P+S175G, L49P+S177L, L49P+R172K, L49P+R185E, L49P+K187M, L49P+K187W, L49P+S159Q, M44N+L176Q, M44N+R185E, L49P+S175Q, L49P+S175M, L49P+E155V, L49P+K187D, L49P+S175W, L49P+L176V, L49P+S173L, M44N+S175G, L49P+R185G, L49P+R143W, L49P+1149T, L49P+R185L, L49P+R185S, L49P+S177H, L49P+K106D, M44N+R185N, L49P+K187V, L49P+K106W, L49P+K135T, M44N+V128I, M44N+R185D, L49P+K106P, L49P+S183M, L49P+S183D, L49P+K156A, L49P+S183L, M44N+K187D, L49P+R185M, L49P+R185N, M44N+A168L, L49P+S175L, L49P+R185Q, L49P+K187G, M44N+S177E, L49P+W163L, L49P+R185W, L49P+K187T, L49P+T109W, M44N+P160E, M44N+K106T, L49P+R185T, L49P+S175I, L49P+S173F, M44N+R185L, L49P+S183E, L49P+K187N, M44N+K187F, L49P+S159D, M44N+K106I, L49P+S175Y, L49P+L184N, L49P+I170L, L49P+V166S, L49P+K187A, L49P+S186D, L49P+L111F, L49P+K154Q, L49P+K106T, L49P+E136D, L49P+K106M, L49P+F107W, M44N+R185Y, M44N+V165I, M44N+K187W, L49P+R185I, M44N+R185T, M44N+R185V, M44N+Q113A, M44N+T178K, L49P+K156V, L49P+K187S, M44N+Q114I, L49P+T131E, M44N+S183E, L49P+Y152W, L49P+V128E, L49P+E155K, L49P+S175T, L49P+E155R, L49P+V166T, and L49P+T178F in the wild-type IFNA2 amino acid sequence (SEQ ID NO: 1).

In some embodiments, the IFNA2 fusion protein has a binding affinity to the human interferon-alpha/beta receptor beta 2 (IFNAR2) that is decreased by 1.5-fold, 2-fold, 3-fold, 5-fold, 10-fold, 50-fold, 100-fold, 500-fold, 1000-fold, 2000-fold, or 3000-fold or more compared to the binding affinity between the wild-type human IFNA2 polypeptide and the human IFNAR2.

Polynucleotides, Vectors, Host Cells

The disclosure also provides polynucleotides encoding any of the IFNA2 variants and IFNA2 fusion proteins as described herein. In one aspect, the disclosure provides methods of making any of the polynucleotides described herein. Polynucleotides can be made and expressed by procedures known in the art.

In another aspect, the disclosure provides compositions (such as pharmaceutical compositions) including any of the polynucleotides described herein. In some embodiments, the composition includes an expression vector having a polynucleotide encoding any of the IFNA2 variants and IFNA2 fusion proteins described herein.

In another aspect, the disclosure provides isolated cell lines that produce the IFNA2 variants and the IFNA2 fusion proteins as described herein. In some embodiments, the cell line is an engineered immune cell, wherein the engineered immune cell includes a chimeric antigen receptor (CAR). In some embodiments, the IFNA2 variants and the IFNA2 fusion proteins, when expressed as polynucleotides in CAR T cells, either as secreted or membrane-tethered versions, are used to enhance CAR T function, including activity and proliferation.

Immune cells producing the IFNA2 variants and the IFNA2 fusion proteins as described herein may be made by introducing a CAR into immune cells, and expanding the cells. For example, the immune cells can be engineered by providing a cell and expressing at the surface of the cell at least one CAR and at least one IFNA2 variant or IFNA2 fusion protein as described herein. Methods for engineering immune cells are described in, for example, PCT Patent Application Publication Nos. WO/2014/039523, WO/2014/184741, WO/2014/191128, WO/2014/184744, and WO/2014/184143, each of which is incorporated herein by reference in its entirety. In some embodiments, the cell can be transformed with at least one polynucleotide encoding a CAR, one polynucleotide encoding the IFNA2 variant or IFNA2 fusion protein as described herein, followed by expressing the polynucleotides in the cell.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide described herein, and a polynucleotide may, but need not, be linked to other molecules and/or support materials. Polynucleotides can include a native sequence (e.g., an endogenous sequence that encodes an antibody or a fragment thereof) or may include a variant of such a sequence. Polynucleotide variants of antibodies or fragments thereof contain one or more substitutions, additions, deletions, and/or insertions such that the immunoreactivity of the encoded polypeptide is not diminished, relative to a native immunoreactive molecule. The effect on the immunoreactivity of the encoded polypeptide may generally be assessed as described herein and by methods known in the relevant field. Variants of antibodies or fragments thereof can exhibit at least about 70% identity, at least about 80% identity, at least about 90% identity, or at least about 95, 96, 97, 98, or 99% identity to a polynucleotide sequence that encodes a native antibody or a fragment thereof.

Variants are substantially homologous to a native gene, or a portion or complement thereof. It will be appreciated by those of ordinary skill in the art that, as a result of the degeneracy of the genetic code, there are many nucleotide sequences that encode polypeptides as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence. For preparing polynucleotides using recombinant methods, a polynucleotide having a desired sequence can be inserted into a suitable vector, and the vector in turn can be introduced into a suitable host cell for replication and amplification, as further discussed herein. Polynucleotides can be inserted into host cells by any means known in the art. Cells are transformed by introducing an exogenous polynucleotide by direct uptake, endocytosis, transfection, F-mating, or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al., 1989.

As is well known, PCR allows reproduction of DNA sequences. See, e.g. U.S. Pat. Nos. 4,683,195, 4,800,159, 4,754,065 and 4,683,202, as well as PCR: The Polymerase Chain Reaction, Mullis et al. eds., Birkauswer Press, Boston, 1994.

RNA can be obtained by using isolated DNA in an appropriate vector and inserting it into a suitable host cell. When the cell replicates and the DNA is transcribed into RNA, the RNA can then be isolated using methods well known to those of skill in the art, as set forth in Sambrook et al., 1989, supra, for example.

Suitable cloning vectors can be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp 18, mp 19, pBR322, pMB9, ColE1, pCRI, RP4, phage DNAs, and shuttle vectors such as pSA3 and pAT28. These and many other cloning vectors are available from commercial vendors such as BioRad, Strategene, and Invitrogen.

Expression vectors are also provided herein. Expression vectors generally are replicable polynucleotide constructs that contain a polynucleotide as described herein. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell. The disclosure also provides host cells including any of the polynucleotides described herein. Any host cells capable of over-expressing heterologous DNAs can be used for the purpose of isolating the genes encoding the antibody, polypeptide, or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtilis*) and yeast (such as *S. cerevisae, S. pombe*; or *K. lactis*). Preferably, the host cells express the cDNAs at a level of about 5 fold higher, 10 fold higher, or 20 fold higher than that of the corresponding endogenous antibody or protein of interest, if present, in the host cells. Screening the host cells for a specific binding to IFNA2 or a IFNA2 domain can be effected by an immunoassay or FACS. A cell overexpressing the antibody or protein of interest can be identified.

An expression vector can be used to direct expression of an IFNA2 variant or an IFNA2 fusion protein. One skilled in the art is familiar with administration of expression vectors to obtain expression of an exogenous protein in vivo. See, e.g., U.S. Pat. Nos. 6,436,908; 6,413,942; and 6,376, 471. Administration of expression vectors includes local or systemic administration, including injection, oral administration, particle gun, catheterized administration, and topical administration. In another embodiment, the expression vector is administered directly to the sympathetic trunk or ganglion, or into a coronary artery, atrium, ventricle, or pericardium.

Targeted delivery of therapeutic compositions containing an expression vector, or subgenomic polynucleotides can also be used. Receptor-mediated DNA delivery techniques are described in, for example, Findeis et al., Trends Biotechnol., 1993, 11:202; Chiou et al., Gene Therapeutics: Methods And Applications Of Direct Gene Transfer, J. A. Wolff, ed., 1994; Wu et al., J. Biol. Chem., 1988, 263:621; Wu et al., J. Biol. Chem., 1994, 269:542; Zenke et al., Proc. Natl. Acad. Sci. USA, 1990, 87:3655; Wu et al., J. Biol. Chem., 1991, 266:338.

Therapeutic compositions containing a polynucleotide are administered in a range of about 100 ng to about 200 mg of DNA for local administration in a gene therapy protocol. Concentration ranges of about 500 ng to about 50 mg, about 1 μg to about 2 mg, about 5 μg to about 500 pg, and about 20 μg to about 100 μg of DNA can also be used during a gene therapy protocol. The therapeutic polynucleotides and polypeptides can be delivered using gene delivery vehicles. The gene delivery vehicle can be of viral or non-viral origin (see generally, Jolly, Cancer Gene Therapy, 1994, 1:51; Kimura, Human Gene Therapy, 1994, 5:845; Connelly, Human Gene Therapy, 1995, 1:185; and Kaplitt, Nature Genetics, 1994, 6:148). Expression of such coding sequences can be induced using endogenous mammalian or heterologous promoters. Expression of the coding sequence can be either constitutive or regulated. Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936: WO 94/03622; WO 93/25698; WO 93/25234; WO 93/11230; WO 93/10218; WO 91/02805; U.S. Pat. Nos. 5,219,740 and 4,777,127; GB Patent No. 2,200,651; and EP Patent No. 0345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, Hum. Gene Ther., 1992, 3:147 can also be employed.

Non-viral delivery vehicles and methods can also be employed, including, but not limited to, polycationic condensed DNA linked or unlinked to killed adenovirus alone (see, e.g., Curiel, Hum. Gene Ther., 1992, 3:147); ligand-linked DNA (see, e.g., Wu, J. Biol. Chem., 1989, 264: 16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP 0524968. Additional approaches are described in Philip, Mol. Cell Biol., 1994, 14:2411, and in Woffendin, Proc. Natl. Acad. Sci., 1994, 91:1581.

Compositions

The disclosure also provides pharmaceutical compositions including an effective amount of an IFNA2 variant or an IFNA2 fusion protein as described herein. Examples of such compositions, as well as how to formulate, are also described herein. In some embodiments, the composition includes one or more IFNA2 variants, combinations with other variant detuned cytokines or other IFNA2 fusion proteins.

In some embodiments, the compositions include an IFNA2 fusion protein including an antibody and a human IFNA2 variant having one or more, e.g., two specific, or more, specific substitutions in SEQ ID NO: 1 as described herein.

It is understood that the compositions can include more than one IFNA2 variant or IFNA2 fusion protein (e.g., a mixture of IFNA2 variants or IFNA2 fusion proteins comprising different IFNA2 variants and/or different antibodies).

The compositions disclosed herein can further include pharmaceutically acceptable carriers, excipients, or stabilizers (Remington: The Science and practice of Pharmacy 20th Ed., 2000, Lippincott Williams and Wilkins, Ed. K. E. Hoover), in the form of lyophilized formulations or aqueous solutions. Acceptable carriers, excipients, or stabilizers are nontoxic to recipients at known dosages and concentrations, and may include buffers such as phosphate, citrate, and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrans; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™, or polyethylene glycol (PEG). Pharmaceutically acceptable excipients are further described herein.

The IFNA2 variants, IFNA2 fusion proteins, and compositions thereof can also be used in conjunction with, or administered separately, simultaneously, or sequentially with other agents that serve to enhance and/or complement the effectiveness of the agents.

The disclosure also provides compositions, including pharmaceutical compositions, including any of the polynucleotides described herein. In some embodiments, the compositions include an expression vector including a polynucleotide encoding the IFNA2 variants and IFNA2 fusion proteins as described herein. In other embodiments, the compositions include an expression vector having a polynucleotide encoding any of the IFNA2 variants and IFNA2 fusion proteins described herein.

Methods of Treatment

The IFNA2 variants and the IFNA2 fusion proteins described herein are useful in various applications including, but are not limited to, therapeutic treatment methods and diagnostic treatment methods.

In one aspect, the disclosure provides methods for treating cancer. In some embodiments, the methods of treating cancer in a subject include administering to the subject in need thereof an effective amount of a composition (e.g., a pharmaceutical composition) including any of the IFNA2 variants and the IFNA2 fusion proteins as described herein. As used herein, a cancer can be a solid cancer or a blood or bone marrow cancer. Solid cancers include, but are not limited to, gastric cancer, small intestine cancer, sarcoma, head and neck cancer (e.g., squamous cell head and neck cancer), thymic cancer, epithelial cancer, salivary cancer, liver cancer, biliary cancer, neuroendocrine tumors, stomach cancer, thyroid cancer, lung cancer, mesothelioma, ovarian cancer, breast cancer, prostate cancer, esophageal cancer, pancreatic cancer, glioma, renal cancer (e.g., renal cell carcinoma), bladder cancer, cervical cancer, uterine cancer, vulvar cancer, penile cancer, testicular cancer, anal cancer, choriocarcinoma, colorectal cancer, oral cancer, skin cancer, Merkel cell carcinoma, glioblastoma, brain tumor, bone cancer, eye cancer, and melanoma.

Blood and bone marrow cancers include, but are not limited to, multiple myeloma, malignant plasma cell neoplasm, Hodgkin's lymphoma, nodular lymphocyte predominant Hodgkin's lymphoma, Kahler's disease and Myelomatosis, plasma cell leukemia, plasmacytoma, B-cell prolymphocytic leukemia, hairy cell leukemia, B-cell non-Hodgkin's lymphoma (NHL), acute myeloid leukemia (AML), chronic lymphocytic leukemia (CLL), acute lymphocytic leukemia (ALL), chronic myeloid leukemia (CML), follicular lymphoma, Burkitt's lymphoma, marginal zone lymphoma, mantle cell lymphoma, large cell lymphoma, precursor B-lymphoblastic lymphoma, myeloid leukemia, Waldenstrom's macroglobulienemia, diffuse large B cell lymphoma, follicular lymphoma, marginal zone lymphoma, mucosa-associated lymphatic tissue lymphoma, small cell lymphocytic lymphoma, mantle cell lymphoma, Burkitt lymphoma, primary mediastinal (thymic) large B-cell lymphoma, lymphoplasmactyic lymphoma, Waldenstrom macroglobulinemia, nodal marginal zone B cell lymphoma, splenic marginal zone lymphoma, intravascular large B-cell lymphoma, primary effusion lymphoma, lymphomatoid granulomatosis, T cell histiocyte-rich large B-cell lymphoma, primary central nervous system lymphoma, primary cutaneous diffuse large B-cell lymphoma (leg type), EBY positive diffuse large B-cell lymphoma of the elderly, diffuse large B-cell lymphoma associated with inflammation, intravascular large B-cell lymphoma, ALK-positive large B-cell lymphoma, plasmablastic lymphoma, large B-cell lymphoma arising in HHVS-associated multicentric Castleman disease, B-cell lymphoma unclassified with features intermediate between diffuse large B-cell lymphoma and Burkitt lymphoma, B-cell lymphoma unclassified with features intermediate between diffuse large B-cell lymphoma and classical Hodgkin lymphoma, and other hematopoietic cell related cancer. In some embodiments, the cancer is relapsed, refractory, or metastatic.

In some embodiments, the methods of inhibiting tumor growth or progression in a subject include administering to the subject in need thereof an effective amount of a composition including the IFNA2 variants or IFNA2 fusion proteins as described herein. In some embodiments, the disclosure includes methods of inhibiting metastasis of cancer cells in a subject, which include administering to a subject in need thereof an effective amount of a composition including any of the IFNA2 variants or IL-fusion proteins as described herein. In other embodiments, the disclosure includes methods of inducing regression of a tumor in a subject, which include administering to the subject in need thereof an effective amount of a composition including any of the IFNA2 variants or IFNA2 fusion proteins as described herein. In another aspect, the disclosure provides methods of detecting, diagnosing, and/or monitoring a cancer. For example, the IFNA2 variants or IFNA2 fusion proteins as described herein can be labeled with a detectable moiety such as an imaging agent and an enzyme-substrate label. The IFNA2 variants or IFNA2 fusion proteins as described herein can also be used for in vivo diagnostic assays, such as in vivo imaging (e.g., PET or SPECT), or a staining reagent.

In some embodiments, the methods described herein further include a step of treating a subject with an additional form of therapy. In some embodiments, the additional form of therapy is an additional anti-cancer therapy including, but not limited to, chemotherapy, radiation, surgery, hormone therapy, checkpoint inhibitor and/or additional immunotherapy.

With respect to all methods described herein, reference to IFNA2 variants or IFNA2 fusion proteins also includes compositions comprising one or more additional agents. These compositions may further comprise suitable excipients, such as pharmaceutically acceptable excipients including buffers, which are well known in the art. The methods and compositions described herein can be used alone or in combination with other methods of treatment.

The IFNA2 variants or IFNA2 fusion proteins as described herein can be administered to a subject via any suitable route. It should be apparent to a person skilled in the art that the examples described herein are not intended to be limiting, but to be illustrative of the techniques available. Accordingly, in some embodiments, the IL-variant or IFNA2 fusion protein is administered to a subject in accord with known methods, such as intravenous administration, e.g., as a bolus or by continuous infusion over a period of time, by intramuscular, intraperitoneal, intracerebrospinal, transdermal, subcutaneous, intra-articular, sublingually, or intrasynovial administration, or via insufflation, intrathecal, oral, inhalation, or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, the IFNA2 variants or IFNA2 fusion proteins can be aerosolized using a fluorocarbon formulation and a metered dose inhaler, or inhaled as a lyophilized and milled powder.

In some embodiments, an IFNA2 variant or IFNA2 fusion protein is administered via site-specific or targeted local delivery techniques. Examples of site-specific or targeted local delivery techniques include direct injection into patient tumor or various implantable depot sources of the IL-variants or IFNA2 fusion proteins or local delivery catheters, such as infusion catheters, indwelling catheters, or needle catheters, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an IFNA2 variant or IFNA2 fusion protein can be used for administration. In some embodiments, the IFNA2 variant or IFNA2 fusion protein can be administered neat. In some embodiments, the IFNA2 variant or IFNA2 fusion protein and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, The Science and Practice of Pharmacy 20th Ed. Mack Publishing, 2000. In some embodiments, these agents are formulated for administration by injection (e.g., intraperitoneally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

Generally, for administration of IFNA2 variants or IFNA2 fusion proteins, the candidate dosage can be administered daily, every other day, every third day, every week, every other week, every three weeks, every four weeks, every five weeks, every six weeks, every seven weeks, every eight weeks, every ten weeks, every twelve weeks, or more than every twelve weeks. For repeated administrations over several days or longer, depending on the condition, the treatment is sustained until a desired suppression of symptoms occurs or until sufficient therapeutic levels are achieved, for example, to reduce symptoms associated with cancer. The progress of this therapy is easily monitored by conventional techniques and assays. The dosing regimen (including the specific IFNA2 variants or IFNA2 fusion proteins used) can vary over time.

In some embodiments, the candidate dosage is administered daily with the dosage ranging from about any of 1 pg/kg to 30 pg/kg to 300 pg/kg to 3 mg/kg, to 30 mg/kg, to 100 mg/kg or more, depending on the factors mentioned above. For example, daily dosage of about 0.01 mg/kg, about 0.03 mg/kg, about 0.1 mg/kg, about 0.3 mg/kg, about 1 mg/kg, about 2.5 mg/kg, about 3 mg/kg, about 5 mg/kg, about 10 mg/kg, about 15 mg/kg, and about 25 mg/kg may be used.

In some embodiments, the candidate dosage is administered every week with the dosage ranging from about any of 1 pg/kg to 30 pg/kg to 300 pg/kg to 3 mg/kg, to 30 mg/kg, to 100 mg/kg or more, depending on the factors mentioned above. For example, a weekly dosage of about 0.01 mg/kg, about 0.03 mg/kg, about 0.1 mg/kg, about 0.3 mg/kg, about 0.5 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every two weeks with the dosage ranging from about any of 1 pg/kg to 30 pg/kg to 300 pg/kg to 3 mg/kg, to 30 mg/kg, to 100 mg/kg or more, depending on the factors mentioned above. For example, a bi-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, and about 30 mg/kg may be used.

In some embodiments, the candidate dosage is administered every three weeks with the dosage ranging from about any of 1 pg/kg to 30 pg/kg to 300 pg/kg to 3 mg/kg, to 30 mg/kg, to 100 mg/kg or more, depending on the factors mentioned above. For example, a tri-weekly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In some embodiments, the candidate dosage is administered every month or every four weeks with the dosage ranging from about any of 1 pg/kg to 30 pg/kg to 300 pg/kg to 3 mg/kg, to 30 mg/kg, to 100 mg/kg or more, depending on the factors mentioned above. For example, a monthly dosage of about 0.1 mg/kg, about 0.3 mg/kg, about 1 mg/kg, about 2.5 mg/kg, about 3 mg/kg, about 5 mg/kg, about 10 mg/kg, about 15 mg/kg, about 25 mg/kg, about 30 mg/kg, about 35 mg/kg, about 40 mg/kg, about 45 mg/kg, and about 50 mg/kg may be used.

In other embodiments, the candidate dosage is administered daily with the dosage ranging from about 0.01 mg to about 1200 mg or more, depending on the factors mentioned above. For example, daily dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, or about 1200 mg may be used.

In other embodiments, the candidate dosage is administered every week with the dosage ranging from about 0.01 mg to about 2000 mg or more, depending on the factors mentioned above. For example, weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every two weeks with the dosage ranging from about 0.01 mg to about 2000 mg or more, depending on the factors mentioned above. For example, bi-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, or about 2000 mg may be used.

In other embodiments, the candidate dosage is administered every three weeks with the dosage ranging from about 0.01 mg to about 2500 mg or more, depending on the factors mentioned above. For example, tri-weekly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, or about 2500 mg may be used.

In other embodiments, the candidate dosage is administered every four weeks or month with the dosage ranging from about 0.01 mg to about 3000 mg or more, depending on the factors mentioned above. For example, monthly dosage of about 0.01 mg, about 0.1 mg, about 1 mg, about 10 mg, about 50 mg, about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg, about 1400 mg, about 1500 mg, about 1600 mg, about 1700 mg, about 1800 mg, about 1900 mg, about 2000 mg, about 2100 mg, about 2200 mg, about 2300 mg, about 2400 mg, about 2500, about 2600 mg, about 2700 mg, about 2800 mg, about 2900 mg, or about 3000 mg may be used.

In some embodiments, a therapeutic of the present invention is administered at a dose ranging from about 1 μg/kg to about 600 μg/kg or more, about 6 μg/kg to about 600 μg/kg, about 6 μg/kg to about 300 μg/kg, about 30 μg/kg to about 600 μg/kg or about 30 μg/kg to about 300 μg/kg. For example, the dose is administered at about 1 μg/kg, about 2 μg/kg, about 3 μg/kg, about 4 μg/kg, about 5 μg/kg, about 6 μg/kg, about 7 μg/kg, about 8 μg/kg, about 9 μg/kg, about 10 μg/kg, about 15 μg/kg, about 20 μg/kg, about 25 μg/kg, about 30 μg/kg, about 35 μg/kg, about 40 μg/kg, about 45 μg/kg, about 50 μg/kg, about 55 μg/kg, about 60 μg/kg, about 65 μg/kg, about 70 μg/kg, about 75 μg/kg, about 80 μg/kg, about 85 μg/kg, about 90 μg/kg, about 95 μg/kg, about 100 μg, about 110 μg/kg, about 120 μg/kg, about 130 μg/kg, about 140 μg/kg, about 150 μg/kg, about 160 μg/kg, about 170 μg/kg, about 180 μg/kg, about 190 μg/kg, about 200 μg/kg, about 210 μg/kg, about 220 μg/kg, about 230 μg/kg, about 240 μg/kg, about 250 μg/kg, about 260 μg/kg, about 270 μg/kg, about 280 μg/kg, about 290 μg/kg, about 300 μg/kg, about 350 μg/kg, about 400 μg/kg, about 450 μg/kg, about 500 μg/kg, about 550 μg/kg or about 600 μg/kg may be used.

For the purposes of the present disclosure, the appropriate dosage of an IFNA2 variant or an IFNA2 fusion protein will depend on the IFNA2 variant or an IFNA2 fusion protein (or compositions thereof) employed, the type and severity of symptoms to be treated, whether the agent is administered for preventive or therapeutic purposes, previous therapy, the patient's clinical history and response to the agent, the patient's clearance rate for the administered agent, and the discretion of the attending physician. Typically the clinician will administer an IFNA2 variant or an IFNA2 fusion protein until a dosage is reached that achieves the desired result. Dose and/or frequency can vary over the course of treatment. In some embodiments, step dosing is performed where the initial dose or doses are lower than incrementally higher doses administered as the regiment continues. Empirical considerations, such as the half-life, generally will contribute to the determination of the dosage. Frequency of administration may be determined and adjusted over the course of therapy, and is generally, but not necessarily, based on treatment and/or suppression and/or amelioration and/or delay of symptoms. Alternatively, sustained continuous release formulations of IFNA2 variants or IFNA2 fusion proteins may be appropriate. Various formulations and devices for achieving sustained release are known in the art.

In one embodiment, dosages for an IFNA2 variant or an IFNA2 fusion protein may be determined empirically in individuals who have been given one or more administration (s) of an IFNA2 variant or an IFNA2 fusion protein. For example, individuals are given incremental dosages of an IFNA2 variant or an IFNA2 fusion protein. To assess efficacy, an indicator of the disease can be followed. Administration of an IFNA2 variant or an IFNA2 fusion protein as described herein in accordance with the method in the present invention can be continuous or intermittent, depending, for example, upon the recipient's physiological condition, whether the purpose of the administration is therapeutic or prophylactic, and other factors known to skilled practitioners. The administration of an IFNA2 variant or an IFNA2 fusion protein may be essentially continuous over a preselected period of time or may be in a series of spaced doses.

In some embodiments, more than one IFNA2 variant or IFNA2 fusion protein may be present. At least one, at least two, at least three, at least four, at least five, or more different IFNA2 variants or IFNA2 fusion proteins can be present. Generally, those IL-variants or IFNA2 fusion proteins may have complementary activities that do not adversely affect each other.

In some embodiments, the IFNA2 variant or the IFNA2 fusion protein may be administered in combination with one or more additional therapeutic agents. These include, but are not limited to, a biotherapeutic agent, a chemotherapeutic agent, a vaccine, a CAR-T cell-based therapy, radiotherapy, another cytokine therapy (e.g., immunostimulatory cytokines including various signaling proteins that stimulate immune response, such as interferons, interleukins, and hematopoietic growth factors), a vaccine, an inhibitor of other immunosuppressive pathways, e.g., anti-PD-1 checkpoint inhibitors, an inhibitors of angiogenesis, a T cell activator, an inhibitor of a metabolic pathway, an mTOR (mechanistic target of rapamycin) inhibitor (e.g., rapamycin, rapamycin derivatives, sirolimus, temsirolimus, everolimus, and deforolimus), an inhibitor of an adenosine pathway, a tyrosine kinase inhibitor including but not limited to inlyta, ALK (anaplastic lymphoma kinase) inhibitors (e.g., crizotinib, ceritinib, alectinib, and sunitinib), a BRAF inhibitor (e.g., vemurafenib and dabrafenib), an epigenetic modifier, an inhibitors or depletor of Treg cells and/or of myeloid-derived suppressor cells, a JAK (Janus Kinase) inhibitor (e.g., ruxolitinib and tofacitinb, varicitinib, filgotinib, gandotinib, lestaurtinib, momelotinib, pacritinib, and upadacitinib), a STAT (Signal Transducers and Activators of Transcription) inhibitor (e.g., STATl, STAT3, and STATS inhibitors such as fludarabine), a cyclin-dependent kinase inhibitor, an immunogenic agent (for example, attenuated cancerous cells, tumor antigens, antigen presenting cells such as dendritic cells pulsed with tumor derived antigen or nucleic acids, a MEK inhibitor (e.g., trametinib, cobimetinib, binimetinib, and selumetinib), a GLSI inhibitor, a PAP inhibitor, an oncolytic virus, an IDO (Indoleamine-pyrrole 2,3-dioxygenase) inhibitor, a PRR (Pattern Recognition Receptors) agonist, and cells transfected with genes encoding immune stimulating cytokines such as but not limited to GM-CSF).

In some embodiments, examples of immunostimulatory cytokines include, but are not limited to, GM-CSF, G-CSF, IFNy, IFNa; IL-2 (e.g. denileukin difitox), IL-6, IL-7, IL-10, IL-11, IL-12, IFNA2, IL-18, IL-21, and TNFa. In some embodiments, the cytokines are pegylated (e.g., pegylated IL-2, IL-10, IFNy, and IFNa).

Pattern recognition receptors (PRRs) are receptors that are expressed by cells of the immune system and that recognize a variety of molecules associated with pathogens and/or cell damage or death. PRRs are involved in both the innate immune response and the adaptive immune response. PRR agonists may be used to stimulate the immune response in a subject. There are multiple classes of PRR molecules, including toll-like receptors (TLRs), RIG-I-like receptors (RLRs), nucleotide-binding oligomerization domain (NOD)-like receptors (NLRs), C-type lectin receptors (CLRs), and Stimulator of Interferon Genes (STING) protein. The terms "TLR" and "toll-like receptor" refer to any toll-like receptor. Toll-like receptors are receptors involved in activating immune responses. TLRs recognize, for example, pathogen-associated molecular patterns (PAMPs) expressed in microbes, as well as endogenous damage-associated molecular patterns (DAMPs), which are released from dead or dying cells.

Molecules that activate TLRs (and thereby activate immune responses) are referred to herein as "TLR agonists." TLR agonists can include, for example, small molecules (e.g. organic molecule having a molecular weight under about 1000 Daltons), as well as large molecules (e.g. oligonucleotides and proteins). Some TLR agonists are specific for a single type ofTLR (e.g. TLR3 or TLR9), while some TLR agonists activate two or more types of TLR (e.g. both TLR7 and TLRS).

Examples of TLR agonists provided herein include agonists of TLR2, TLR3, TLR4, TLR5, TLR6, TLR7, TLRS, and TLR9.

Examples of small molecule TLR agonists include those disclosed in, for example, U.S. Pat. Nos. 4,689,338; 4,929,624; 5,266,575; 5,268,376; 5,346,905; 5,352,784; 5,389,640; 5,446,153; 5,482,936; 5,756,747; 6,110,929; 6,194,425; 6,331,539; 6,376,669; 6,451,810; 6,525,064; 6,541,485; 6,545,016; 6,545,017; 6,573,273; 6,656,938; 6,660,735; 6,660,747; 6,664,260; 6,664,264; 6,664,265; 6,667,312; 6,670,372; 6,677,347; 6,677,348; 6,677,349; 6,683,088; 6,756,382; 6,797,718; 6,818,650; and 7,7091, 214; U.S. Patent Publication Nos. 2004/0091491, 2004/0176367, and 2006/0100229; and International Publication Nos. WO 2005/18551, WO 2005/18556, WO 2005/20999, WO 2005/032484, WO 2005/048933, WO 2005/048945, WO 2005/051317, WO 2005/051324, WO 2005/066169, WO 2005/066170, WO 2005/066172, WO 2005/076783, WO 2005/079195, WO 2005/094531, WO 2005/123079, WO 2005/123080, WO 2006/009826, WO 2006/009832, WO 2006/026760, WO 2006/028451, WO 2006/028545, WO 2006/028962, WO 2006/029115, WO 2006/038923, WO 2006/065280, WO 2006/074003, WO 2006/083440, WO 2006/086449, WO 2006/091394, WO 2006/086633, WO 2006/086634, WO 2006/091567, WO 2006/091568, WO 2006/091647, WO 2006/093514, and WO 2006/098852.

Additional examples of small molecule TLR agonists include certain purine derivatives (such as those described in U.S. Pat. Nos. 6,376,501, and 6,028,076), certain imidazoquinoline amide derivatives (such as those described in U.S. Pat. No. 6,069,149), certain imidazopyridine derivatives (such as those described in U.S. Pat. No. 6,518,265), certain benzimidazole derivatives (such as those described in U.S. Pat. No. 6,387,938), certain derivatives of a 4-aminopyrimidine fused to a five membered nitrogen containing heterocyclic ring (such as adenine derivatives described in U.S. Pat. Nos. 6,376,501; 6,028,076 and 6,329, 381; and in WO 02/08905), and certain 3-.beta.-D-ribofuranosylthiazolo[4,5-d]pyrimidine derivatives (such as those described in U.S. Publication No. 2003/0199461), and certain small molecule immuno-potentiator compounds such as those described, for example, in U.S. Patent Publication No. 2005/0136065.

Examples of large molecule TLR agonists include TLR agonist oligonucleotide sequences. Some TLR agonist oligonucleotide sequences contain cytosine-guanine dinucleotides (CpG) and are described, for example, in U.S. Pat. Nos. 6,194,388; 6,207,646; 6,239,116; 6,339,068; and 6,406,705. Some CpG-containing oligonucleotides can include synthetic immunomodulatory structural motifs such as those described, for example, in U.S. Pat. Nos. 6,426,334 and 6,476,000. Other TLR agonist nucleotide sequences lack CpG sequences and are described, for example, in International Patent Publication No. WO 00/75304. Still other TLR agonist nucleotide sequences include guanosine- and uridine-rich single-stranded RNA (ssRNA) such as those described, for example, in Heil et ah, Science, vol. 303, pp. 1526-1529 Mar. 5, 2004.

Other TLR agonists include biological molecules such as aminoalkyl glucosaminide phosphates (AGPs) and are described, for example, in U.S. Pat. Nos. 6,113,918; 6,303,347; 6,525,028; and 6,649,172.

TLR agonists also include inactivated pathogens or fractions thereof, which may activate multiple different types of TLR receptor. Exemplary pathogen-derived TLR agonists include BCG, *Mycobacterium obuense* extract, Talimogene laherparepvec (T-Vec) (derived from HSV-1), and Pexa-Vec (derived from vaccina virus).

In some embodiments, a TLR agonist may be an agonist antibody that binds specifically to the TLR.

In some embodiments, the biotherapeutic agent is an antibody, including but not limited to, an anti-CTLA-4 antibody, an anti-CD3 antibody, an anti-CD4 antibody, an anti-CD8 antibody, an anti-4-1BB antibody, an anti-PD-1 antibody, an anti-PD-L1 antibody, an anti-TIM3 antibody, an anti-LAG3 antibody, an anti-TIGIT antibody, an anti-OX40 antibody, an anti-IL-7Ralpha (CD127) antibody, an anti-IL-8 antibody, an anti-IL-15 antibody, an anti-HVEM antibody, an anti-BTLA antibody, an anti-CD40 antibody, an anti-CD40L antibody, anti-CD47 antibody, an anti-CSFIR antibody, an anti-CSFI antibody, an anti-IL-7R antibody, an anti-MARCO antibody, an anti-CXCR4 antibodies, an anti-VEGF antibody, an anti-VEGFR1 antibody, an anti-VEGFR2 antibody, an anti-TNFRl antibody, an antiTNFR2 antibody, an anti-CD3 bispecific antibody, an anti-CD19 antibody, an anti-CD20, an anti-Her2 antibody, an anti-EGFR antibody, an anti-ICOS antibody, an anti-CD22 antibody, an anti-CD52 antibody, an anti-CCR4 antibody, an anti-CCRS antibody, an anti-CD200R antibody, an anti-VISG4 antibody, an anti-CCR2 antibody, an anti-LILRb2 antibody, an anti-CXCR4 antibody, an anti-CD206 antibody, an anti-CD163 antibody, an anti-KLRGl antibody, an anti-FLT3 antibody, an anti-B7-H4 antibody, an anti-B7-H3 antibody, an KLRG1 antibody, a BTNlAl antibody, a BCMA antibody, a CLEC9A antibody, a LILRB4 antibody, or an anti-GITR antibody.

In some embodiments, an IFNA2 variant or an IFNA2 fusion protein is used in combination with an immunocytokine. In some embodiments, the immunocytokine includes an antibody, or fragment thereof, conjugated or fused to a cytokine (e.g., fusion protein). In some embodiments, the antibody, or fragment thereof, binds to the Extra Domain-A (EDA) isoform of fibronectin (e.g. anti-EDA antibody). Accordingly, in some embodiments, an IFNA2 variant or an IFNA2 fusion protein is used in conjunction with, for example, an anti-PD-LI antagonist antibody; an anti-PD-I antagonist antibody such as for example, nivolumab (OPDIVO®), pembrolizumab (KEYTRUDA®), mAb7 (e.g., as described in US Pub. No. US20160i59905, hereby incorporated by reference), and pidilizumab; an anti-CTLA-4 antagonist antibody such as for example ipilimumab (YERVOY®); an anti-LAG-3 antagonist antibody such as BMS-986016 and IMP70i; an anti-TIM-3 antagonist antibody; an anti-17-1H3 antagonist antibody such as for example MGA27i; an-anti-VISTA antagonist antibody; an anti-TIGIT antagonist antibody; an anti-CD28 antagonist antibody; an anti-CD8 antibody; an anti-CD86 antibody; an anti-B7-H4 antagonist antibody; an anti-ICOS agonist antibody; an anti-CD28 agonist antibody; an innate immune response modulator (e.g., TLRs, KIR, NKG2A), and an IDO inhibitor. In some embodiments, an IFNA2 variant or an IFNA2 fusion protein is used in conjunction with a 4-18B (CD137) agonist such as, for example, PF-05082566 or urelumab (BMS-663513). In some embodiments, an IFNA2 variant or an IFNA2 fusion protein is used in conjunction with an OX40 agonist such as, for example, an anti-OX-40 agonist antibody. In some embodiments, an IFNA2 variant or an IFNA2 fusion protein is used in conjunction with a GITR agonist such as, for example, TRX518. In some embodiments, an IFNA2 variant or an IFNA2 fusion protein is used in conjunction with an IDO inhibitor. In some embodiments, an IFNA2 variant or an IFNA2 fusion protein is used in conjunction with a cytokine therapy such as, for example without limitation, (pegylated or non-pegylated) IL-2, IL-10, IL-12, IL-7, IL-15, IL-21, IL-33, CSF-1, MCSF-1, etc.

In some embodiments, other examples of the antibody for the combination use with the IFNA2 variant or the IFNA2 fusion protein of the present invention can be directed to, 5T4; A33; alpha-folate receptor 1 (e.g. mirvetuximab soravtansine); Alk-1; CA-125 (e.g. abagovomab); Carboanhydrase IX; CCR2; CCR4 (e.g. mogamulizumab); CCR5 (e.g. Ieronlimab); CCR8; CD3 [e.g. blinatumomab (CD3/CD19 bispecific), PF-06671008 (CD3/P-cadherin bispecific), PF-06863135 (CD3/BCMA bispecific), CD25; CD28; CD30 (e.g. brentuximab vedotin); CD33 (e.g. gemtuzumab ozogamicin); CD38 (e.g. daratumumab, isatuximab), CD44v6; CD63; CD79 (e.g. polatuzumab vedotin); CD80; CD123; CD276/B7-H3 (e.g. omburtamab); CDH17; CEA; ClhCG; desmoglein 4; DLL3 (e.g. rovalpituzumab tesirine); DLL4; E-cadherin; EDA; EDB; EFNA4; EGFR (e.g. cetuximab, depatuxizumab mafodotin, necitumumab, panitumumab); EGFRvIII; Endosialin; EpCAM (e.g. oportuzumab monatox); FAP; Fetal Acetylcholine Receptor; FLT3 (e.g. see WO2018/220584); GD2 (e.g. dinutuximab, 3F8); GD3; GloboH; GMl; GM2; HER2/neu [e.g. margetuximab, pertuzumab, trastuzumab; ado-trastuzumab emtansine, trastuzumab duocarmazine, PF-06804103 (see U.S. Pat. No. 8,828,401)]; HER3; HER4; ICOS; ITG-AvB6; LAG-3 (e.g. relatlimab); Lewis-Y; LG; Ly-6; M-CSF [e.g. PD-0360324 (see U.S. Pat. No. 7,326,414)]; MCSP; mesothelin; MUCl; MUC2; MUC3; MUC4; MUCSAC; MUCSB; MUC7; MUC16; Notchl; Notch3; Nectin-4 (e.g. enfortumab vedotin); P-Cadherein [e.g. PF-06671008 (see WO2016/001810)]; PCDHB2; PDGFRA (e.g. olaratumab); Plasma Cell Antigen; PolySA; PSCA; PSMA; PTK7 [e.g. PF-06647020 (see U.S. Pat. No. 9,409,995)]; Rorl; SAS; SCRx6; SLAMF7 (e.g. elotuzumab); SHH; SIRPa (e.g. ED9, Effi-DEM); STEAP; TGF-beta; TIGIT; TMPRSS3; TNF-alpha precursor; TROP-2 (e.g., sacituzumab govitecan); TSPAN8; and Wue-1. Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylolomelamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CBI-TMI); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as the enediyne antibiotics (e.g. calicheamicin, especially calicheamicin gammall and calicheamicin phill, see, e.g., Agnew, Chem. Intl. Ed. Engl., 33:183-186 (1994); dynemicin, including dynemicin A; bisphosphonates, such as clodronate; an esperamicin; as well as neocarzinostatin chromophore and related chromoprotein enediyne antibiotic chromomophores), aclacinomysins, actinomycin, authramycin, azaserine, bleomycins, cactinomycin, carabicin, caminomycin, carzinophilin, chromomycins, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidamine; maytansinoids such as maytansine and ansamitocins; mitoguazone; mitoxantrone; mopidamol; nitracrine; pentostatin; phenamet; pirarubicin; losoxantrone; podophyllinic acid; 2-ethylhydrazide; procarbazine; razoxane; rhizoxin; sizofuran; spirogermanium; tenuazonic acid; triaziquone; 2, 2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g. paclitaxel and doxetaxel; chlorambucil; gemcitabine; 6-thioguanine; mercaptopurine; methotrexate; platinum analogs such as carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; CPT-11; topoisomerase inhibitor RFS 2000; difluoromethylomithine (DMFO); retinoids such as retinoic acid;

capecitabine; and pharmaceutically acceptable salts, acids or derivatives of any of the above. Also included are antihormonal agents that act to regulate or inhibit hormone action on tumors such as anti-estrogens and selective estrogen receptor modulators (SERMs), including, for example, tamoxifen, raloxifene, droloxifene, 4-hydroxytamoxifen, trioxifene, keoxifene, LYll 7018, onapristone, and toremifene (Fareston); aromatase inhibitors that inhibit the enzyme aromatase, which regulates estrogen production in the adrenal glands, such as, for example, 4(5)-imidazoles, aminoglutethimide, megestrol acetate, exemestane, formestane, fadrozole, vorozole, letrozole, and anastrozole; and antiandrogens such as flutamide, nilutamide, bicalutamide, leuprolide, fluridil, apalutamide, enzalutamide, cimetidine and goserelin; KRAS inhibitors; MCT4 inhibitors; MAT2a inhibitors; tyrosine kinase inhibitors such as sunitinib, axitinib; alk/c-Met/ROS inhibitors such as crizotinib, lorlatinib; mTOR inhibitors such as temsirolimus, gedatolisib; src/abl inhibitors such as bosutinib; cyclin-dependent kinase (CDK) inhibitors such as palbociclib, PF-06873600; erb inhibitors such as dacomitinib; PARP inhibitors such as talazoparib; SMO inhibitors such as glasdegib, PF-5274857; EGFR T790M inhibitors such as PF-06747775; EZH2 inhibitors such as PF-06821497; PRMT5 inhibitors such as PF-06939999; TGFR~rl inhibitors such as PF-06952229; and pharmaceutically acceptable salts, acids or derivatives of any of the above.

In some embodiments, an IFNA2 variant or an IFNA2 fusion protein is used in conjunction with one or more other therapeutic agents targeting an immune checkpoint modulator, such as, for example without limitation, an agent targeting PD-1, PDL-1, CTLA-4, LAG-3, B7-H3, B7-H4, B7-DC (PD-L2), B7-H5, B7-H6, B7-H8, B7-H2, B7-1, B7-2, ICOS, ICOS-L, TIGIT, CD2, CD47, CD80, CD86, CD48, CD58, CD226, CD155, CD112, LAIR1, 2B4, BTLA, CD160, TIMI, TIM-3, TIM4, VISTA (PD-Hl), OX40, OX40L, GITRL, CD70, CD27, 4-18B, 4-BBL, DR3, TLlA, CD40, CD40L, CD30, CD30L, LIGHT, HVEM, SLAM (SLAMFl, CD150), SLAMF2 (CD48), SLAMF3 (CD229), SLAMF4 (2B4, CD244), SLAMF5 (CD84), SLAMF6 (NTB-A), SLAMCF7 (CS!), SLAMF8 (BLAME), SLAMF9 (CD2F), CD28, CEACAM1 (CD66a), CEACAM3, CEACAM4, CEACAM5, CEACAM6, CEACAM7, CEACAM8, CEACAM1-3AS CEACAM3C2, CEACAMl-15, PSGl-11, CEACAM1-4Cl, CEACAM1-4S, CEACAM1-4L, IDO, TDO, CCR2, CD39-CD73-adenosine pathway (A2AR), BTKs, TIKs, CXCR2, CCR4, CCR8, CCR5, VEGF pathway, CSF-1, or an innate immune response modulator.

In some embodiments, an IFNA2 variant or an IFNA2 fusion protein is used in conjunction with a biotherapeutic agent and a chemotherapeutic agent. For example, provided is a method for treating cancer in a subject in need thereof including administering to the subject an effective amount of the IFNA2 variant or IFNA2 fusion protein as described herein, a therapeutic antibody, and a chemotherapeutic agent (e.g., gemcitabine, methotrexate, or a platinum analog). In some embodiments, provided is a method for treating cancer in a subject in need thereof comprising administering to the subject an effective amount of the IFNA2 variant or IFNA2 fusion protein as described wherein, a therapeutic antibody (e.g., nivolumab (OPDIVO®), mAb7 (e.g., as described in US Pub. No. US20160159905, hereby incorporated by reference), or pembrolizumab (KEYTRUDA®), and a chemotherapeutic agent (e.g., gemcitabine, methotrexate, or a platinum analog). In some embodiments, provided is a method for treating cancer in a subject in need thereof comprising administering to the subject an effective amount of the IFNA2 variant or IFNA2 fusion protein as described wherein, an anti-CTLA-4 antagonist antibody (e.g., ipilimumab (YERVOY®)), and a chemotherapeutic agent (e.g., gemcitabine, methotrexate, or a platinum analog).

In some embodiments, the IFNA2 variant or IFNA2 fusion protein therapy may precede or follow the other agent treatment by intervals ranging from minutes to weeks. In embodiments where the other agents and/or a proteins or polynucleotides are administered separately, one would generally ensure that a significant period of time did not expire between each delivery, such that the agent and the composition of the present invention would still be able to exert an advantageously combined effect on the subject. In such instances, it is contemplated that one may administer both modalities within about 12-24 h of each other and, more preferably, within about 6-12 h of each other. In some situations, it may be desirable to extend the time period for administration significantly, however, where several days (2, 3, 4, 5, 6 or 7) to several weeks (1, 2, 3, 4, 5, 6, 7 or 8) lapse between the respective administrations.

In some embodiments, an IFNA2 variant or an IFNA2 fusion protein composition comprises a second agent selected from crizotinib, palbociclib, gemcitabine, cyclophosphamide, fluorouracil, FOLFOX, folinic acid, oxaliplatin, axitinib, sunitinib malate, tofacitinib, bevacizumab, rituximab, and trastuzumab.

In some embodiments, an IFNA2 variant or IFNA2 fusion protein composition is combined with a treatment regimen further comprising a traditional therapy selected from the group consisting of: surgery, radiation therapy, chemotherapy, targeted therapy, immunotherapy, hormonal therapy, angiogenesis inhibition and palliative care.

Formulations

Therapeutic formulations of the IFNA2 variant or IFNA2 fusion protein used in accordance with the present disclosure are prepared for storage by mixing the protein having the desired degree of purity with optional pharmaceutically acceptable carriers, excipients, or stabilizers (Remington, The Science and Practice of Pharmacy 20th Ed. Mack Publishing, 2000), e.g., in the form of lyophilized formulations or aqueous solutions. Acceptable carriers, excipients, or stabilizers are nontoxic to recipients at the dosages and concentrations employed, and may include buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEWM, PLURONICS™ or polyethylene glycol (PEG).

Liposomes containing the IFNA2 variant or IFNA2 fusion protein are prepared by methods known in the art, such as described in Epstein, et al., Proc. Natl. Acad. Sci. USA 82:3688 (1985); Hwang, et al., Proc. Natl Acad. Sci. USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. The active ingredients may also be entrapped in microcapsules prepared, for example, by coacervation techniques or by interfacial polymerization, for example, hydroxymethylcellulose or gelatin-microcapsules and poly (methylmethacrylate) microcapsules, respectively, in colloidal drug delivery systems (for example, liposomes, albumin microspheres, microemulsions, nano-particles and nanocapsules) or in macroemulsions. Such techniques are disclosed in Remington, The Science and Practice of Pharmacy $20^{th}$ Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and 7 ethyl-L-glutamate, nondegradable ethylene-vinyl acetate, degradable lactic acidglycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic IFNA2 variant or IFNA2 fusion protein compositions are generally placed into a container having a sterile access port, for example, an intravenous solution bag or vial having a stopper pierceable by a hypodermic injection needle.

The compositions according to the present invention may be in unit dosage forms such as tablets, pills, capsules, powders, granules, solutions or suspensions, or suppositories, for oral, parenteral, or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from about 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g., Tween™ 20, 40, 60, 80 or 85) and other sorbitans (e.g. Span™ 20, 40, 60, 80 or 85). Compositions with a surface-active agent will conveniently comprise between 0.05 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example glycerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing an IFNA2 variant or IFNA2 fusion protein with Intralipid™ or the components thereof (soy bean oil, egg phospholipids, glycerol and water). Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulizing device or the nebulising device may be attached to a face mask, tent or intermittent positive pressure breathing machine. Solution, suspension or powder compositions may be administered, preferably orally or nasally, from devices which deliver the formulation in an appropriate manner. Kits The invention also provides kits comprising any or all of the IFNA2 variants or IFNA2-fusion proteins described herein. Kits of the invention include one or more containers comprising an IFNA2 variant or IFNA2 fusion protein described herein and instructions for use in accordance with any of the methods of the invention described herein. Generally, these instructions comprise a description of administration of the IFNA2 variant or IFNA2 fusion protein for the above described therapeutic treatments. In some embodiments, kits are provided for producing a single-dose administration unit. In certain embodiments, the kit can contain both a first container having a dried protein and a second container having an aqueous formulation. In certain embodiments, kits containing single and multi-chambered pre-filled syringes (e.g., liquid syringes and lyosyringes) are included.

The instructions relating to the use of an IFNA2 variant or an IFNA2 fusion protein generally include information as to dosage, dosing schedule, and route of administration for the intended treatment. The containers may be unit doses, bulk packages (e.g., multi-dose packages) or sub-unit doses. Instructions supplied in the kits of the invention are typically written instructions on a label or package insert (e.g., a paper sheet included in the kit), but machine-readable instructions (e.g., instructions carried on a magnetic or optical storage disk) are also acceptable.

The kits of this invention are in suitable packaging. Suitable packaging includes, but is not limited to, vials, bottles, jars, flexible packaging (e.g., sealed Mylar or plastic bags), and the like. Also contemplated are packages for use in combination with a specific device, such as an inhaler, nasal administration device (e.g., an atomizer) or an infusion device such as a minipump. A kit may have a sterile access port (for example the container may be an intravenous solution bag or a vial having a stopper pierceable by a hypodermic injection needle). The container may also have a sterile access port (for example the container may be an intravenous solution bag or a vial having a stopper pierceable by a hypodermic injection needle). At least one active agent in the composition is an IFNA2 variant or an IFNA2 fusion protein. The container may further comprise a second pharmaceutically active agent.

Kits may optionally provide additional components such as buffers and interpretive information. Normally, the kit comprises a container and a label or package insert(s) on or associated with the container.

EXAMPLES

The invention is further described in the following examples, which do not limit the scope of the invention described in the claims.

Example 1: Validating IFNA2/IFNAR2 Interaction Network Using AlphaSeq™

Prior to measuring binding affinities of IFNA2 variants against the IFNAR2 receptor, the wild-type IFNA2 and IFNAR2 interactions were validated using the AlphaSeq™ assay for PPI screening. Various construct designs for human, cynomolgus monkey, mouse, and rat IFNA2 and IFNAR2 were designed and constructed into AlphaSeq™ yeast strains. An AlphaSeq™ assay was performed to measure all the pairwise interactions between IFNA2 and IFNAR2 construct designs.

AlphaSeq™ predicted affinities (log 10 Kd nM) for the IFNA2/IFNAR2 validation network are shown in FIG. 1. Strong binding is considered below 3 (dark gray), weak binding is considered between 3 and 4 (medium gray), no detectable binding is considered above 4 (lightest gray).

Strong binding was observed between human IFNA2 to human, cynomolgus, and rat IFNAR2 (AlphaSeq™ Kd<3) and weak binding of human IFNA2 to mouse IFNAR2 (AlphaSeq™ Kd 3.5). For cynomolgus IFNA2 strong binding to human and cynomolgus IFNAR2 (AlphaSeq™ Kd<3), weak binding to rat IFNAR2 (AlphaSeq™ Kd 3.7) and no detectable binding to mouse IFNAR2 (AlphaSeq™ Kd 4.2) was observed. Weak binding of mouse IFNA2 was observed to human and mouse IFNAR2 (AlphaSeq™ Kd<4) and no detectable binding to cynomolgus or rat IFNAR2 (AlphaSeq™ Kd >4). Lastly, rat IFNA2b bound strongly to mouse and rat IFNAR2 (AlphaSeq™ Kd<3) and did not bind human or cynomolgus IFNAR2 (AlphaSeq™ Kd >4).

Example 2: Measuring Binding Affinities of IFNA2 Variants Using AlphaSeq

To identify IFNA2 variants with decreased affinity for human IFNAR2 using AlphaSeq™, a site saturation mutagenesis (SSM) library of IFNA2 was constructed, such that each of the 161 amino acid residues in the displayed protein was mutated to every other amino acid, excluding cysteine. The variant library consisted of 2898 total variant IFNA2 proteins, which was combined with 161 copies of the wild-type IFNA2 sequence, such that the total library consisted of 3059 proteins. These 3059 proteins were synthesized and cloned into yeast display libraries and associated with nucleotide barcodes as described above. Each protein was displayed as a synthetic adhesion protein (SAP) fusion protein to the yeast agglutination factor AGA2 and the c-myc epitope tag.

Using AlphaSeq™, affinity predictions were obtained for interactions between each IFNA2 SSM variant and human, cynomolgus monkey (cyno), mouse, and rat IFNAR2. Variants of interest were those with decreased affinity (higher Kd values) than the wild-type IFNA2/IFNAR2 interaction. In the AlphaSeq™ assay, if a given variant has apparently decreased affinity, this could be due to true detuning—i.e., the affinity between IFNA2 and IFNAR2 is actually decreased—or from a decrease in expression or stability of the particular IFNA2 variant relative to wild-type. For therapeutic applications, the former is preferred. Thus, a parallel assay was performed to measure the surface expression of each displayed IFNA2 variant.

To measure surface expression, the library of variants was labeled with a FITC-conjugated anti-c-myc antibody. Labeled cells were then sorted by FACS into one of three bins—low (bin 1), medium (bin 2), or high (bin 3)—based on fluorescence intensity. Cells expressing higher levels of IFNA2 were expected to be enriched in the high bin and vice versa for those cells expressing lower levels of IFNA2. DNA was extracted from each of the three sorted samples and subjected to deep Illumina™ sequencing at the barcode locus. The number of reads aligning to each barcode was counted for each bin and normalized to the total number of reads in that bin and to the number of reads in the unsorted library, which results in an enrichment score for each barcode in each bin.

Figure 2B:
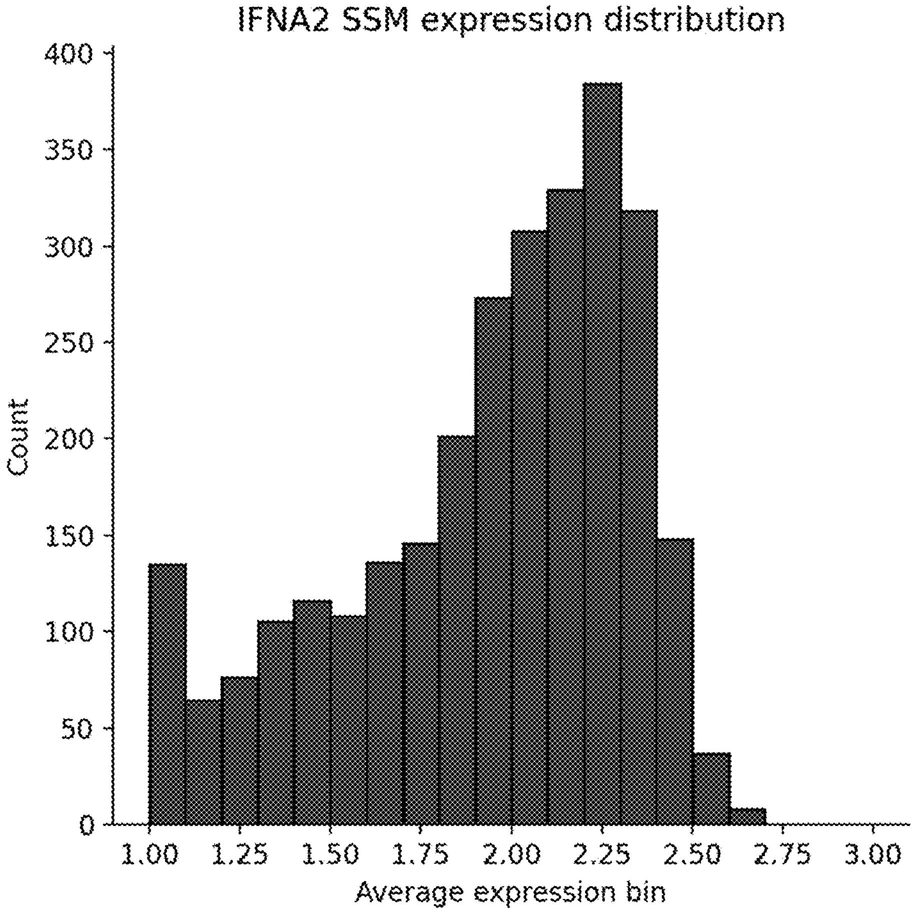
FIG. 2B is a histogram of expression values for site-saturation mutagenesis (SSM) variants of IFNA2. A value of 3 is the maximum possible expression in this assay and a value of 1 is the minimum possible expression.

The enrichment scores for the 3 bins were combined into an expression value using the formula (1*bin1_enrichment+2*bin2_enrichment+3*bin3_enrichment)/(bin1_enrichment+bin2_enrichment+bin3_enrichment). This expression metric is termed the average expression bin for each barcode and returns a value between 1 and 3. Very highly expressing variants (i.e., those with most barcode reads in bin 3) have an average expression bin value approaching 3, while very lowly expressing variants (i.e., those with most reads in bin 1) have a value approaching 1. The average expression bin values for the various barcodes associated with each single IFNA2 variant were combined as a weighted average based on frequency in the unsorted population to obtain a value for each protein. The distribution of average expression bin values for the wild-type copies of IFNA2 are shown in FIG. 2A and the values for the members of the IFNA2 SSM library are shown in FIG. 2B.

Figure 3:
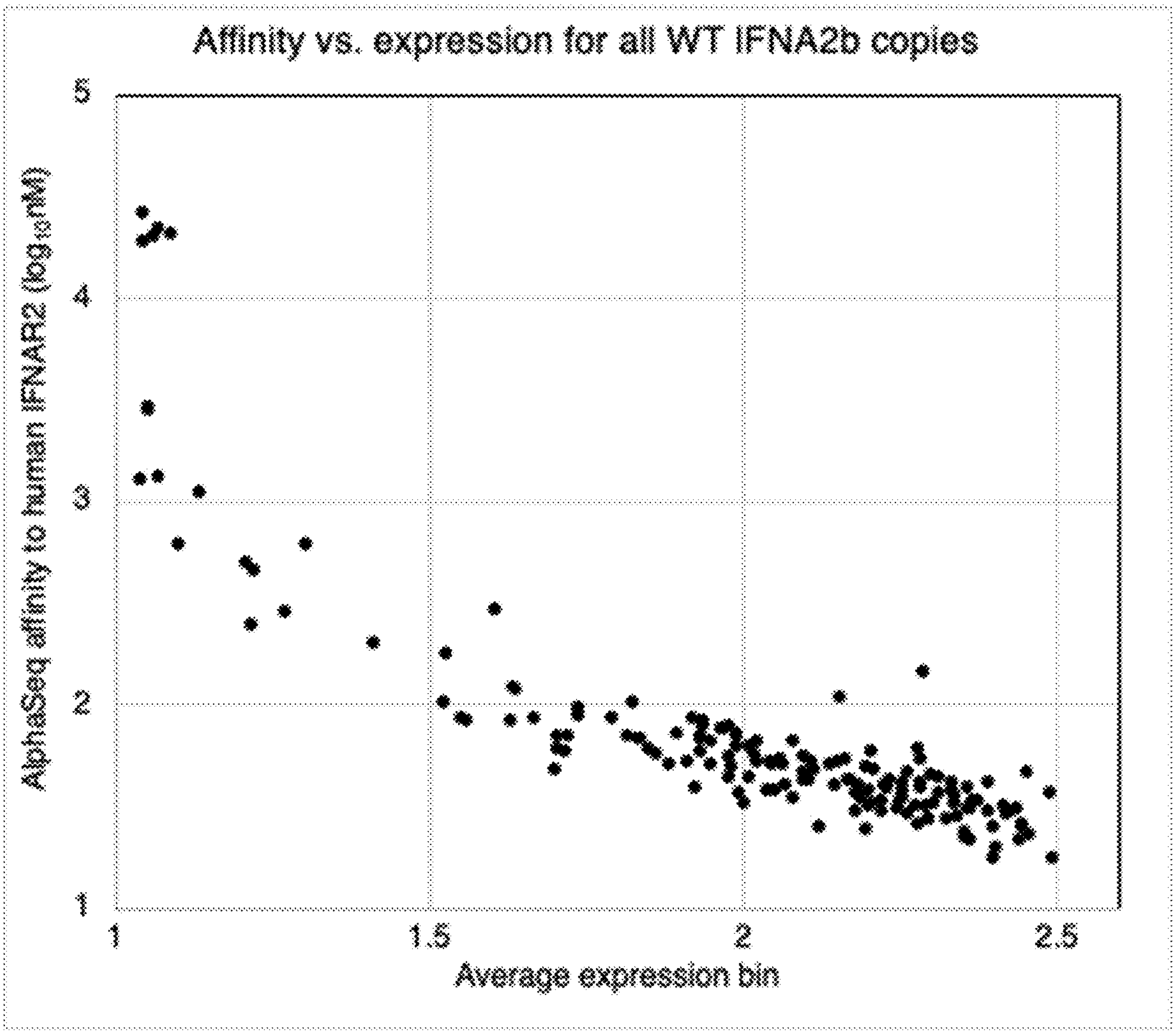
FIG. 3 is a scatter plot showing the relationship between expression (x-axis) and affinity for IFNAR2 in AlphaSeq™ (y-axis) for each wild-type replicate of IFNA2 in the IFNA2 SSM library.

Using the 161 library-encoded copies of wild-type IFNA2, the relationship between expression and AlphaSeq™ affinity to human IFNAR2 was measured. As shown in FIG. 3, this analysis revealed a clear correlation where, as expected, poorly expressing proteins also show weaker binding. Based on this analysis, an average expression bin cutoff of 2.0 was set for selecting detuned IFNA2 variants, since below that expression level, weaker affinity was likely to be dependent on poor expression as opposed to bona fide detuning.

Figure 4A:
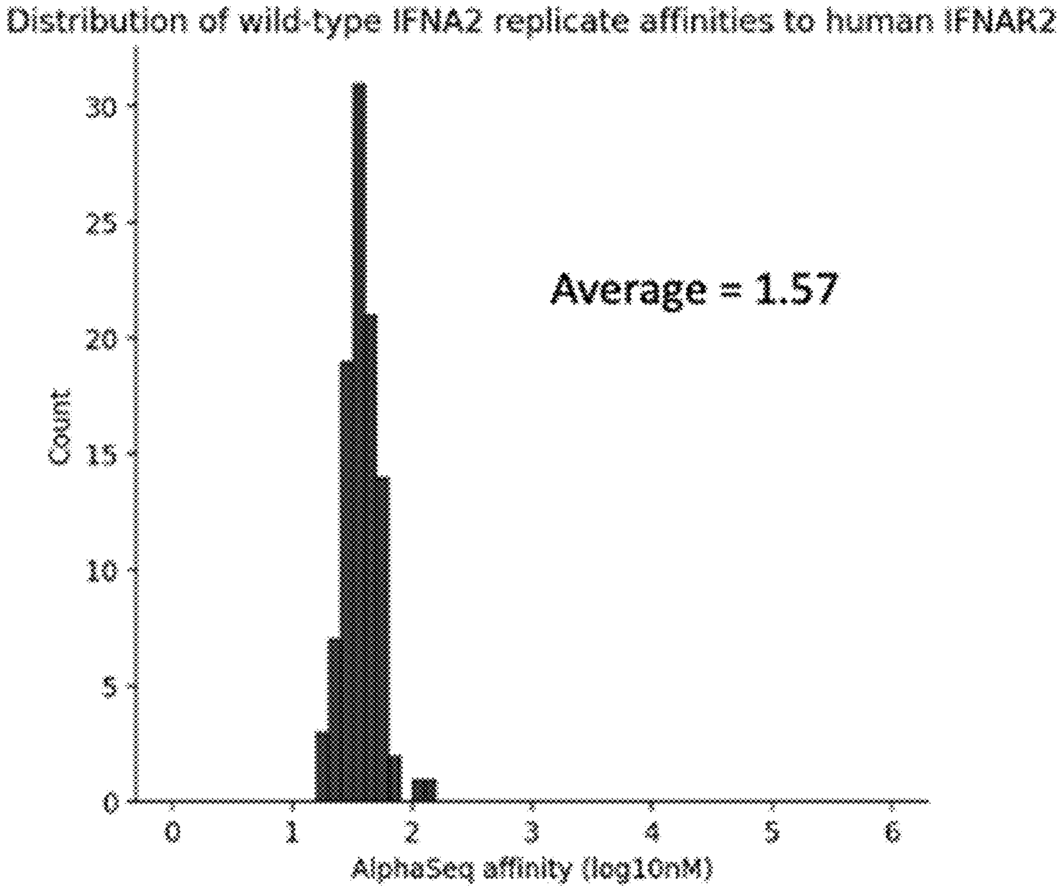
FIG. 4A is a histogram of AlphaSeq™ affinity values for the replicates of wild-type IFNA2 binding to human IFNAR2.
Figure 4B:
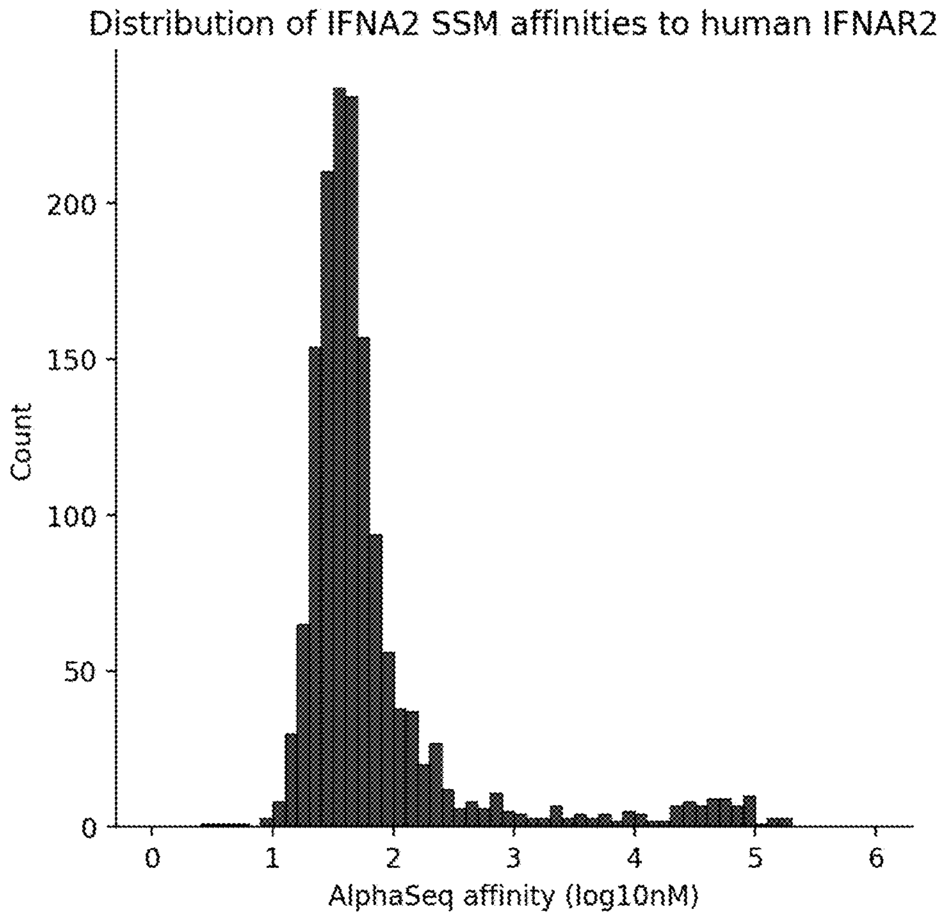
FIG. 4B is a histogram of AlphaSeq™ affinity values for the full IFNA2 SSM binding to human IFNAR2.

After filtering AlphaSeq™ results to include only variants with the average expression bin >2.0, the average affinity between the 161 wild-type IFNA2 replicates and human IFNAR2 was found to be 37 nM ($log_{10}$ nM=1.57 in FIG. 4A). While the 161 wild-type copies of IFNA2 had a tight affinity range centered at 37 nM, the IFNA2 SSM displayed a wide range of affinities to human IFNAR2: most variants bind with wild-type or near-wild-type affinity to IFNAR2, but a range of affinities was observed ranging from minimally detuned (~100 nM Kd/$log_{10}$ nM=2) to background-level binding (~100 uM Kd or weaker/$log_{10}$ nM=4 or greater) (FIG. 4B). Any variant found to bind human IFNAR2 with an affinity weaker than 100 nM ($log_{10}$ nM=2) was designated as "detuned." These detuned IFNA2 variants are listed in Table 1, including affinity to human IFNAR2 (nM) and average expression bin.

Figure 5A:
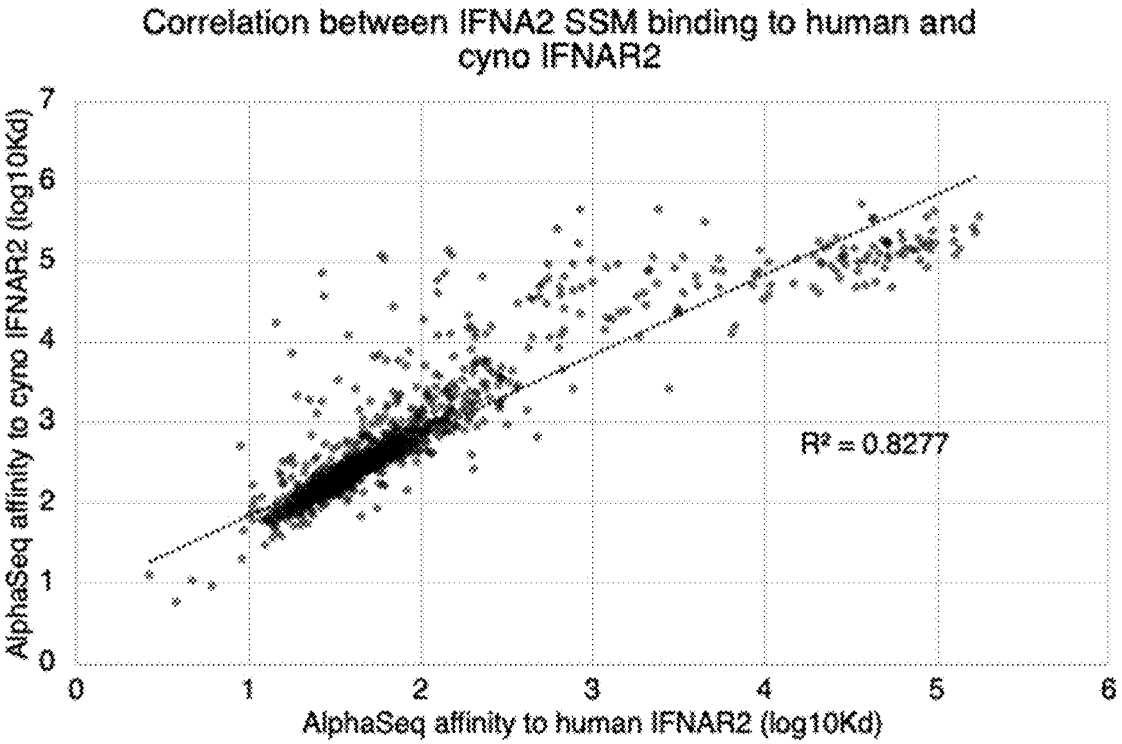
FIG. 5A is a scatter plot showing the relationship between AlphaSeq™ affinity to human IFNAR2 (x-axis) and AlphaSeq™ affinity to cynomolgus IFNAR2 (y-axis) for each variant in the IFNA2 SSM library.
Figure 5B:
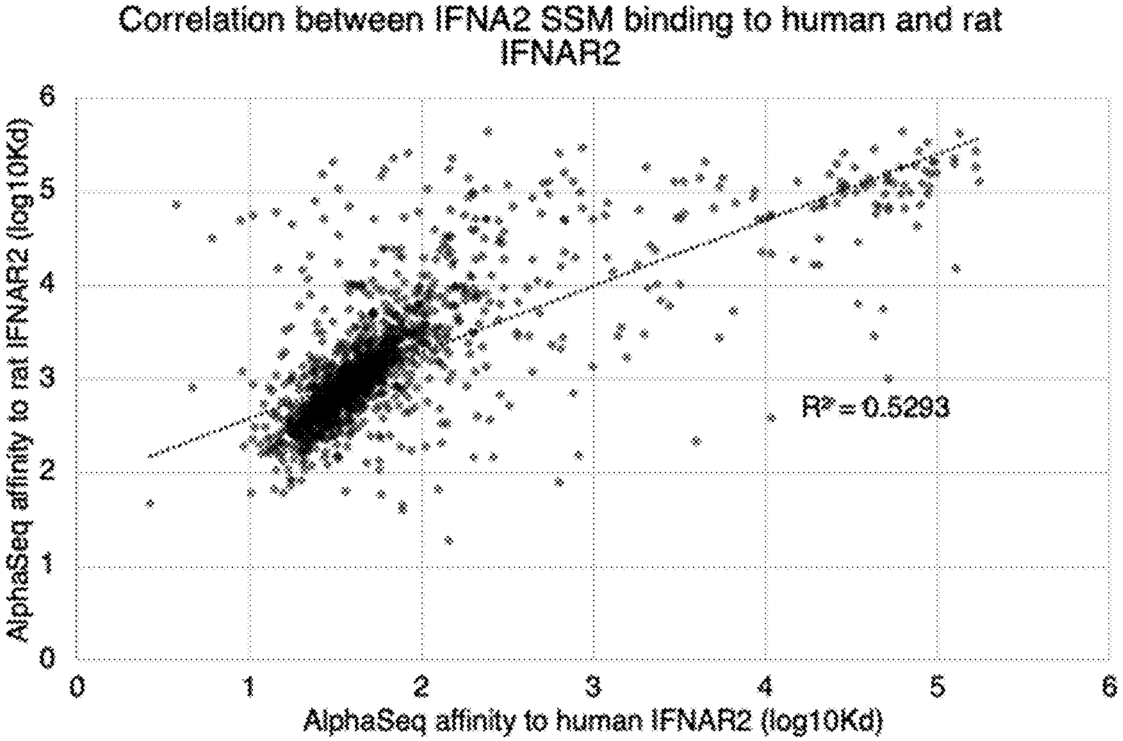
FIG. 5B is a scatter plot showing the relationship between AlphaSeq™ affinity to human IFNAR2 (x-axis) and AlphaSeq™ affinity to rat IFNAR2 (y-axis) for each variant in the IFNA2 SSM library.
Figure 5C:
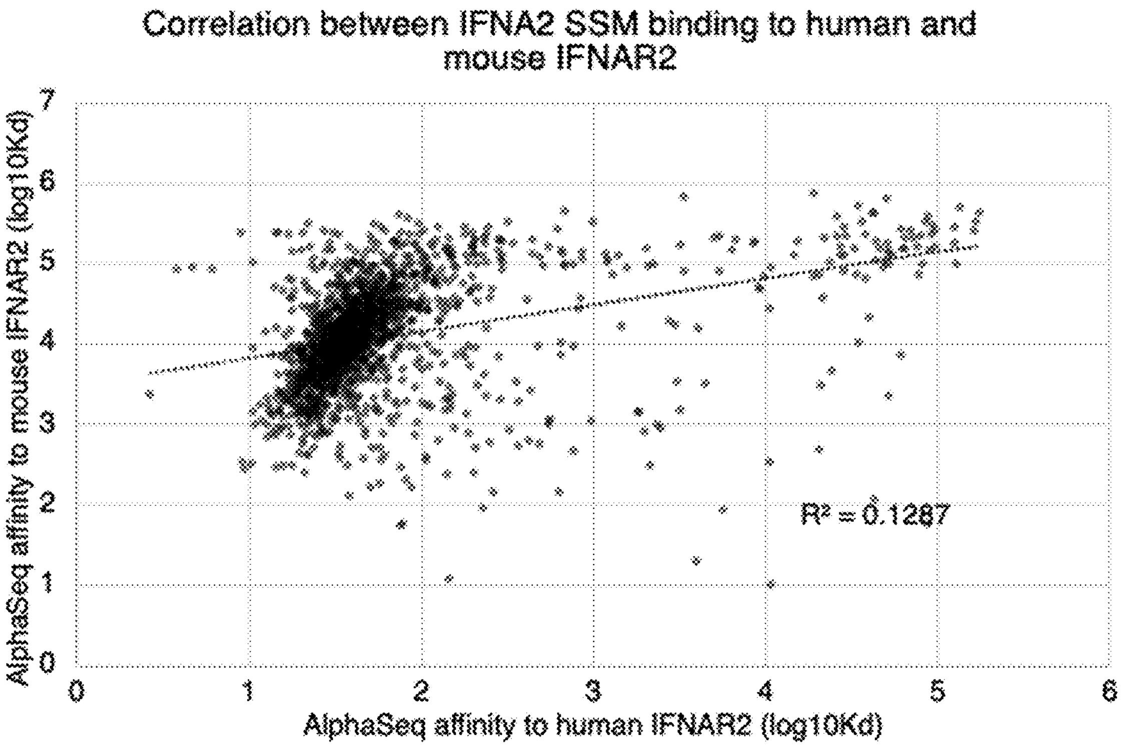
FIG. 5C is a scatter plot showing the relationship between AlphaSeq™ affinity to human IFNAR2 (x-axis) and AlphaSeq™ affinity to mouse IFNAR2 (y-axis) for each variant in the IFNA2 SSM library.

The AlphaSeq™ platform allowed simultaneous measurement of IFNA2 variant affinities to the cynomolgus, rat, and mouse orthologs of IFNAR2. IFNA2 variants showed highly correlated degrees of detuning to human and cynomolgus IFNAR2 (FIG. 5A). Detuning to rat IFNAR2 was moderately correlated with human (FIG. 5B). IFNA2 bound only weakly to mouse IFNAR2, which led to minimal correlation between human detuning and mouse detuning (FIG. 5C).

In addition to the above criteria for identifying all detuned variants, a more selective set of criteria were used for identifying and ranking high-confidence detuned variants for prioritization and further characterization. To qualify for prioritization and further characterization first, >50 diploids must have formed between the IFNA2 variant and human IFNAR2 during the AlphaSeq™ assay. In addition, >2 different substitutions at the specific position in IFNA2 must have given rise to detuning. For a given position, the number of substitutions that led to detuning was termed the "multiplicity" for that position. Preference was also given to variants at positions conserved in cynomolgus, mouse, and rat, as well as variants with similar degrees of detuning in cynomolgus and rat. Identifying variants with similar degrees of detuning in mouse was not possible given the weak interaction between human IFNA2 and mouse IFNAR2. Using these criteria, 12 initial variants were identified that spanned 4 affinity bins ranging from ~300 nM (~10-fold weaker than wild-type) to ~10 μM (~300-fold weaker than wild-type). These variants are described in Table 2.

Figure 6:
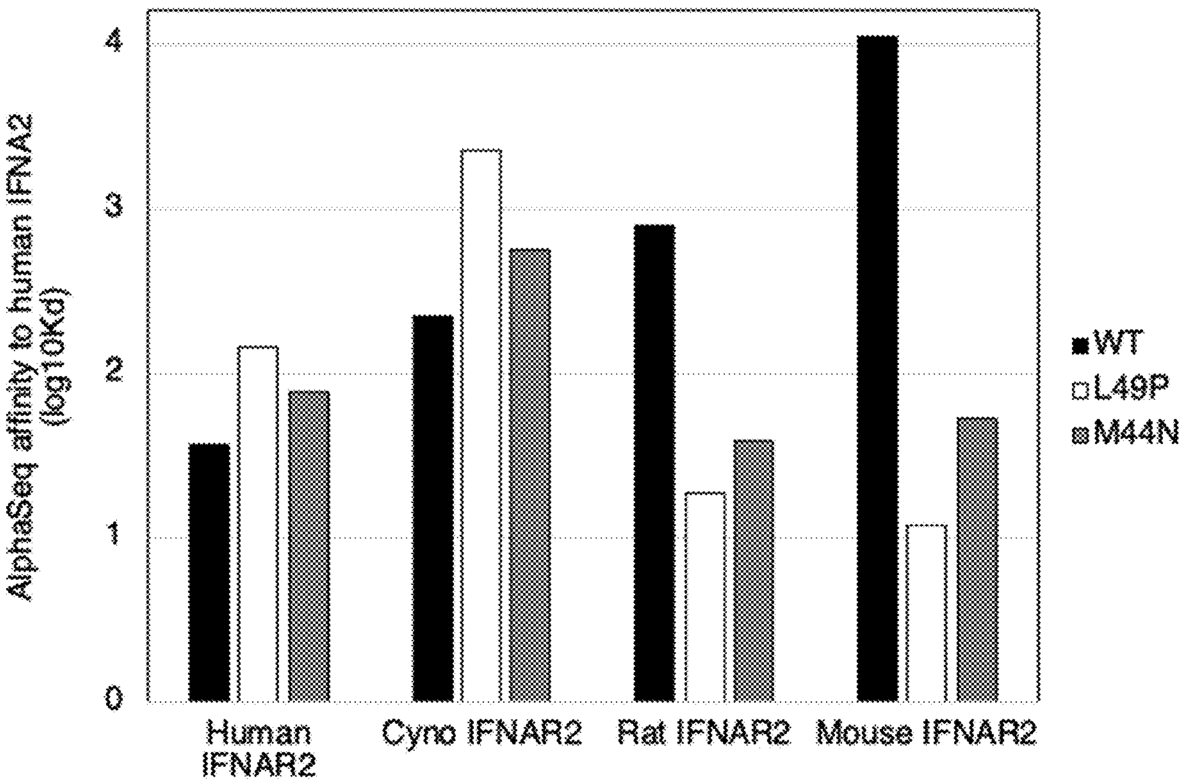
FIG. 6 is a bar graph showing the affinity of wild-type IFNA2 to human, cynomolgus, rat and mouse IFNAR2 (black bars), along with two single mutants that show increased affinity to mouse and rat IFNAR2 (L49P: white bars; M44N: gray bars)

While wild-type IFNA2 bound only weakly to mouse IFNAR2 (FIG. 5C), two IFNA2 variants, L49P and M44N, were identified that bound to mouse IFNAR2 with substantially increased affinity, i.e., substantially decreased Kd values (FIG. 6). To identify IFNA2 variants with detuned affinities to both human and mouse IFNAR2, two further SSM sub-libraries were constructed in which either the L49P or M44N substitution was held constant. These libraries contained SSM mutations only in the second half of the IFNA2 protein, beginning with residue K106. These libraries were subjected to the same expression analysis and filtering as described for the wild-type library above, and IFNA2 variants were identified based on having an average expression bin >2.0 and demonstrating detuning against human IFNAR2, mouse IFNAR2 or both.

Figure 7A:
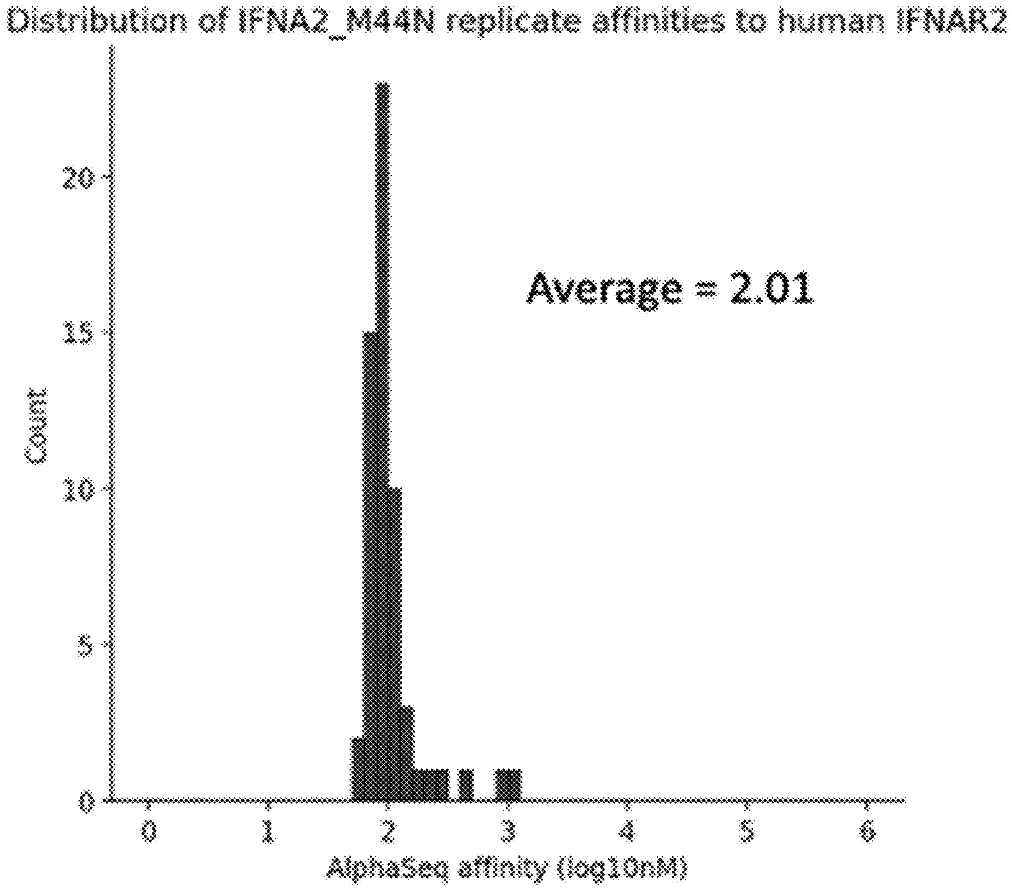
FIG. 7A is a histogram of AlphaSeq™ affinity values for the replicates of IFNA2_M44N binding to human IFNAR2.
Figure 7B:
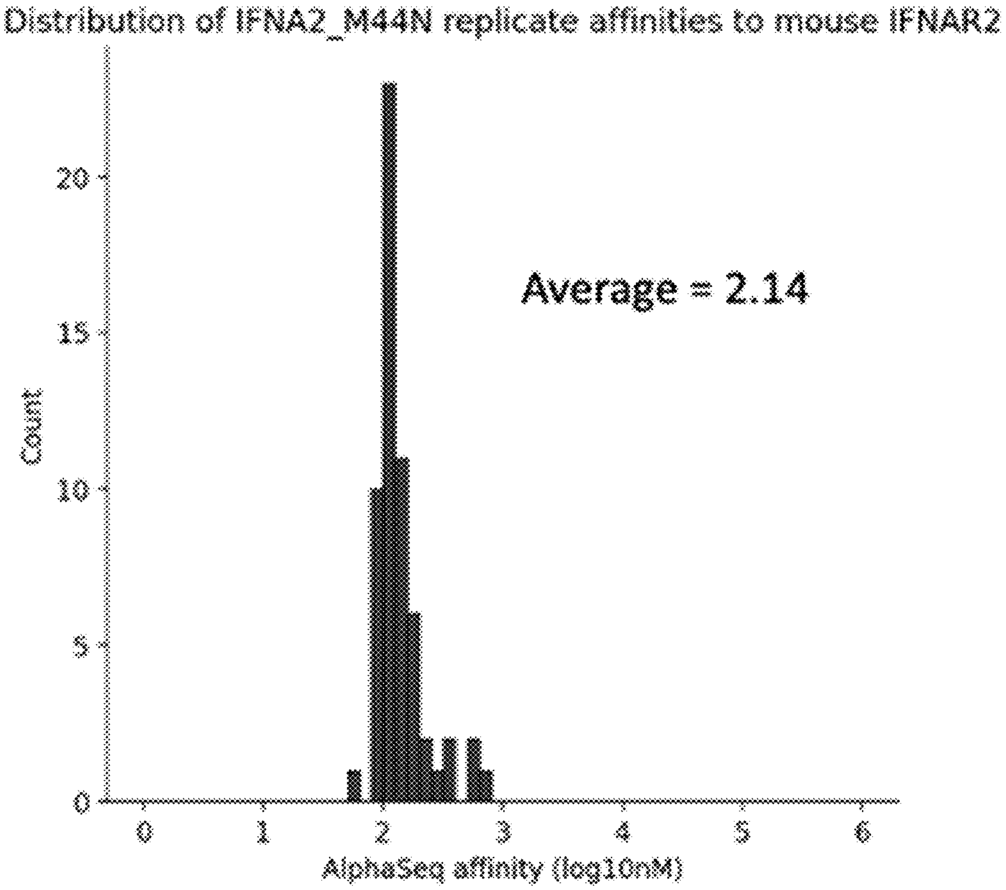
FIG. 7B is a histogram of AlphaSeq™ affinity values for the replicates of IFNA2_M44N binding to mouse IFNAR2.
Figure 7C:
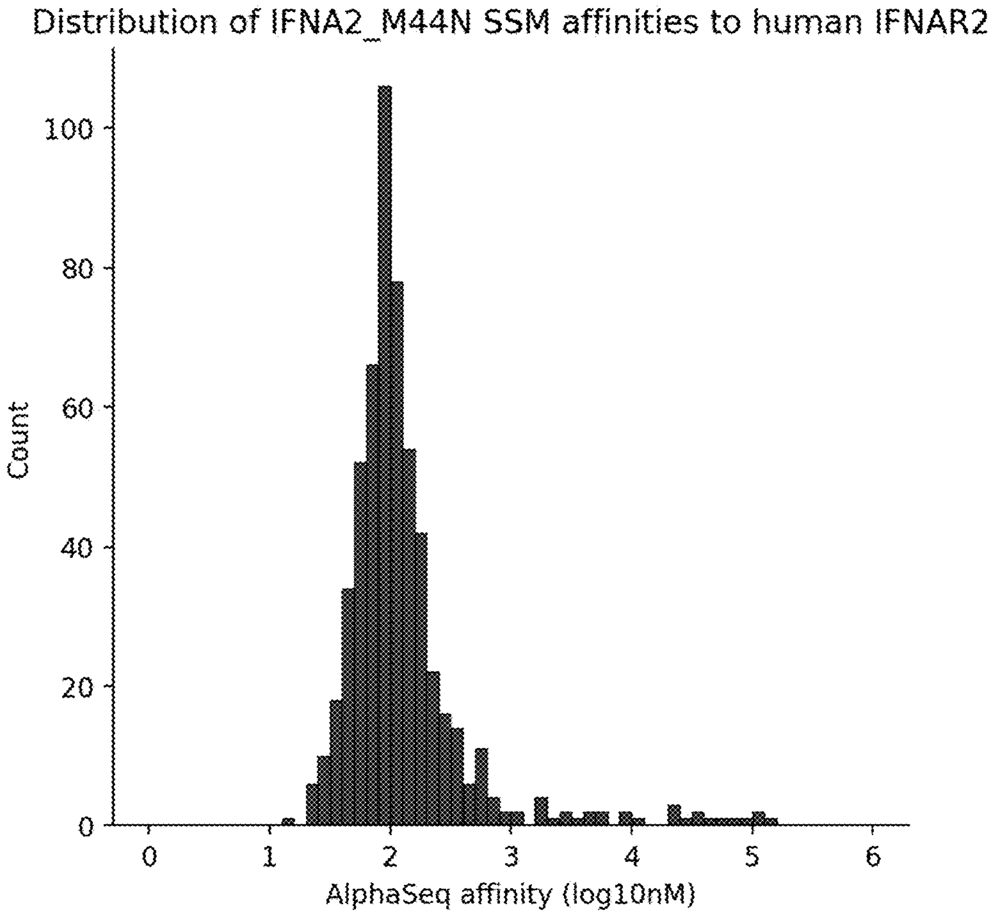
FIG. 7C is histogram of AlphaSeq™ affinity values for the full IFNA2_M44N SSM library binding to human IFNAR2.
Figure 7D:
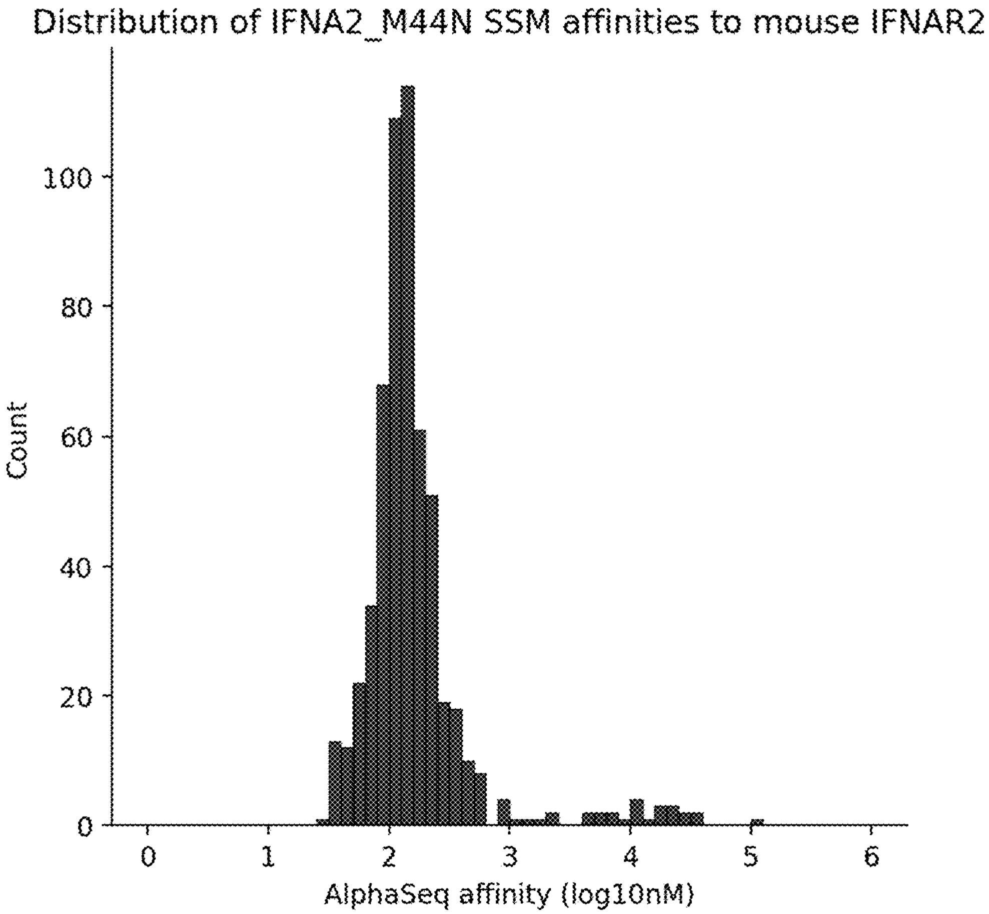
FIG. 7D is a histogram of AlphaSeq™ affinity values for the full IFNA2_M44N SSM library binding to mouse IFNAR2.

IFNA2_M44N bound to human IFNAR2 with an average replicate Kd of 102 nM ($log_{10}$ nM=2.01 in FIG. 7A) and to mouse IFNAR2 with an average replicate Kd of 138 nM ($log_{10}$ nM=2.14 in FIG. 7B). The M44N SSM library demonstrated a range of binding affinities against human and mouse receptors (FIG. 7C, FIG. 7D).

Figure 8A:
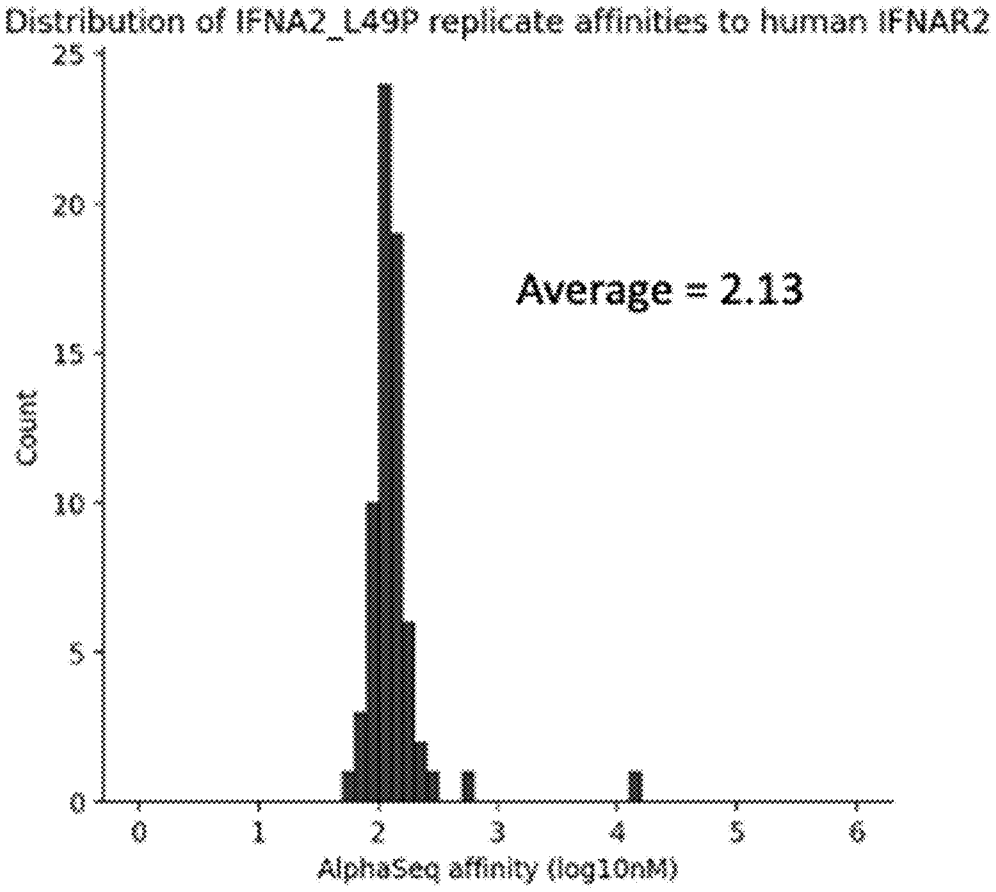
FIG. 8A is a histogram of AlphaSeq™ affinity values for the replicates of IFNA2_L49P binding to human IFNAR2.
Figure 8B:
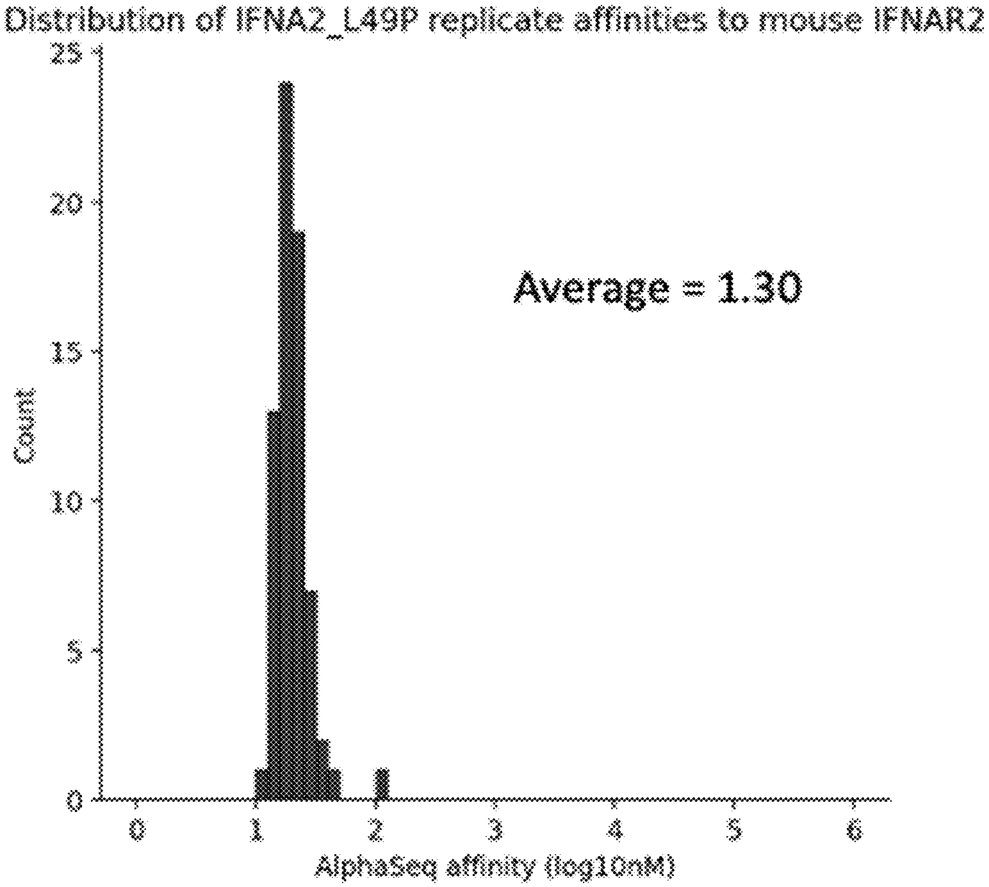
FIG. 8B is a histogram of AlphaSeq™ affinity values for the replicates of IFNA2_L49P binding to mouse IFNAR2.
Figure 8C:
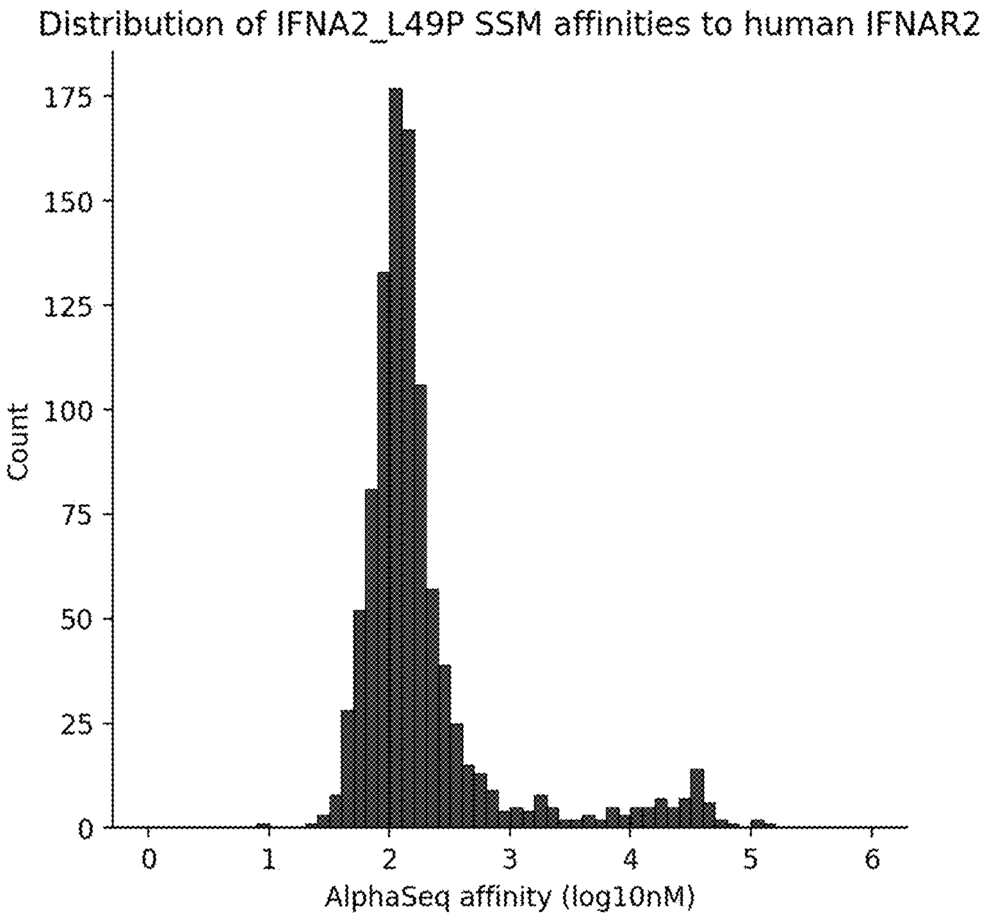
FIG. 8C is histogram of AlphaSeq™ affinity values for the full IFNA2 L49P SSM library binding to human IFNAR2.
Figure 8D:
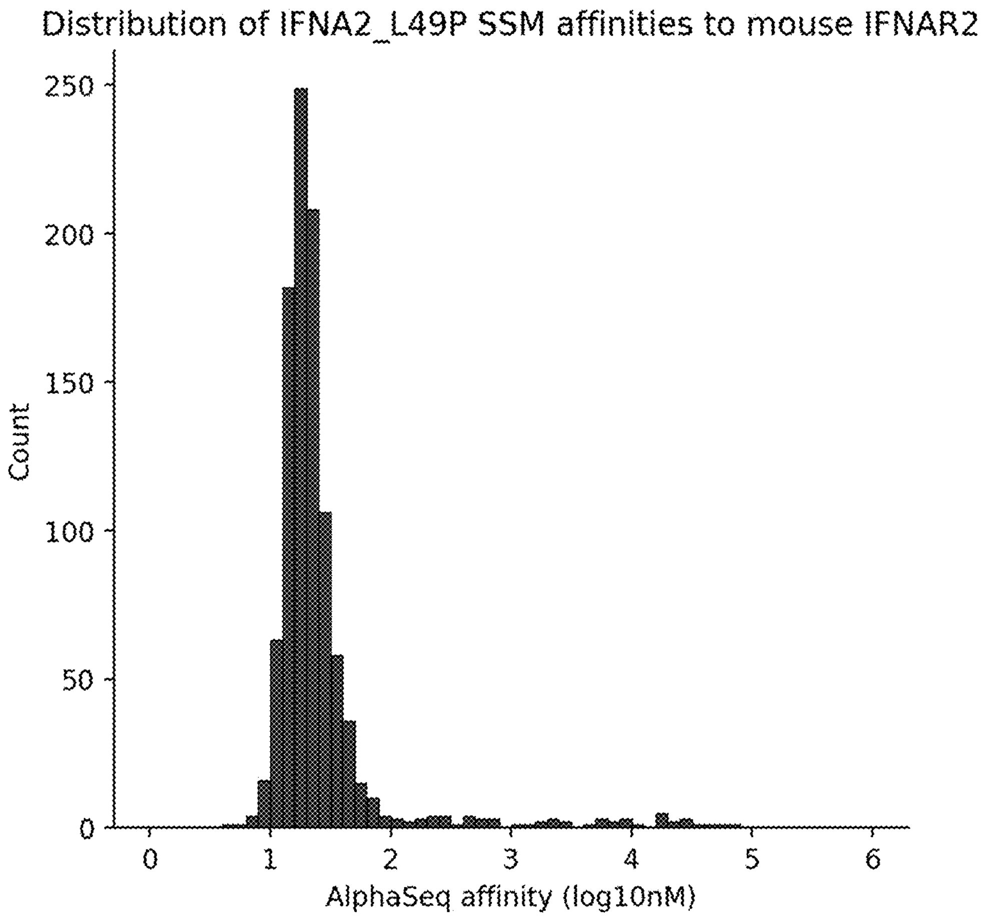
FIG. 8D is a histogram of AlphaSeq™ affinity values for the full IFNA2 L49P SSM library binding to mouse IFNAR2.

IFNA2 L49P bound to human IFNAR2 with an affinity of 135 nM ($log_{10}$ nM=2.13 in FIG. 8A) and to mouse IFNAR2 with an affinity of 20 nM ($log_{10}$ nM=1.30 in FIG. 8B). The L49P SSM library demonstrated a range of binding affinities against human and mouse receptors (FIG. 8C, FIG. 8D).

For both the M44N and L49P SSM libraries, any variant binding to human IFNAR2 with an affinity weaker than 316 nM (~0.5-log weaker than the L49P and M44N single mutants bind to human IFNAR2) was deemed a detuned variant. Because L49P and M44N bound mouse IFNAR2 with significantly different affinities, a different affinity cutoff was used for each sub-library in determining detuned variants: 407 nM in the case of M44N and 63 nM in the case of L49P (~0.5-log weaker than IFNA2_M44N and IFNA2 L49P bound mouse IFNAR2 respectively). From the M44N and L49P libraries, 127 variants were identified with detuned affinity against human IFNAR2 (Table 3), 22 variants were identified with detuned affinity against mouse IFNAR2 (Table 4), and 100 variants were identified with detuned affinity against both mouse and human IFNAR2 (Table 5).

Example 3: Mammalian Protein Expression and Purification of Detuned IFNA2 Variant Fc Fusion Proteins Cytokine variant sequences identified with appropriate AlphaSeq™ expression and affinity bins of interest were nominated for recombinant protein expression. Double stranded DNA fragments coding the identified variant sequence were synthesized by Twist Biosciences which included flanking sequences to facilitate cloning into the pCDNA3.1(+) mammalian cell expression vector. The commercial vector had been modified to encode the human IgG1 Fc sequence containing effectorless function mutations. Variant cytokine insert fragments were cloned into the modified expression vector using Gibson Assembly and transformed into host TOP10 *E. Coli* competent cells. Cytokine sequence of interest was verified by Sanger sequencing. Confirmed sequence plasmid DNA was isolated from bacteria cultures using commercial DNA miniprep kits. The ExpiCHO mammalian cell line was thawed and cultured according to manufacturer instructions. Transient transfection of ExpiCHO cells was performed with detuned cytokine Fc construct DNA according to ExpiCHO transfection kit specifications and cultured supernatants were harvested 7 days later. Cultured supernatants containing proteins of interest were passed through a Protein A column using an AKTA FPLC instrument and eluted with low pH buffer. Purified protein was formulated in 20 mM histidine at pH 6.0 and quantitated using Nanodrop A280 measurements with yields of expression titers reported in Table 6. Table 6 also provides the polypeptide sequences of the IFNA2-Fc fusion proteins as SEQ ID NOs 539-550.

TABLE 6

Protein Expression Yields for IFNA2 Fc Fusion Proteins

| Variant | Expression titers (ug/ml) | Polypeptide Sequence | SEQ ID NO |
|---|---|---|---|
| IFNA2b_ I47P | 45 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRPSLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRAEIMRSFSLSTNLQESLRSKE | 539 |
| IFNA2b_ A168G | 72 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRISLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRGEIMRSFSLSTNLQESLRSKE | 540 |
| IFNA2b_ R172T | 30 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRISLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRAEIMTSFSLSTNLQESLRSKE | 541 |
| IFNA2b_ R46F | 16 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRFISLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRAEIMRSFSLSTNLQESLRSKE | 542 |
| IFNA2b_ S175K | 54 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRISLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRAEIMRSFKLSTNLQESLRSKE | 543 |
| IFNA2b_ M171L | 62 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRISLFSCLKDRHDFGFPQEEF GNQFQKAETIPVLHEMIQQIFNLFSTKDSSAAWDETLLDKF YTELYQQLNDLEACVIQGVGVTETPLMKEDSILAVRKYFQR ITLYLKEKKYSPCAWEVVRAEILRSFSLSTNLQESLRSKE | 544 |
| IFNA2b_ S183W | 78 | DIEPKSSDKTHTCPPCPAPEAAGGPSVFLFPPKPKDTLMIS RTPEVTCVVVDVSHEDPEVKFNWYVDGVEVHNAKTKPREEQ YNSTYRVVSVLTVLHQDWLNGKEYKCKVSNKALGAPIEKTI SKAKGQPREPQVYTLPPSRDELTKNQVSLTCLVKGFYPSDI AVEWESNGQPENNYKTTPPVLDSDGSFFLYSKLTVDKSRWQ QGNVFSCSVMHEALHNHYTQKSLSLSPGKGGGGSGGGGSCD LPQTHSLGSRRTLMLLAQMRRISLFSCLKDRHDFGFPQEEF GNQFQKAETIPVLHEMIQQIFNLFSTKDSSAAWDETLLDKF | 545 |

TABLE 6-continued

Protein Expression Yields for IFNA2 Fc Fusion Proteins

| Variant | Expression titers (ug/ml) | Polypeptide Sequence | SEQ ID NO |
|---|---|---|---|
| | | YTELYQQLNDLEACVIQGVGVTETPLMKEDSILAVRKYFQR<br>ITLYLKEKKYSPCAWEVVRAEIMRSFSLSTNLQEWLRSKE | |
| IFNA2b_<br>N116W | 40 | DIEPKSSDKTHTCPPCPAPEAAGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALGAPIEKTI<br>SKAKGQPREPQVYTLPPSRDELTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSGGGGSCD<br>LPQTHSLGSRRTLMLLAQMRRISLFSCLKDRHDFGFPQEEF<br>GNQFQKAETIPVLHEMIQQIFNLFSTKDSSAAWDETLLDKF<br>YTELYQQLWDLEACVIQGVGVTETPLMKEDSILAVRKYFQR<br>ITLYLKEKKYSPCAWEVVRAEIMRSFSLSTNLQESLRSKE | 546 |
| IFNA2b_<br>F50G | 54 | DIEPKSSDKTHTCPPCPAPEAAGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALGAPIEKTI<br>SKAKGQPREPQVYTLPPSRDELTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSGGGGSCD<br>LPQTHSLGSRRTLMLLAQMRRISLGSCLKDRHDFGFPQEEF<br>GNQFQKAETIPVLHEMIQQIFNLFSTKDSSAAWDETLLDKF<br>YTELYQQLNDLEACVIQGVGVTETPLMKEDSILAVRKYFQR<br>ITLYLKEKKYSPCAWEVVRAEIMRSFSLSTNLQESLRSKE | 547 |
| IFNA2b_<br>M82G | 4 | DIEPKSSDKTHTCPPCPAPEAAGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALGAPIEKTI<br>SKAKGQPREPQVYTLPPSRDELTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSGGGGSCD<br>LPQTHSLGSRRTLMLLAQMRRISLFSCLKDRHDFGFPQEEF<br>GNQFQKAETIPVLHEGIQQIFNLFSTKDSSAAWDETLLDKF<br>YTELYQQLNDLEACVIQGVGVTETPLMKEDSILAVRKYFQR<br>ITLYLKEKKYSPCAWEVVRAEIMRSFSLSTNLQESLRSKE | 548 |
| IFNA2b_<br>F61G | 104 | DIEPKSSDKTHTCPPCPAPEAAGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALGAPIEKTI<br>SKAKGQPREPQVYTLPPSRDELTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSGGGGSCD<br>LPQTHSLGSRRTLMLLAQMRRISLFSCLKDRHDFGGPQEEF<br>GNQFQKAETIPVLHEMIQQIFNLFSTKDSSAAWDETLLDKF<br>YTELYQQLNDLEACVIQGVGVTETPLMKEDSILAVRKYFQR<br>ITLYLKEKKYSPCAWEVVRAEIMRSFSLSTNLQESLRSKE | 549 |
| IFNA2b_<br>R185D | 51 | DIEPKSSDKTHTCPPCPAPEAAGGPSVFLFPPKPKDTLMIS<br>RTPEVTCVVVDVSHEDPEVKFNWYVDGVEVHNAKTKPREEQ<br>YNSTYRVVSVLTVLHQDWLNGKEYKCKVSNKALGAPIEKTI<br>SKAKGQPREPQVYTLPPSRDELTKNQVSLTCLVKGFYPSDI<br>AVEWESNGQPENNYKTTPPVLDSDGSFFLYSKLTVDKSRWQ<br>QGNVFSCSVMHEALHNHYTQKSLSLSPGKGGGGSGGGGSCD<br>LPQTHSLGSRRTLMLLAQMRRISLFSCLKDRHDFGFPQEEF<br>GNQFQKAETIPVLHEMIQQIFNLFSTKDSSAAWDETLLDKF<br>YTELYQQLNDLEACVIQGVGVTETPLMKEDSILAVRKYFQR<br>ITLYLKEKKYSPCAWEVVRAEIMRSFSLSTNLQESLDSKE | 550 |

Figure 9:
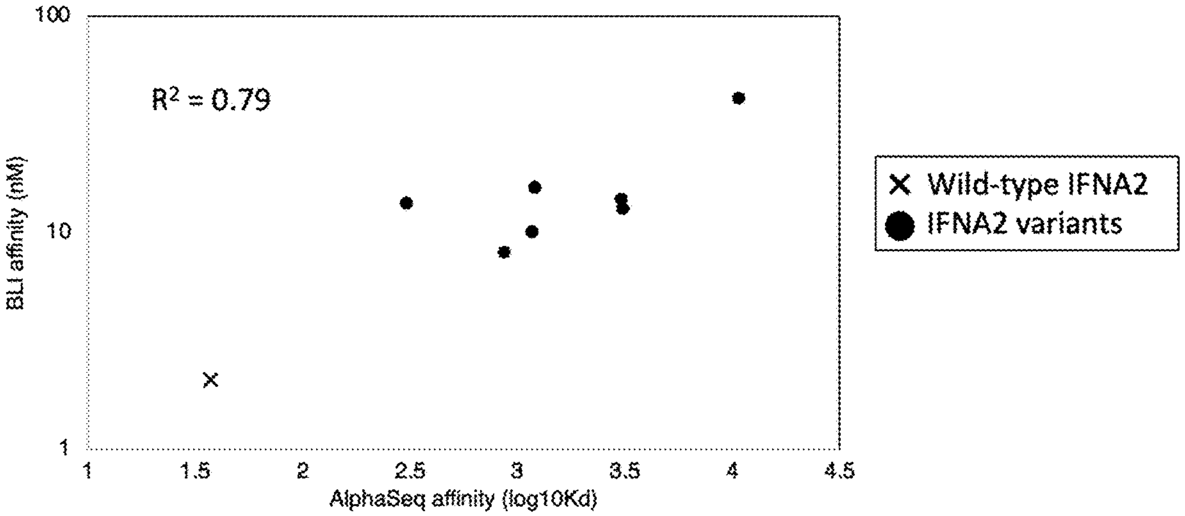
FIG. 9 is a scatter plot showing the relation between AlphaSeq™ affinity values and Kd rates measured by bio-layer interferometry (BLI) for a subset of IFNA2 variants binding to wild-type human IFNAR2.

Example 4: Biolayer Interferometry Affinity Determination of Detuned IFNA2 Variant Fc Fusion Proteins The binding kinetics for IFNA2 variant Fc fusion proteins was determined by bio-layer interferometry analysis on a Gator Prime instrument. This assay was performed by immobilizing commercially available recombinant human IFNalpha-beta R2, his tag (Acro Biosystems) to anti-His biosensors (Gator). Protein A purified IFNA2 variant Fc fusion proteins association to and dissociation from the immobilized IFNalpha-beta R2 was observed at the following dilution range (164 nM, 54 nM, 18 nM, 6 nM, 2 nM, 0.6 nM, and 0.2 nM) for all variants observed. Specifically, anti-his probes were hydrated in kinetics buffer (1×PBS with 0.2% BSA and 0.02% Tween-20) for 10 minutes and IFNalpha-beta R2, his tag antigen was immobilized to the anti-his probe for 180 seconds. Association was observed by placing probes with immobilized antigen into wells containing IFNA2 variant Fc fusion proteins for 60 seconds. Dissociation was measured after transferring the biosensors into wells containing only kinetics buffer for 60 seconds. All assay steps were performed with shaking at 1000 rpm at 30° C. Affinity constant (KD) analysis for this assay were determined using the Gator software provided from the manufacturer using data points collected from 60 seconds of the association step and the first 20 seconds of dissociation step, using a 1:1 global binding fit. Results of the kinetic studies are presented in Table 7. The bio-layer interferometry affinity measurements were highly correlated with AlphaSeq™ affinity measurements (FIG. 9).

TABLE 7

Affinity Determination of IFNA2 Fc Fusion Proteins

| Variant | KD affinity (nM) |
|---|---|
| IFNA2b_I47P | na |
| IFNA2b_A168G | 41.9 |
| IFNA2b_R172T | na |
| IFNA2b_R46F | na |
| IFNA2b_S175K | 12.9 |
| IFNA2b_M171L | 14.3 |
| IFNA2b_S183W | 16.2 |
| IFNA2b_N116W | 10.1 |
| IFNA2b_F50G | 8.13 |
| IFNA2b_M82G | na |
| IFNA2b_F61G | 13.7 |
| IFNA2b_R185D | na |
| IFNA2b_WT | 2.11 |

Example 5: pSTAT1 T Cell Signaling Potency Determination of Detuned IFNA2 Variant Fc Fusion Proteins Successfully expressed IFNA2 Fc fusion variant signaling potency in primary human PBMCs was determined using a phosphorylated STAT1 flow cytometry assay (pSTAT1 phosflow). Previously frozen human PBMCs (Bloodworks-Bio) were thawed and counted to determine cell number and viability. Cell concentration was adjusted to 2 million viable human PBMC/ml and 100 μl was plated in round-well bottom 96 well tissue culture plates for a total of 200,000 cells per well. A 2X working stock of wild-type and variant IFNA2 Fc fusion proteins was prepared at a concentration of 2 μM before performing an five point serial dilution using 1:10 dilutions. 100 μl of the 2× titrated cytokines were added to 100 μl of human PBMC and the cells were cultured for 30 minutes. Cytokine signaling was stopped by the addition of 50 μl of 4% paraformaldehyde for an additional 30 minutes.

Cells were centrifuged and washed with PBS/1% BSA followed by resuspension in ice cold methanol to permeabilize cells. After 30 minutes, cells were washed twice in PBS/1% BSA before resuspending in 50 μl PBS/1% BSA containing human Fc block (ThermoFisher) at recommended concentration. Cells were incubated on ice for 20 minutes and staining antibody panel was prepared.

Figure 10:
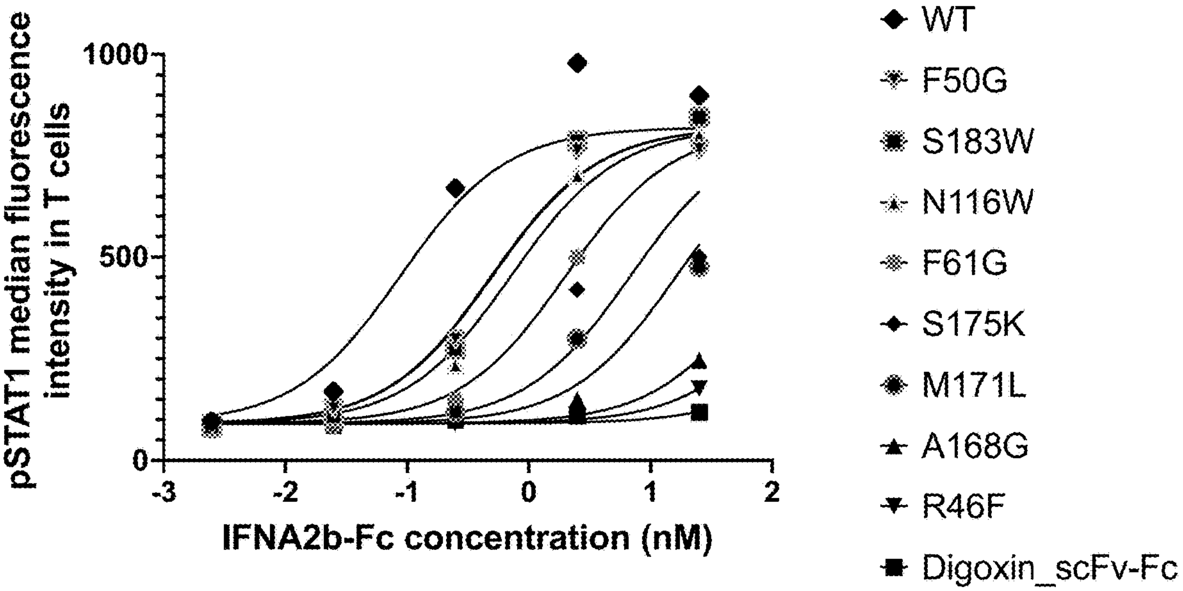
FIG. 10 is a graph that shows STAT1 phosphorylation (pSTAT1) in human peripheral blood mononuclear cells stimulated with IFNA2 variants or a negative control protein (Digoxin_scFv-Fc). Plotted is the median fluorescence intensity (MFI) of pSTAT1 in T cells. Dose-response curves were analyzed for EC50 calculations.
Figure 11:
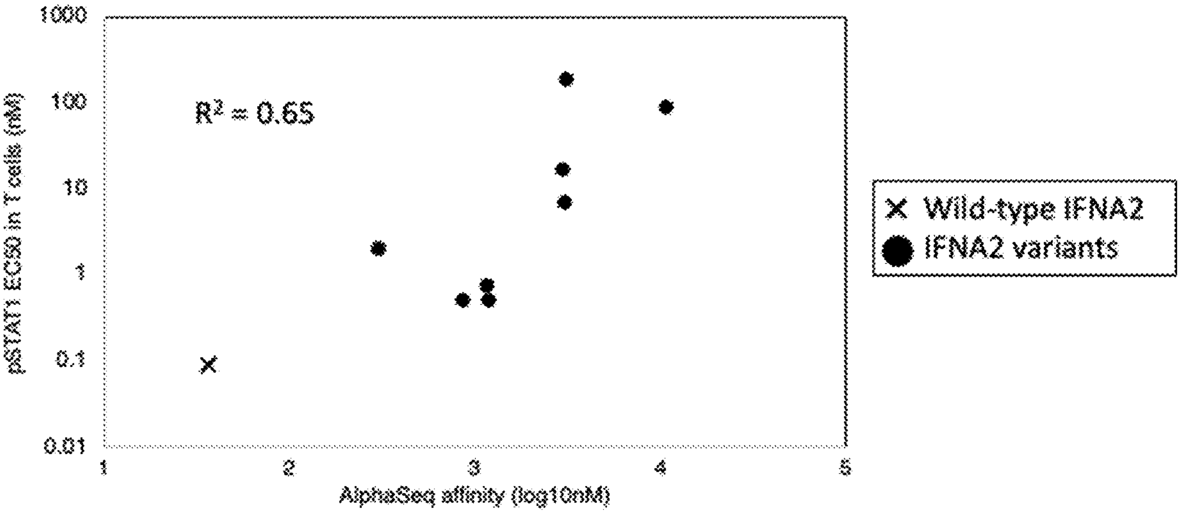
FIG. 11 is a scatter plot showing the relation between AlphaSeq™ affinity values and pSTAT1 EC50 in T cells, calculated from the dose-response curves shown in FIG. 10.

Anti-human CD14-BV421, anti-human CD20-PE, anti-human CD3-PECy5, and anti-human CD4-e450 were added to cells at recommended concentrations in an addition 50 μl volume. Cells were stained with antibodies for 30 minutes before washing twice with PBS/1% BSA and analyzing on a ZE5 (Biorad) flow cytometer. Data was analyzed using Flowjo software and EC50 potency curves determined using Graphpad Prism and reported in Table 8 and FIG. 10. The potency determined by STAT1 phosphorylation flow cytometry showed a strong correlation with affinity measurements between IFNA2 variants and IFNAR2 in AlphaSeq™. (FIG. 11)

TABLE 8

Signaling Potency Determination of IFNA2 Fc Fusion Proteins in Primary Human PBMCs

| Variant | EC50 in T cells (nM) |
|---|---|
| IFNA2b_WT | 0.08891 |
| IFNA2b_A168G | 88.01 |
| IFNA2b_R46F | 185.8 |
| IFNA2b_S175K | 6.923 |
| IFNA2b_M171L | 16.5 |
| IFNA2b_S183W | 0.5114 |
| IFNA2b_N116W | 0.7271 |
| IFNA2b_F50G | 0.5013 |
| IFNA2b_F61G | 2.035 |

Table 8 shows EC50 values for a subset of IFNA2-Fc fusion proteins as measured by phosphorylation of STAT1 in a phospho-specific flow cytometry assay. EC50 was measured in T cells (CD3+). IFNA2 variants showed a range of EC50 values, with the weakest variant (R46F) being ~2000-fold less potent than wild-type (185.8 nM vs. 0.0889 nM).

Example 6: IFNA2 Detuned Variant Candidate Immunocytokine Generation and Characterization Lead IFNA2 variants displaying a range of correlated affinity and potency are selected for antibody fusion to generate immunocytokine candidates by cloning into modified pCDNA3.4 vector encoding scFv sequence that binds to CD8 and is fused to the same effectorless Fc described previously. IFNA2 immunocytokines are produced in ExpiCHO and are purified as described in Example 3. IFNA2 immunocytokine affinity and potency are determined as shown in Example 4 and Example 5, respectively. Detuned IFNA2 immunocytokine candidates that demonstrate cell specific signaling in CD8 cells with greatly reduced signaling in CD4 and other immune subsets are selected for further in vivo characterization.

Example 7: Mouse Syngeneic Tumor Modeling Efficacy Study with IFNA2 Immunocytokines Lead immunocytokine candidates are produced in ExpiCHO cells as before and purified proteins formulated in physiological buffer. Balb/c mice are implanted with 1 million CT26 colorectal carcinoma cells subcutaneously in the flank of the mice and tumor volume growth is measured with hand calipers. Dosing with IFNA2 detuned immunoctyokine commences when tumor volume reaches 100 mm3. 1 ug/kg immunocytokine is administered intravenously weekly for 3 weeks and tumor volumes are measured every three days. Mice are euthanized when tumor volumes exceed 2000 mm3. Percent tumor growth inhibition is calculated by dividing experimental tumor volumes by the average tumor volume of saline treated mice and multiplying by 100.

Example 8: Detuned IFNA2 Immunocytokines Exhibit Increased Potency on CD8 T Cells Lead IFNA2 variants displaying a range of correlated affinity as measured by AlphaSeq™ and potency were selected for antibody fusion to generate immunocytokine candidates by cloning into a modified pCDNA3.4 vector encoding scFv sequence that binds to CD8 and is fused to a human IgG1 effectorless Fc region. The expression vector therefore encoded IFNA2-anti-CD8 fusion proteins comprising an anti-CD8 antibody and each lead IFNA2 variant. Immunocytokines were produced in ExpiCHO cells and purified as described above in Example 3. Affinity constants ($K_D$) for IFNA2-anti-CD8 (IFNA2-aCD8) fusion proteins binding to IFNalpha-beta R2 (IFNAR2) were determined using BLI as described above in Example 4. Results of the kinetic studies are presented in Table 9. As was the case for IFNA2-Fc fusion proteins, the variant IFNA2 proteins in the context of IFNA2-anti-CD8 fusion proteins demonstrated a range of affinities to IFNAR2. Table 9 also provides the polypeptide sequences of the IFNA2-aCD8 fusion proteins as SEQ ID NOs 551-559.

TABLE 9

Affinity Determination of IFNA2-aCD8 Fusion proteins

| Variant | $K_D$ affinity (nM) | Polypeptide Sequence | SEQ ID NO |
|---|---|---|---|
| IFNA2b_ WT | $K_{off}$ below limit of detection | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFSLSTNLQESLRSKE | 551 |
| IFNA2b_ I47P | 5.16 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKENWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVESCS<br>VMHEALHNHYTQKSLSLSPGKGGGGSGGGGSCDLPQTHSLG<br>SRRTLMLLAQMRRPSLFSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFSLSTNLQESLRSKE | 552 |
| IFNA2b_ R172T | 4.56 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMTSFSLSTNLQESLRSKE | 553 |
| IFNA2b_ S175K | 0.93 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRESGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGFPQEEFGNQFQKAE | 554 |

TABLE 9-continued

Affinity Determination of IFNA2-aCD8 Fusion proteins

| Variant | $K_D$ affinity (nM) | Polypeptide Sequence | SEQ ID NO |
|---|---|---|---|
| | | TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFKLSTNLQESLRSKE | |
| IFNA2b_ M171L | 5.93 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKENWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEILRSFSLSTNLQESLRSKE | 555 |
| IFNA2b_ S183W | $K_{off}$ below limit of detection | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFSLSTNLQEWLRSKE | 556 |
| IFNA2b_ F50G | 0.40 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVESCS<br>VMHEALHNHYTQKSLSLSPGKGGGGSGGGGSCDLPQTHSLG<br>SRRTLMLLAQMRRISLGSCLKDRHDFGFPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFSLSTNLQESLRSKE | 557 |
| IFNA2b_ F61G | 1.96 | EVQLVESGGGLVQPGGSLRLSCAASGFNIKDTYIHFVRQAP<br>GKGLEWIGRIDPANDNTLYASKFQGKATISADTSKNTAYLQ<br>MNSLRAEDTAVYYCGRGYGYYVFDHWGQGTLVTVSSGGGGS<br>GGGGSGGGGSDVQITQSPSSLSASVGDRVTITCRTSRSISQ<br>YLAWYQQKPGKVPKLLIYSGSTLQSGVPSRFSGSGSGTDFT<br>LTISSLQPEDVATYYCQQHNENPLTFGGGTKVEIKEPKSSD<br>KTHTCPPCPAPEAAGGPSVFLFPPKPKDTLMISRTPEVTCV<br>VVDVSHEDPEVKFNWYVDGVEVHNAKTKPREEQYNSTYRVV<br>SVLTVLHQDWLNGKEYKCKVSNKALGAPIEKTISKAKGQPR<br>EPQVYTLPPSRDELTKNQVSLTCLVKGFYPSDIAVEWESNG<br>QPENNYKTTPPVLDSDGSFFLYSKLTVDKSRWQQGNVFSCS<br>VMHEALHNHYTQKSLSLSPGKGGGGSGGGGSCDLPQTHSLG<br>SRRTLMLLAQMRRISLFSCLKDRHDFGGPQEEFGNQFQKAE<br>TIPVLHEMIQQIFNLFSTKDSSAAWDETLLDKFYTELYQQL<br>NDLEACVIQGVGVTETPLMKEDSILAVRKYFQRITLYLKEK<br>KYSPCAWEVVRAEIMRSFSLSTNLQESLRSKE | 558 |

TABLE 9-continued

Affinity Determination of IFNA2-aCD8 Fusion proteins

| Variant | $K_D$ affinity (nM) | Polypeptide Sequence | SEQ ID NO |
|---|---|---|---|
| IFNA2b_ R185D | 0.50 | EVQLVESGGGLVQPGGSLRLSCAASGENIKDTYIHFVRQAP GKGLEWIGRIDPANDNTLYASKFQGKATISADTSKNTAYLQ MNSLRAEDTAVYYCGRGYGYYVFDHWGQGTLVTVSSGGGGS GGGGSGGGGSDVQITQSPSSLSASVGDRVTITCRTSRSISQ YLAWYQQKPGKVPKLLIYSGSTLQSGVPSRFSGSGSGTDFT LTISSLQPEDVATYYCQQHNENPLTFGGGTKVEIKEPKSSD KTHTCPPCPAPEAAGGPSVFLFPPKPKDTLMISRTPEVTCV VVDVSHEDPEVKENWYVDGVEVHNAKTKPREEQYNSTYRVV SVLTVLHQDWLNGKEYKCKVSNKALGAPIEKTISKAKGQPR EPQVYTLPPSRDELTKNQVSLTCLVKGFYPSDIAVEWESNG QPENNYKTTPPVLDSDGSFFLYSKLTVDKSRWQQGNVFSCS VMHEALHNHYTQKSLSLSPGKGGGGSGGGGSCDLPQTHSLG SRRTLMLLAQMRRISLFSCLKDRHDFGFPQEEFGNQFQKAE TIPVLHEMIQQIFNLFSTKDSSAAWDETLLDKFYTELYQQL NDLEACVIQGVGVTETPLMKEDSILAVRKYFQRITLYLKEK KYSPCAWEVVRAEIMRSFSLSTNLQESLDSKE | 559 |

Figure 12:
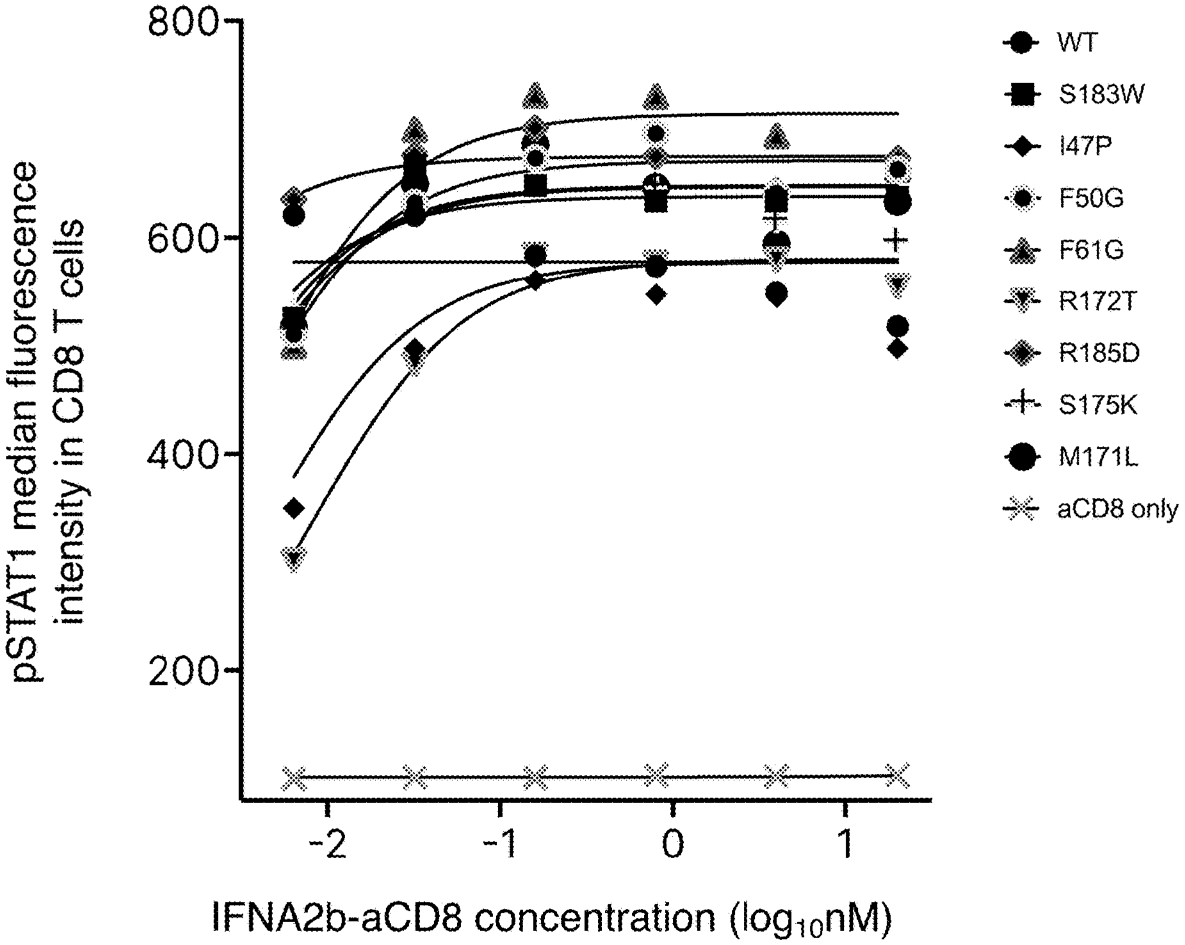
FIG. 12 is a graph of the dose-response curves for STAT1 phosphorylation as measured by flow cytometry for candidate IFNA2b immunocytokines in CD8 T cells.
Figure 13:
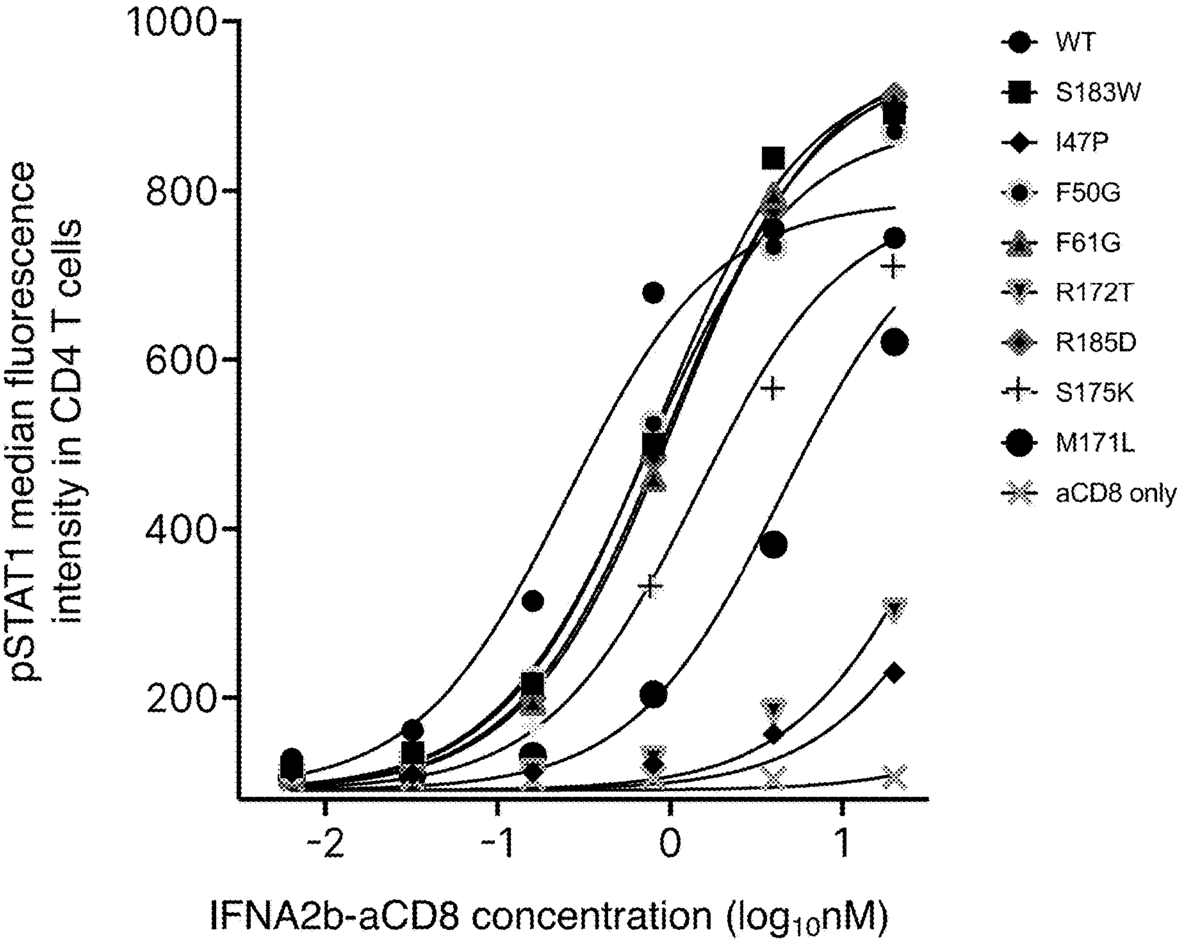
FIG. 13 is a graph of the dose-response curves for STAT1 phosphorylation as measured by flow cytometry for candidate IFNA2b immunocytokines in CD4 T cells.
Figure 14:
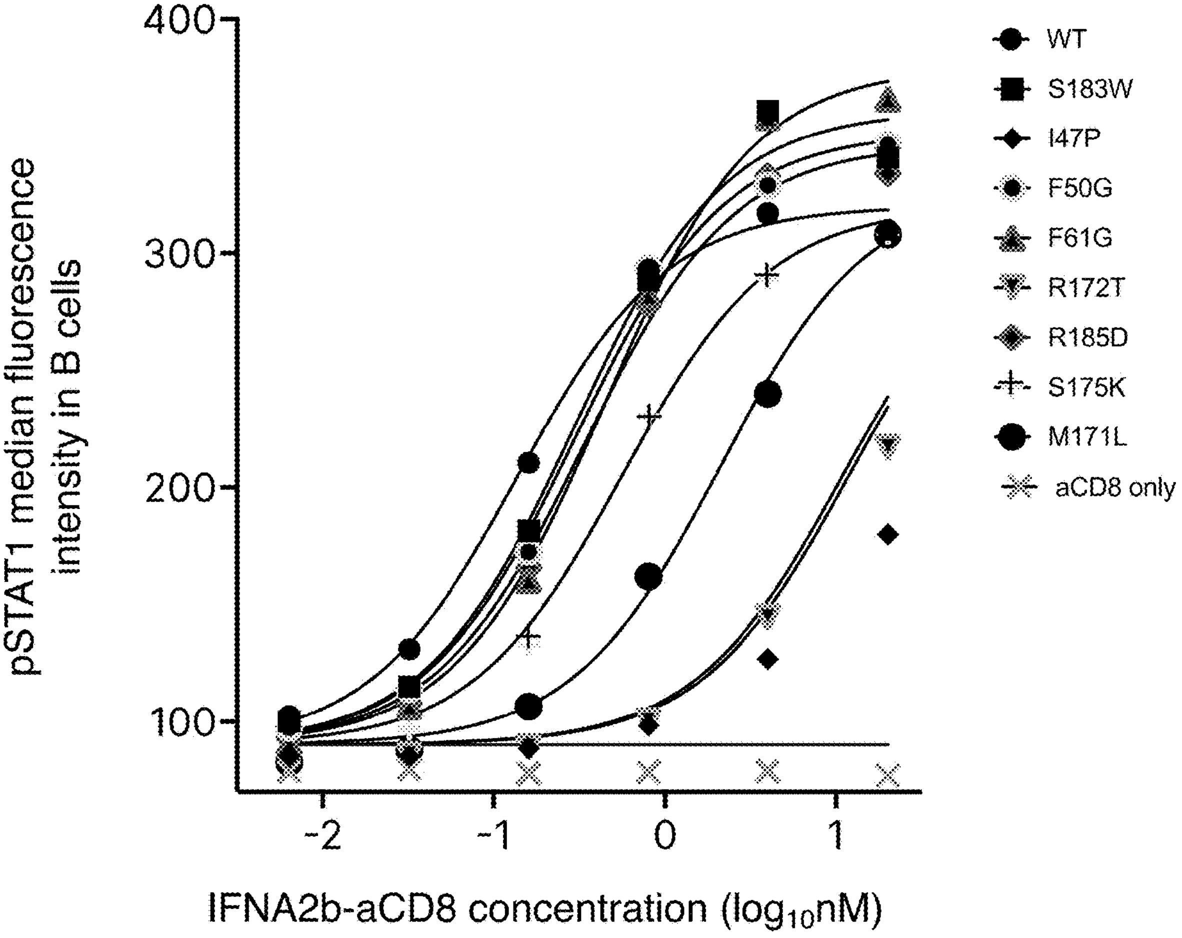
FIG. 14 is a graph of the dose-response curves for STAT1 phosphorylation as measured by flow cytometry for candidate IFNA2b immunocytokines in B cells.
Figure 15:
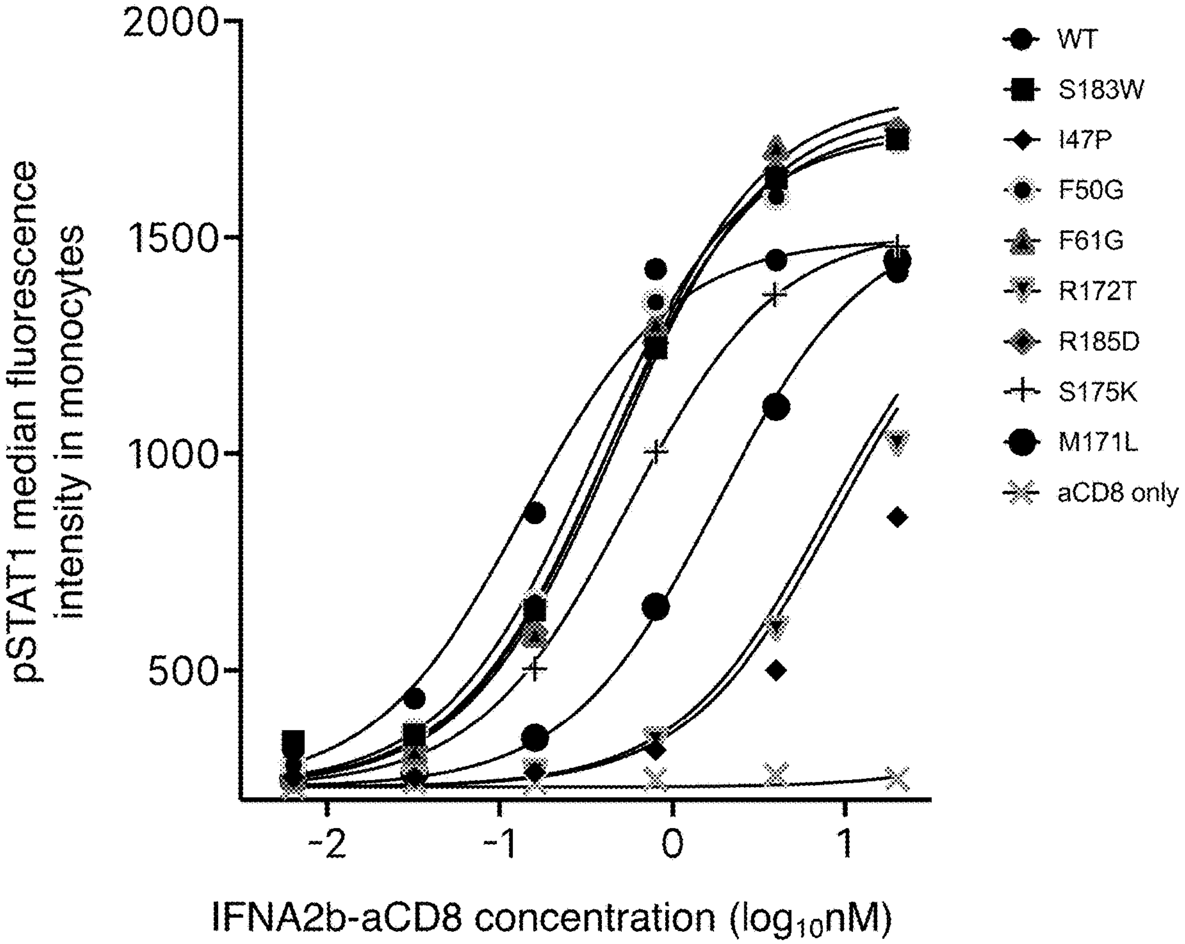
FIG. 15 is a graph of the dose-response curves for STAT1 phosphorylation as measured by flow cytometry for candidate IFNA2b immunocytokines in monocytes.

Cell-type-specific signaling potency was identified for each IFNA2-aCD8 fusion using the same PBMC pSTAT1 assay described in Example 5. Signaling was measured in the targeted CD8+ T cell population, as well as for three non-targeted cell populations (CD4+ T cells, B cells, and monocytes). Dose-response curves for STAT1 phosphorylation are shown in CD8 T cells (FIG. 12), CD4 T cells (FIG. 13), B cells (FIG. 14), and monocytes (FIG. 15). EC50 values are shown in Table 10. The concentrations of protein added in this assay ranged from 6.4 pM to 20 nM and those values are set as the minimum and maximum measurable EC50s, respectively, in Table 10. IFNA2-aCD8 fusions all showed higher potency in the targeted CD8 T cells than the non-targeted cell populations. For example, IFNA2_R172T had an EC50 of ~8 pM in CD8 cells, but ~8 nM, ~11 nM, and >20 nM respectively in monocytes, B cells, and CD4 cells, a >1000-fold potency difference in targeted vs. non-targeted cells. These results indicate that detuned IFNA2-anti-CD8 immunocytokines comprising the IFNA2 variants disclosed herein mediated cis-dependent signaling in CD8 cells, with reduced affinity to IFNAR2 relative to wild-type IFNA2.

TABLE 10

Signaling Potency Determination of IFNA2-aCD8 Fusion Proteins in Primary Human PBMCs

| | EC50 in CD8 cells (nM) | EC50 in CD4 cells (nM) | EC50 in B cells (nM) | EC50 in monocytes (nM) |
|---|---|---|---|---|
| WT | <0.0064 | 0.2555 | 0.1388 | 0.1392 |
| S183W | <0.0064 | 0.8285 | 0.2942 | 0.4177 |
| I47P | <0.0064 | >20 | 11.88 | 8.987 |
| F50G | <0.0064 | 0.7211 | 0.298 | 0.3474 |
| F61G | <0.0064 | 1.06 | 0.4401 | 0.4533 |
| R172T | 0.008421 | >20 | 10.93 | 7.952 |

TABLE 10-continued

Signaling Potency Determination of IFNA2-aCD8 Fusion Proteins in Primary Human PBMCs

| | EC50 in CD8 cells (nM) | EC50 in CD4 cells (nM) | EC50 in B cells (nM) | EC50 in monocytes (nM) |
|---|---|---|---|---|
| R185D | <0.0064 | 0.9832 | 0.3375 | 0.4687 |
| S175K | <0.0064 | 1.417 | 0.5614 | 0.5493 |
| M171L | <0.0064 | 4.458 | 2.109 | 1.825 |

Example 9: Selection of Further Detuned IFNA2 Variants

Figure 16:
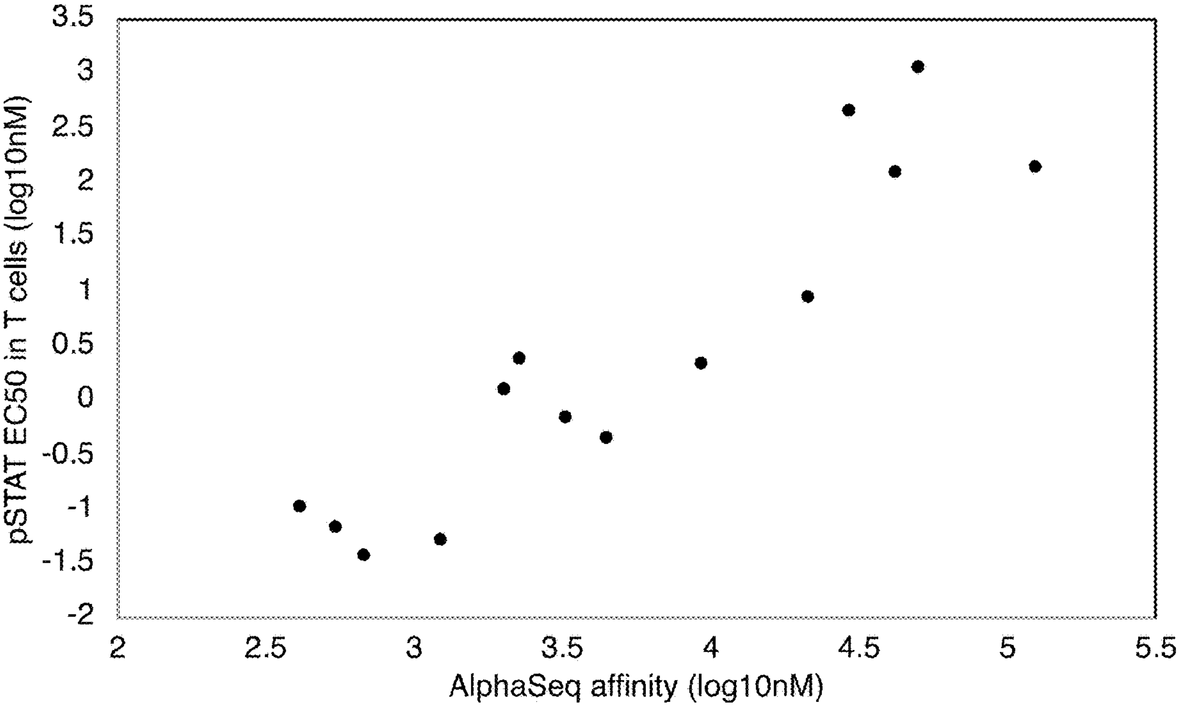
FIG. 16 is a scatter plot showing the relation between the AlphaSeq™ affinity values and BLI-measured Kd for a second set of IFNA2 Fc fusion proteins comprising IFNA2 variants.
Figure 17:
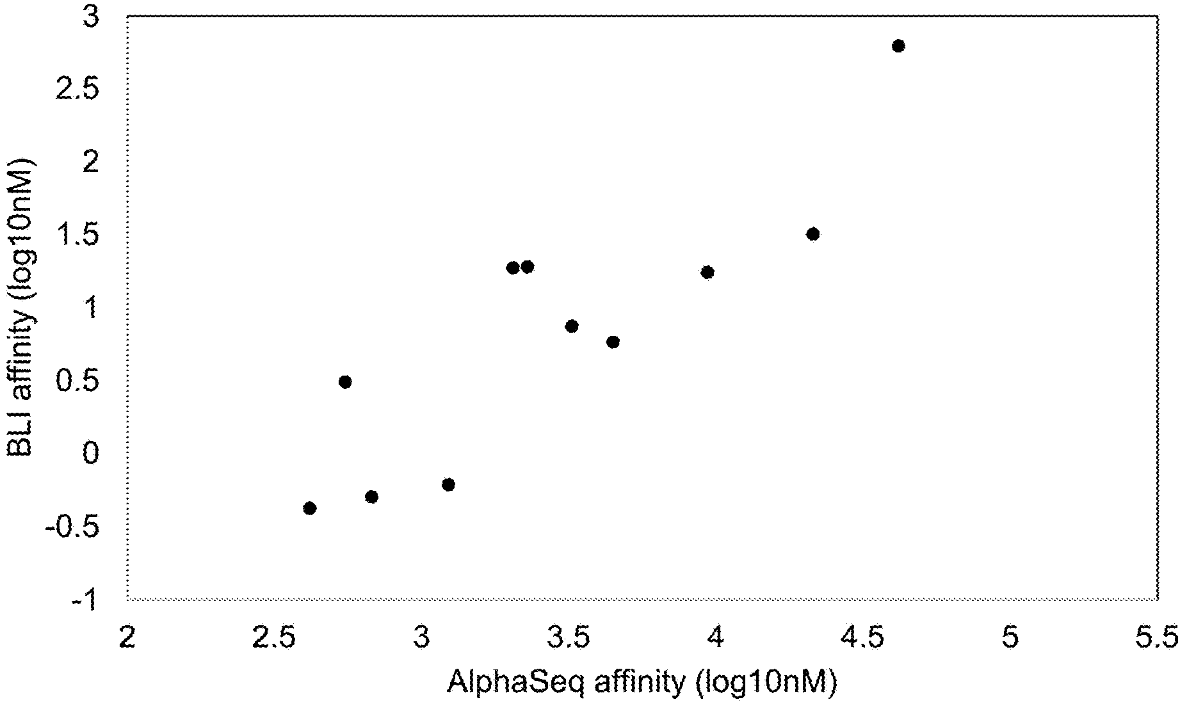
FIG. 17 is a scatter plot showing the correlation between the AlphaSeq™ affinity values and Phosflow-measured pSTAT1 EC50 in T cells for a second set of IFNA2 Fc fusion proteins comprising IFNA2 variants.

After characterizing the first batch of detuned IFNA2 variants described in Table 2, a further set of 15 IFNA2 variants was selected based on criteria described in Example 2 for selecting top detuned variants, but with a wider range of affinities, ranging from ~400 nM to >100 μM (affinities shown in Table 11). These proteins were produced as described in Example 8 as Fc-fusion proteins and tested for binding to IFNAR2 by BLI and for signaling in a human PBMC Phosflow assay using the same protocol as described in Example 8. Affinities of IFNA2 Fc fusion proteins to IFNAR2 as measured by BLI are shown in Table 12, with variants showing binding weaker than the limit of detection marked as "na." Signaling potencies in human T cells are shown in Table 13. As in Examples 4 and 5, there was a strong correlation between AlphaSeq™ predicted affinity for IFNA2 variants and both BLI-measured affinity and Phosflow-measured signaling potency. FIG. 16 is a scatter plot showing the relation between the AlphaSeq™ affinity values and BLI-measured Kd for a second set of IFNA2 Fc fusion proteins comprising IFNA2 variants. FIG. 17 is a scatter plot showing the correlation between the AlphaSeq™ affinity values and Phosflow-measured pSTAT1 EC50 in T cells for a second set of IFNA2 Fc fusion proteins comprising IFNA2 variants. Table 11 also provides the polypeptide sequences of the IFNA2-Fc fusion proteins as SEQ ID NOs 560-574.

TABLE 11

Detuned IFNA2 variants produced as soluble Fc fusions

| Affinity bin ($log_{10}$nM) | Variant | IFNAR2 affinity ($log_{10}$nM) | Position conserved in mouse/cyno/rat? | Multiplicity | Polypeptide Sequence | SEQ ID NO |
|---|---|---|---|---|---|---|
| >4.5 | A168R | 5.10 | yes | 9 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRREI<br>MRSFSLSTNLQESLRSK<br>E | 560 |
| | R172D | 4.70 | yes | 12 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MDSFSLSTNLQESLRSK<br>E | 561 |
| | R172N | 4.62 | yes | 12 | DIEPKSSDKTHTCPPCP<br>APEAAGGPSVFLFPPKP<br>KDTLMISRTPEVTCVVV<br>DVSHEDPEVKENWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL | 562 |

TABLE 11-continued

Detuned IFNA2 variants produced as soluble Fc fusions

| Affinity bin ($log_{10}$nM) | Variant | IFNAR2 affinity ($log_{10}$nM) | Position conserved in mouse/cyno/rat? | Multiplicity | Polypeptide Sequence | SEQ ID NO |
|---|---|---|---|---|---|---|
| | | | | | KEKKYSPCAWEVVRAEI MNSFSLSTNLQESLRSK E | |
| 4-4.5 | R56L | 4.47 | yes | 9 | DIEPKSSDKTHTCPPCP APEAAGGPSVFLFPPKP KDTLMISRTPEVTCVVV DVSHEDPEVKENWYVDG VEVHNAKTKPREEQYNS TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDLHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSPCAWEVVRAEI MRSFSLSTNLQESLRSK E | 563 |
| | R167E | 4.35 | yes | 10 | DIEPKSSDKTHTCPPCP APEAAGGPSVFLFPPKP KDTLMISRTPEVTCVVV DVSHEDPEVKFNWYVDG VEVHNAKTKPREEQYNS TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDRHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSPCAWEVVEAEI MRSFSLSTNLQESLRSK E | 564 |
| | M171Y | 4.33 | cyno only | 14 | DIEPKSSDKTHTCPPCP APEAAGGPSVFLFPPKP KDTLMISRTPEVTCVVV DVSHEDPEVKFNWYVDG VEVHNAKTKPREEQYNS TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDRHDFGFPQEEFGN QFQKAETIPVLHEMIQQ | 565 |

TABLE 11-continued

Detuned IFNA2 variants produced as soluble Fc fusions

| Affinity bin ($log_{10}nM$) | Variant | IFNAR2 affinity ($log_{10}nM$) | Position conserved in mouse/cyno/ rat? | Multiplicity | Polypeptide Sequence | SEQ ID NO |
|---|---|---|---|---|---|---|
| | | | | | IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>YRSFSLSTNLQESLRSK<br>E | |
| 3.5-4 | R46D | 3.97 | yes | 11 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRDISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MRSFSLSTNLQESLRSK<br>E | 566 |
| | S173H | 3.65 | cyno only | 7 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MRHFSLSTNLQESLRSK<br>E | 567 |
| | I47D | 3.51 | cyno only | 4 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG | 568 |

TABLE 11-continued

Detuned IFNA2 variants produced as soluble Fc fusions

| Affinity bin ($log_{10}$nM) | Variant | IFNAR2 affinity ($log_{10}$nM) | Position conserved in mouse/cyno/rat? | Multiplicity | Polypeptide Sequence | SEQ ID NO |
|---|---|---|---|---|---|---|
| | | | | | SGGGGSCDLPQTHSLGS RRTLMLLAQMRRDSLFS CLKDRHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSPCAWEVVRAEI MRSFSLSTNLQESLRSK E | |
| 3-3.5 | A168F | 3.36 | yes | 9 | DIEPKSSDKTHTCPPCP APEAAGGPSVFLFPPKP KDTLMISRTPEVTCVVV DVSHEDPEVKFNWYVDG VEVHNAKTKPREEQYNS TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDRHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSPCAWEVVRFEI MRSFSLSTNLQESLRSK E | 569 |
| | V165N | 3.31 | yes | 14 | DIEPKSSDKTHTCPPCP APEAAGGPSVFLFPPKP KDTLMISRTPEVTCVVV DVSHEDPEVKFNWYVDG VEVHNAKTKPREEQYNS TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDRHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSPCAWENVRAEI MRSFSLSTNLQESLRSK E | 570 |
| | S34A | 3.09 | no | 1 | DIEPKSSDKTHTCPPCP APEAAGGPSVFLFPPKP KDTLMISRTPEVTCVVV DVSHEDPEVKENWYVDG VEVHNAKTKPREEQYNS TYRVVSVLTVLHQDWLN GKEYKCKVSNKALGAPI EKTISKAKGQPREPQVY TLPPSRDELTKNQVSLT | 571 |

TABLE 11-continued

| Affinity bin ($log_{10}$nM) | Variant | IFNAR2 affinity ($log_{10}$nM) | Position conserved in mouse/cyno/rat? | Multiplicity | Polypeptide Sequence | SEQ ID NO |
|---|---|---|---|---|---|---|
| Detuned IFNA2 variants produced as soluble Fc fusions | | | | | | |
| | | | | | CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGA<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MRSFSLSTNLQESLRSK<br>E | |
| 2.5-3 | K187R | 2.83 | cyno only | 10 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLFS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MRSFSLSTNLQESLRSR<br>E | 572 |
| | F50S | 2.74 | cyno only | 8 | DIEPKSSDKTHTCPPCP<br>APEAAGGPSVFLFPPKP<br>KDTLMISRTPEVTCVVV<br>DVSHEDPEVKFNWYVDG<br>VEVHNAKTKPREEQYNS<br>TYRVVSVLTVLHQDWLN<br>GKEYKCKVSNKALGAPI<br>EKTISKAKGQPREPQVY<br>TLPPSRDELTKNQVSLT<br>CLVKGFYPSDIAVEWES<br>NGQPENNYKTTPPVLDS<br>DGSFFLYSKLTVDKSRW<br>QQGNVFSCSVMHEALHN<br>HYTQKSLSLSPGKGGGG<br>SGGGGSCDLPQTHSLGS<br>RRTLMLLAQMRRISLSS<br>CLKDRHDFGFPQEEFGN<br>QFQKAETIPVLHEMIQQ<br>IFNLFSTKDSSAAWDET<br>LLDKFYTELYQQLNDLE<br>ACVIQGVGVTETPLMKE<br>DSILAVRKYFQRITLYL<br>KEKKYSPCAWEVVRAEI<br>MRSFSLSTNLQESLRSK<br>E | 573 |
| | P160E | 2.62 | mouse/rat | 5 | DIEPKSSDKTHTCPPCP<br>APEAAGGPSVFLFPPKP<br>KDTLMISRTPEVTCVVV<br>DVSHEDPEVKENWYVDG<br>VEVHNAKTKPREEQYNS | 574 |

TABLE 11-continued

| Detuned IFNA2 variants produced as soluble Fc fusions | | | | | | |
|---|---|---|---|---|---|---|
| Affinity bin ($log_{10}$nM) | Variant | IFNAR2 affinity ($log_{10}$nM) | Position conserved in mouse/cyno/rat? | Multiplicity | Polypeptide Sequence | SEQ ID NO |
| | | | | | TYRVVSVLTVLHQDWLN GKEYKCKVSNKALGAPI EKTISKAKGQPREPQVY TLPPSRDELTKNQVSLT CLVKGFYPSDIAVEWES NGQPENNYKTTPPVLDS DGSFFLYSKLTVDKSRW QQGNVFSCSVMHEALHN HYTQKSLSLSPGKGGGG SGGGGSCDLPQTHSLGS RRTLMLLAQMRRISLFS CLKDRHDFGFPQEEFGN QFQKAETIPVLHEMIQQ IFNLFSTKDSSAAWDET LLDKFYTELYQQLNDLE ACVIQGVGVTETPLMKE DSILAVRKYFQRITLYL KEKKYSECAWEVVRAEI MRSFSLSTNLQESLRSK E | |

TABLE 12

| Affinity Determination of IFNA2 Fc Fusion Proteins | |
|---|---|
| Variant | IFNAR2 KD (nM) |
| A168R | na |
| R172D | na |
| R172N | 625 |
| R56L | na |
| R167E | na |
| M171Y | 32.0 |
| R46D | 17.5 |
| S173H | 5.79 |
| I47D | 7.51 |
| A168F | 19.1 |
| V165N | 18.8 |
| S34A | 0.612 |
| K187R | 0.505 |
| F50S | 3.08 |
| P160E | 0.422 |

TABLE 13

| Signaling Potency Determination of IFNA2 Fc Fusion Proteins in Primary Human PBMCs | |
|---|---|
| Variant | EC50 in T cells (nM) |
| A168R | 139.2 |
| R172D | 1181 |
| R172N | 124.2 |
| R56L | 459.5 |
| R167E | 8.978 |
| M171Y | 2.175 |
| R46D | 0.464 |
| S173H | 0.697 |
| I47D | 2.46 |
| A168F | 1.278 |
| V165N | 0.05168 |
| S34A | 0.03695 |
| K187R | 0.06664 |
| F50S | 0.1069 |
| P160E | 139.2 |

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

SEQUENCE LISTING

```
Sequence total quantity: 578
SEQ ID NO: 1           moltype = AA  length = 188
FEATURE                Location/Qualifiers
source                 1..188
                       mol_type = protein
                       organism = Homo sapiens
SEQUENCE: 1
MALTFALLVA LLVLSCKSSC SVGCDLPQTH SLGSRRTLML LAQMRRISLF SCLKDRHDFG  60
FPQEEFGNQF QKAETIPVLH EMIQQIFNLF STKDSSAAWD ETLLDKFYTE LYQQLNDLEA  120
```

-continued

```
CVIQGVGVTE TPLMKEDSIL AVRKYFQRIT LYLKEKKYSP CAWEVVRAEI MRSFSLSTNL  180
QESLRSKE                                                           188

SEQ ID NO: 2            moltype = AA  length = 515
FEATURE                 Location/Qualifiers
source                  1..515
                        mol_type = protein
                        organism = Homo sapiens
SEQUENCE: 2
MLLSQNAFIF RSLNLVLMVY ISLVFGISYD SPDYTDESCT FKISLRNFRS ILSWELKNHS  60
IVPTHYTLLY TIMSKPEDLK VVKNCANTTR SFCDLTDEWR STHEAYVTVL EGFSGNTTLF  120
SCSHNFWLAI DMSFEPPEFE IVGFTNHINV MVKFPSIVEE ELQFDLSLVI EEQSEGIVKK  180
HKPEIKGNMS GNFTYIIDKL IPNTNYCVSV YLEHSDEQAV IKSPLKCTLL PPGQESESAE  240
SAKIGGIITV FLIALVLTST IVTLKWIGYI CLRNSLPKVL NFHNFLAWPF PNLPPLEAMD  300
MVEVIYINRK KKVWDYNYDD ESDSDTEAAP RTSGGGYTMH GLTVRPLGQA SATSTESQLI  360
DPESEEEPDL PEVDVELPTM PKDSPQQLEL LSGPCERRKS PLQDPFPEED YSSTEGSGGR  420
ITFNVDLNSV FLRVLDDEDS DDLEAPLMLS SHLEEMVDPE DPDNVQSNHL LASGEGTQPT  480
FPSPSSEGLW SEDAPSDQSD TSESDVDLGD GYIMR                             515

SEQ ID NO: 3            moltype = AA  length = 513
FEATURE                 Location/Qualifiers
source                  1..513
                        mol_type = protein
                        organism = Mus sp.
SEQUENCE: 3
MRSRCTVSAV GLLSLCLVVS ASLETITPSA FDGYPDEPCT INITIRNSRL ILSWELENKS  60
GPPANYTLWY TVMSKDENLT KVKNCSDTTK SSCDVTDKWL EGMESYVVAI VIVHRGDLTV  120
CRCSDYIVPA NAPLEPPEFE IVGFTDHINV TMEFPPVTSK IIQEKMKTTP FVIKEQIGDS  180
VRKKHEPKVN NVTGNFTFVL RDLLPKTNYC VSLYFDDDPA IKSPLKCIVL QPGQESGLSE  240
SAIVGITTSC LVVMVFVSTI VMLKRIGYIC LKDNLPNVLN FRHFLTWIIP ERSPSEAIDR  300
LEIIPTNKKK RLWNYDYEDG SDSDEEVPTA SVTGYTMHGL TGKPLQQTSD TSASPEDPLH  360
EEDSGAEESD EAGAGAGAEP ELPTEAGAGP SEDPTGPYER RKSVLEDSFP REDNSSMDEP  420
GDNIIFNVNL NSVFLRVLHD EDASETLSLE EDTILLDEGP QRTESDLRIA GGDRTQPPLP  480
SLPSQDLWTE DGSSEKSDTS DSDADVGDGY IMR                               513

SEQ ID NO: 4            moltype = AA  length = 118
FEATURE                 Location/Qualifiers
source                  1..118
                        mol_type = protein
                        organism = synthetic construct
SEQUENCE: 4
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSS    118

SEQ ID NO: 5            moltype = AA  length = 107
FEATURE                 Location/Qualifiers
source                  1..107
                        mol_type = protein
                        organism = synthetic construct
SEQUENCE: 5
DVQITQSPSS LSASVGDRVT ITCRTSRSIS QYLAWYQQKP GKVPKLLIYS GSTLQSGVPS  60
RFSGSGSGTD FTLTISSLQP EDVATYYCQQ HNENPLTFGG GTKVEIK                107

SEQ ID NO: 6            moltype = AA  length = 119
FEATURE                 Location/Qualifiers
source                  1..119
                        mol_type = protein
                        organism = synthetic construct
SEQUENCE: 6
EVQLVQSGAE VKKPGSSVKV SCKASGYTFS SYVMHWVRQA PGQGLEWIGY IDPYNDGAKY  60
AQKFQGRVTL TSDKSTSTAY MELSSLRSED TAVYYCARGG PYGWYFDVWG QGTTVTVSS   119

SEQ ID NO: 7            moltype = AA  length = 107
FEATURE                 Location/Qualifiers
source                  1..107
                        mol_type = protein
                        organism = synthetic construct
SEQUENCE: 7
DIQMTQSPSS LSASVGDRVT ITCRASEHIY SYLSWYQQKP GKVPKLLIYN AKTLAEGVPS  60
RFSGSGSGTD FTLTISSLQP EDVATYYCQH HFGSPLTFGQ GTRLEIK                107

SEQ ID NO: 8            moltype = AA  length = 119
FEATURE                 Location/Qualifiers
source                  1..119
                        mol_type = protein
                        organism = synthetic construct
SEQUENCE: 8
QVQLVQSGAE VKKPGASVKL SCKASGYNFK HTYAHWVRQA PGQGLEWIGR IDPANGNTKY  60
DPKFQGRATM TADTASNTAY LELSSLRSED TAVYYCVADH YGSSLLDYWG QGTLVTVSS   119
```

```
SEQ ID NO: 9            moltype = AA  length = 112
FEATURE                 Location/Qualifiers
source                  1..112
                        mol_type = protein
                        organism = synthetic construct
SEQUENCE: 9
DVVMTQTPLS LSVTPGQPAS ISCKSSQSLL DSDGKTYLNW FQQRPGQSPR RLIYLVSKLD  60
SGVPDRFSGS GSGTDFTLKI SRVEAEDVGV YYCWQGTYFP YTFGQGTKLE IK          112

SEQ ID NO: 10           moltype = AA  length = 165
FEATURE                 Location/Qualifiers
source                  1..165
                        mol_type = protein
                        organism = synthetic construct
SEQUENCE: 10
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EYVRAEIMRS FSLSTNLQES LRSKE                 165

SEQ ID NO: 11           moltype = AA  length = 165
FEATURE                 Location/Qualifiers
source                  1..165
                        mol_type = protein
                        organism = synthetic construct
SEQUENCE: 11
CDLPQTHSLG SRRTLMLLAQ MRRISLFSCL KDDHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 12           moltype = AA  length = 165
FEATURE                 Location/Qualifiers
source                  1..165
                        mol_type = protein
                        organism = synthetic construct
SEQUENCE: 12
CDLPQTHSLG SRRTLMLLAQ MRRISLFSCL KDRHDQGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 13           moltype = AA  length = 165
FEATURE                 Location/Qualifiers
source                  1..165
                        mol_type = protein
                        organism = synthetic construct
SEQUENCE: 13
CDLPQTHSLG SRRTLMLLAQ MRRISLDSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 14           moltype = AA  length = 165
FEATURE                 Location/Qualifiers
source                  1..165
                        mol_type = protein
                        organism = synthetic construct
SEQUENCE: 14
CDLPQTHSLG SRRTLMLHAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 15           moltype = AA  length = 165
FEATURE                 Location/Qualifiers
source                  1..165
                        mol_type = protein
                        organism = synthetic construct
SEQUENCE: 15
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRREIMRS FSLSTNLQES LRSKE                 165

SEQ ID NO: 16           moltype = AA  length = 165
FEATURE                 Location/Qualifiers
source                  1..165
                        mol_type = protein
                        organism = synthetic construct
SEQUENCE: 16
CDLPQTHSLG SRRTLMLLAQ MRRISLFSCL KDRHDEGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165
```

```
SEQ ID NO: 17          moltype = AA  length = 165
FEATURE                Location/Qualifiers
source                 1..165
                       mol_type = protein
                       organism = synthetic construct
SEQUENCE: 17
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EEVRAEIMRS FSLSTNLQES LRSKE                  165

SEQ ID NO: 18          moltype = AA  length = 165
FEATURE                Location/Qualifiers
source                 1..165
                       mol_type = protein
                       organism = synthetic construct
SEQUENCE: 18
CDLPQTHSLG SRRTLMLLAQ MRRISLFSCL KDGHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 19          moltype = AA  length = 165
FEATURE                Location/Qualifiers
source                 1..165
                       mol_type = protein
                       organism = synthetic construct
SEQUENCE: 19
CDLPQTHSLG SRRTLMLLAQ MRRISLFSCD KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 20          moltype = AA  length = 165
FEATURE                Location/Qualifiers
source                 1..165
                       mol_type = protein
                       organism = synthetic construct
SEQUENCE: 20
CDLPQTHSLG SRRTLMLLAQ MRRISLFSCE KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 21          moltype = AA  length = 165
FEATURE                Location/Qualifiers
source                 1..165
                       mol_type = protein
                       organism = synthetic construct
SEQUENCE: 21
CDLPQTHSLG SRRTLMLLAQ MRRISLFSCG KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 22          moltype = AA  length = 165
FEATURE                Location/Qualifiers
source                 1..165
                       mol_type = protein
                       organism = synthetic construct
SEQUENCE: 22
CDLPQTHSLG SRRTLMLLAQ MRRISLFSCA KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 23          moltype = AA  length = 165
FEATURE                Location/Qualifiers
source                 1..165
                       mol_type = protein
                       organism = synthetic construct
SEQUENCE: 23
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIRRS FSLSTNLQES LRSKE                  165

SEQ ID NO: 24          moltype = AA  length = 165
FEATURE                Location/Qualifiers
source                 1..165
                       mol_type = protein
                       organism = synthetic construct
SEQUENCE: 24
CDLPQTHSLG SRRTLMLLAQ MRRISLFSCL KDKHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRITLYL KEKKYSPCAW EVVRAEIMRS FSLSTNLQES LRSKE                  165

SEQ ID NO: 25          moltype = AA  length = 165
FEATURE                Location/Qualifiers
source                 1..165
                       mol_type = protein
                       organism = synthetic construct
SEQUENCE: 25
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EHVRAEIMRS FSLSTNLQES LRSKE                  165

SEQ ID NO: 26          moltype = AA  length = 165
FEATURE                Location/Qualifiers
source                 1..165
                       mol_type = protein
                       organism = synthetic construct
SEQUENCE: 26
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EKVRAEIMRS FSLSTNLQES LRSKE                  165

SEQ ID NO: 27          moltype = AA  length = 165
FEATURE                Location/Qualifiers
source                 1..165
                       mol_type = protein
                       organism = synthetic construct
SEQUENCE: 27
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEISRS FSLSTNLQES LRSKE                  165

SEQ ID NO: 28          moltype = AA  length = 165
FEATURE                Location/Qualifiers
source                 1..165
                       mol_type = protein
                       organism = synthetic construct
SEQUENCE: 28
CDLPQTHSLG SRRTLMLDAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 29          moltype = AA  length = 165
FEATURE                Location/Qualifiers
source                 1..165
                       mol_type = protein
                       organism = synthetic construct
SEQUENCE: 29
CDLPQTHSLG SRRTLMLLAQ MRRISLFSCL KDRHDIGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 30          moltype = AA  length = 165
FEATURE                Location/Qualifiers
source                 1..165
                       mol_type = protein
                       organism = synthetic construct
SEQUENCE: 30
CDLPQTHSLG SRRTLMLLAQ MRRISLFSCL KDNHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 31          moltype = AA  length = 165
FEATURE                Location/Qualifiers
source                 1..165
                       mol_type = protein
                       organism = synthetic construct
SEQUENCE: 31
CDLPQTHSLG SRRTLMLLAQ MRRISLFSCL KDRPDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 32          moltype = AA  length = 165
FEATURE                Location/Qualifiers
source                 1..165
                       mol_type = protein
                       organism = synthetic construct
SEQUENCE: 32
CDLPQTHSLG SRRTLMLLAQ MRRISLFSCL KDRHDFGFPQ EEFGNQFQKA ETIPVLHEMI  60
```

-continued

```
QQIFNLFSTK DSSAAWDETL LDKFYTELYQ QLNDLEACVI QGVGVTETPL MKEDSILAVR  120
KYFQRITLYL KEKKYSPCAW EVVWAEIMRS FSLSTNLQES LRSKE                  165

SEQ ID NO: 33          moltype = AA  length = 165
FEATURE                Location/Qualifiers
source                 1..165
                       mol_type = protein
                       organism = synthetic construct
SEQUENCE: 33
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRHEIMRS FSLSTNLQES LRSKE                  165

SEQ ID NO: 34          moltype = AA  length = 165
FEATURE                Location/Qualifiers
source                 1..165
                       mol_type = protein
                       organism = synthetic construct
SEQUENCE: 34
CDLPQTHSLG SRRTLMLLAQ MRRISLFSCL KDRHDNGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 35          moltype = AA  length = 165
FEATURE                Location/Qualifiers
source                 1..165
                       mol_type = protein
                       organism = synthetic construct
SEQUENCE: 35
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEITRS FSLSTNLQES LRSKE                  165

SEQ ID NO: 36          moltype = AA  length = 165
FEATURE                Location/Qualifiers
source                 1..165
                       mol_type = protein
                       organism = synthetic construct
SEQUENCE: 36
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EWVRAEIMRS FSLSTNLQES LRSKE                  165

SEQ ID NO: 37          moltype = AA  length = 165
FEATURE                Location/Qualifiers
source                 1..165
                       mol_type = protein
                       organism = synthetic construct
SEQUENCE: 37
CDLPQTHSLG SRRTLMLLAQ MRRISHFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 38          moltype = AA  length = 165
FEATURE                Location/Qualifiers
source                 1..165
                       mol_type = protein
                       organism = synthetic construct
SEQUENCE: 38
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EFVRAEIMRS FSLSTNLQES LRSKE                  165

SEQ ID NO: 39          moltype = AA  length = 165
FEATURE                Location/Qualifiers
source                 1..165
                       mol_type = protein
                       organism = synthetic construct
SEQUENCE: 39
CDLPQTHSLG SRRTLMLLAQ MRRISLFSCN KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 40          moltype = AA  length = 165
FEATURE                Location/Qualifiers
source                 1..165
                       mol_type = protein
                       organism = synthetic construct
SEQUENCE: 40
```

```
CDLPQTHSLG SRRTLMLLAQ MRRISLFSCL KDRHDAGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 41          moltype = AA  length = 165
FEATURE                Location/Qualifiers
source                 1..165
                       mol_type = protein
                       organism = synthetic construct
SEQUENCE: 41
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRKEIMRS FSLSTNLQES LRSKE                  165

SEQ ID NO: 42          moltype = AA  length = 165
FEATURE                Location/Qualifiers
source                 1..165
                       mol_type = protein
                       organism = synthetic construct
SEQUENCE: 42
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMDS FSLSTNLQES LRSKE                  165

SEQ ID NO: 43          moltype = AA  length = 165
FEATURE                Location/Qualifiers
source                 1..165
                       mol_type = protein
                       organism = synthetic construct
SEQUENCE: 43
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVIAEIMRS FSLSTNLQES LRSKE                  165

SEQ ID NO: 44          moltype = AA  length = 165
FEATURE                Location/Qualifiers
source                 1..165
                       mol_type = protein
                       organism = synthetic construct
SEQUENCE: 44
CDLPQTHSLG SRRTLMLKAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 45          moltype = AA  length = 165
FEATURE                Location/Qualifiers
source                 1..165
                       mol_type = protein
                       organism = synthetic construct
SEQUENCE: 45
CDLPQTHSLG SRRTLMLLAQ MRRISLFSCL KDRHDGGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 46          moltype = AA  length = 165
FEATURE                Location/Qualifiers
source                 1..165
                       mol_type = protein
                       organism = synthetic construct
SEQUENCE: 46
CDLPQTHSLG SRRTLMLLAQ MRRISLFSCL KDVHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 47          moltype = AA  length = 165
FEATURE                Location/Qualifiers
source                 1..165
                       mol_type = protein
                       organism = synthetic construct
SEQUENCE: 47
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMWS FSLSTNLQES LRSKE                  165

SEQ ID NO: 48          moltype = AA  length = 165
FEATURE                Location/Qualifiers
source                 1..165
                       mol_type = protein
                       organism = synthetic construct
```

```
SEQUENCE: 48
CDLPQTHSLG SRRTLMLLAQ MRRISLFSCL KDTHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 49          moltype = AA  length = 165
FEATURE                Location/Qualifiers
source                 1..165
                       mol_type = protein
                       organism = synthetic construct
SEQUENCE: 49
CDLPQTHSLG SRRTLMLLAQ MRRISIFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 50          moltype = AA  length = 165
FEATURE                Location/Qualifiers
source                 1..165
                       mol_type = protein
                       organism = synthetic construct
SEQUENCE: 50
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMNS FSLSTNLQES LRSKE                  165

SEQ ID NO: 51          moltype = AA  length = 165
FEATURE                Location/Qualifiers
source                 1..165
                       mol_type = protein
                       organism = synthetic construct
SEQUENCE: 51
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEINRS FSLSTNLQES LRSKE                  165

SEQ ID NO: 52          moltype = AA  length = 165
FEATURE                Location/Qualifiers
source                 1..165
                       mol_type = protein
                       organism = synthetic construct
SEQUENCE: 52
CDLPQTHSLG SRRTLMLLAQ MRRISKFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 53          moltype = AA  length = 165
FEATURE                Location/Qualifiers
source                 1..165
                       mol_type = protein
                       organism = synthetic construct
SEQUENCE: 53
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EQVRAEIMRS FSLSTNLQES LRSKE                  165

SEQ ID NO: 54          moltype = AA  length = 165
FEATURE                Location/Qualifiers
source                 1..165
                       mol_type = protein
                       organism = synthetic construct
SEQUENCE: 54
CDLPQTHSLG SRRTLMLLAQ MRRISLFSCV KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 55          moltype = AA  length = 165
FEATURE                Location/Qualifiers
source                 1..165
                       mol_type = protein
                       organism = synthetic construct
SEQUENCE: 55
CDLPQTHSLG SRRTLMLLAQ MRRISLFSCS KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 56          moltype = AA  length = 165
FEATURE                Location/Qualifiers
source                 1..165
                       mol_type = protein
```

```
                         organism = synthetic construct
SEQUENCE: 56
CDLPQTHSLG SRRTLMLGAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 57            moltype = AA  length = 165
FEATURE                  Location/Qualifiers
source                   1..165
                         mol_type = protein
                         organism = synthetic construct
SEQUENCE: 57
CDLPQTHSLG SRRTLMLLAQ MRRISLFSCL KDAHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 58            moltype = AA  length = 165
FEATURE                  Location/Qualifiers
source                   1..165
                         mol_type = protein
                         organism = synthetic construct
SEQUENCE: 58
CDLPQTHSLG SRRTLMLLAQ MRRISLFSCL KDRHDTGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 59            moltype = AA  length = 165
FEATURE                  Location/Qualifiers
source                   1..165
                         mol_type = protein
                         organism = synthetic construct
SEQUENCE: 59
CDLPQTHSLG SRRTLMLLAQ MRRISLFSCL KDLHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 60            moltype = AA  length = 165
FEATURE                  Location/Qualifiers
source                   1..165
                         mol_type = protein
                         organism = synthetic construct
SEQUENCE: 60
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRK FSLSTNLQES LRSKE                  165

SEQ ID NO: 61            moltype = AA  length = 165
FEATURE                  Location/Qualifiers
source                   1..165
                         mol_type = protein
                         organism = synthetic construct
SEQUENCE: 61
CDLPQTHSLG SRRTLMLLAQ MRRISLFSCL KDHHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 62            moltype = AA  length = 165
FEATURE                  Location/Qualifiers
source                   1..165
                         mol_type = protein
                         organism = synthetic construct
SEQUENCE: 62
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVMAEIMRS FSLSTNLQES LRSKE                  165

SEQ ID NO: 63            moltype = AA  length = 165
FEATURE                  Location/Qualifiers
source                   1..165
                         mol_type = protein
                         organism = synthetic construct
SEQUENCE: 63
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMAS FSLSTNLQES LRSKE                  165

SEQ ID NO: 64            moltype = AA  length = 165
FEATURE                  Location/Qualifiers
source                   1..165
```

```
                        mol_type = protein
                        organism = synthetic construct
SEQUENCE: 64
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVSAEIMRS FSLSTNLQES LRSKE                  165

SEQ ID NO: 65           moltype = AA  length = 165
FEATURE                 Location/Qualifiers
source                  1..165
                        mol_type = protein
                        organism = synthetic construct
SEQUENCE: 65
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMVS FSLSTNLQES LRSKE                  165

SEQ ID NO: 66           moltype = AA  length = 165
FEATURE                 Location/Qualifiers
source                  1..165
                        mol_type = protein
                        organism = synthetic construct
SEQUENCE: 66
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ELVRAEIMRS FSLSTNLQES LRSKE                  165

SEQ ID NO: 67           moltype = AA  length = 165
FEATURE                 Location/Qualifiers
source                  1..165
                        mol_type = protein
                        organism = synthetic construct
SEQUENCE: 67
CDLPQTHSLG SRRTLMLLAQ MRRPSLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 68           moltype = AA  length = 165
FEATURE                 Location/Qualifiers
source                  1..165
                        mol_type = protein
                        organism = synthetic construct
SEQUENCE: 68
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRR FSLSTNLQES LRSKE                  165

SEQ ID NO: 69           moltype = AA  length = 165
FEATURE                 Location/Qualifiers
source                  1..165
                        mol_type = protein
                        organism = synthetic construct
SEQUENCE: 69
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVEAEIMRS FSLSTNLQES LRSKE                  165

SEQ ID NO: 70           moltype = AA  length = 165
FEATURE                 Location/Qualifiers
source                  1..165
                        mol_type = protein
                        organism = synthetic construct
SEQUENCE: 70
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIARS FSLSTNLQES LRSKE                  165

SEQ ID NO: 71           moltype = AA  length = 165
FEATURE                 Location/Qualifiers
source                  1..165
                        mol_type = protein
                        organism = synthetic construct
SEQUENCE: 71
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIYRS FSLSTNLQES LRSKE                  165

SEQ ID NO: 72           moltype = AA  length = 165
FEATURE                 Location/Qualifiers
```

```
source                 1..165
                       mol_type = protein
                       organism = synthetic construct
SEQUENCE: 72
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIWRS FSLSTNLQES LRSKE                  165

SEQ ID NO: 73          moltype = AA  length = 165
FEATURE                Location/Qualifiers
source                 1..165
                       mol_type = protein
                       organism = synthetic construct
SEQUENCE: 73
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EMVRAEIMRS FSLSTNLQES LRSKE                  165

SEQ ID NO: 74          moltype = AA  length = 165
FEATURE                Location/Qualifiers
source                 1..165
                       mol_type = protein
                       organism = synthetic construct
SEQUENCE: 74
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIFRS FSLSTNLQES LRSKE                  165

SEQ ID NO: 75          moltype = AA  length = 165
FEATURE                Location/Qualifiers
source                 1..165
                       mol_type = protein
                       organism = synthetic construct
SEQUENCE: 75
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRYEIMRS FSLSTNLQES LRSKE                  165

SEQ ID NO: 76          moltype = AA  length = 165
FEATURE                Location/Qualifiers
source                 1..165
                       mol_type = protein
                       organism = synthetic construct
SEQUENCE: 76
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ESVRAEIMRS FSLSTNLQES LRSKE                  165

SEQ ID NO: 77          moltype = AA  length = 165
FEATURE                Location/Qualifiers
source                 1..165
                       mol_type = protein
                       organism = synthetic construct
SEQUENCE: 77
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ERVRAEIMRS FSLSTNLQES LRSKE                  165

SEQ ID NO: 78          moltype = AA  length = 165
FEATURE                Location/Qualifiers
source                 1..165
                       mol_type = protein
                       organism = synthetic construct
SEQUENCE: 78
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FRLSTNLQES LRSKE                  165

SEQ ID NO: 79          moltype = AA  length = 165
FEATURE                Location/Qualifiers
source                 1..165
                       mol_type = protein
                       organism = synthetic construct
SEQUENCE: 79
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRGEIMRS FSLSTNLQES LRSKE                  165

SEQ ID NO: 80          moltype = AA  length = 165
```

```
FEATURE                Location/Qualifiers
source                 1..165
                       mol_type = protein
                       organism = synthetic construct
SEQUENCE: 80
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMGS FSLSTNLQES LRSKE                  165

SEQ ID NO: 81          moltype = AA  length = 165
FEATURE                Location/Qualifiers
source                 1..165
                       mol_type = protein
                       organism = synthetic construct
SEQUENCE: 81
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIKRS FSLSTNLQES LRSKE                  165

SEQ ID NO: 82          moltype = AA  length = 165
FEATURE                Location/Qualifiers
source                 1..165
                       mol_type = protein
                       organism = synthetic construct
SEQUENCE: 82
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIERS FSLSTNLQES LRSKE                  165

SEQ ID NO: 83          moltype = AA  length = 165
FEATURE                Location/Qualifiers
source                 1..165
                       mol_type = protein
                       organism = synthetic construct
SEQUENCE: 83
CDLPQTHSLG SRRTLMLLAQ MRPISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 84          moltype = AA  length = 165
FEATURE                Location/Qualifiers
source                 1..165
                       mol_type = protein
                       organism = synthetic construct
SEQUENCE: 84
CDLPQTHSLG SRRTLMLLAQ MRDISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 85          moltype = AA  length = 165
FEATURE                Location/Qualifiers
source                 1..165
                       mol_type = protein
                       organism = synthetic construct
SEQUENCE: 85
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMTS FSLSTNLQES LRSKE                  165

SEQ ID NO: 86          moltype = AA  length = 165
FEATURE                Location/Qualifiers
source                 1..165
                       mol_type = protein
                       organism = synthetic construct
SEQUENCE: 86
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVLAEIMRS FSLSTNLQES LRSKE                  165

SEQ ID NO: 87          moltype = AA  length = 165
FEATURE                Location/Qualifiers
source                 1..165
                       mol_type = protein
                       organism = synthetic construct
SEQUENCE: 87
CDLPQTHSLG SRRTLMLLAQ MRRISLFSCL KDRHDYGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165
```

```
SEQ ID NO: 88          moltype = AA  length = 165
FEATURE                Location/Qualifiers
source                 1..165
                       mol_type = protein
                       organism = synthetic construct
SEQUENCE: 88
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSNSTNLQES LRSKE                  165

SEQ ID NO: 89          moltype = AA  length = 165
FEATURE                Location/Qualifiers
source                 1..165
                       mol_type = protein
                       organism = synthetic construct
SEQUENCE: 89
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRATIMRS FSLSTNLQES LRSKE                  165

SEQ ID NO: 90          moltype = AA  length = 165
FEATURE                Location/Qualifiers
source                 1..165
                       mol_type = protein
                       organism = synthetic construct
SEQUENCE: 90
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSGSTNLQES LRSKE                  165

SEQ ID NO: 91          moltype = AA  length = 165
FEATURE                Location/Qualifiers
source                 1..165
                       mol_type = protein
                       organism = synthetic construct
SEQUENCE: 91
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVVAEIMRS FSLSTNLQES LRSKE                  165

SEQ ID NO: 92          moltype = AA  length = 165
FEATURE                Location/Qualifiers
source                 1..165
                       mol_type = protein
                       organism = synthetic construct
SEQUENCE: 92
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMSS FSLSTNLQES LRSKE                  165

SEQ ID NO: 93          moltype = AA  length = 165
FEATURE                Location/Qualifiers
source                 1..165
                       mol_type = protein
                       organism = synthetic construct
SEQUENCE: 93
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRH FSLSTNLQES LRSKE                  165

SEQ ID NO: 94          moltype = AA  length = 165
FEATURE                Location/Qualifiers
source                 1..165
                       mol_type = protein
                       organism = synthetic construct
SEQUENCE: 94
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIGRS FSLSTNLQES LRSKE                  165

SEQ ID NO: 95          moltype = AA  length = 165
FEATURE                Location/Qualifiers
source                 1..165
                       mol_type = protein
                       organism = synthetic construct
SEQUENCE: 95
CDLPQTHSLG SRRTLMLLAQ MRRISVFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165
```

```
SEQ ID NO: 96          moltype = AA  length = 165
FEATURE                Location/Qualifiers
source                 1..165
                       mol_type = protein
                       organism = synthetic construct
SEQUENCE: 96
CDLPQTHSLG SRRTLMLLAQ MRRISLNSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 97          moltype = AA  length = 165
FEATURE                Location/Qualifiers
source                 1..165
                       mol_type = protein
                       organism = synthetic construct
SEQUENCE: 97
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVAAEIMRS FSLSTNLQES LRSKE                  165

SEQ ID NO: 98          moltype = AA  length = 165
FEATURE                Location/Qualifiers
source                 1..165
                       mol_type = protein
                       organism = synthetic construct
SEQUENCE: 98
CDLPQTHSLG SRRTLMLLAQ MRRDSLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 99          moltype = AA  length = 165
FEATURE                Location/Qualifiers
source                 1..165
                       mol_type = protein
                       organism = synthetic construct
SEQUENCE: 99
CDLPQTHSLG SRRTLMLLAQ MRFISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 100         moltype = AA  length = 165
FEATURE                Location/Qualifiers
source                 1..165
                       mol_type = protein
                       organism = synthetic construct
SEQUENCE: 100
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FKLSTNLQES LRSKE                  165

SEQ ID NO: 101         moltype = AA  length = 165
FEATURE                Location/Qualifiers
source                 1..165
                       mol_type = protein
                       organism = synthetic construct
SEQUENCE: 101
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEILRS FSLSTNLQES LRSKE                  165

SEQ ID NO: 102         moltype = AA  length = 165
FEATURE                Location/Qualifiers
source                 1..165
                       mol_type = protein
                       organism = synthetic construct
SEQUENCE: 102
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGWGVTETPL MKEDSILAVR  120
KYFQRITLYL KEKKYSPCAW EVVRAEIMRS FSLSTNLQES LRSKE                  165

SEQ ID NO: 103         moltype = AA  length = 165
FEATURE                Location/Qualifiers
source                 1..165
                       mol_type = protein
                       organism = synthetic construct
SEQUENCE: 103
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRITLYL KEKKYSPCAW EVVRAEIMRS FMLSTNLQES LRSKE                165

SEQ ID NO: 104          moltype = AA  length = 165
FEATURE                 Location/Qualifiers
source                  1..165
                        mol_type = protein
                        organism = synthetic construct
SEQUENCE: 104
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSHSTNLQES LRSKE                165

SEQ ID NO: 105          moltype = AA  length = 165
FEATURE                 Location/Qualifiers
source                  1..165
                        mol_type = protein
                        organism = synthetic construct
SEQUENCE: 105
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRFEIMRS FSLSTNLQES LRSKE                165

SEQ ID NO: 106          moltype = AA  length = 165
FEATURE                 Location/Qualifiers
source                  1..165
                        mol_type = protein
                        organism = synthetic construct
SEQUENCE: 106
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIIRS FSLSTNLQES LRSKE                165

SEQ ID NO: 107          moltype = AA  length = 165
FEATURE                 Location/Qualifiers
source                  1..165
                        mol_type = protein
                        organism = synthetic construct
SEQUENCE: 107
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVGAEIMRS FSLSTNLQES LRSKE                165

SEQ ID NO: 108          moltype = AA  length = 165
FEATURE                 Location/Qualifiers
source                  1..165
                        mol_type = protein
                        organism = synthetic construct
SEQUENCE: 108
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ENVRAEIMRS FSLSTNLQES LRSKE                165

SEQ ID NO: 109          moltype = AA  length = 165
FEATURE                 Location/Qualifiers
source                  1..165
                        mol_type = protein
                        organism = synthetic construct
SEQUENCE: 109
CDLPQTHSLG SRRTLMLLAQ MRYISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                165

SEQ ID NO: 110          moltype = AA  length = 165
FEATURE                 Location/Qualifiers
source                  1..165
                        mol_type = protein
                        organism = synthetic construct
SEQUENCE: 110
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIVRS FSLSTNLQES LRSKE                165

SEQ ID NO: 111          moltype = AA  length = 165
FEATURE                 Location/Qualifiers
source                  1..165
                        mol_type = protein
                        organism = synthetic construct
SEQUENCE: 111
CDLPQTHSLG SRRTHMLLAQ MRRISLFSCL KDRHDFGFPQ EEFGNQFQKA ETIPVLHEMI  60
```

-continued

```
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 112          moltype = AA  length = 165
FEATURE                 Location/Qualifiers
source                  1..165
                        mol_type = protein
                        organism = synthetic construct
SEQUENCE: 112
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSASTNLQES LRSKE                  165

SEQ ID NO: 113          moltype = AA  length = 165
FEATURE                 Location/Qualifiers
source                  1..165
                        mol_type = protein
                        organism = synthetic construct
SEQUENCE: 113
CDLPQTHSLG SRRTLMLAAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 114          moltype = AA  length = 165
FEATURE                 Location/Qualifiers
source                  1..165
                        mol_type = protein
                        organism = synthetic construct
SEQUENCE: 114
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSPSTNLQES LRSKE                  165

SEQ ID NO: 115          moltype = AA  length = 165
FEATURE                 Location/Qualifiers
source                  1..165
                        mol_type = protein
                        organism = synthetic construct
SEQUENCE: 115
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSDSTNLQES LRSKE                  165

SEQ ID NO: 116          moltype = AA  length = 165
FEATURE                 Location/Qualifiers
source                  1..165
                        mol_type = protein
                        organism = synthetic construct
SEQUENCE: 116
CDLPQTHSLG ARRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 117          moltype = AA  length = 165
FEATURE                 Location/Qualifiers
source                  1..165
                        mol_type = protein
                        organism = synthetic construct
SEQUENCE: 117
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEW LRSKE                  165

SEQ ID NO: 118          moltype = AA  length = 165
FEATURE                 Location/Qualifiers
source                  1..165
                        mol_type = protein
                        organism = synthetic construct
SEQUENCE: 118
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLWDLEACVI QGVGVTETPL MKEDSILAVR  120
KYFQRITLYL KEKKYSPCAW EVVRAEIMRS FSLSTNLQES LRSKE                  165

SEQ ID NO: 119          moltype = AA  length = 165
FEATURE                 Location/Qualifiers
source                  1..165
                        mol_type = protein
                        organism = synthetic construct
SEQUENCE: 119
```

```
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRE FSLSTNLQES LRSKE                 165

SEQ ID NO: 120         moltype = AA  length = 165
FEATURE                Location/Qualifiers
source                 1..165
                       mol_type = protein
                       organism = synthetic construct
SEQUENCE: 120
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FLLSTNLQES LRSKE                 165

SEQ ID NO: 121         moltype = AA  length = 165
FEATURE                Location/Qualifiers
source                 1..165
                       mol_type = protein
                       organism = synthetic construct
SEQUENCE: 121
CDLPQTHSLG SRRTLMLLAQ MRRISLGSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 122         moltype = AA  length = 165
FEATURE                Location/Qualifiers
source                 1..165
                       mol_type = protein
                       organism = synthetic construct
SEQUENCE: 122
CDLPQTHSLG SRRTLMLLAQ MRRISLFSCL KDRHDFGFPQ EEFGNQFQKA ETIPVLHEWI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 123         moltype = AA  length = 165
FEATURE                Location/Qualifiers
source                 1..165
                       mol_type = protein
                       organism = synthetic construct
SEQUENCE: 123
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSRSTNLQES LRSKE                 165

SEQ ID NO: 124         moltype = AA  length = 165
FEATURE                Location/Qualifiers
source                 1..165
                       mol_type = protein
                       organism = synthetic construct
SEQUENCE: 124
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FPLSTNLQES LRSKE                 165

SEQ ID NO: 125         moltype = AA  length = 165
FEATURE                Location/Qualifiers
source                 1..165
                       mol_type = protein
                       organism = synthetic construct
SEQUENCE: 125
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKI                 165

SEQ ID NO: 126         moltype = AA  length = 165
FEATURE                Location/Qualifiers
source                 1..165
                       mol_type = protein
                       organism = synthetic construct
SEQUENCE: 126
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FILSTNLQES LRSKE                 165

SEQ ID NO: 127         moltype = AA  length = 165
FEATURE                Location/Qualifiers
source                 1..165
                       mol_type = protein
                       organism = synthetic construct
```

-continued

```
SEQUENCE: 127
CDLPQTHSLG SRRTLMLLAQ MRRISLFSCL KTRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 128          moltype = AA  length = 165
FEATURE                 Location/Qualifiers
source                  1..165
                        mol_type = protein
                        organism = synthetic construct
SEQUENCE: 128
CDLPQTHSLG SRRTLMLLAQ MRRISYFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 129          moltype = AA  length = 165
FEATURE                 Location/Qualifiers
source                  1..165
                        mol_type = protein
                        organism = synthetic construct
SEQUENCE: 129
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMYS FSLSTNLQES LRSKE                  165

SEQ ID NO: 130          moltype = AA  length = 165
FEATURE                 Location/Qualifiers
source                  1..165
                        mol_type = protein
                        organism = synthetic construct
SEQUENCE: 130
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSYLAVR  120
KYFQRITLYL KEKKYSPCAW EVVRAEIMRS FSLSTNLQES LRSKE                  165

SEQ ID NO: 131          moltype = AA  length = 165
FEATURE                 Location/Qualifiers
source                  1..165
                        mol_type = protein
                        organism = synthetic construct
SEQUENCE: 131
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSRE                  165

SEQ ID NO: 132          moltype = AA  length = 165
FEATURE                 Location/Qualifiers
source                  1..165
                        mol_type = protein
                        organism = synthetic construct
SEQUENCE: 132
CDLPQTHSLG SRRTLMLLAQ MRRISLFSCL KDRHDFGFPQ EEFGNQFQKA ETIPVLHEKI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 133          moltype = AA  length = 165
FEATURE                 Location/Qualifiers
source                  1..165
                        mol_type = protein
                        organism = synthetic construct
SEQUENCE: 133
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLDTNLQES LRSKE                  165

SEQ ID NO: 134          moltype = AA  length = 165
FEATURE                 Location/Qualifiers
source                  1..165
                        mol_type = protein
                        organism = synthetic construct
SEQUENCE: 134
CDLPQTHSLG SRRTLMLLAQ MRRISLFSCL KDRHDFGFPQ EEFGNQFQKA ETIPVLHERI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 135          moltype = AA  length = 165
FEATURE                 Location/Qualifiers
source                  1..165
                        mol_type = protein
```

-continued

```
                      organism = synthetic construct
SEQUENCE: 135
CDLPQTHSLG SRRTLMLLAP MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 136        moltype = AA  length = 165
FEATURE               Location/Qualifiers
source                1..165
                      mol_type = protein
                      organism = synthetic construct
SEQUENCE: 136
CDLPQTHSLG SRRTLMLLAQ MRRISLQSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 137        moltype = AA  length = 165
FEATURE               Location/Qualifiers
source                1..165
                      mol_type = protein
                      organism = synthetic construct
SEQUENCE: 137
CDLPQTHSLG SRRTLMLLAQ MRNISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 138        moltype = AA  length = 165
FEATURE               Location/Qualifiers
source                1..165
                      mol_type = protein
                      organism = synthetic construct
SEQUENCE: 138
CDLPQTHSLG SRRTYMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 139        moltype = AA  length = 165
FEATURE               Location/Qualifiers
source                1..165
                      mol_type = protein
                      organism = synthetic construct
SEQUENCE: 139
CDLPQTHSLG SRRTLMLLAQ MRRISLSSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 140        moltype = AA  length = 165
FEATURE               Location/Qualifiers
source                1..165
                      mol_type = protein
                      organism = synthetic construct
SEQUENCE: 140
CDLPQTHSLG SRRTGMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 141        moltype = AA  length = 165
FEATURE               Location/Qualifiers
source                1..165
                      mol_type = protein
                      organism = synthetic construct
SEQUENCE: 141
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMLS FSLSTNLQES LRSKE                 165

SEQ ID NO: 142        moltype = AA  length = 165
FEATURE               Location/Qualifiers
source                1..165
                      mol_type = protein
                      organism = synthetic construct
SEQUENCE: 142
CDLPQTHSLG SRRTLMLLAQ MRRISLFSCL KDRHDFGFPE EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 143        moltype = AA  length = 165
FEATURE               Location/Qualifiers
source                1..165
```

```
                         mol_type = protein
                         organism = synthetic construct
SEQUENCE: 143
CDLPQTHSLG SRRTLMLLAQ MRRISFFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 144           moltype = AA  length = 165
FEATURE                  Location/Qualifiers
source                   1..165
                         mol_type = protein
                         organism = synthetic construct
SEQUENCE: 144
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QVVGVTETPL MKEDSILAVR  120
KYFQRITLYL KEKKYSPCAW EVVRAEIMRS FSLSTNLQES LRSKE                  165

SEQ ID NO: 145           moltype = AA  length = 165
FEATURE                  Location/Qualifiers
source                   1..165
                         mol_type = protein
                         organism = synthetic construct
SEQUENCE: 145
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMMS FSLSTNLQES LRSKE                  165

SEQ ID NO: 146           moltype = AA  length = 165
FEATURE                  Location/Qualifiers
source                   1..165
                         mol_type = protein
                         organism = synthetic construct
SEQUENCE: 146
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSQSTNLQES LRSKE                  165

SEQ ID NO: 147           moltype = AA  length = 165
FEATURE                  Location/Qualifiers
source                   1..165
                         mol_type = protein
                         organism = synthetic construct
SEQUENCE: 147
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FVLSTNLQES LRSKE                  165

SEQ ID NO: 148           moltype = AA  length = 165
FEATURE                  Location/Qualifiers
source                   1..165
                         mol_type = protein
                         organism = synthetic construct
SEQUENCE: 148
CDLPQTHSLG SRRTPMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 149           moltype = AA  length = 165
FEATURE                  Location/Qualifiers
source                   1..165
                         mol_type = protein
                         organism = synthetic construct
SEQUENCE: 149
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSECAW EVVRAEIMRS FSLSTNLQES LRSKE                  165

SEQ ID NO: 150           moltype = AA  length = 165
FEATURE                  Location/Qualifiers
source                   1..165
                         mol_type = protein
                         organism = synthetic construct
SEQUENCE: 150
CDLPQTHSLG SRRTLMLLAQ MRSISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 151           moltype = AA  length = 165
FEATURE                  Location/Qualifiers
```

```
source                  1..165
                        mol_type = protein
                        organism = synthetic construct
SEQUENCE: 151
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRN FSLSTNLQES LRSKE                  165

SEQ ID NO: 152          moltype = AA  length = 165
FEATURE                 Location/Qualifiers
source                  1..165
                        mol_type = protein
                        organism = synthetic construct
SEQUENCE: 152
CDLPQTHSLG SRRTLMRLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 153          moltype = AA  length = 165
FEATURE                 Location/Qualifiers
source                  1..165
                        mol_type = protein
                        organism = synthetic construct
SEQUENCE: 153
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQYITLYL KEKKYSPCAW EVVRAEIMRS FSLSTNLQES LRSKE                  165

SEQ ID NO: 154          moltype = AA  length = 165
FEATURE                 Location/Qualifiers
source                  1..165
                        mol_type = protein
                        organism = synthetic construct
SEQUENCE: 154
CDLPQTHSLG SRRTLMLLAQ MRRIYLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 155          moltype = AA  length = 165
FEATURE                 Location/Qualifiers
source                  1..165
                        mol_type = protein
                        organism = synthetic construct
SEQUENCE: 155
CDLPQTHSLG SRRTLMLLAQ MRRISLMSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 156          moltype = AA  length = 165
FEATURE                 Location/Qualifiers
source                  1..165
                        mol_type = protein
                        organism = synthetic construct
SEQUENCE: 156
CDLPQTHSLG SRRTLMLLAQ MRIISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 157          moltype = AA  length = 165
FEATURE                 Location/Qualifiers
source                  1..165
                        mol_type = protein
                        organism = synthetic construct
SEQUENCE: 157
CDLPQTHSLG SRRTLMLLAQ MRRISLFSCL KDRHDFGFPQ EEFGNQFQKA ETIPVLHEMI  60
QQIFNLFSTK DSSAAWDETL LDLFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 158          moltype = AA  length = 165
FEATURE                 Location/Qualifiers
source                  1..165
                        mol_type = protein
                        organism = synthetic construct
SEQUENCE: 158
CDLPQTHDLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 159          moltype = AA  length = 165
```

-continued

```
FEATURE                Location/Qualifiers
source                 1..165
                       mol_type = protein
                       organism = synthetic construct
SEQUENCE: 159
CDLPQTHSLG SRRTLMLLAQ MRRISLFSCL KDRHDFGGPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 160         moltype = AA  length = 165
FEATURE                Location/Qualifiers
source                 1..165
                       mol_type = protein
                       organism = synthetic construct
SEQUENCE: 160
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSFLAVR  120
KYFQRITLYL KEKKYSPCAW EVVRAEIMRS FSLSTNLQES LRSKE                  165

SEQ ID NO: 161         moltype = AA  length = 165
FEATURE                Location/Qualifiers
source                 1..165
                       mol_type = protein
                       organism = synthetic construct
SEQUENCE: 161
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LDSKE                  165

SEQ ID NO: 162         moltype = AA  length = 165
FEATURE                Location/Qualifiers
source                 1..165
                       mol_type = protein
                       organism = synthetic construct
SEQUENCE: 162
CDLPQTHSLG SRRTLMLLAQ MRGISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 163         moltype = AA  length = 165
FEATURE                Location/Qualifiers
source                 1..165
                       mol_type = protein
                       organism = synthetic construct
SEQUENCE: 163
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFSRITLYL KEKKYSPCAW EVVRAEIMRS FSLSTNLQES LRSKE                  165

SEQ ID NO: 164         moltype = AA  length = 165
FEATURE                Location/Qualifiers
source                 1..165
                       mol_type = protein
                       organism = synthetic construct
SEQUENCE: 164
CDLPQTHSLG SRRTLMLLAQ MPRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 165         moltype = AA  length = 165
FEATURE                Location/Qualifiers
source                 1..165
                       mol_type = protein
                       organism = synthetic construct
SEQUENCE: 165
CDLPQTHSLG SRRTLMLLAQ MRRISLFSCL KDRHDFGFPQ EEFGNQFQKA ETIPVLHEGI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 166         moltype = AA  length = 165
FEATURE                Location/Qualifiers
source                 1..165
                       mol_type = protein
                       organism = synthetic construct
SEQUENCE: 166
CDLPQTHSLG SRRTLMLLAQ MRRISGFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165
```

-continued

```
SEQ ID NO: 167          moltype = AA  length = 165
FEATURE                 Location/Qualifiers
source                  1..165
                        mol_type = protein
                        organism = synthetic construct
SEQUENCE: 167
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSESTNLQES LRSKE                  165

SEQ ID NO: 168          moltype = AA  length = 165
FEATURE                 Location/Qualifiers
source                  1..165
                        mol_type = protein
                        organism = synthetic construct
SEQUENCE: 168
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSLE                  165

SEQ ID NO: 169          moltype = AA  length = 165
FEATURE                 Location/Qualifiers
source                  1..165
                        mol_type = protein
                        organism = synthetic construct
SEQUENCE: 169
CDLPQTHSLG SRRTLMGLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 170          moltype = AA  length = 165
FEATURE                 Location/Qualifiers
source                  1..165
                        mol_type = protein
                        organism = synthetic construct
SEQUENCE: 170
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMKS FSLSTNLQES LRSKE                  165

SEQ ID NO: 171          moltype = AA  length = 165
FEATURE                 Location/Qualifiers
source                  1..165
                        mol_type = protein
                        organism = synthetic construct
SEQUENCE: 171
CDLPQTHSLG SRRTLMLLAQ MRRISLFSCL KDRHDFGFPQ EEFGNQFQKA ETIPELHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 172          moltype = AA  length = 165
FEATURE                 Location/Qualifiers
source                  1..165
                        mol_type = protein
                        organism = synthetic construct
SEQUENCE: 172
CDLPQTHSLG SRRTLMLLAQ MRRISLFSCL KDRHDFGIPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 173          moltype = AA  length = 165
FEATURE                 Location/Qualifiers
source                  1..165
                        mol_type = protein
                        organism = synthetic construct
SEQUENCE: 173
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSVSTNLQES LRSKE                  165

SEQ ID NO: 174          moltype = AA  length = 165
FEATURE                 Location/Qualifiers
source                  1..165
                        mol_type = protein
                        organism = synthetic construct
SEQUENCE: 174
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRASIMRS FSLSTNLQES LRSKE                  165
```

```
SEQ ID NO: 175          moltype = AA  length = 165
FEATURE                 Location/Qualifiers
source                  1..165
                        mol_type = protein
                        organism = synthetic construct
SEQUENCE: 175
CDLPQTHSLG SRRTLMLLAQ MRRISLFSCL LDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 176          moltype = AA  length = 165
FEATURE                 Location/Qualifiers
source                  1..165
                        mol_type = protein
                        organism = synthetic construct
SEQUENCE: 176
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAGIMRS FSLSTNLQES LRSKE                  165

SEQ ID NO: 177          moltype = AA  length = 165
FEATURE                 Location/Qualifiers
source                  1..165
                        mol_type = protein
                        organism = synthetic construct
SEQUENCE: 177
CDLPQTHSLG SRRTLMLLAQ MRRISLFSCL KDRHDFGVPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 178          moltype = AA  length = 165
FEATURE                 Location/Qualifiers
source                  1..165
                        mol_type = protein
                        organism = synthetic construct
SEQUENCE: 178
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRW FSLSTNLQES LRSKE                  165

SEQ ID NO: 179          moltype = AA  length = 165
FEATURE                 Location/Qualifiers
source                  1..165
                        mol_type = protein
                        organism = synthetic construct
SEQUENCE: 179
CDLPQTHSLG SRRTLMLLAQ MRRISLFSCL KDRHDFGPPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 180          moltype = AA  length = 165
FEATURE                 Location/Qualifiers
source                  1..165
                        mol_type = protein
                        organism = synthetic construct
SEQUENCE: 180
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRLKE                  165

SEQ ID NO: 181          moltype = AA  length = 165
FEATURE                 Location/Qualifiers
source                  1..165
                        mol_type = protein
                        organism = synthetic construct
SEQUENCE: 181
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSEE                  165

SEQ ID NO: 182          moltype = AA  length = 165
FEATURE                 Location/Qualifiers
source                  1..165
                        mol_type = protein
                        organism = synthetic construct
SEQUENCE: 182
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRITLYL KEKKYSPCAW EVVRAEIMRS FSLSTNLQES LRSYE               165

SEQ ID NO: 183          moltype = AA  length = 165
FEATURE                 Location/Qualifiers
source                  1..165
                        mol_type = protein
                        organism = synthetic construct
SEQUENCE: 183
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FWLSTNLQES LRSKE               165

SEQ ID NO: 184          moltype = AA  length = 165
FEATURE                 Location/Qualifiers
source                  1..165
                        mol_type = protein
                        organism = synthetic construct
SEQUENCE: 184
CDLPQTHSLG SRRTSMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE               165

SEQ ID NO: 185          moltype = AA  length = 165
FEATURE                 Location/Qualifiers
source                  1..165
                        mol_type = protein
                        organism = synthetic construct
SEQUENCE: 185
CDLPQTHSLG SRRTLMLLAQ MRRISEFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE               165

SEQ ID NO: 186          moltype = AA  length = 165
FEATURE                 Location/Qualifiers
source                  1..165
                        mol_type = protein
                        organism = synthetic construct
SEQUENCE: 186
CDLPQTHSLG SRRTLMLLAQ MRRISLFSCL KDRHDFGQPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE               165

SEQ ID NO: 187          moltype = AA  length = 165
FEATURE                 Location/Qualifiers
source                  1..165
                        mol_type = protein
                        organism = synthetic construct
SEQUENCE: 187
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYW QLNDLEACVI QGVGVTETPL MKEDSILAVR  120
KYFQRITLYL KEKKYSPCAW EVVRAEIMRS FSLSTNLQES LRSKE               165

SEQ ID NO: 188          moltype = AA  length = 165
FEATURE                 Location/Qualifiers
source                  1..165
                        mol_type = protein
                        organism = synthetic construct
SEQUENCE: 188
CDLPQTHSLG SRRTLMLLAQ MRRISLFSCL IDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE               165

SEQ ID NO: 189          moltype = AA  length = 165
FEATURE                 Location/Qualifiers
source                  1..165
                        mol_type = protein
                        organism = synthetic construct
SEQUENCE: 189
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEDKYSPCAW EVVRAEIMRS FSLSTNLQES LRSKE               165

SEQ ID NO: 190          moltype = AA  length = 165
FEATURE                 Location/Qualifiers
source                  1..165
                        mol_type = protein
                        organism = synthetic construct
SEQUENCE: 190
CDLPQTHSLG SRRTLMLLAQ MRRISLFSCL KDRHDFGFPQ EEFGNQFQKA ETIPVLHEMI  60
```

```
QQIFNLFSTK DSSAAWDETL LDKFYTELYQ QLNDLEACVI QGVGVTETWL MKEDSILAVR    120
KYFQRITLYL KEKKYSPCAW EVVRAEIMRS FSLSTNLQES LRSKE                   165

SEQ ID NO: 191          moltype = AA  length = 165
FEATURE                 Location/Qualifiers
source                  1..165
                        mol_type = protein
                        organism = synthetic construct
SEQUENCE: 191
CDLPQTHSLG SRRTLMLLAQ MRRISLFDCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKE                   165

SEQ ID NO: 192          moltype = AA  length = 165
FEATURE                 Location/Qualifiers
source                  1..165
                        mol_type = protein
                        organism = synthetic construct
SEQUENCE: 192
CDLPQTHSLG SRRTLMLLAQ QRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKE                   165

SEQ ID NO: 193          moltype = AA  length = 165
FEATURE                 Location/Qualifiers
source                  1..165
                        mol_type = protein
                        organism = synthetic construct
SEQUENCE: 193
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLYACVI QGVGVTETPL MKEDSILAVR    120
KYFQRITLYL KEKKYSPCAW EVVRAEIMRS FSLSTNLQES LRSKE                   165

SEQ ID NO: 194          moltype = AA  length = 165
FEATURE                 Location/Qualifiers
source                  1..165
                        mol_type = protein
                        organism = synthetic construct
SEQUENCE: 194
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRDEIMRS FSLSTNLQES LRSKE                   165

SEQ ID NO: 195          moltype = AA  length = 165
FEATURE                 Location/Qualifiers
source                  1..165
                        mol_type = protein
                        organism = synthetic construct
SEQUENCE: 195
CDLPQTHSLG SRRTLMLLAQ MRRISLHSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKE                   165

SEQ ID NO: 196          moltype = AA  length = 165
FEATURE                 Location/Qualifiers
source                  1..165
                        mol_type = protein
                        organism = synthetic construct
SEQUENCE: 196
CDLPQTHSLG SRRTLMLLAQ MRRISLFECL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQES LRSKE                   165

SEQ ID NO: 197          moltype = AA  length = 165
FEATURE                 Location/Qualifiers
source                  1..165
                        mol_type = protein
                        organism = synthetic construct
SEQUENCE: 197
CDLPQTHSLG SRRTLMLLAQ MRRISLFSCL KDRHDFGFPQ EEFGNQFQKA ETIPVLHEMI    60
QQIFNLFSTK DSSAAWDETL LDKFYTELYQ QLNDLEACVI QGVGVTETPL MKEDSILAVR    120
KYFQRITLYL KEKKYSPCAW EVVRAEIMRS FSLSTNLQEF LRSKE                   165

SEQ ID NO: 198          moltype = AA  length = 165
FEATURE                 Location/Qualifiers
source                  1..165
                        mol_type = protein
                        organism = synthetic construct
SEQUENCE: 198
```

-continued

```
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSFCAW EVVRAEIMRS FSLSTNLQES LRSKE                  165

SEQ ID NO: 199         moltype = AA  length = 165
FEATURE                Location/Qualifiers
source                 1..165
                       mol_type = protein
                       organism = synthetic construct
SEQUENCE: 199
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTPLYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 200         moltype = AA  length = 165
FEATURE                Location/Qualifiers
source                 1..165
                       mol_type = protein
                       organism = synthetic construct
SEQUENCE: 200
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAELMRS FSLSTNLQES LRSKE                  165

SEQ ID NO: 201         moltype = AA  length = 165
FEATURE                Location/Qualifiers
source                 1..165
                       mol_type = protein
                       organism = synthetic construct
SEQUENCE: 201
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FYLSTNLQES LRSKE                  165

SEQ ID NO: 202         moltype = AA  length = 165
FEATURE                Location/Qualifiers
source                 1..165
                       mol_type = protein
                       organism = synthetic construct
SEQUENCE: 202
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FGLSTNLQES LRSKE                  165

SEQ ID NO: 203         moltype = AA  length = 165
FEATURE                Location/Qualifiers
source                 1..165
                       mol_type = protein
                       organism = synthetic construct
SEQUENCE: 203
CDLPQTHSLG SRRTLMQLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 204         moltype = AA  length = 165
FEATURE                Location/Qualifiers
source                 1..165
                       mol_type = protein
                       organism = synthetic construct
SEQUENCE: 204
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSVE                  165

SEQ ID NO: 205         moltype = AA  length = 165
FEATURE                Location/Qualifiers
source                 1..165
                       mol_type = protein
                       organism = synthetic construct
SEQUENCE: 205
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKYYSPCAW EVVRAEIMRS FSLSTNLQES LRSKE                  165

SEQ ID NO: 206         moltype = AA  length = 165
FEATURE                Location/Qualifiers
source                 1..165
                       mol_type = protein
                       organism = synthetic construct
```

```
SEQUENCE: 206
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLMDLEACVI QGVGVTETPL MKEDSILAVR  120
KYFQRITLYL KEKKYSPCAW EVVRAEIMRS FSLSTNLQES LRSKE                  165

SEQ ID NO: 207          moltype = AA  length = 165
FEATURE                 Location/Qualifiers
source                  1..165
                        mol_type = protein
                        organism = synthetic construct
SEQUENCE: 207
CDLPQTHSLG SRRTLMLLAQ MRRISLFSCL KDRHDFGFPQ EEFGNQFQKA ETIPVLHEMI  60
QQLFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 208          moltype = AA  length = 165
FEATURE                 Location/Qualifiers
source                  1..165
                        mol_type = protein
                        organism = synthetic construct
SEQUENCE: 208
CDLPQTHSLG SRRTLMLLAQ MRRISLFSCL KDRHDFGFIQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 209          moltype = AA  length = 165
FEATURE                 Location/Qualifiers
source                  1..165
                        mol_type = protein
                        organism = synthetic construct
SEQUENCE: 209
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KHFQRITLYL KEKKYSPCAW EVVRAEIMRS FSLSTNLQES LRSKE                  165

SEQ ID NO: 210          moltype = AA  length = 165
FEATURE                 Location/Qualifiers
source                  1..165
                        mol_type = protein
                        organism = synthetic construct
SEQUENCE: 210
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGYGVTETPL MKEDSILAVR  120
KYFQRITLYL KEKKYSPCAW EVVRAEIMRS FSLSTNLQES LRSKE                  165

SEQ ID NO: 211          moltype = AA  length = 165
FEATURE                 Location/Qualifiers
source                  1..165
                        mol_type = protein
                        organism = synthetic construct
SEQUENCE: 211
CDLPQTHSLG SRRTLMLLAQ MRRISLFSCL KDRHDFGFPQ EEFGNSFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 212          moltype = AA  length = 165
FEATURE                 Location/Qualifiers
source                  1..165
                        mol_type = protein
                        organism = synthetic construct
SEQUENCE: 212
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSME                  165

SEQ ID NO: 213          moltype = AA  length = 165
FEATURE                 Location/Qualifiers
source                  1..165
                        mol_type = protein
                        organism = synthetic construct
SEQUENCE: 213
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLFDLEACVI QGVGVTETPL MKEDSILAVR  120
KYFQRITLYL KEKKYSPCAW EVVRAEIMRS FSLSTNLQES LRSKE                  165

SEQ ID NO: 214          moltype = AA  length = 165
FEATURE                 Location/Qualifiers
source                  1..165
                        mol_type = protein
```

-continued

```
                         organism = synthetic construct
SEQUENCE: 214
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSWCAW EVVRAEIMRS FSLSTNLQES LRSKE                  165

SEQ ID NO: 215           moltype = AA  length = 165
FEATURE                  Location/Qualifiers
source                   1..165
                         mol_type = protein
                         organism = synthetic construct
SEQUENCE: 215
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSFE                  165

SEQ ID NO: 216           moltype = AA  length = 165
FEATURE                  Location/Qualifiers
source                   1..165
                         mol_type = protein
                         organism = synthetic construct
SEQUENCE: 216
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSIE                  165

SEQ ID NO: 217           moltype = AA  length = 165
FEATURE                  Location/Qualifiers
source                   1..165
                         mol_type = protein
                         organism = synthetic construct
SEQUENCE: 217
CDLPQTHSLG SRRTTMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 218           moltype = AA  length = 165
FEATURE                  Location/Qualifiers
source                   1..165
                         mol_type = protein
                         organism = synthetic construct
SEQUENCE: 218
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEM LRSKE                  165

SEQ ID NO: 219           moltype = AA  length = 165
FEATURE                  Location/Qualifiers
source                   1..165
                         mol_type = protein
                         organism = synthetic construct
SEQUENCE: 219
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EDVRAEIMRS FSLSTNLQES LRSKE                  165

SEQ ID NO: 220           moltype = AA  length = 165
FEATURE                  Location/Qualifiers
source                   1..165
                         mol_type = protein
                         organism = synthetic construct
SEQUENCE: 220
CDLPQTHSLG SRRTLMLLGQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 221           moltype = AA  length = 165
FEATURE                  Location/Qualifiers
source                   1..165
                         mol_type = protein
                         organism = synthetic construct
SEQUENCE: 221
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KELKYSPCAW EVVRAEIMRS FSLSTNLQES LRSKE                  165

SEQ ID NO: 222           moltype = AA  length = 165
FEATURE                  Location/Qualifiers
source                   1..165
```

```
                        mol_type = protein
                        organism = synthetic construct
SEQUENCE: 222
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEE LRSKE                  165

SEQ ID NO: 223          moltype = AA  length = 165
FEATURE                 Location/Qualifiers
source                  1..165
                        mol_type = protein
                        organism = synthetic construct
SEQUENCE: 223
CDLPQTHSLG SRRTLMLLAQ MRRISLFSCL KDRHDFGFPQ EEFGNQFQKA ETIPVLHEMI  60
QQIFNLFSTK DSSAAWDETL LDKFKTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 224          moltype = AA  length = 165
FEATURE                 Location/Qualifiers
source                  1..165
                        mol_type = protein
                        organism = synthetic construct
SEQUENCE: 224
CDLPQTHSLG SRRTLMLLAQ MRRISLFSCL KNRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 225          moltype = AA  length = 165
FEATURE                 Location/Qualifiers
source                  1..165
                        mol_type = protein
                        organism = synthetic construct
SEQUENCE: 225
CDLPQTHSLG SRRTQMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 226          moltype = AA  length = 165
FEATURE                 Location/Qualifiers
source                  1..165
                        mol_type = protein
                        organism = synthetic construct
SEQUENCE: 226
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LESKE                  165

SEQ ID NO: 227          moltype = AA  length = 165
FEATURE                 Location/Qualifiers
source                  1..165
                        mol_type = protein
                        organism = synthetic construct
SEQUENCE: 227
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRIKE                  165

SEQ ID NO: 228          moltype = AA  length = 165
FEATURE                 Location/Qualifiers
source                  1..165
                        mol_type = protein
                        organism = synthetic construct
SEQUENCE: 228
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FELSTNLQES LRSKE                  165

SEQ ID NO: 229          moltype = AA  length = 165
FEATURE                 Location/Qualifiers
source                  1..165
                        mol_type = protein
                        organism = synthetic construct
SEQUENCE: 229
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 230          moltype = AA  length = 165
FEATURE                 Location/Qualifiers
```

```
source                 1..165
                       mol_type = protein
                       organism = synthetic construct
SEQUENCE: 230
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEY LRSKE                  165

SEQ ID NO: 231         moltype = AA  length = 165
FEATURE                Location/Qualifiers
source                 1..165
                       mol_type = protein
                       organism = synthetic construct
SEQUENCE: 231
CDLPQTHSLG SRRTLMLLAQ MRAISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 232         moltype = AA  length = 165
FEATURE                Location/Qualifiers
source                 1..165
                       mol_type = protein
                       organism = synthetic construct
SEQUENCE: 232
CDLPQTASLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 233         moltype = AA  length = 165
FEATURE                Location/Qualifiers
source                 1..165
                       mol_type = protein
                       organism = synthetic construct
SEQUENCE: 233
CDLPQTHSLG SRRTLMLLAQ MRHISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 234         moltype = AA  length = 165
FEATURE                Location/Qualifiers
source                 1..165
                       mol_type = protein
                       organism = synthetic construct
SEQUENCE: 234
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTSLYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 235         moltype = AA  length = 165
FEATURE                Location/Qualifiers
source                 1..165
                       mol_type = protein
                       organism = synthetic construct
SEQUENCE: 235
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEWKYSPCAW EVVRAEIMRS FSLSTNLQES LRSKE                  165

SEQ ID NO: 236         moltype = AA  length = 165
FEATURE                Location/Qualifiers
source                 1..165
                       mol_type = protein
                       organism = synthetic construct
SEQUENCE: 236
CDLPQTHSLG SRRTLMLLAQ MRTISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 237         moltype = AA  length = 165
FEATURE                Location/Qualifiers
source                 1..165
                       mol_type = protein
                       organism = synthetic construct
SEQUENCE: 237
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FQLSTNLQES LRSKE                  165

SEQ ID NO: 238         moltype = AA  length = 165
```

-continued

```
FEATURE                 Location/Qualifiers
source                  1..165
                        mol_type = protein
                        organism = synthetic construct
SEQUENCE: 238
CDLPQTHSLG SRRTLMLLAQ MRRISLFSCL KDRHQFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 239          moltype = AA  length = 165
FEATURE                 Location/Qualifiers
source                  1..165
                        mol_type = protein
                        organism = synthetic construct
SEQUENCE: 239
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KHKKYSPCAW EVVRAEIMRS FSLSTNLQES LRSKE                  165

SEQ ID NO: 240          moltype = AA  length = 165
FEATURE                 Location/Qualifiers
source                  1..165
                        mol_type = protein
                        organism = synthetic construct
SEQUENCE: 240
CDLPQTHSLG SRRTLMDLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 241          moltype = AA  length = 165
FEATURE                 Location/Qualifiers
source                  1..165
                        mol_type = protein
                        organism = synthetic construct
SEQUENCE: 241
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEMCVI QGVGVTETPL MKEDSILAVR  120
KYFQRITLYL KEKKYSPCAW EVVRAEIMRS FSLSTNLQES LRSKE                  165

SEQ ID NO: 242          moltype = AA  length = 165
FEATURE                 Location/Qualifiers
source                  1..165
                        mol_type = protein
                        organism = synthetic construct
SEQUENCE: 242
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVHAEIMRS FSLSTNLQES LRSKE                  165

SEQ ID NO: 243          moltype = AA  length = 165
FEATURE                 Location/Qualifiers
source                  1..165
                        mol_type = protein
                        organism = synthetic construct
SEQUENCE: 243
CDLPQTHSLG SRRTLMLLAQ MRRISLFSCL KDRHDFGFPQ EEFGNQFQKA ETIPVLHESI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 244          moltype = AA  length = 165
FEATURE                 Location/Qualifiers
source                  1..165
                        mol_type = protein
                        organism = synthetic construct
SEQUENCE: 244
CDLPQTHSLG SRRTLMLLMQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 245          moltype = AA  length = 165
FEATURE                 Location/Qualifiers
source                  1..165
                        mol_type = protein
                        organism = synthetic construct
SEQUENCE: 245
CDLPQTHSLG SRRTLMLLAQ MRRIHLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165
```

```
SEQ ID NO: 246         moltype = AA  length = 165
FEATURE                Location/Qualifiers
source                 1..165
                       mol_type = protein
                       organism = synthetic construct
SEQUENCE: 246
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVF  120
KYFQRITLYL KEKKYSPCAW EVVRAEIMRS FSLSTNLQES LRSKE                  165

SEQ ID NO: 247         moltype = AA  length = 165
FEATURE                Location/Qualifiers
source                 1..165
                       mol_type = protein
                       organism = synthetic construct
SEQUENCE: 247
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSWE                  165

SEQ ID NO: 248         moltype = AA  length = 165
FEATURE                Location/Qualifiers
source                 1..165
                       mol_type = protein
                       organism = synthetic construct
SEQUENCE: 248
CDLPQTHSLG SRRTLMLLAQ MRRSSLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 249         moltype = AA  length = 165
FEATURE                Location/Qualifiers
source                 1..165
                       mol_type = protein
                       organism = synthetic construct
SEQUENCE: 249
CDLPQTHSLG SNRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 250         moltype = AA  length = 165
FEATURE                Location/Qualifiers
source                 1..165
                       mol_type = protein
                       organism = synthetic construct
SEQUENCE: 250
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FTLSTNLQES LRSKE                  165

SEQ ID NO: 251         moltype = AA  length = 165
FEATURE                Location/Qualifiers
source                 1..165
                       mol_type = protein
                       organism = synthetic construct
SEQUENCE: 251
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRY FSLSTNLQES LRSKE                  165

SEQ ID NO: 252         moltype = AA  length = 165
FEATURE                Location/Qualifiers
source                 1..165
                       mol_type = protein
                       organism = synthetic construct
SEQUENCE: 252
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRMEIMRS FSLSTNLQES LRSKE                  165

SEQ ID NO: 253         moltype = AA  length = 165
FEATURE                Location/Qualifiers
source                 1..165
                       mol_type = protein
                       organism = synthetic construct
SEQUENCE: 253
CDLPQTHSLG SRRTLMLLAQ MRRISLFSCL KDRHDFGFPQ EEFGNQFQKA ETIPVLHEMI  60
QQIFNLFSTK DSSAEWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165
```

```
SEQ ID NO: 254         moltype = AA  length = 165
FEATURE                Location/Qualifiers
source                 1..165
                       mol_type = protein
                       organism = synthetic construct
SEQUENCE: 254
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRDKE                  165

SEQ ID NO: 255         moltype = AA  length = 165
FEATURE                Location/Qualifiers
source                 1..165
                       mol_type = protein
                       organism = synthetic construct
SEQUENCE: 255
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL YKEDSILAVR  120
KYFQRITLYL KEKKYSPCAW EVVRAEIMRS FSLSTNLQES LRSKE                  165

SEQ ID NO: 256         moltype = AA  length = 165
FEATURE                Location/Qualifiers
source                 1..165
                       mol_type = protein
                       organism = synthetic construct
SEQUENCE: 256
CDLPQTDSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 257         moltype = AA  length = 165
FEATURE                Location/Qualifiers
source                 1..165
                       mol_type = protein
                       organism = synthetic construct
SEQUENCE: 257
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLFACVI QGVGVTETPL MKEDSILAVR  120
KYFQRITLYL KEKKYSPCAW EVVRAEIMRS FSLSTNLQES LRSKE                  165

SEQ ID NO: 258         moltype = AA  length = 165
FEATURE                Location/Qualifiers
source                 1..165
                       mol_type = protein
                       organism = synthetic construct
SEQUENCE: 258
CDLPQTHSLG SRRTLMLLAQ MRRISLFSCL KDRHDFGFPQ EEFGNQFQKA ETIPGLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 259         moltype = AA  length = 165
FEATURE                Location/Qualifiers
source                 1..165
                       mol_type = protein
                       organism = synthetic construct
SEQUENCE: 259
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LQSKE                  165

SEQ ID NO: 260         moltype = AA  length = 165
FEATURE                Location/Qualifiers
source                 1..165
                       mol_type = protein
                       organism = synthetic construct
SEQUENCE: 260
CDLPQTHSLG SRRTLMLLAQ MRRISLFSCL MDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 261         moltype = AA  length = 165
FEATURE                Location/Qualifiers
source                 1..165
                       mol_type = protein
                       organism = synthetic construct
SEQUENCE: 261
CDLPQTHSDG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRITLYL KEKKYSPCAW EVVRAEIMRS FSLSTNLQES LRSKE                165

SEQ ID NO: 262         moltype = AA  length = 165
FEATURE                Location/Qualifiers
source                 1..165
                       mol_type = protein
                       organism = synthetic construct
SEQUENCE: 262
CDLPQTHSLG SRRTLMLLAQ MRRISLFSCL KDRHDFGFPQ EEFGNQFQKA ETIPVLHEMI  60
QQIFNLFSTK DSSAAWDETE LDKFYTELYQ QLNDLEACVI QGVGVTETPL MKEDSILAVR  120
KYFQRITLYL KEKKYSPCAW EVVRAEIMRS FSLSTNLQES LRSKE                165

SEQ ID NO: 263         moltype = AA  length = 165
FEATURE                Location/Qualifiers
source                 1..165
                       mol_type = protein
                       organism = synthetic construct
SEQUENCE: 263
CDLPQTHSLG SRRTLMLLAQ MRRISLFSCL KDRHDFGFPQ EEFGNQFQKA ETIPVLHEMI  60
QQIFNLFSTK DSSAAWDETL LDDFYTELYQ QLNDLEACVI QGVGVTETPL MKEDSILAVR  120
KYFQRITLYL KEKKYSPCAW EVVRAEIMRS FSLSTNLQES LRSKE                165

SEQ ID NO: 264         moltype = AA  length = 165
FEATURE                Location/Qualifiers
source                 1..165
                       mol_type = protein
                       organism = synthetic construct
SEQUENCE: 264
CDLPQTHSLG SRRTNMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                165

SEQ ID NO: 265         moltype = AA  length = 165
FEATURE                Location/Qualifiers
source                 1..165
                       mol_type = protein
                       organism = synthetic construct
SEQUENCE: 265
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTGLQES LRSKE                165

SEQ ID NO: 266         moltype = AA  length = 165
FEATURE                Location/Qualifiers
source                 1..165
                       mol_type = protein
                       organism = synthetic construct
SEQUENCE: 266
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EIVRAEIMRS FSLSTNLQES LRSKE                165

SEQ ID NO: 267         moltype = AA  length = 165
FEATURE                Location/Qualifiers
source                 1..165
                       mol_type = protein
                       organism = synthetic construct
SEQUENCE: 267
CDLPQTHSLG SRRTLMLLAQ MRRISLFSCL KDRHDFGFPQ EEFGNQFQKA ETIPVLHEMI  60
QQIFNLFSTK DSSAAWDETD LDKFYTELYQ QLNDLEACVI QGVGVTETPL MKEDSILAVR  120
KYFQRITLYL KEKKYSPCAW EVVRAEIMRS FSLSTNLQES LRSKE                165

SEQ ID NO: 268         moltype = AA  length = 165
FEATURE                Location/Qualifiers
source                 1..165
                       mol_type = protein
                       organism = synthetic construct
SEQUENCE: 268
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSGE                165

SEQ ID NO: 269         moltype = AA  length = 165
FEATURE                Location/Qualifiers
source                 1..165
                       mol_type = protein
                       organism = synthetic construct
SEQUENCE: 269
CDLPQTHSLG SRGTLMLLAQ MRRISLFSCL KDRHDFGFPQ EEFGNQFQKA ETIPVLHEMI  60
```

-continued

```
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 270          moltype = AA  length = 165
FEATURE                 Location/Qualifiers
source                  1..165
                        mol_type = protein
                        organism = synthetic construct
SEQUENCE: 270
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILEVR  120
KYFQRITLYL KEKKYSPCAW EVVRAEIMRS FSLSTNLQES LRSKE                  165

SEQ ID NO: 271          moltype = AA  length = 165
FEATURE                 Location/Qualifiers
source                  1..165
                        mol_type = protein
                        organism = synthetic construct
SEQUENCE: 271
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVGETPL MKEDSILAVR  120
KYFQRITLYL KEKKYSPCAW EVVRAEIMRS FSLSTNLQES LRSKE                  165

SEQ ID NO: 272          moltype = AA  length = 165
FEATURE                 Location/Qualifiers
source                  1..165
                        mol_type = protein
                        organism = synthetic construct
SEQUENCE: 272
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRQEIMRS FSLSTNLQES LRSKE                  165

SEQ ID NO: 273          moltype = AA  length = 165
FEATURE                 Location/Qualifiers
source                  1..165
                        mol_type = protein
                        organism = synthetic construct
SEQUENCE: 273
CDLPQTHSLG SRRTLMLLAQ MRRISLFSCL KQRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 274          moltype = AA  length = 165
FEATURE                 Location/Qualifiers
source                  1..165
                        mol_type = protein
                        organism = synthetic construct
SEQUENCE: 274
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEK LRSKE                  165

SEQ ID NO: 275          moltype = AA  length = 165
FEATURE                 Location/Qualifiers
source                  1..165
                        mol_type = protein
                        organism = synthetic construct
SEQUENCE: 275
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEL LRSKE                  165

SEQ ID NO: 276          moltype = AA  length = 165
FEATURE                 Location/Qualifiers
source                  1..165
                        mol_type = protein
                        organism = synthetic construct
SEQUENCE: 276
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLQDLEACVI QGVGVTETPL MKEDSILAVR  120
KYFQRITLYL KEKKYSPCAW EVVRAEIMRS FSLSTNLQES LRSKE                  165

SEQ ID NO: 277          moltype = AA  length = 165
FEATURE                 Location/Qualifiers
source                  1..165
                        mol_type = protein
                        organism = synthetic construct
SEQUENCE: 277
```

-continued

```
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLRTNLQES LRSKE                  165

SEQ ID NO: 278          moltype = AA  length = 165
FEATURE                 Location/Qualifiers
source                  1..165
                        mol_type = protein
                        organism = synthetic construct
SEQUENCE: 278
CDLPQTHSLG SRRTLMLLAQ MRRISLFSCL KDRHDFGFPQ EEFGNQFQKA ETIPVLHEMI  60
QQIFNLFSTE DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 279          moltype = AA  length = 165
FEATURE                 Location/Qualifiers
source                  1..165
                        mol_type = protein
                        organism = synthetic construct
SEQUENCE: 279
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILIVR  120
KYFQRITLYL KEKKYSPCAW EVVRAEIMRS FSLSTNLQES LRSKE                  165

SEQ ID NO: 280          moltype = AA  length = 165
FEATURE                 Location/Qualifiers
source                  1..165
                        mol_type = protein
                        organism = synthetic construct
SEQUENCE: 280
CDLPQTHSLG SRRTLMLLAQ MRRISLFSCL KDRHDFGFPQ EEFGNQFQKA ETIPVLHEMI  60
QQIFNLFSTK DSSAAWDETL LDKFYWELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 281          moltype = AA  length = 165
FEATURE                 Location/Qualifiers
source                  1..165
                        mol_type = protein
                        organism = synthetic construct
SEQUENCE: 281
CDLPQTHSLG SRRTLMLLAQ MRRISLFSCL KDRHDFGFPQ EEFGNQFQDA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 282          moltype = AA  length = 165
FEATURE                 Location/Qualifiers
source                  1..165
                        mol_type = protein
                        organism = synthetic construct
SEQUENCE: 282
CDLPQTHSLG SRRTLMLLAQ MRRISLASCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 283          moltype = AA  length = 165
FEATURE                 Location/Qualifiers
source                  1..165
                        mol_type = protein
                        organism = synthetic construct
SEQUENCE: 283
CDLPQTHSLG SRRTLMLLAQ MRRISLFSCL KDRHDFGAPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 284          moltype = AA  length = 165
FEATURE                 Location/Qualifiers
source                  1..165
                        mol_type = protein
                        organism = synthetic construct
SEQUENCE: 284
CDLPQTHSLG SRRTLMLLAQ MRRISLFSCL KDRHDFGSPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 285          moltype = AA  length = 165
FEATURE                 Location/Qualifiers
source                  1..165
                        mol_type = protein
                        organism = synthetic construct
```

-continued

```
SEQUENCE: 285
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSYCAW EVVRAEIMRS FSLSTNLQES LRSKE                  165

SEQ ID NO: 286         moltype = AA  length = 165
FEATURE                Location/Qualifiers
source                 1..165
                       mol_type = protein
                       organism = synthetic construct
SEQUENCE: 286
CDLPQTHSEG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 287         moltype = AA  length = 165
FEATURE                Location/Qualifiers
source                 1..165
                       mol_type = protein
                       organism = synthetic construct
SEQUENCE: 287
CDLPQTHSLG SRRTLMLLAQ MRRISLFSCL KDRHDFGFPQ EEFGNQFQKA ETIPVLHEMI  60
QQIFNLFSTV DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 288         moltype = AA  length = 165
FEATURE                Location/Qualifiers
source                 1..165
                       mol_type = protein
                       organism = synthetic construct
SEQUENCE: 288
CDLPQTHSLG SRRTLMLLAQ MRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSTCAW EVVRAEIMRS FSLSTNLQES LRSKE                  165

SEQ ID NO: 289         moltype = AA  length = 165
FEATURE                Location/Qualifiers
source                 1..165
                       mol_type = protein
                       organism = synthetic construct
SEQUENCE: 289
CDLPQTHSLG SRRTLMLLAQ MRRESLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 290         moltype = AA  length = 165
FEATURE                Location/Qualifiers
source                 1..165
                       mol_type = protein
                       organism = synthetic construct
SEQUENCE: 290
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRREIMRS FSLSTNLQES LRSKE                  165

SEQ ID NO: 291         moltype = AA  length = 165
FEATURE                Location/Qualifiers
source                 1..165
                       mol_type = protein
                       organism = synthetic construct
SEQUENCE: 291
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FPLSTNLQES LRSKE                  165

SEQ ID NO: 292         moltype = AA  length = 165
FEATURE                Location/Qualifiers
source                 1..165
                       mol_type = protein
                       organism = synthetic construct
SEQUENCE: 292
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRH FSLSTNLQES LRSKE                  165

SEQ ID NO: 293         moltype = AA  length = 165
FEATURE                Location/Qualifiers
source                 1..165
                       mol_type = protein
```

```
                         organism = synthetic construct
SEQUENCE: 293
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIWRS FSLSTNLQES LRSKE                  165

SEQ ID NO: 294           moltype = AA  length = 165
FEATURE                  Location/Qualifiers
source                   1..165
                         mol_type = protein
                         organism = synthetic construct
SEQUENCE: 294
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIGRS FSLSTNLQES LRSKE                  165

SEQ ID NO: 295           moltype = AA  length = 165
FEATURE                  Location/Qualifiers
source                   1..165
                         mol_type = protein
                         organism = synthetic construct
SEQUENCE: 295
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRR FSLSTNLQES LRSKE                  165

SEQ ID NO: 296           moltype = AA  length = 165
FEATURE                  Location/Qualifiers
source                   1..165
                         mol_type = protein
                         organism = synthetic construct
SEQUENCE: 296
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FPLSTNLQES LRSKE                  165

SEQ ID NO: 297           moltype = AA  length = 165
FEATURE                  Location/Qualifiers
source                   1..165
                         mol_type = protein
                         organism = synthetic construct
SEQUENCE: 297
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIVRS FSLSTNLQES LRSKE                  165

SEQ ID NO: 298           moltype = AA  length = 165
FEATURE                  Location/Qualifiers
source                   1..165
                         mol_type = protein
                         organism = synthetic construct
SEQUENCE: 298
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIKRS FSLSTNLQES LRSKE                  165

SEQ ID NO: 299           moltype = AA  length = 165
FEATURE                  Location/Qualifiers
source                   1..165
                         mol_type = protein
                         organism = synthetic construct
SEQUENCE: 299
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEISRS FSLSTNLQES LRSKE                  165

SEQ ID NO: 300           moltype = AA  length = 165
FEATURE                  Location/Qualifiers
source                   1..165
                         mol_type = protein
                         organism = synthetic construct
SEQUENCE: 300
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FRLSTNLQES LRSKE                  165

SEQ ID NO: 301           moltype = AA  length = 165
FEATURE                  Location/Qualifiers
source                   1..165
```

```
                         mol_type = protein
                         organism = synthetic construct
SEQUENCE: 301
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIRRS FSLSTNLQES LRSKE                  165

SEQ ID NO: 302           moltype = AA  length = 165
FEATURE                  Location/Qualifiers
source                   1..165
                         mol_type = protein
                         organism = synthetic construct
SEQUENCE: 302
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSGSTNLQES LRSKE                  165

SEQ ID NO: 303           moltype = AA  length = 165
FEATURE                  Location/Qualifiers
source                   1..165
                         mol_type = protein
                         organism = synthetic construct
SEQUENCE: 303
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIYRS FSLSTNLQES LRSKE                  165

SEQ ID NO: 304           moltype = AA  length = 165
FEATURE                  Location/Qualifiers
source                   1..165
                         mol_type = protein
                         organism = synthetic construct
SEQUENCE: 304
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSNSTNLQES LRSKE                  165

SEQ ID NO: 305           moltype = AA  length = 165
FEATURE                  Location/Qualifiers
source                   1..165
                         mol_type = protein
                         organism = synthetic construct
SEQUENCE: 305
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRQ FSLSTNLQES LRSKE                  165

SEQ ID NO: 306           moltype = AA  length = 165
FEATURE                  Location/Qualifiers
source                   1..165
                         mol_type = protein
                         organism = synthetic construct
SEQUENCE: 306
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSHSTNLQES LRSKE                  165

SEQ ID NO: 307           moltype = AA  length = 165
FEATURE                  Location/Qualifiers
source                   1..165
                         mol_type = protein
                         organism = synthetic construct
SEQUENCE: 307
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSRSTNLQES LRSKE                  165

SEQ ID NO: 308           moltype = AA  length = 165
FEATURE                  Location/Qualifiers
source                   1..165
                         mol_type = protein
                         organism = synthetic construct
SEQUENCE: 308
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIARS FSLSTNLQES LRSKE                  165

SEQ ID NO: 309           moltype = AA  length = 165
FEATURE                  Location/Qualifiers
```

```
source                  1..165
                        mol_type = protein
                        organism = synthetic construct
SEQUENCE: 309
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEITRS FSLSTNLQES LRSKE                 165

SEQ ID NO: 310          moltype = AA  length = 165
FEATURE                 Location/Qualifiers
source                  1..165
                        mol_type = protein
                        organism = synthetic construct
SEQUENCE: 310
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSASTNLQES LRSKE                 165

SEQ ID NO: 311          moltype = AA  length = 165
FEATURE                 Location/Qualifiers
source                  1..165
                        mol_type = protein
                        organism = synthetic construct
SEQUENCE: 311
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIFRS FSLSTNLQES LRSKE                 165

SEQ ID NO: 312          moltype = AA  length = 165
FEATURE                 Location/Qualifiers
source                  1..165
                        mol_type = protein
                        organism = synthetic construct
SEQUENCE: 312
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FKLSTNLQES LRSKE                 165

SEQ ID NO: 313          moltype = AA  length = 165
FEATURE                 Location/Qualifiers
source                  1..165
                        mol_type = protein
                        organism = synthetic construct
SEQUENCE: 313
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FKLSTNLQES LRSKE                 165

SEQ ID NO: 314          moltype = AA  length = 165
FEATURE                 Location/Qualifiers
source                  1..165
                        mol_type = protein
                        organism = synthetic construct
SEQUENCE: 314
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSESTNLQES LRSKE                 165

SEQ ID NO: 315          moltype = AA  length = 165
FEATURE                 Location/Qualifiers
source                  1..165
                        mol_type = protein
                        organism = synthetic construct
SEQUENCE: 315
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRATIMRS FSLSTNLQES LRSKE                 165

SEQ ID NO: 316          moltype = AA  length = 165
FEATURE                 Location/Qualifiers
source                  1..165
                        mol_type = protein
                        organism = synthetic construct
SEQUENCE: 316
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEILRS FSLSTNLQES LRSKE                 165

SEQ ID NO: 317          moltype = AA  length = 165
```

```
FEATURE                Location/Qualifiers
source                 1..165
                       mol_type = protein
                       organism = synthetic construct
SEQUENCE: 317
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSQSTNLQES LRSKE                  165

SEQ ID NO: 318         moltype = AA  length = 165
FEATURE                Location/Qualifiers
source                 1..165
                       mol_type = protein
                       organism = synthetic construct
SEQUENCE: 318
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSEE                  165

SEQ ID NO: 319         moltype = AA  length = 165
FEATURE                Location/Qualifiers
source                 1..165
                       mol_type = protein
                       organism = synthetic construct
SEQUENCE: 319
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRN FSLSTNLQES LRSKE                  165

SEQ ID NO: 320         moltype = AA  length = 165
FEATURE                Location/Qualifiers
source                 1..165
                       mol_type = protein
                       organism = synthetic construct
SEQUENCE: 320
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSHSTNLQES LRSKE                  165

SEQ ID NO: 321         moltype = AA  length = 165
FEATURE                Location/Qualifiers
source                 1..165
                       mol_type = protein
                       organism = synthetic construct
SEQUENCE: 321
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FRLSTNLQES LRSKE                  165

SEQ ID NO: 322         moltype = AA  length = 165
FEATURE                Location/Qualifiers
source                 1..165
                       mol_type = protein
                       organism = synthetic construct
SEQUENCE: 322
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLNTNLQES LRSKE                  165

SEQ ID NO: 323         moltype = AA  length = 165
FEATURE                Location/Qualifiers
source                 1..165
                       mol_type = protein
                       organism = synthetic construct
SEQUENCE: 323
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRW FSLSTNLQES LRSKE                  165

SEQ ID NO: 324         moltype = AA  length = 165
FEATURE                Location/Qualifiers
source                 1..165
                       mol_type = protein
                       organism = synthetic construct
SEQUENCE: 324
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLDTNLQES LRSKE                  165
```

```
SEQ ID NO: 325          moltype = AA  length = 165
FEATURE                 Location/Qualifiers
source                  1..165
                        mol_type = protein
                        organism = synthetic construct
SEQUENCE: 325
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LDSKE                  165

SEQ ID NO: 326          moltype = AA  length = 165
FEATURE                 Location/Qualifiers
source                  1..165
                        mol_type = protein
                        organism = synthetic construct
SEQUENCE: 326
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRASIMRS FSLSTNLQES LRSKE                  165

SEQ ID NO: 327          moltype = AA  length = 165
FEATURE                 Location/Qualifiers
source                  1..165
                        mol_type = protein
                        organism = synthetic construct
SEQUENCE: 327
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FGLSTNLQES LRSKE                  165

SEQ ID NO: 328          moltype = AA  length = 165
FEATURE                 Location/Qualifiers
source                  1..165
                        mol_type = protein
                        organism = synthetic construct
SEQUENCE: 328
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLLTNLQES LRSKE                  165

SEQ ID NO: 329          moltype = AA  length = 165
FEATURE                 Location/Qualifiers
source                  1..165
                        mol_type = protein
                        organism = synthetic construct
SEQUENCE: 329
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMKS FSLSTNLQES LRSKE                  165

SEQ ID NO: 330          moltype = AA  length = 165
FEATURE                 Location/Qualifiers
source                  1..165
                        mol_type = protein
                        organism = synthetic construct
SEQUENCE: 330
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LESKE                  165

SEQ ID NO: 331          moltype = AA  length = 165
FEATURE                 Location/Qualifiers
source                  1..165
                        mol_type = protein
                        organism = synthetic construct
SEQUENCE: 331
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSME                  165

SEQ ID NO: 332          moltype = AA  length = 165
FEATURE                 Location/Qualifiers
source                  1..165
                        mol_type = protein
                        organism = synthetic construct
SEQUENCE: 332
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSWE                  165
```

```
SEQ ID NO: 333         moltype = AA  length = 165
FEATURE                Location/Qualifiers
source                 1..165
                       mol_type = protein
                       organism = synthetic construct
SEQUENCE: 333
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYQPCAW EVVRAEIMRS FSLSTNLQES LRSKE                  165

SEQ ID NO: 334         moltype = AA  length = 165
FEATURE                Location/Qualifiers
source                 1..165
                       mol_type = protein
                       organism = synthetic construct
SEQUENCE: 334
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSQSTNLQES LRSKE                  165

SEQ ID NO: 335         moltype = AA  length = 165
FEATURE                Location/Qualifiers
source                 1..165
                       mol_type = protein
                       organism = synthetic construct
SEQUENCE: 335
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LESKE                  165

SEQ ID NO: 336         moltype = AA  length = 165
FEATURE                Location/Qualifiers
source                 1..165
                       mol_type = protein
                       organism = synthetic construct
SEQUENCE: 336
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FQLSTNLQES LRSKE                  165

SEQ ID NO: 337         moltype = AA  length = 165
FEATURE                Location/Qualifiers
source                 1..165
                       mol_type = protein
                       organism = synthetic construct
SEQUENCE: 337
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FMLSTNLQES LRSKE                  165

SEQ ID NO: 338         moltype = AA  length = 165
FEATURE                Location/Qualifiers
source                 1..165
                       mol_type = protein
                       organism = synthetic construct
SEQUENCE: 338
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KVKKYSPCAW EVVRAEIMRS FSLSTNLQES LRSKE                  165

SEQ ID NO: 339         moltype = AA  length = 165
FEATURE                Location/Qualifiers
source                 1..165
                       mol_type = protein
                       organism = synthetic construct
SEQUENCE: 339
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSDE                  165

SEQ ID NO: 340         moltype = AA  length = 165
FEATURE                Location/Qualifiers
source                 1..165
                       mol_type = protein
                       organism = synthetic construct
SEQUENCE: 340
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

```
KYFQRITLYL KEKKYSPCAW EVVRAEIMRS FWLSTNLQES LRSKE                165

SEQ ID NO: 341          moltype = AA  length = 165
FEATURE                 Location/Qualifiers
source                  1..165
                        mol_type = protein
                        organism = synthetic construct
SEQUENCE: 341
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSVSTNLQES LRSKE                165

SEQ ID NO: 342          moltype = AA  length = 165
FEATURE                 Location/Qualifiers
source                  1..165
                        mol_type = protein
                        organism = synthetic construct
SEQUENCE: 342
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRL FSLSTNLQES LRSKE                165

SEQ ID NO: 343          moltype = AA  length = 165
FEATURE                 Location/Qualifiers
source                  1..165
                        mol_type = protein
                        organism = synthetic construct
SEQUENCE: 343
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FGLSTNLQES LRSKE                165

SEQ ID NO: 344          moltype = AA  length = 165
FEATURE                 Location/Qualifiers
source                  1..165
                        mol_type = protein
                        organism = synthetic construct
SEQUENCE: 344
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LGSKE                165

SEQ ID NO: 345          moltype = AA  length = 165
FEATURE                 Location/Qualifiers
source                  1..165
                        mol_type = protein
                        organism = synthetic construct
SEQUENCE: 345
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVW  120
KYFQRITLYL KEKKYSPCAW EVVRAEIMRS FSLSTNLQES LRSKE                165

SEQ ID NO: 346          moltype = AA  length = 165
FEATURE                 Location/Qualifiers
source                  1..165
                        mol_type = protein
                        organism = synthetic construct
SEQUENCE: 346
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRTTLYL KEKKYSPCAW EVVRAEIMRS FSLSTNLQES LRSKE                165

SEQ ID NO: 347          moltype = AA  length = 165
FEATURE                 Location/Qualifiers
source                  1..165
                        mol_type = protein
                        organism = synthetic construct
SEQUENCE: 347
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LLSKE                165

SEQ ID NO: 348          moltype = AA  length = 165
FEATURE                 Location/Qualifiers
source                  1..165
                        mol_type = protein
                        organism = synthetic construct
SEQUENCE: 348
CDLPQTHSLG SRRTLMLLAQ MRRISPFSCL KDRHDFGFPQ EEFGNQFQKA ETIPVLHEMI  60
```

```
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LSSKE                 165

SEQ ID NO: 349         moltype = AA  length = 165
FEATURE                Location/Qualifiers
source                 1..165
                       mol_type = protein
                       organism = synthetic construct
SEQUENCE: 349
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLHTNLQES LRSKE                 165

SEQ ID NO: 350         moltype = AA  length = 165
FEATURE                Location/Qualifiers
source                 1..165
                       mol_type = protein
                       organism = synthetic construct
SEQUENCE: 350
CDLPQTHSLG SRRTLMLLAQ MRRISPFSCL KDRHDFGFPQ EEFGNQFQKA ETIPVLHEMI  60
QQIFNLFSTK DSSAAWDETL LDDFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 351         moltype = AA  length = 165
FEATURE                Location/Qualifiers
source                 1..165
                       mol_type = protein
                       organism = synthetic construct
SEQUENCE: 351
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LNSKE                 165

SEQ ID NO: 352         moltype = AA  length = 165
FEATURE                Location/Qualifiers
source                 1..165
                       mol_type = protein
                       organism = synthetic construct
SEQUENCE: 352
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSVE                 165

SEQ ID NO: 353         moltype = AA  length = 165
FEATURE                Location/Qualifiers
source                 1..165
                       mol_type = protein
                       organism = synthetic construct
SEQUENCE: 353
CDLPQTHSLG SRRTLMLLAQ MRRISPFSCL KDRHDFGFPQ EEFGNQFQKA ETIPVLHEMI  60
QQIFNLFSTK DSSAAWDETL LDWFYTELYQ QLNDLEACVI QGVGVTETPL MKEDSILAVR  120
KYFQRITLYL KEKKYSPCAW EVVRAEIMRS FSLSTNLQES LRSKE                 165

SEQ ID NO: 354         moltype = AA  length = 165
FEATURE                Location/Qualifiers
source                 1..165
                       mol_type = protein
                       organism = synthetic construct
SEQUENCE: 354
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MTEDSILAVR  120
KYFQRITLYL KEKKYSPCAW EVVRAEIMRS FSLSTNLQES LRSKE                 165

SEQ ID NO: 355         moltype = AA  length = 165
FEATURE                Location/Qualifiers
source                 1..165
                       mol_type = protein
                       organism = synthetic construct
SEQUENCE: 355
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGITETPL MKEDSILAVR  120
KYFQRITLYL KEKKYSPCAW EVVRAEIMRS FSLSTNLQES LRSKE                 165

SEQ ID NO: 356         moltype = AA  length = 165
FEATURE                Location/Qualifiers
source                 1..165
                       mol_type = protein
                       organism = synthetic construct
SEQUENCE: 356
```

```
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LDSKE                  165

SEQ ID NO: 357          moltype = AA  length = 165
FEATURE                 Location/Qualifiers
source                  1..165
                        mol_type = protein
                        organism = synthetic construct
SEQUENCE: 357
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 358          moltype = AA  length = 165
FEATURE                 Location/Qualifiers
source                  1..165
                        mol_type = protein
                        organism = synthetic construct
SEQUENCE: 358
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEM LRSKE                  165

SEQ ID NO: 359          moltype = AA  length = 165
FEATURE                 Location/Qualifiers
source                  1..165
                        mol_type = protein
                        organism = synthetic construct
SEQUENCE: 359
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQED LRSKE                  165

SEQ ID NO: 360          moltype = AA  length = 165
FEATURE                 Location/Qualifiers
source                  1..165
                        mol_type = protein
                        organism = synthetic construct
SEQUENCE: 360
CDLPQTHSLG SRRTLMLLAQ MRRISPFSCL KDRHDFGFPQ EEFGNQFQKA ETIPVLHEMI  60
QQIFNLFSTK DSSAAWDETL LDPFYTELYQ QLNDLEACVI QGVGVTETPL MKEDSILAVR  120
KYFQRITLYL KEAKYSPCAW EVVRAEIMRS FSLSTNLQES LRSKE                  165

SEQ ID NO: 361          moltype = AA  length = 165
FEATURE                 Location/Qualifiers
source                  1..165
                        mol_type = protein
                        organism = synthetic construct
SEQUENCE: 361
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEL LRSKE                  165

SEQ ID NO: 362          moltype = AA  length = 165
FEATURE                 Location/Qualifiers
source                  1..165
                        mol_type = protein
                        organism = synthetic construct
SEQUENCE: 362
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSDE                  165

SEQ ID NO: 363          moltype = AA  length = 165
FEATURE                 Location/Qualifiers
source                  1..165
                        mol_type = protein
                        organism = synthetic construct
SEQUENCE: 363
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LMSKE                  165

SEQ ID NO: 364          moltype = AA  length = 165
FEATURE                 Location/Qualifiers
source                  1..165
                        mol_type = protein
                        organism = synthetic construct
```

```
SEQUENCE: 364
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LNSKE                  165

SEQ ID NO: 365         moltype = AA  length = 165
FEATURE                Location/Qualifiers
source                 1..165
                       mol_type = protein
                       organism = synthetic construct
SEQUENCE: 365
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRLEIMRS FSLSTNLQES LRSKE                  165

SEQ ID NO: 366         moltype = AA  length = 165
FEATURE                Location/Qualifiers
source                 1..165
                       mol_type = protein
                       organism = synthetic construct
SEQUENCE: 366
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FLLSTNLQES LRSKE                  165

SEQ ID NO: 367         moltype = AA  length = 165
FEATURE                Location/Qualifiers
source                 1..165
                       mol_type = protein
                       organism = synthetic construct
SEQUENCE: 367
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LQSKE                  165

SEQ ID NO: 368         moltype = AA  length = 165
FEATURE                Location/Qualifiers
source                 1..165
                       mol_type = protein
                       organism = synthetic construct
SEQUENCE: 368
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSGE                  165

SEQ ID NO: 369         moltype = AA  length = 165
FEATURE                Location/Qualifiers
source                 1..165
                       mol_type = protein
                       organism = synthetic construct
SEQUENCE: 369
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLETNLQES LRSKE                  165

SEQ ID NO: 370         moltype = AA  length = 165
FEATURE                Location/Qualifiers
source                 1..165
                       mol_type = protein
                       organism = synthetic construct
SEQUENCE: 370
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAL EVVRAEIMRS FSLSTNLQES LRSKE                  165

SEQ ID NO: 371         moltype = AA  length = 165
FEATURE                Location/Qualifiers
source                 1..165
                       mol_type = protein
                       organism = synthetic construct
SEQUENCE: 371
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LWSKE                  165

SEQ ID NO: 372         moltype = AA  length = 165
FEATURE                Location/Qualifiers
source                 1..165
                       mol_type = protein
```

```
                        organism = synthetic construct
SEQUENCE: 372
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSTE                  165

SEQ ID NO: 373          moltype = AA  length = 165
FEATURE                 Location/Qualifiers
source                  1..165
                        mol_type = protein
                        organism = synthetic construct
SEQUENCE: 373
CDLPQTHSLG SRRTLMLLAQ MRRISPFSCL KDRHDFGFPQ EEFGNQFQKA ETIPVLHEMI  60
QQIFNLFSTK DSSAAWDETL LDKFYWELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 374          moltype = AA  length = 165
FEATURE                 Location/Qualifiers
source                  1..165
                        mol_type = protein
                        organism = synthetic construct
SEQUENCE: 374
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSECAW EVVRAEIMRS FSLSTNLQES LRSKE                  165

SEQ ID NO: 375          moltype = AA  length = 165
FEATURE                 Location/Qualifiers
source                  1..165
                        mol_type = protein
                        organism = synthetic construct
SEQUENCE: 375
CDLPQTHSLG SRRTLMLLAQ NRRISLFSCL KDRHDFGFPQ EEFGNQFQKA ETIPVLHEMI  60
QQIFNLFSTK DSSAAWDETL LDTFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 376          moltype = AA  length = 165
FEATURE                 Location/Qualifiers
source                  1..165
                        mol_type = protein
                        organism = synthetic construct
SEQUENCE: 376
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LTSKE                  165

SEQ ID NO: 377          moltype = AA  length = 165
FEATURE                 Location/Qualifiers
source                  1..165
                        mol_type = protein
                        organism = synthetic construct
SEQUENCE: 377
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FILSTNLQES LRSKE                  165

SEQ ID NO: 378          moltype = AA  length = 165
FEATURE                 Location/Qualifiers
source                  1..165
                        mol_type = protein
                        organism = synthetic construct
SEQUENCE: 378
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRF FSLSTNLQES LRSKE                  165

SEQ ID NO: 379          moltype = AA  length = 165
FEATURE                 Location/Qualifiers
source                  1..165
                        mol_type = protein
                        organism = synthetic construct
SEQUENCE: 379
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LLSKE                  165

SEQ ID NO: 380          moltype = AA  length = 165
FEATURE                 Location/Qualifiers
source                  1..165
```

```
                         mol_type = protein
                         organism = synthetic construct
SEQUENCE: 380
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEE LRSKE                  165

SEQ ID NO: 381           moltype = AA  length = 165
FEATURE                  Location/Qualifiers
source                   1..165
                         mol_type = protein
                         organism = synthetic construct
SEQUENCE: 381
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSNE                  165

SEQ ID NO: 382           moltype = AA  length = 165
FEATURE                  Location/Qualifiers
source                   1..165
                         mol_type = protein
                         organism = synthetic construct
SEQUENCE: 382
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSFE                  165

SEQ ID NO: 383           moltype = AA  length = 165
FEATURE                  Location/Qualifiers
source                   1..165
                         mol_type = protein
                         organism = synthetic construct
SEQUENCE: 383
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYDPCAW EVVRAEIMRS FSLSTNLQES LRSKE                  165

SEQ ID NO: 384           moltype = AA  length = 165
FEATURE                  Location/Qualifiers
source                   1..165
                         mol_type = protein
                         organism = synthetic construct
SEQUENCE: 384
CDLPQTHSLG SRRTLMLLAQ NRRISLFSCL KDRHDFGFPQ EEFGNQFQKA ETIPVLHEMI  60
QQIFNLFSTK DSSAAWDETL LDIFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 385           moltype = AA  length = 165
FEATURE                  Location/Qualifiers
source                   1..165
                         mol_type = protein
                         organism = synthetic construct
SEQUENCE: 385
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FYLSTNLQES LRSKE                  165

SEQ ID NO: 386           moltype = AA  length = 165
FEATURE                  Location/Qualifiers
source                   1..165
                         mol_type = protein
                         organism = synthetic construct
SEQUENCE: 386
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES NRSKE                  165

SEQ ID NO: 387           moltype = AA  length = 165
FEATURE                  Location/Qualifiers
source                   1..165
                         mol_type = protein
                         organism = synthetic construct
SEQUENCE: 387
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAELMRS FSLSTNLQES LRSKE                  165

SEQ ID NO: 388           moltype = AA  length = 165
FEATURE                  Location/Qualifiers
```

```
source                  1..165
                        mol_type = protein
                        organism = synthetic construct
SEQUENCE: 388
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVSRAEIMRS FSLSTNLQES LRSKE                  165

SEQ ID NO: 389          moltype = AA  length = 165
FEATURE                 Location/Qualifiers
source                  1..165
                        mol_type = protein
                        organism = synthetic construct
SEQUENCE: 389
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSAE                  165

SEQ ID NO: 390          moltype = AA  length = 165
FEATURE                 Location/Qualifiers
source                  1..165
                        mol_type = protein
                        organism = synthetic construct
SEQUENCE: 390
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRDKE                  165

SEQ ID NO: 391          moltype = AA  length = 165
FEATURE                 Location/Qualifiers
source                  1..165
                        mol_type = protein
                        organism = synthetic construct
SEQUENCE: 391
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTEFYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 392          moltype = AA  length = 165
FEATURE                 Location/Qualifiers
source                  1..165
                        mol_type = protein
                        organism = synthetic construct
SEQUENCE: 392
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL QEKKYSPCAW EVVRAEIMRS FSLSTNLQES LRSKE                  165

SEQ ID NO: 393          moltype = AA  length = 165
FEATURE                 Location/Qualifiers
source                  1..165
                        mol_type = protein
                        organism = synthetic construct
SEQUENCE: 393
CDLPQTHSLG SRRTLMLLAQ MRRISPFSCL KDRHDFGFPQ EEFGNQFQKA ETIPVLHEMI  60
QQIFNLFSTK DSSAAWDETL LDTFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 394          moltype = AA  length = 165
FEATURE                 Location/Qualifiers
source                  1..165
                        mol_type = protein
                        organism = synthetic construct
SEQUENCE: 394
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKDDSILAVR  120
KYFQRITLYL KEKKYSPCAW EVVRAEIMRS FSLSTNLQES LRSKE                  165

SEQ ID NO: 395          moltype = AA  length = 165
FEATURE                 Location/Qualifiers
source                  1..165
                        mol_type = protein
                        organism = synthetic construct
SEQUENCE: 395
CDLPQTHSLG SRRTLMLLAQ MRRISPFSCL KDRHDFGFPQ EEFGNQFQKA ETIPVLHEMI  60
QQIFNLFSTK DSSAAWDETL LDMFYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 396          moltype = AA  length = 165
```

-continued

```
FEATURE                 Location/Qualifiers
source                  1..165
                        mol_type = protein
                        organism = synthetic construct
SEQUENCE: 396
CDLPQTHSLG SRRTLMLLAQ MRRISPFSCL KDRHDFGFPQ EEFGNQFQKA ETIPVLHEMI  60
QQIFNLFSTK DSSAAWDETL LDKWYTELYQ QLNDLEACVI QGVGVTETPL MKEDSILAVR  120
KYFQRITLYL KEKKYSPCAW EVVRAEIMRS FSLSTNLQES LRSKE                  165

SEQ ID NO: 397          moltype = AA  length = 165
FEATURE                 Location/Qualifiers
source                  1..165
                        mol_type = protein
                        organism = synthetic construct
SEQUENCE: 397
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LYSKE                  165

SEQ ID NO: 398          moltype = AA  length = 165
FEATURE                 Location/Qualifiers
source                  1..165
                        mol_type = protein
                        organism = synthetic construct
SEQUENCE: 398
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EIVRAEIMRS FSLSTNLQES LRSKE                  165

SEQ ID NO: 399          moltype = AA  length = 165
FEATURE                 Location/Qualifiers
source                  1..165
                        mol_type = protein
                        organism = synthetic construct
SEQUENCE: 399
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSWE                  165

SEQ ID NO: 400          moltype = AA  length = 165
FEATURE                 Location/Qualifiers
source                  1..165
                        mol_type = protein
                        organism = synthetic construct
SEQUENCE: 400
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LISKE                  165

SEQ ID NO: 401          moltype = AA  length = 165
FEATURE                 Location/Qualifiers
source                  1..165
                        mol_type = protein
                        organism = synthetic construct
SEQUENCE: 401
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LTSKE                  165

SEQ ID NO: 402          moltype = AA  length = 165
FEATURE                 Location/Qualifiers
source                  1..165
                        mol_type = protein
                        organism = synthetic construct
SEQUENCE: 402
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LVSKE                  165

SEQ ID NO: 403          moltype = AA  length = 165
FEATURE                 Location/Qualifiers
source                  1..165
                        mol_type = protein
                        organism = synthetic construct
SEQUENCE: 403
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYA QLNDLEACVI QGVGVTETPL MKEDSILAVR  120
KYFQRITLYL KEKKYSPCAW EVVRAEIMRS FSLSTNLQES LRSKE                  165
```

-continued

```
SEQ ID NO: 404          moltype = AA  length = 165
FEATURE                 Location/Qualifiers
source                  1..165
                        mol_type = protein
                        organism = synthetic construct
SEQUENCE: 404
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSKNLQES LRSKE                  165

SEQ ID NO: 405          moltype = AA  length = 165
FEATURE                 Location/Qualifiers
source                  1..165
                        mol_type = protein
                        organism = synthetic construct
SEQUENCE: 405
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEVKYSPCAW EVVRAEIMRS FSLSTNLQES LRSKE                  165

SEQ ID NO: 406          moltype = AA  length = 165
FEATURE                 Location/Qualifiers
source                  1..165
                        mol_type = protein
                        organism = synthetic construct
SEQUENCE: 406
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSSE                  165

SEQ ID NO: 407          moltype = AA  length = 165
FEATURE                 Location/Qualifiers
source                  1..165
                        mol_type = protein
                        organism = synthetic construct
SEQUENCE: 407
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ ILNDLEACVI QGVGVTETPL MKEDSILAVR  120
KYFQRITLYL KEKKYSPCAW EVVRAEIMRS FSLSTNLQES LRSKE                  165

SEQ ID NO: 408          moltype = AA  length = 165
FEATURE                 Location/Qualifiers
source                  1..165
                        mol_type = protein
                        organism = synthetic construct
SEQUENCE: 408
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTEEPL MKEDSILAVR  120
KYFQRITLYL KEKKYSPCAW EVVRAEIMRS FSLSTNLQES LRSKE                  165

SEQ ID NO: 409          moltype = AA  length = 165
FEATURE                 Location/Qualifiers
source                  1..165
                        mol_type = protein
                        organism = synthetic construct
SEQUENCE: 409
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEE LRSKE                  165

SEQ ID NO: 410          moltype = AA  length = 165
FEATURE                 Location/Qualifiers
source                  1..165
                        mol_type = protein
                        organism = synthetic construct
SEQUENCE: 410
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLWL KEKKYSPCAW EVVRAEIMRS FSLSTNLQES LRSKE                  165

SEQ ID NO: 411          moltype = AA  length = 165
FEATURE                 Location/Qualifiers
source                  1..165
                        mol_type = protein
                        organism = synthetic construct
SEQUENCE: 411
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGETETPL MKEDSILAVR  120
KYFQRITLYL KEKKYSPCAW EVVRAEIMRS FSLSTNLQES LRSKE                  165
```

```
SEQ ID NO: 412          moltype = AA  length = 165
FEATURE                 Location/Qualifiers
source                  1..165
                        mol_type = protein
                        organism = synthetic construct
SEQUENCE: 412
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KKKKYSPCAW EVVRAEIMRS FSLSTNLQES LRSKE                  165

SEQ ID NO: 413          moltype = AA  length = 165
FEATURE                 Location/Qualifiers
source                  1..165
                        mol_type = protein
                        organism = synthetic construct
SEQUENCE: 413
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FTLSTNLQES LRSKE                  165

SEQ ID NO: 414          moltype = AA  length = 165
FEATURE                 Location/Qualifiers
source                  1..165
                        mol_type = protein
                        organism = synthetic construct
SEQUENCE: 414
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KRKKYSPCAW EVVRAEIMRS FSLSTNLQES LRSKE                  165

SEQ ID NO: 415          moltype = AA  length = 165
FEATURE                 Location/Qualifiers
source                  1..165
                        mol_type = protein
                        organism = synthetic construct
SEQUENCE: 415
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVTRAEIMRS FSLSTNLQES LRSKE                  165

SEQ ID NO: 416          moltype = AA  length = 165
FEATURE                 Location/Qualifiers
source                  1..165
                        mol_type = protein
                        organism = synthetic construct
SEQUENCE: 416
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSFNLQES LRSKE                  165

SEQ ID NO: 417          moltype = AA  length = 165
FEATURE                 Location/Qualifiers
source                  1..165
                        mol_type = protein
                        organism = synthetic construct
SEQUENCE: 417
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRWEIMRS FSLSTNLQES LRSKE                  165

SEQ ID NO: 418          moltype = AA  length = 165
FEATURE                 Location/Qualifiers
source                  1..165
                        mol_type = protein
                        organism = synthetic construct
SEQUENCE: 418
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVTAEIMRS FSLSTNLQES LRSKE                  165

SEQ ID NO: 419          moltype = AA  length = 165
FEATURE                 Location/Qualifiers
source                  1..165
                        mol_type = protein
                        organism = synthetic construct
SEQUENCE: 419
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRITLYL KEKKYSPCAW EVVLAEIMRS FSLSTNLQES LRSKE               165

SEQ ID NO: 420         moltype = AA  length = 165
FEATURE                Location/Qualifiers
source                 1..165
                       mol_type = protein
                       organism = synthetic construct
SEQUENCE: 420
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVVAEIMRS FSLSTNLQES LRSKE               165

SEQ ID NO: 421         moltype = AA  length = 165
FEATURE                Location/Qualifiers
source                 1..165
                       mol_type = protein
                       organism = synthetic construct
SEQUENCE: 421
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRYEIMRS FSLSTNLQES LRSKE               165

SEQ ID NO: 422         moltype = AA  length = 165
FEATURE                Location/Qualifiers
source                 1..165
                       mol_type = protein
                       organism = synthetic construct
SEQUENCE: 422
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MIEDSILAVR  120
KYFQRITLYL KEKKYSPCAW EVVRAEIMRS FSLSTNLQES LRSKE               165

SEQ ID NO: 423         moltype = AA  length = 165
FEATURE                Location/Qualifiers
source                 1..165
                       mol_type = protein
                       organism = synthetic construct
SEQUENCE: 423
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTMTPL MKEDSILAVR  120
KYFQRITLYL KEKKYSPCAW EVVRAEIMRS FSLSTNLQES LRSKE               165

SEQ ID NO: 424         moltype = AA  length = 165
FEATURE                Location/Qualifiers
source                 1..165
                       mol_type = protein
                       organism = synthetic construct
SEQUENCE: 424
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVDVTETPL MKEDSILAVR  120
KYFQRITLYL KEKKYSPCAW EVVRAEIMRS FSLSTNLQES LRSKE               165

SEQ ID NO: 425         moltype = AA  length = 165
FEATURE                Location/Qualifiers
source                 1..165
                       mol_type = protein
                       organism = synthetic construct
SEQUENCE: 425
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVIAEIMRS FSLSTNLQES LRSKE               165

SEQ ID NO: 426         moltype = AA  length = 165
FEATURE                Location/Qualifiers
source                 1..165
                       mol_type = protein
                       organism = synthetic construct
SEQUENCE: 426
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLETCVI QGVGVTETPL MKEDSILAVR  120
KYFQRITLYL KEKKYSPCAW EVVRAEIMRS FSLSTNLQES LRSKE               165

SEQ ID NO: 427         moltype = AA  length = 165
FEATURE                Location/Qualifiers
source                 1..165
                       mol_type = protein
                       organism = synthetic construct
SEQUENCE: 427
CDLPQTHSLG SRRTLMLLAQ MRRISPFSCL KDRHDFGFPQ EEFGNQFQKA ETIPVLHEMI  60
```

```
QQIFNLFSTK DSSAAWDETL LDKFYTELYQ QLNDLEACVI QGVGVTETPL MKEDSILAVR      120
KYFQRITLYL KEKKYSPCAW EVVRDEIMRS FSLSTNLQES LRSKE                     165

SEQ ID NO: 428          moltype = AA   length = 165
FEATURE                 Location/Qualifiers
source                  1..165
                        mol_type = protein
                        organism = synthetic construct
SEQUENCE: 428
CDLPQTHSLG SRRTLMLLAQ NRRISLFSCL KDRHDFGFPQ EEFGNQFQKA ETIPVLHEMI      60
QQIFNLFSTK DSSAAWDETL LDKFYTELYQ QLNDLEACVI QGVGVTETPL MKEDSILAVR      120
KYFQRITLYL KEKKYSPCAW EVVRAEIMRS FSLSTNLQES LRSKR                     165

SEQ ID NO: 429          moltype = AA   length = 165
FEATURE                 Location/Qualifiers
source                  1..165
                        mol_type = protein
                        organism = synthetic construct
SEQUENCE: 429
CDLPQTHSLG SRRTLMLLAQ NRRISLFSCL KDRHDFGFPQ EEFGNQFQKA ETIPVLHEMI      60
QQIFNLFSTK DSSAAWDETL LDKFYTELYQ QLNDLEACVI QGEGVTETPL MKEDSILAVR      120
KYFQRITLYL KEKKYSPCAW EVVRAEIMRS FSLSTNLQES LRSKE                     165

SEQ ID NO: 430          moltype = AA   length = 165
FEATURE                 Location/Qualifiers
source                  1..165
                        mol_type = protein
                        organism = synthetic construct
SEQUENCE: 430
CDLPQTHSLG SRRTLMLLAQ NRRISLFSCL KDRHDFGFPQ EEFGNQFQKA ETIPVLHEMI      60
QQIFNLFSTK DSSAAWDETL LDLFYTELYQ QLNDLEACVI QGVGVTETPL MKEDSILAVR      120
KYFQRITLYL KEKKYSPCAW EVVRAEIMRS FSLSTNLQES LRSKE                     165

SEQ ID NO: 431          moltype = AA   length = 165
FEATURE                 Location/Qualifiers
source                  1..165
                        mol_type = protein
                        organism = synthetic construct
SEQUENCE: 431
CDLPQTHSLG SRRTLMLLAQ MRRISPFSCL KDRHDFGFPQ EEFGNQFQKA ETIPVLHEMI      60
QQIFNLFSTK DSSAAWDETL LDKFYTELYQ QLNDLEACVI QGVGVTETPL MKEDSINAVR      120
KYFQRITLYL KEKKYSPCAW EVVRAEIMRS FSLSTNLQES LRSKE                     165

SEQ ID NO: 432          moltype = AA   length = 165
FEATURE                 Location/Qualifiers
source                  1..165
                        mol_type = protein
                        organism = synthetic construct
SEQUENCE: 432
CDLPQTHSLG SRRTLMLLAQ NRRISLFSCL KDRHDFGFPQ EEFGNQFQKA ETIPVLHEMI      60
QQIFNLFSTK DSSAAWDETL LDKFYTELYQ QLNDLEACVI QGVGGTETPL MKEDSILAVR      120
KYFQRITLYL KEKKYSPCAW EVVRAEIMRS FSLSTNLQES LRSKE                     165

SEQ ID NO: 433          moltype = AA   length = 165
FEATURE                 Location/Qualifiers
source                  1..165
                        mol_type = protein
                        organism = synthetic construct
SEQUENCE: 433
CDLPQTHSLG SRRTLMLLAQ NRRISLFSCL KDRHDFGFPQ EEFGNQFQKA ETIPVLHEMI      60
QQIFNLFSTK DSSAAWDETL LDKFYTELYQ QLNDLEACVI QGVGVTETPL MKEDSILAVR      120
KYFQRITLYL KEKKYSPCAW EVVRAEIMRS FSLSTNEQES LRSKE                     165

SEQ ID NO: 434          moltype = AA   length = 165
FEATURE                 Location/Qualifiers
source                  1..165
                        mol_type = protein
                        organism = synthetic construct
SEQUENCE: 434
CDLPQTHSLG SRRTLMLLAQ MRRISPFSCL KDRHDFGFPQ EEFGNQFQKA ETIPVLHEMI      60
QQIFNLFSTK DSSAAWDETL LDKFYTELYQ QLNDLEACVI QGVGVTETPL MKEDSILAVR      120
KYFQRITLYL KEKKYSPCAW EVVRFEIMRS FSLSTNLQES LRSKE                     165

SEQ ID NO: 435          moltype = AA   length = 165
FEATURE                 Location/Qualifiers
source                  1..165
                        mol_type = protein
                        organism = synthetic construct
SEQUENCE: 435
```

-continued

```
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRWEIMRS FSLSTNLQES LRSKE                  165

SEQ ID NO: 436          moltype = AA  length = 165
FEATURE                 Location/Qualifiers
source                  1..165
                        mol_type = protein
                        organism = synthetic construct
SEQUENCE: 436
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FDLSTNLQES LRSKE                  165

SEQ ID NO: 437          moltype = AA  length = 165
FEATURE                 Location/Qualifiers
source                  1..165
                        mol_type = protein
                        organism = synthetic construct
SEQUENCE: 437
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEQKYSPCAW EVVRAEIMRS FSLSTNLQES LRSKE                  165

SEQ ID NO: 438          moltype = AA  length = 165
FEATURE                 Location/Qualifiers
source                  1..165
                        mol_type = protein
                        organism = synthetic construct
SEQUENCE: 438
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRHEIMRS FSLSTNLQES LRSKE                  165

SEQ ID NO: 439          moltype = AA  length = 165
FEATURE                 Location/Qualifiers
source                  1..165
                        mol_type = protein
                        organism = synthetic construct
SEQUENCE: 439
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMNS FSLSTNLQES LRSKE                  165

SEQ ID NO: 440          moltype = AA  length = 165
FEATURE                 Location/Qualifiers
source                  1..165
                        mol_type = protein
                        organism = synthetic construct
SEQUENCE: 440
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVSAEIMRS FSLSTNLQES LRSKE                  165

SEQ ID NO: 441          moltype = AA  length = 165
FEATURE                 Location/Qualifiers
source                  1..165
                        mol_type = protein
                        organism = synthetic construct
SEQUENCE: 441
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVGAEIMRS FSLSTNLQES LRSKE                  165

SEQ ID NO: 442          moltype = AA  length = 165
FEATURE                 Location/Qualifiers
source                  1..165
                        mol_type = protein
                        organism = synthetic construct
SEQUENCE: 442
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMES FSLSTNLQES LRSKE                  165

SEQ ID NO: 443          moltype = AA  length = 165
FEATURE                 Location/Qualifiers
source                  1..165
                        mol_type = protein
                        organism = synthetic construct
```

```
SEQUENCE: 443
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMGS FSLSTNLQES LRSKE                  165

SEQ ID NO: 444         moltype = AA  length = 165
FEATURE                Location/Qualifiers
source                 1..165
                       mol_type = protein
                       organism = synthetic construct
SEQUENCE: 444
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYDPCAW EVVRAEIMRS FSLSTNLQES LRSKE                  165

SEQ ID NO: 445         moltype = AA  length = 165
FEATURE                Location/Qualifiers
source                 1..165
                       mol_type = protein
                       organism = synthetic construct
SEQUENCE: 445
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EGVRAEIMRS FSLSTNLQES LRSKE                  165

SEQ ID NO: 446         moltype = AA  length = 165
FEATURE                Location/Qualifiers
source                 1..165
                       mol_type = protein
                       organism = synthetic construct
SEQUENCE: 446
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVREEIMRS FSLSTNLQES LRSKE                  165

SEQ ID NO: 447         moltype = AA  length = 165
FEATURE                Location/Qualifiers
source                 1..165
                       mol_type = protein
                       organism = synthetic construct
SEQUENCE: 447
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EKVRAEIMRS FSLSTNLQES LRSKE                  165

SEQ ID NO: 448         moltype = AA  length = 165
FEATURE                Location/Qualifiers
source                 1..165
                       mol_type = protein
                       organism = synthetic construct
SEQUENCE: 448
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSRE                  165

SEQ ID NO: 449         moltype = AA  length = 165
FEATURE                Location/Qualifiers
source                 1..165
                       mol_type = protein
                       organism = synthetic construct
SEQUENCE: 449
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVI  120
KYFQRITLYL KEKKYSPCAW EVVRAEIMRS FSLSTNLQES LRSKE                  165

SEQ ID NO: 450         moltype = AA  length = 165
FEATURE                Location/Qualifiers
source                 1..165
                       mol_type = protein
                       organism = synthetic construct
SEQUENCE: 450
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EDVRAEIMRS FSLSTNLQES LRSKE                  165

SEQ ID NO: 451         moltype = AA  length = 165
FEATURE                Location/Qualifiers
source                 1..165
                       mol_type = protein
```

```
                        organism = synthetic construct
SEQUENCE: 451
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEEKYSPCAW EVVRAEIMRS FSLSTNLQES LRSKE                  165

SEQ ID NO: 452          moltype = AA  length = 165
FEATURE                 Location/Qualifiers
source                  1..165
                        mol_type = protein
                        organism = synthetic construct
SEQUENCE: 452
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRKEIMRS FSLSTNLQES LRSKE                  165

SEQ ID NO: 453          moltype = AA  length = 165
FEATURE                 Location/Qualifiers
source                  1..165
                        mol_type = protein
                        organism = synthetic construct
SEQUENCE: 453
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EFVRAEIMRS FSLSTNLQES LRSKE                  165

SEQ ID NO: 454          moltype = AA  length = 165
FEATURE                 Location/Qualifiers
source                  1..165
                        mol_type = protein
                        organism = synthetic construct
SEQUENCE: 454
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMDS FSLSTNLQES LRSKE                  165

SEQ ID NO: 455          moltype = AA  length = 165
FEATURE                 Location/Qualifiers
source                  1..165
                        mol_type = protein
                        organism = synthetic construct
SEQUENCE: 455
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRQEIMRS FSLSTNLQES LRSKE                  165

SEQ ID NO: 456          moltype = AA  length = 165
FEATURE                 Location/Qualifiers
source                  1..165
                        mol_type = protein
                        organism = synthetic construct
SEQUENCE: 456
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EQVRAEIMRS FSLSTNLQES LRSKE                  165

SEQ ID NO: 457          moltype = AA  length = 165
FEATURE                 Location/Qualifiers
source                  1..165
                        mol_type = protein
                        organism = synthetic construct
SEQUENCE: 457
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMNS FSLSTNLQES LRSKE                  165

SEQ ID NO: 458          moltype = AA  length = 165
FEATURE                 Location/Qualifiers
source                  1..165
                        mol_type = protein
                        organism = synthetic construct
SEQUENCE: 458
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRDEIMRS FSLSTNLQES LRSKE                  165

SEQ ID NO: 459          moltype = AA  length = 165
FEATURE                 Location/Qualifiers
source                  1..165
```

```
                        mol_type = protein
                        organism = synthetic construct
SEQUENCE: 459
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEQKYSPCAW EVVRAEIMRS FSLSTNLQES LRSKE                  165

SEQ ID NO: 460          moltype = AA  length = 165
FEATURE                 Location/Qualifiers
source                  1..165
                        mol_type = protein
                        organism = synthetic construct
SEQUENCE: 460
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ESVRAEIMRS FSLSTNLQES LRSKE                  165

SEQ ID NO: 461          moltype = AA  length = 165
FEATURE                 Location/Qualifiers
source                  1..165
                        mol_type = protein
                        organism = synthetic construct
SEQUENCE: 461
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRKKE                  165

SEQ ID NO: 462          moltype = AA  length = 165
FEATURE                 Location/Qualifiers
source                  1..165
                        mol_type = protein
                        organism = synthetic construct
SEQUENCE: 462
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EYVRAEIMRS FSLSTNLQES LRSKE                  165

SEQ ID NO: 463          moltype = AA  length = 165
FEATURE                 Location/Qualifiers
source                  1..165
                        mol_type = protein
                        organism = synthetic construct
SEQUENCE: 463
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EEVRAEIMRS FSLSTNLQES LRSKE                  165

SEQ ID NO: 464          moltype = AA  length = 165
FEATURE                 Location/Qualifiers
source                  1..165
                        mol_type = protein
                        organism = synthetic construct
SEQUENCE: 464
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KKKKYSPCAW EVVRAEIMRS FSLSTNLQES LRSKE                  165

SEQ ID NO: 465          moltype = AA  length = 165
FEATURE                 Location/Qualifiers
source                  1..165
                        mol_type = protein
                        organism = synthetic construct
SEQUENCE: 465
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLDTNLQES LRSKE                  165

SEQ ID NO: 466          moltype = AA  length = 165
FEATURE                 Location/Qualifiers
source                  1..165
                        mol_type = protein
                        organism = synthetic construct
SEQUENCE: 466
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIERS FSLSTNLQES LRSKE                  165

SEQ ID NO: 467          moltype = AA  length = 165
FEATURE                 Location/Qualifiers
```

```
source                 1..165
                       mol_type = protein
                       organism = synthetic construct
SEQUENCE: 467
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMDS FSLSTNLQES LRSKE                 165

SEQ ID NO: 468         moltype = AA  length = 165
FEATURE                Location/Qualifiers
source                 1..165
                       mol_type = protein
                       organism = synthetic construct
SEQUENCE: 468
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EMVRAEIMRS FSLSTNLQES LRSKE                 165

SEQ ID NO: 469         moltype = AA  length = 165
FEATURE                Location/Qualifiers
source                 1..165
                       mol_type = protein
                       organism = synthetic construct
SEQUENCE: 469
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMWS FSLSTNLQES LRSKE                 165

SEQ ID NO: 470         moltype = AA  length = 165
FEATURE                Location/Qualifiers
source                 1..165
                       mol_type = protein
                       organism = synthetic construct
SEQUENCE: 470
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ERVRAEIMRS FSLSTNLQES LRSKE                 165

SEQ ID NO: 471         moltype = AA  length = 165
FEATURE                Location/Qualifiers
source                 1..165
                       mol_type = protein
                       organism = synthetic construct
SEQUENCE: 471
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMWS FSLSTNLQES LRSKE                 165

SEQ ID NO: 472         moltype = AA  length = 165
FEATURE                Location/Qualifiers
source                 1..165
                       mol_type = protein
                       organism = synthetic construct
SEQUENCE: 472
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMQS FSLSTNLQES LRSKE                 165

SEQ ID NO: 473         moltype = AA  length = 165
FEATURE                Location/Qualifiers
source                 1..165
                       mol_type = protein
                       organism = synthetic construct
SEQUENCE: 473
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KRKKYSPCAW EVVRAEIMRS FSLSTNLQES LRSKE                 165

SEQ ID NO: 474         moltype = AA  length = 165
FEATURE                Location/Qualifiers
source                 1..165
                       mol_type = protein
                       organism = synthetic construct
SEQUENCE: 474
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVTAEIMRS FSLSTNLQES LRSKE                 165

SEQ ID NO: 475         moltype = AA  length = 165
```

-continued

```
FEATURE                 Location/Qualifiers
source                  1..165
                        mol_type = protein
                        organism = synthetic construct
SEQUENCE: 475
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMAS FSLSTNLQES LRSKE                  165

SEQ ID NO: 476          moltype = AA  length = 165
FEATURE                 Location/Qualifiers
source                  1..165
                        mol_type = protein
                        organism = synthetic construct
SEQUENCE: 476
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVWAEIMRS FSLSTNLQES LRSKE                  165

SEQ ID NO: 477          moltype = AA  length = 165
FEATURE                 Location/Qualifiers
source                  1..165
                        mol_type = protein
                        organism = synthetic construct
SEQUENCE: 477
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMTS FSLSTNLQES LRSKE                  165

SEQ ID NO: 478          moltype = AA  length = 165
FEATURE                 Location/Qualifiers
source                  1..165
                        mol_type = protein
                        organism = synthetic construct
SEQUENCE: 478
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMSS FSLSTNLQES LRSKE                  165

SEQ ID NO: 479          moltype = AA  length = 165
FEATURE                 Location/Qualifiers
source                  1..165
                        mol_type = protein
                        organism = synthetic construct
SEQUENCE: 479
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ETVRAEIMRS FSLSTNLQES LRSKE                  165

SEQ ID NO: 480          moltype = AA  length = 165
FEATURE                 Location/Qualifiers
source                  1..165
                        mol_type = protein
                        organism = synthetic construct
SEQUENCE: 480
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QYVGVTETPL MKEDSILAVR  120
KYFQRITLYL KEKKYSPCAW EVVRAEIMRS FSLSTNLQES LRSKE                  165

SEQ ID NO: 481          moltype = AA  length = 165
FEATURE                 Location/Qualifiers
source                  1..165
                        mol_type = protein
                        organism = synthetic construct
SEQUENCE: 481
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVAAEIMRS FSLSTNLQES LRSKE                  165

SEQ ID NO: 482          moltype = AA  length = 165
FEATURE                 Location/Qualifiers
source                  1..165
                        mol_type = protein
                        organism = synthetic construct
SEQUENCE: 482
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVIAEIMRS FSLSTNLQES LRSKE                  165
```

-continued

```
SEQ ID NO: 483          moltype = AA  length = 165
FEATURE                 Location/Qualifiers
source                  1..165
                        mol_type = protein
                        organism = synthetic construct
SEQUENCE: 483
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVFAEIMRS FSLSTNLQES LRSKE                  165

SEQ ID NO: 484          moltype = AA  length = 165
FEATURE                 Location/Qualifiers
source                  1..165
                        mol_type = protein
                        organism = synthetic construct
SEQUENCE: 484
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNGQES LRSKE                  165

SEQ ID NO: 485          moltype = AA  length = 165
FEATURE                 Location/Qualifiers
source                  1..165
                        mol_type = protein
                        organism = synthetic construct
SEQUENCE: 485
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW ENVRAEIMRS FSLSTNLQES LRSKE                  165

SEQ ID NO: 486          moltype = AA  length = 165
FEATURE                 Location/Qualifiers
source                  1..165
                        mol_type = protein
                        organism = synthetic construct
SEQUENCE: 486
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVMAEIMRS FSLSTNLQES LRSKE                  165

SEQ ID NO: 487          moltype = AA  length = 165
FEATURE                 Location/Qualifiers
source                  1..165
                        mol_type = protein
                        organism = synthetic construct
SEQUENCE: 487
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVLAEIMRS FSLSTNLQES LRSKE                  165

SEQ ID NO: 488          moltype = AA  length = 165
FEATURE                 Location/Qualifiers
source                  1..165
                        mol_type = protein
                        organism = synthetic construct
SEQUENCE: 488
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMGS FSLSTNLQES LRSKE                  165

SEQ ID NO: 489          moltype = AA  length = 165
FEATURE                 Location/Qualifiers
source                  1..165
                        mol_type = protein
                        organism = synthetic construct
SEQUENCE: 489
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVAAEIMRS FSLSTNLQES LRSKE                  165

SEQ ID NO: 490          moltype = AA  length = 165
FEATURE                 Location/Qualifiers
source                  1..165
                        mol_type = protein
                        organism = synthetic construct
SEQUENCE: 490
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRR FSLSTNLQES LRSKE                  165
```

```
SEQ ID NO: 491          moltype = AA  length = 165
FEATURE                 Location/Qualifiers
source                  1..165
                        mol_type = protein
                        organism = synthetic construct
SEQUENCE: 491
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ KLNDLEACVI QGVGVTETPL MKEDSILAVR  120
KYFQRITLYL KEKKYSPCAW EVVRAEIMRS FSLSTNLQES LRSKE                 165

SEQ ID NO: 492          moltype = AA  length = 165
FEATURE                 Location/Qualifiers
source                  1..165
                        mol_type = protein
                        organism = synthetic construct
SEQUENCE: 492
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRNEIMRS FSLSTNLQES LRSKE                 165

SEQ ID NO: 493          moltype = AA  length = 165
FEATURE                 Location/Qualifiers
source                  1..165
                        mol_type = protein
                        organism = synthetic construct
SEQUENCE: 493
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EHVRAEIMRS FSLSTNLQES LRSKE                 165

SEQ ID NO: 494          moltype = AA  length = 165
FEATURE                 Location/Qualifiers
source                  1..165
                        mol_type = protein
                        organism = synthetic construct
SEQUENCE: 494
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDWILAVR  120
KYFQRITLYL KEKKYSPCAW EVVRAEIMRS FSLSTNLQES LRSKE                 165

SEQ ID NO: 495          moltype = AA  length = 165
FEATURE                 Location/Qualifiers
source                  1..165
                        mol_type = protein
                        organism = synthetic construct
SEQUENCE: 495
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES ERSKE                 165

SEQ ID NO: 496          moltype = AA  length = 165
FEATURE                 Location/Qualifiers
source                  1..165
                        mol_type = protein
                        organism = synthetic construct
SEQUENCE: 496
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRHEIMRS FSLSTNLQES LRSKE                 165

SEQ ID NO: 497          moltype = AA  length = 165
FEATURE                 Location/Qualifiers
source                  1..165
                        mol_type = protein
                        organism = synthetic construct
SEQUENCE: 497
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MIEDSILAVR  120
KYFQRITLYL KEKKYSPCAW EVVRAEIMRS FSLSTNLQES LRSKE                 165

SEQ ID NO: 498          moltype = AA  length = 165
FEATURE                 Location/Qualifiers
source                  1..165
                        mol_type = protein
                        organism = synthetic construct
SEQUENCE: 498
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
```

-continued

```
KYFQRILLYL KEKKYSPCAW EVVRAEIMRS FSLSTNLQES LRSKE                 165

SEQ ID NO: 499          moltype = AA  length = 165
FEATURE                 Location/Qualifiers
source                  1..165
                        mol_type = protein
                        organism = synthetic construct
SEQUENCE: 499
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMVS FSLSTNLQES LRSKE                 165

SEQ ID NO: 500          moltype = AA  length = 165
FEATURE                 Location/Qualifiers
source                  1..165
                        mol_type = protein
                        organism = synthetic construct
SEQUENCE: 500
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSFNLQES LRSKE                 165

SEQ ID NO: 501          moltype = AA  length = 165
FEATURE                 Location/Qualifiers
source                  1..165
                        mol_type = protein
                        organism = synthetic construct
SEQUENCE: 501
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRSEIMRS FSLSTNLQES LRSKE                 165

SEQ ID NO: 502          moltype = AA  length = 165
FEATURE                 Location/Qualifiers
source                  1..165
                        mol_type = protein
                        organism = synthetic construct
SEQUENCE: 502
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSRSTNLQES LRSKE                 165

SEQ ID NO: 503          moltype = AA  length = 165
FEATURE                 Location/Qualifiers
source                  1..165
                        mol_type = protein
                        organism = synthetic construct
SEQUENCE: 503
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRIGLYL KEKKYSPCAW EVVRAEIMRS FSLSTNLQES LRSKE                 165

SEQ ID NO: 504          moltype = AA  length = 165
FEATURE                 Location/Qualifiers
source                  1..165
                        mol_type = protein
                        organism = synthetic construct
SEQUENCE: 504
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEW LRSKE                 165

SEQ ID NO: 505          moltype = AA  length = 165
FEATURE                 Location/Qualifiers
source                  1..165
                        mol_type = protein
                        organism = synthetic construct
SEQUENCE: 505
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSESTNLQES LRSKE                 165

SEQ ID NO: 506          moltype = AA  length = 165
FEATURE                 Location/Qualifiers
source                  1..165
                        mol_type = protein
                        organism = synthetic construct
SEQUENCE: 506
CDLPQTHSLG SRRTLMLLAQ NRRISLFSCL KDRHDFGFPQ EEFGNQFQKA ETIPVLHEMI  60
```

-continued

```
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FELSTNLQES LRSKE                  165

SEQ ID NO: 507          moltype = AA  length = 165
FEATURE                 Location/Qualifiers
source                  1..165
                        mol_type = protein
                        organism = synthetic construct
SEQUENCE: 507
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVHAEIMRS FSLSTNLQES LRSKE                  165

SEQ ID NO: 508          moltype = AA  length = 165
FEATURE                 Location/Qualifiers
source                  1..165
                        mol_type = protein
                        organism = synthetic construct
SEQUENCE: 508
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRKEIMRS FSLSTNLQES LRSKE                  165

SEQ ID NO: 509          moltype = AA  length = 165
FEATURE                 Location/Qualifiers
source                  1..165
                        mol_type = protein
                        organism = synthetic construct
SEQUENCE: 509
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FDLSTNLQES LRSKE                  165

SEQ ID NO: 510          moltype = AA  length = 165
FEATURE                 Location/Qualifiers
source                  1..165
                        mol_type = protein
                        organism = synthetic construct
SEQUENCE: 510
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MGEDSILAVR  120
KYFQRITLYL KEKKYSPCAW EVVRAEIMRS FSLSTNLQES LRSKE                  165

SEQ ID NO: 511          moltype = AA  length = 165
FEATURE                 Location/Qualifiers
source                  1..165
                        mol_type = protein
                        organism = synthetic construct
SEQUENCE: 511
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSRE                  165

SEQ ID NO: 512          moltype = AA  length = 165
FEATURE                 Location/Qualifiers
source                  1..165
                        mol_type = protein
                        organism = synthetic construct
SEQUENCE: 512
CDLPQTHSLG SRRTLMLLAQ NRRISLFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSEE                  165

SEQ ID NO: 513          moltype = AA  length = 165
FEATURE                 Location/Qualifiers
source                  1..165
                        mol_type = protein
                        organism = synthetic construct
SEQUENCE: 513
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRQEIMRS FSLSTNLQES LRSKE                  165

SEQ ID NO: 514          moltype = AA  length = 165
FEATURE                 Location/Qualifiers
source                  1..165
                        mol_type = protein
                        organism = synthetic construct
SEQUENCE: 514
```

-continued

```
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMIS FSLSTNLQES LRSKE                  165

SEQ ID NO: 515         moltype = AA  length = 165
FEATURE                Location/Qualifiers
source                 1..165
                       mol_type = protein
                       organism = synthetic construct
SEQUENCE: 515
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRMEIMRS FSLSTNLQES LRSKE                  165

SEQ ID NO: 516         moltype = AA  length = 165
FEATURE                Location/Qualifiers
source                 1..165
                       mol_type = protein
                       organism = synthetic construct
SEQUENCE: 516
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMFS FSLSTNLQES LRSKE                  165

SEQ ID NO: 517         moltype = AA  length = 165
FEATURE                Location/Qualifiers
source                 1..165
                       mol_type = protein
                       organism = synthetic construct
SEQUENCE: 517
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMMS FSLSTNLQES LRSKE                  165

SEQ ID NO: 518         moltype = AA  length = 165
FEATURE                Location/Qualifiers
source                 1..165
                       mol_type = protein
                       organism = synthetic construct
SEQUENCE: 518
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSDSTNLQES LRSKE                  165

SEQ ID NO: 519         moltype = AA  length = 165
FEATURE                Location/Qualifiers
source                 1..165
                       mol_type = protein
                       organism = synthetic construct
SEQUENCE: 519
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMYS FSLSTNLQES LRSKE                  165

SEQ ID NO: 520         moltype = AA  length = 165
FEATURE                Location/Qualifiers
source                 1..165
                       mol_type = protein
                       organism = synthetic construct
SEQUENCE: 520
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIERS FSLSTNLQES LRSKE                  165

SEQ ID NO: 521         moltype = AA  length = 165
FEATURE                Location/Qualifiers
source                 1..165
                       mol_type = protein
                       organism = synthetic construct
SEQUENCE: 521
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEDKYSPCAW EVVRAEIMRS FSLSTNLQES LRSKE                  165

SEQ ID NO: 522         moltype = AA  length = 165
FEATURE                Location/Qualifiers
source                 1..165
                       mol_type = protein
                       organism = synthetic construct
```

SEQUENCE: 522
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRGEIMRS FSLSTNLQES LRSKE 165

SEQ ID NO: 523 moltype = AA length = 165
FEATURE Location/Qualifiers
source 1..165
mol_type = protein
organism = synthetic construct
SEQUENCE: 523
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRREIMRS FSLSTNLQES LRSKE 165

SEQ ID NO: 524 moltype = AA length = 165
FEATURE Location/Qualifiers
source 1..165
mol_type = protein
organism = synthetic construct
SEQUENCE: 524
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIMLS FSLSTNLQES LRSKE 165

SEQ ID NO: 525 moltype = AA length = 165
FEATURE Location/Qualifiers
source 1..165
mol_type = protein
organism = synthetic construct
SEQUENCE: 525
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIMRS FSLSTNLQEF LRSKE 165

SEQ ID NO: 526 moltype = AA length = 165
FEATURE Location/Qualifiers
source 1..165
mol_type = protein
organism = synthetic construct
SEQUENCE: 526
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIMRS FSLSTNLQES LRSIE 165

SEQ ID NO: 527 moltype = AA length = 165
FEATURE Location/Qualifiers
source 1..165
mol_type = protein
organism = synthetic construct
SEQUENCE: 527
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIDRS FSLSTNLQES LRSKE 165

SEQ ID NO: 528 moltype = AA length = 165
FEATURE Location/Qualifiers
source 1..165
mol_type = protein
organism = synthetic construct
SEQUENCE: 528
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIMRS FSLSTNLQES LRSYE 165

SEQ ID NO: 529 moltype = AA length = 165
FEATURE Location/Qualifiers
source 1..165
mol_type = protein
organism = synthetic construct
SEQUENCE: 529
CDLPQTHSLG SRRTLMLLAQ MRRISPFSCL KDRHDFGFPQ EEFGNQFQKA ETIPVLHEMI 60
QQIFNLFSTK DSSAAWDETL LDKFYTELYQ QLNDLEACVI QGVGVTETPL MKEDSILAVR 120
KYFQRITLYL KEKKYSPCAW EVVRAEIMRS FSLSTNLQES LRSLE 165

SEQ ID NO: 530 moltype = AA length = 165
FEATURE Location/Qualifiers
source 1..165
mol_type = protein

```
                        organism = synthetic construct
SEQUENCE: 530
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTGLQES LRSKE                  165

SEQ ID NO: 531          moltype = AA  length = 165
FEATURE                 Location/Qualifiers
source                  1..165
                        mol_type = protein
                        organism = synthetic construct
SEQUENCE: 531
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEEKYSPCAW EVVRAEIMRS FSLSTNLQES LRSKE                  165

SEQ ID NO: 532          moltype = AA  length = 165
FEATURE                 Location/Qualifiers
source                  1..165
                        mol_type = protein
                        organism = synthetic construct
SEQUENCE: 532
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVKAEIMRS FSLSTNLQES LRSKE                  165

SEQ ID NO: 533          moltype = AA  length = 165
FEATURE                 Location/Qualifiers
source                  1..165
                        mol_type = protein
                        organism = synthetic construct
SEQUENCE: 533
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQEY LRSKE                  165

SEQ ID NO: 534          moltype = AA  length = 165
FEATURE                 Location/Qualifiers
source                  1..165
                        mol_type = protein
                        organism = synthetic construct
SEQUENCE: 534
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW DVVRAEIMRS FSLSTNLQES LRSKE                  165

SEQ ID NO: 535          moltype = AA  length = 165
FEATURE                 Location/Qualifiers
source                  1..165
                        mol_type = protein
                        organism = synthetic construct
SEQUENCE: 535
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSPSTNLQES LRSKE                  165

SEQ ID NO: 536          moltype = AA  length = 165
FEATURE                 Location/Qualifiers
source                  1..165
                        mol_type = protein
                        organism = synthetic construct
SEQUENCE: 536
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYSPCAW EVVRAEIMRS FSLSTNLQES LRSFE                  165

SEQ ID NO: 537          moltype = AA  length = 165
FEATURE                 Location/Qualifiers
source                  1..165
                        mol_type = protein
                        organism = synthetic construct
SEQUENCE: 537
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KETKYSPCAW EVVRAEIMRS FSLSTNLQES LRSKE                  165

SEQ ID NO: 538          moltype = AA  length = 165
FEATURE                 Location/Qualifiers
source                  1..165
```

```
                        mol_type = protein
                        organism = synthetic construct
SEQUENCE: 538
CDLPQTHSLG SRRTLMLLAQ MRRISPFSCL KDRHDFGFPQ EEFGNQFQKA ETIPVLHEMI  60
QQIFNLFSTK DSSAAWDETL LDKFYTELYQ QLNDLEACVI QGVGVTETPL MKEDSILAVR  120
KYFQRITLYL KEKKYHPCAW EVVRAEIMRS FSLSTNLQES LRSKE                  165

SEQ ID NO: 539          moltype = AA  length = 409
FEATURE                 Location/Qualifiers
source                  1..409
                        mol_type = protein
                        organism = synthetic construct
SEQUENCE: 539
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRPSL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 540          moltype = AA  length = 409
FEATURE                 Location/Qualifiers
source                  1..409
                        mol_type = protein
                        organism = synthetic construct
SEQUENCE: 540
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRGE IMRSFSLSTN LQESLRSKE              409

SEQ ID NO: 541          moltype = AA  length = 409
FEATURE                 Location/Qualifiers
source                  1..409
                        mol_type = protein
                        organism = synthetic construct
SEQUENCE: 541
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMTSFSLSTN LQESLRSKE              409

SEQ ID NO: 542          moltype = AA  length = 409
FEATURE                 Location/Qualifiers
source                  1..409
                        mol_type = protein
                        organism = synthetic construct
SEQUENCE: 542
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRFISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 543          moltype = AA  length = 409
FEATURE                 Location/Qualifiers
source                  1..409
                        mol_type = protein
                        organism = synthetic construct
SEQUENCE: 543
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFKLSTN LQESLRSKE              409

SEQ ID NO: 544          moltype = AA  length = 409
FEATURE                 Location/Qualifiers
```

```
source                  1..409
                        mol_type = protein
                        organism = synthetic construct
SEQUENCE: 544
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE ILRSFSLSTN LQESLRSKE              409

SEQ ID NO: 545          moltype = AA  length = 409
FEATURE                 Location/Qualifiers
source                  1..409
                        mol_type = protein
                        organism = synthetic construct
SEQUENCE: 545
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQEWLRSKE              409

SEQ ID NO: 546          moltype = AA  length = 409
FEATURE                 Location/Qualifiers
source                  1..409
                        mol_type = protein
                        organism = synthetic construct
SEQUENCE: 546
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLWDLE ACVIQGVGVT ETPLMKEDSI  360
LAVRKYFQRI TLYLKEKKYS PCAWEVVRAE IMRSFSLSTN LQESLRSKE              409

SEQ ID NO: 547          moltype = AA  length = 409
FEATURE                 Location/Qualifiers
source                  1..409
                        mol_type = protein
                        organism = synthetic construct
SEQUENCE: 547
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL GSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 548          moltype = AA  length = 409
FEATURE                 Location/Qualifiers
source                  1..409
                        mol_type = protein
                        organism = synthetic construct
SEQUENCE: 548
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEGIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 549          moltype = AA  length = 409
FEATURE                 Location/Qualifiers
source                  1..409
                        mol_type = protein
                        organism = synthetic construct
SEQUENCE: 549
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GGPQEEFGNQ FQKAETIPVL  300
```

-continued

```
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 550          moltype = AA  length = 409
FEATURE                 Location/Qualifiers
source                  1..409
                        mol_type = protein
                        organism = synthetic construct
SEQUENCE: 550
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLDSKE              409

SEQ ID NO: 551          moltype = AA  length = 647
FEATURE                 Location/Qualifiers
source                  1..647
                        mol_type = protein
                        organism = synthetic construct
SEQUENCE: 551
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ ESLRSKE                647

SEQ ID NO: 552          moltype = AA  length = 647
FEATURE                 Location/Qualifiers
source                  1..647
                        mol_type = protein
                        organism = synthetic construct
SEQUENCE: 552
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRPSLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ ESLRSKE                647

SEQ ID NO: 553          moltype = AA  length = 647
FEATURE                 Location/Qualifiers
source                  1..647
                        mol_type = protein
                        organism = synthetic construct
SEQUENCE: 553
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM TSFSLSTNLQ ESLRSKE                647

SEQ ID NO: 554          moltype = AA  length = 647
FEATURE                 Location/Qualifiers
source                  1..647
                        mol_type = protein
                        organism = synthetic construct
SEQUENCE: 554
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
```

-continued

```
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFKLSTNLQ ESLRSKE                647

SEQ ID NO: 555         moltype = AA  length = 647
FEATURE                Location/Qualifiers
source                 1..647
                       mol_type = protein
                       organism = synthetic construct
SEQUENCE: 555
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIL RSFSLSTNLQ ESLRSKE                647

SEQ ID NO: 556         moltype = AA  length = 647
FEATURE                Location/Qualifiers
source                 1..647
                       mol_type = protein
                       organism = synthetic construct
SEQUENCE: 556
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ EWLRSKE                647

SEQ ID NO: 557         moltype = AA  length = 647
FEATURE                Location/Qualifiers
source                 1..647
                       mol_type = protein
                       organism = synthetic construct
SEQUENCE: 557
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLGS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ ESLRSKE                647

SEQ ID NO: 558         moltype = AA  length = 647
FEATURE                Location/Qualifiers
source                 1..647
                       mol_type = protein
                       organism = synthetic construct
SEQUENCE: 558
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGG PQEEFGNQFQ KAETIPVLHE  540
```

```
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ ESLRSKE                647

SEQ ID NO: 559         moltype = AA  length = 647
FEATURE                Location/Qualifiers
source                 1..647
                       mol_type = protein
                       organism = synthetic construct
SEQUENCE: 559
EVQLVESGGG LVQPGGSLRL SCAASGFNIK DTYIHFVRQA PGKGLEWIGR IDPANDNTLY  60
ASKFQGKATI SADTSKNTAY LQMNSLRAED TAVYYCGRGY GYYVFDHWGQ GTLVTVSSGG  120
GGSGGGGSGG GGSDVQITQS PSSLSASVGD RVTITCRTSR SISQYLAWYQ QKPGKVPKLL  180
IYSGSTLQSG VPSRFSGSGS GTDFTLTISS LQPEDVATYY CQQHNENPLT FGGGTKVEIK  240
EPKSSDKTHT CPPCPAPEAA GGPSVFLFPP KPKDTLMISR TPEVTCVVVD VSHEDPEVKF  300
NWYVDGVEVH NAKTKPREEQ YNSTYRVVSV LTVLHQDWLN GKEYKCKVSN KALGAPIEKT  360
ISKAKGQPRE PQVYTLPPSR DELTKNQVSL TCLVKGFYPS DIAVEWESNG QPENNYKTTP  420
PVLDSDGSFF LYSKLTVDKS RWQQGNVFSC SVMHEALHNH YTQKSLSLSP GKGGGGSGGG  480
GSCDLPQTHS LGSRRTLMLL AQMRRISLFS CLKDRHDFGF PQEEFGNQFQ KAETIPVLHE  540
MIQQIFNLFS TKDSSAAWDE TLLDKFYTEL YQQLNDLEAC VIQGVGVTET PLMKEDSILA  600
VRKYFQRITL YLKEKKYSPC AWEVVRAEIM RSFSLSTNLQ ESLDSKE                647

SEQ ID NO: 560         moltype = AA  length = 409
FEATURE                Location/Qualifiers
source                 1..409
                       mol_type = protein
                       organism = synthetic construct
SEQUENCE: 560
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRRE IMRSFSLSTN LQESLRSKE              409

SEQ ID NO: 561         moltype = AA  length = 409
FEATURE                Location/Qualifiers
source                 1..409
                       mol_type = protein
                       organism = synthetic construct
SEQUENCE: 561
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMDSFSLSTN LQESLRSKE              409

SEQ ID NO: 562         moltype = AA  length = 409
FEATURE                Location/Qualifiers
source                 1..409
                       mol_type = protein
                       organism = synthetic construct
SEQUENCE: 562
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMNSFSLSTN LQESLRSKE              409

SEQ ID NO: 563         moltype = AA  length = 409
FEATURE                Location/Qualifiers
source                 1..409
                       mol_type = protein
                       organism = synthetic construct
SEQUENCE: 563
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDLHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE              409

SEQ ID NO: 564         moltype = AA  length = 409
FEATURE                Location/Qualifiers
```

```
source                  1..409
                        mol_type = protein
                        organism = synthetic construct
SEQUENCE: 564
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVEAE IMRSFSLSTN LQESLRSKE             409

SEQ ID NO: 565          moltype = AA  length = 409
FEATURE                 Location/Qualifiers
source                  1..409
                        mol_type = protein
                        organism = synthetic construct
SEQUENCE: 565
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IYRSFSLSTN LQESLRSKE             409

SEQ ID NO: 566          moltype = AA  length = 409
FEATURE                 Location/Qualifiers
source                  1..409
                        mol_type = protein
                        organism = synthetic construct
SEQUENCE: 566
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRDISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE             409

SEQ ID NO: 567          moltype = AA  length = 409
FEATURE                 Location/Qualifiers
source                  1..409
                        mol_type = protein
                        organism = synthetic construct
SEQUENCE: 567
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRHFSLSTN LQESLRSKE             409

SEQ ID NO: 568          moltype = AA  length = 409
FEATURE                 Location/Qualifiers
source                  1..409
                        mol_type = protein
                        organism = synthetic construct
SEQUENCE: 568
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRDSL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE             409

SEQ ID NO: 569          moltype = AA  length = 409
FEATURE                 Location/Qualifiers
source                  1..409
                        mol_type = protein
                        organism = synthetic construct
SEQUENCE: 569
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
```

-continued

```
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRFE IMRSFSLSTN LQESLRSKE             409

SEQ ID NO: 570         moltype = AA  length = 409
FEATURE                Location/Qualifiers
source                 1..409
                       mol_type = protein
                       organism = synthetic construct
SEQUENCE: 570
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWENVRAE IMRSFSLSTN LQESLRSKE             409

SEQ ID NO: 571         moltype = AA  length = 409
FEATURE                Location/Qualifiers
source                 1..409
                       mol_type = protein
                       organism = synthetic construct
SEQUENCE: 571
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGARRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE             409

SEQ ID NO: 572         moltype = AA  length = 409
FEATURE                Location/Qualifiers
source                 1..409
                       mol_type = protein
                       organism = synthetic construct
SEQUENCE: 572
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSRE             409

SEQ ID NO: 573         moltype = AA  length = 409
FEATURE                Location/Qualifiers
source                 1..409
                       mol_type = protein
                       organism = synthetic construct
SEQUENCE: 573
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL SSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS PCAWEVVRAE IMRSFSLSTN LQESLRSKE             409

SEQ ID NO: 574         moltype = AA  length = 409
FEATURE                Location/Qualifiers
source                 1..409
                       mol_type = protein
                       organism = synthetic construct
SEQUENCE: 574
DIEPKSSDKT HTCPPCPAPE AAGGPSVFLF PPKPKDTLMI SRTPEVTCVV VDVSHEDPEV  60
KFNWYVDGVE VHNAKTKPRE EQYNSTYRVV SVLTVLHQDW LNGKEYKCKV SNKALGAPIE  120
KTISKAKGQP REPQVYTLPP SRDELTKNQV SLTCLVKGFY PSDIAVEWES NGQPENNYKT  180
TPPVLDSDGS FFLYSKLTVD KSRWQQGNVF SCSVMHEALH NHYTQKSLSL SPGKGGGGSG  240
GGGSCDLPQT HSLGSRRTLM LLAQMRRISL FSCLKDRHDF GFPQEEFGNQ FQKAETIPVL  300
HEMIQQIFNL FSTKDSSAAW DETLLDKFYT ELYQQLNDLE ACVIQGVGVT ETPLMKEDSI  360
LAVRKYFQRI TLYLKEKKYS ECAWEVVRAE IMRSFSLSTN LQESLRSKE             409

SEQ ID NO: 575         moltype = AA  length = 10
FEATURE                Location/Qualifiers
source                 1..10
                       mol_type = protein
                       organism = synthetic construct
SEQUENCE: 575
```

-continued

```
GGGGSGGGGS                                                                  10

SEQ ID NO: 576          moltype = AA  length = 15
FEATURE                 Location/Qualifiers
source                  1..15
                        mol_type = protein
                        organism = synthetic construct
SEQUENCE: 576
GGGGSGGGGS GGGGS                                                            15

SEQ ID NO: 577          moltype = AA  length = 6
FEATURE                 Location/Qualifiers
source                  1..6
                        mol_type = protein
                        organism = synthetic construct
SEQUENCE: 577
HHHHHH                                                                      6

SEQ ID NO: 578          moltype = AA  length = 8
FEATURE                 Location/Qualifiers
source                  1..8
                        mol_type = protein
                        organism = synthetic construct
SEQUENCE: 578
HHHHHHHH                                                                    8
```

What is claimed is:

1. An isolated human interferon alpha-2 (IFNA2) variant, wherein the IFNA2 variant has decreased or no detectable binding to the human interferon-alpha/beta receptor beta 2 (IFNAR2) as compared to the wild-type human IFNA2 polypeptide, and wherein the IFNA2 variant comprises a polypeptide sequence of any one of SEQ ID NOs 67, 85, 99, 100, 101, 117, 118, 121, 159, 161, and 165.

2. An isolated nucleic acid encoding the IFNA2 variant of claim 1.

3. A recombinant expression vector comprising the nucleic acid of claim 2.

4. A host cell comprising the recombinant expression vector of claim 3.

5. An isolated fusion protein comprising:

an antibody or binding fragment thereof; and an isolated human IFNA2 variant, wherein the IFNA2 variant is covalently linked to the antibody or binding fragment thereof, and wherein the IFNA2 variant has decreased or no detectable binding to the human interferon-alpha/beta receptor beta (IFNAR2) as compared to the wild-type human IFNA2 polypeptide, and wherein the IFNA2 variant comprises a polypeptide sequence of any one of SEQ ID NOs 67, 85, 99, 100, 101, 117, 118, 121, 159, 161, and 165.

6. The isolated fusion protein of claim 5, wherein the IFNA2 variant is covalently linked to the antibody by a polypeptide linker.

7. The isolated fusion protein of claim 6, wherein the polypeptide linker is selected from the group consisting of (G4S) 2 and (G4S) 3.

8. The isolated fusion protein of claim 6, wherein the polypeptide linker is a polypeptide tag selected from the group consisting of FLAG, MYC, HA, and 6Xhis.

9. An isolated cell line that produces the fusion protein of claim 5.

10. An isolated nucleic acid encoding the fusion protein of claim 5.

11. A recombinant expression vector comprising the nucleic acid of claim 10.

12. A host cell comprising the recombinant expression vector of claim 11.

13. The isolated fusion protein of claim 5, wherein the antibody or binding fragment thereof comprises an Fc domain.

14. The isolated fusion protein of claim 5, wherein the isolated fusion protein comprises a polypeptide sequence of any one of SEQ ID NOs 539, 541-550, and 560-574.

15. The isolated fusion protein of claim 5, wherein the antibody is an anti-CD8 antibody.

16. The isolated fusion protein of claim 5, wherein the isolated fusion protein comprises a polypeptide sequence of any one of SEQ ID NOs 552-559.

* * * * *